US011807618B2

(12) United States Patent
Meldrum et al.

(10) Patent No.: US 11,807,618 B2
(45) Date of Patent: Nov. 7, 2023

(54) THIOPHENE DERIVATIVES AS ANTIVIRAL AGENTS

(71) Applicant: ENYO PHARMA, Lyons (FR)

(72) Inventors: Eric Meldrum, Riehen (CH); Benoît De Chassey, Lyons (FR); Laëtitia Lines, Villeurbanne (FR); Jérôme Amaudrut, Dijon (FR); Benaissa Boubia, Saint Apollinaire (FR); Vincent Derain, Prenois (FR); Fabrice Guillier, Belleneuve (FR); Christian Montalbetti, Fontaine-les-Dijon (FR); Calum Macleod, Bishop's Stortford (GB); Karine Fabienne Malagu, Cambridge (GB); David Robert Vesey, Harlow (GB); Paul Colin Michael Winship, Cambridge (GB)

(73) Assignee: ENYO PHARMA, Lyons (FR)

( * ) Notice: Subject to any disclaimer, the term of this patent is extended or adjusted under 35 U.S.C. 154(b) by 0 days.

(21) Appl. No.: 17/697,981

(22) Filed: Mar. 18, 2022

(65) Prior Publication Data

US 2022/0213053 A1 Jul. 7, 2022

Related U.S. Application Data

(62) Division of application No. 16/473,660, filed as application No. PCT/EP2017/084726 on Dec. 28, 2017, now Pat. No. 11,279,683.

(30) Foreign Application Priority Data

Dec. 29, 2016 (EP) .................................. 16306843

(51) Int. Cl.
| | |
|---|---|
| *C07D 333/78* | (2006.01) |
| *A61P 31/12* | (2006.01) |
| *C07D 333/38* | (2006.01) |
| *C07D 333/68* | (2006.01) |
| *C07D 409/12* | (2006.01) |
| *C07D 413/12* | (2006.01) |
| *C07D 417/12* | (2006.01) |
| *C07D 493/08* | (2006.01) |
| *C07D 495/04* | (2006.01) |

(52) U.S. Cl.
CPC ............ *C07D 333/78* (2013.01); *A61P 31/12* (2018.01); *C07D 333/38* (2013.01); *C07D 333/68* (2013.01); *C07D 409/12* (2013.01); *C07D 413/12* (2013.01); *C07D 417/12* (2013.01); *C07D 493/08* (2013.01); *C07D 495/04* (2013.01)

(58) Field of Classification Search
CPC ................................................. C07D 333/78
See application file for complete search history.

(56) References Cited

U.S. PATENT DOCUMENTS 11,279,683 B2    3/2022   Meldrum et al.

FOREIGN PATENT DOCUMENTS

| WO | WO 01/12189 | 2/2001 | |
|---|---|---|---|
| WO | WO-2001098290 A2 * | 12/2001 | |
| WO | WO 2004/069149 | 8/2004 | |
| WO | WO 2005/023818 | 3/2005 | |
| WO | WO 2006/026619 | 3/2006 | |
| WO | WO 2006/093518 | 9/2006 | |
| WO | WO 2007/044565 | 4/2007 | |
| WO | WO 2009/079373 | 6/2009 | |
| WO | WO-2015018823 A1 * | 2/2015 | ............. A61K 31/38 |

OTHER PUBLICATIONS

STN chemical database Registry entry for 2-[(2-acetylbenzoyl)amino]-3-[[(4-ethoxyphenyl)amino]carbonyl]-4,7-dihydro-thieno[2,3-c]pyridine-6(5H)-carboxylic acid ethyl ester, RN 885942-82-5, ED Entered STN: May 29, 2006, SR Chemical Library Supplier: MicroChemistry Ltd.*
Schönherr "Profound Methyl Effects in Drug Discovery and a Call for New C-H Methylation Reactions" Angew. Chem. Int. Ed. 2013, 52, 12256-12267.*
Leitão, A. et al. "In silico screening of HIV-1 non-nucleoside reverse transcriptase and protease inhibitors" European Journal of Medicinal Chemistry, 2008, pp. 1412-1422, vol. 43, No. 7.
Nathans, R. et al. "Small-molecule inhibition of HIV-1 Vif" Nature Biotechnology, Oct. 2008, pp. 1187-1192, vol. 26, No. 10.
Chung, S. et al. "Structure-Activity Analysis of Vinylogous Urea Inhibitors of Human Immunodeficiency Virus-Encoded Ribonuclease H" Antimicrobial Agents and Chemotherapy, Sep. 2010, pp. 3913-3921, vol. 54, No. 9.
Written Opinion in International Application No. PCT/EP2017/084726, dated Feb. 26, 2018, pp. 1-6.
De Clercq, E. "Clinical Potential of the Acyclic Nucleoside Phosphonates Cidofovir, Adefovir, and Tenofovir in Treatment of DNA Virus and Retrovirus Infections" Clinical Microbiology Reviews, Oct. 2003, vol. 16, No. 4, pp. 569-596.
Kranzusch, P. J. et al. "Assembly of a functional Machupo virus polymerase complex" PNAS, Nov. 16, 2010, pp. 20069-20074, vol. 107, No. 46.
Bae, Y. H. et al. "Cancer Targeted Drug Delivery", Springer: New York, 2013, p. v., pp. 1-3.
Mainz, L. "Autophagy and cancer—insights from mouse model" The FEBS Journal, 2018, pp. 792-808, vol. 285.
Mulcahy Levy, J. M. "Targeting autophagy during cancer therapy to improve clinical outcomes" Pharmacology & Therapeutics, 2011, pp. 130-141, vol. 131, No. 1.
Damia, G. et al. "Contemporary pre-clinical development of anti-cancer agents—What are the optimal preclinical models?" European Journal of Cancer, 2009, pp. 2768-2781, vol. 45.
Sharma, S. V. et al. "Cell line-based platforms to evaluate the therapeutic efficacy of candidate anticancer agents" Nature Reviews Cancer, Apr. 2010, pp. 241-253, vol. 10.

(Continued)

*Primary Examiner* — David K O'Dell
(74) *Attorney, Agent, or Firm* — SALIWANCHIK, LLOYD & EISENSCHENK

(57) ABSTRACT

The present invention relates to a new class of compounds having an antiviral effect and the uses thereof.

7 Claims, No Drawings

(56) References Cited

OTHER PUBLICATIONS

Ocana, A. et al. "Preclinical development of molecular targeted agents for cancer" *Nat. Rev. Clin. Oncol.*, 2011 (published online Dec. 7, 2010), pp. 200-209, vol. 8.
Ledford, H. "US cancer institute overhauls cell lines" *Nature*, Feb. 25, 2016, p. 391, vol. 530.
Johnson, J. et al. "Relationships between drug activity in NCI preclinical in vitro and in vivo models and early clinical trials" *British Journal of Cancer*, 2001, pp. 1424-1431, vol. 84, No. 10.
Makrilakis, K. "Pathophysiology of Type 2 diabetes" *Chapters in Diabetes in Clinical Practice: Questions and Answers from Case Studies*, Nicholas Katsilambros et al., eds. John Wiley & Sons, 2006, pp. 43-58.
Vickers, S. P. et al. "The utility of animal models to evaluate novel anti-obesity agents" *British Journal of Pharmacology*, 2011, pp. 1248-1262, vol. 164.
Lutz, T. A. et al. "Overview of Animal Models of Obesity" *Curr Protoc Pharmacol*, Sep. 2012, Chapter: Unit 5.61, pp. 1-22.
Tatti, M. et al. "Autophagy in Gaucher disease due to saposin C deficiency" *Autophagy*, Jan. 2011, pp. 94-95, vol. 7, Issue 1.
Maley, C. C. et al. "Frontiers in Cancer Research" Springer, 2016, pp. 18-19.

Viret, C. et al. "Autophagy during Early Virus-Host Cell Interactions" CIRI, International Center for Infectiology Research, 2018, pp. 1-45.
Zhang, Y. et al. "Autophagy as an emerging target in cardiorenal metabolic disease: From pathophysiology to management" *Pharmacology & Therapeutics*, 2018, pp. 1-22.
Wileman, T. "Aggresomes and Autophagy Generate Sites for Virus Replication" *Science*, May 12, 2006, pp. 875-878, vol. 312, No. 5775.
Jordan, T. X. et al. "Manipulation or capitulation: virus interactions with autophagy" *Microbes and Infection*, 2012, pp. 126-139, vol. 14.
Yun, C. W. et al. "The Dual Role of Autophagy in Cancer Development and a Therapeutic Strategy for Cancer by Targeting Autophagy" *International Journal of Molecular Sciences*, 2020, pp. 1-22, vol. 22, No. 179.
Muller, B. et al. "Antiviral Strategies" Handbook of Experimental Pharmacology, vol. 189, Chapter 1, 2009, pp. 1-24.
Massari, S. et al. "Structural Investigation of Cycloheptathiophene-3-carboxamide Derivatives Targeting Influenza Virus Polymerase Assembly "*Journal of Medicinal Chemistry*, 2013, pp. 10118-10131, vol. 56.

\* cited by examiner

THIOPHENE DERIVATIVES AS ANTIVIRAL AGENTS

CROSS-REFERENCE TO RELATED APPLICATIONS

This application is a divisional of U.S. application Ser. No. 16/473,660, filed Jun. 26, 2019, now U.S. Pat. No. 11,279,683, which is the U.S. national stage application of International Patent Application No. PCT/EP2017/084726, filed Dec. 28, 2017.

FIELD OF THE INVENTION

The present invention relates to the field of medicine, in particular antiviral drugs.

BACKGROUND OF THE INVENTION

Viruses are small infectious agents that replicates only inside living cells of other organisms. They can infect all types of life forms, from animals and plants to microorganisms, including bacteria and archaea. Among them, more than 400 species of virus are known to be responsible of diseases in humans, many of them leading to serious pathologies and eventually death. In particular, HIV was classified at the sixth leading cause of death worldwide in 2012 with 1.5 million deaths per year (WHO, Fact sheet No 310, 2014). Seasonal influenza viruses are responsible of flu that affects approximately 20% of the world population and causes 250,000 to 500,000 deaths per year (WHO, Fact sheet No 211, 2014). Among other examples, Hepatitis B and C are responsible altogether for about 1.4 million of death each year and human Papillomaviruses are responsible of cervix cancer, the second most common women cancer worldwide, leading to 270,000 death in 2012 (WHO, Fact sheets, 2016).

Because viruses use vital metabolic pathways within host cells to replicate, they are difficult to eliminate without using drugs that cause toxic effects to host cells in general. The most effective medical approaches to viral diseases are vaccinations to provide immunity to infection, and antiviral drugs that selectively interfere with viral replication. Vaccines are very effective on stable viruses for a preventive use. However, vaccines are of limited use in treating a patient who has already been infected. They are also difficult to successfully deploy against rapidly mutating viruses, such as influenza (the vaccine for which is updated every year) and HIV. Antiviral drugs may be particularly useful in these cases.

Antiviral drugs are a class of medication used specifically for treating viral infections. Antiviral drugs do not destroy their target pathogens, instead they inhibit their development. Antiviral drugs may target any stage of the viral life cycle: attachment to a host cell, release of viral genes and possibly enzymes into the host cell, replication of viral components using host-cell machinery, assembly of viral components into complete viral particles, and release of viral particles to infect new host cells. The most common antiviral drugs are nucleoside analogues that block viruses' replication. Most antiviral drugs are used for specific viral infections, while broad-spectrum antiviral drugs are effective against a wide range of viruses.

Soon after the development of antiviral drugs, resistance appeared. Antiviral drug resistance can be defined as a decreased susceptibility to a drug through either a minimally effective, or completely ineffective, treatment response to prevent associated illnesses from a particular virus. Antiviral drug resistance remains a major obstacle to antiviral therapy as it has developed to almost all specific and effective antiviral drugs. For example, there are two main groups of antiviral drugs available for treatment and prophylaxis of influenza: M2 inhibitors (amantadine and rimantadine) and neuraminidase inhibitors (oseltamivir and zanamivir). Despite the effectiveness of these drugs in reducing influenza-related morbidity and mortality, the emergence of drug resistance poses a critical limitation on their application and have raised an urgent need for developing new anti-influenza drugs against resistant forms.

Thus, there is nowadays a strong need for the development of new antiviral drugs, and in particular broad-spectrum antiviral drugs. The present invention seeks to meet these and other needs.

SUMMARY OF THE INVENTION

The present invention relates to a compound for use as an antiviral drug, having the following formula (I):

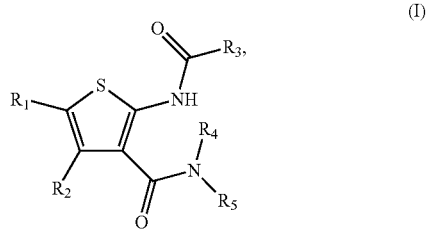

wherein:
$R_1$ and $R_2$ represent independently:
  H;
  a $(C_1-C_6)$alkyl; or
  $R_1$ and $R_2$ may form together a 5-7 membered ring, saturated or unsaturated,
    said 5-7 membered ring optionally comprises one or more heteroatoms chosen among:
    N, optionally substituted by a radical selected in the group consisting of
      a $(C_1-C_6)$alkyl, a $(C_2-C_6)$alkenyl, a $(C_2-C_6)$alkynyl,
      a 5-10 membered ring, saturated or unsaturated, selected from the group consisting of cycloalkyl, aryl, heterocycloalkyl, and heteroaryl,
      a saturated or unsaturated $(C_1-C_6)$alkylcycloalkyl, $(C_1-C_6)$alkylaryl, $(C_1-C_6)$alkylheterocycloalkyl), or $(C_1-C_6)$alkylheteroaryl, and
      a CO—$(C_1-C_6)$alkyl, a $CO_2$—$(C_1-C_6)$alkyl, a CO—$(C_1-C_6)$alkylaryl, a CO-aryl, a CO-heteroaryl, a $SO_2$-aryl, or a $SO_2$-heteroaryl, said radical is optionally substituted by at least one —OH, halogen, $(C_1-C_6)$alkyl, or $(C_1-C_6)$alkyloxy,
    O, and
    S, and
    said 5-7 membered ring is optionally substituted by:
      a $(C_1-C_6)$alkyl, a $(C_1-C_6)$alkyloxy, a $(C_2-C_6)$alkenyl, a $(C_2-C_6)$alkynyl, optionally substituted by at least one halogen, or —OH,
      a 5-10 membered ring, saturated or unsaturated, selected from the group consisting of cycloalkyl, aryl, heterocycloalkyl, and heteroaryl, optionally substituted by at least one —OH, halogen, $(C_1$-$C_6)$alkyl, or $(C_1$-$C_6)$alkyloxy, a saturated or unsaturated $(C_1$-$C_6)$alkylcycloalkyl, $(C_1$-$C_6)$alkylaryl, $(C_1$-$C_6)$alkylheterocycloalkyl), or $(C_1$-$C_6)$alkylheteroaryl, optionally substituted by at least one —OH, halogen, $(C_1$-$C_6)$alkyl, or $(C_1$-$C_6)$alkyloxy, a halogen, —CN, or —$NO_2$, —C(O)R, —C(O)$_2$R, —C(O)NRR', —CONHOR, —CONHSO$_2$R, —NRR', —N(R)C(O)R', —N(R)NR'R'', —N(R)C(O)$_2$R', —N(R)C(O)NR'R'', —N(R)S(O)$_2$R', —OR, —SR, —S(O)R, —S(O$_2$)R, —S(O)NRR', or —S(O)$_2$NRR', R, R', and R'' being independently H, $(C_1$-$C_6)$alkyl, cycloalkyl, aryl, heterocycloalkyl, heteroaryl, $(C_1$-$C_6)$alkylcycloalkyl, $(C_1$-$C_6)$alkylaryl, $(C_1$-$C_6)$alkylheterocycloalkyl), $(C_1$-$C_6)$alkylheteroaryl, or R and R' or R' and R'' may form a 5-7 membered ring, optionally interrupted by one or several heteroatoms, said 5-7 membered ring is optionally substituted by at least one —OH, halogen, $(C_1$-$C_6)$alkyl, or $(C_1$-$C_6)$alkyloxy;

$R_3$ represents:

a radical selected from the group consisting of:
a $(C_1$-$C_6)$alkyl, a $(C_2$-$C_6)$alkenyl, a $(C_2$-$C_6)$alkynyl, a 4-10 membered ring, saturated or unsaturated, selected from the group consisting of a cycloalkyl, a cycloalkanonyl, a heterocycloalkanonyl, an aryl, a heterocycloalkyl, a heteroaryl, a 5-10 membered bridged carbocyclyl or heterocyclyl, and a saturated or unsaturated $(C_1$-$C_6)$alkylcycloalkyl, $(C_1$-$C_6)$alkylaryl, $(C_1$-$C_6)$alkylheterocycloalkyl, and $(C_1$-$C_6)$alkylheteroaryl, said radicals being optionally substituted by:
a $(C_1$-$C_6)$alkyl or a $(C_1$-$C_6)$alkoxy, optionally substituted by at least one halogen, preferably a fluorine, a 5-10 membered ring, saturated or unsaturated, selected from the group consisting of a cycloalkyl, a spironocycloalkyl, an aryl, a heterocycloalkyl, and a heteroaryl, or a saturated or unsaturated $(C_1$-$C_6)$alkylcycloalkyl, $(C_1$-$C_6)$alkylaryl, $(C_1$-$C_6)$alkylheterocycloalkyl, or $(C_1$-$C_6)$alkylheteroaryl; and said optionally substituted radical being optionally substituted by at least one group (A) selected in the group consisting of:

—C(O)R, —C(O)$_2$R, —C(O)NRR', —CONHOR, —CONHSO$_2$R, —NRR', —N(R)C(O)R', —N(R)NR'R'', —N(R)C(O)$_2$R', —N(R)C(O)NR'R'', —N(R)S(O)$_2$R', —R—OH, —OR, —SR, —S(O)R, —S(O$_2$)R, —S(O)NRR', —S(O)$_2$NRR', R, R', and R'' are such as above defined, and a tetrazolyl;

a —X—Y unit, in which:
X is O or NH, and
Y is selected from the radical consisting of:
a $(C_1$-$C_6)$alkyl, a $(C_2$-$C_6)$alkenyl, a $(C_2$-$C_6)$alkynyl, a 5-10 membered ring, saturated or unsaturated, selected from the group consisting of a cycloalkyl, a cycloalkanonyl, an aryl, a heterocycloalkyl, a heteroaryl, and a 5-10 membered bridged carbocyclyl or heterocyclyl, and a saturated or unsaturated $(C_1$-$C_6)$alkylcycloalkyl, $(C_1$-$C_6)$alkylaryl, $(C_1$-$C_6)$alkylheterocycloalkyl, $(C_1$-$C_6)$alkylheteroaryl, said radicals being optionally substituted by:
a $(C_1$-$C_6)$alkyl or a $(C_1$-$C_6)$alkoxy, a 5-10 membered ring, saturated or unsaturated, selected from the group consisting of a cycloalkyl, a spironocycloalkyl, an aryl, a heterocycloalkyl, and a heteroaryl, or a saturated or unsaturated $(C_1$-$C_6)$alkylcycloalkyl, $(C_1$-$C_6)$alkylaryl, $(C_1$-$C_6)$alkylheterocycloalkyl, or $(C_1$-$C_6)$alkylheteroaryl, and said optionally substituted radical being optionally substituted by at least one group (A) as above defined; or $R_3$ may form with the nitrogen atom of the group —NH—CO—$R_3$ a moiety having the following formula (A):

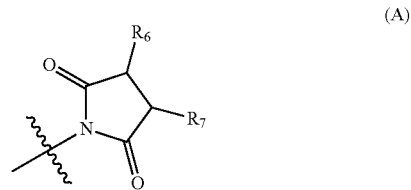

(A)

in which $R_6$ and $R_7$ represent independently H, or a $(C_1$-$C_6)$alkyl or $R_6$ and $R_7$ may form a 5-10 membered ring saturated or unsaturated, selected from the group consisting of a cycloalkyl, an aryl, a heterocycloalkyl, and a heteroaryl, said 5-10 membered ring being optionally substituted by at least one —OH, halogen, $(C_1$-$C_6)$alkyl, or $(C_1$-$C_6)$alkyloxy;

$R_4$ represents a radical selected in the group of:
a 5-14 membered ring, saturated or unsaturated, selected from the group consisting of a cycloalkyl, an aryl, a heterocycloalkyl, a heteroaryl, a fused arylheterocycloalkyl, and a fused arylcycloalkyl, a $(C_1$-$C_6)$alkylcycloalkyl, a $(C_1$-$C_6)$alkylaryl, a $(C_1$-$C_6)$alkylheterocycloalkyl, and a $(C_1$-$C_6)$alkylheteroaryl, and a $(C_1$-$C_6)$alkyl, said radicals being optionally substituted by at least one group (B) selected in the group consisting of:
a $(C_1$-$C_6)$alkyl or a $(C_1$-$C_6)$alkoxy, optionally substituted by at least one OH, one halogen or one —NRR', R, R', and R'' are such as defined above, a halogen, —CN, or —$NO_2$, a 5-10 membered ring, saturated or unsaturated, selected from the group consisting of a cycloalkyl, an aryl, a heterocycloalkyl, and a heteroaryl, optionally substituted by at least one OH, one halogen, one $(C_1$-$C_6)$alkyl, one $(C_1$-$C_6)$alkyloxy or one —NRR', R, R', and R'' are such as defined above, a saturated or unsaturated $(C_1$-$C_6)$alkylcycloalkyl, $(C_1$-$C_6)$alkylaryl, $(C_1$-$C_6)$alkylheterocycloalkyl, or $(C_1$-$C_6)$alkylheteroaryl, optionally substituted by at least one —OH, halogen, $(C_1$-$C_6)$alkyl, or $(C_1$-$C_6)$alkyloxy —C(O)R, —C(O)$_2$R, —C(O)NRR', —CONHOR, —CONHSO$_2$R, —NRR', —N(R)C(O)R', —N(R)NR'R'', —N(R)C(O)$_2$R', —N(R)C(O)NR'R'', —N(R)S(O)$_2$R', —OR, —SR, —S(O)R, —S(O$_2$)R, —S(O)NRR', or —S(O)$_2$NRR', R, R', and R" are such as defined above; and R$_5$ represents H, a (C$_1$-C$_6$)alkyl, a (C$_2$-C$_6$)alkenyl, or a (C$_2$-C$_6$)alkynyl; or R$_4$ and R$_5$ may form together a 5-14 membered ring, optionally interrupted by one or several heteroatoms, said 5-14 membered ring is optionally substituted by at least one —OH, halogen, (C$_1$-C$_6$)alkyl, (C$_1$-C$_6$)alkyloxy, cycloalkyl, or a 5-10 membered ring selected in the group of an aryl, a heterocycloalkyl, and a heteroaryl, optionally substituted by at least one —OH, halogen, (C$_1$-C$_6$)alkyl, or (C$_1$-C$_6$)alkyloxy; and the pharmaceutical salts thereof.

In a particular embodiment,

R$_1$ and R$_2$ form together a 5- or 6-membered ring, saturated or unsaturated, selected in the group of a cycloalkyl and an aryl,
    said 5- or 6-membered ring optionally comprises one O or one S, and
    said 5- or 6-membered ring is optionally substituted by a (C$_1$-C$_6$)alkyl.

In a preferred embodiment,

R$_1$ and R$_2$ form together a cyclopentyl, a cyclohexyl, a tetrahydro-2H-pyran, a tetrahydrofuran optionally substituted by a (C$_1$-C$_6$)alkyl, preferably a methyl, a thiophene, a tetrahydro-thiophene, or a phenyl, preferably a cyclopentyl.

In a further particular embodiment,

R$_4$ represents a radical selected in the group consisting of:
    a 5-10 membered ring, saturated or unsaturated, selected from the group consisting of:
        a cycloalkyl, preferably a cyclohexyl, optionally substituted by at least one group (B) selected from the group consisting of:
            a (C$_1$-C$_6$)alkyl, preferably a methyl, optionally substituted by at least one halogen, or one hydroxy,
            a (C$_1$-C$_6$)alkoxy, preferably a methoxy,
            a halogen, preferably a fluorine,
            a cyano,
            a cycloalkyl, a heterocycloalkyl, an aryl, or a heteroaryl, optionally substituted by at least one —OH, halogen, (C$_1$-C$_6$)alkyl, or (C$_1$-C$_6$)alkyloxy, and
            —C(O)R or —S(O$_2$)R with R being a (C$_1$-C$_6$)alkyl,
        an aryl, preferably a phenyl, optionally substituted by at least one group (B) selected from the group consisting of:
            a (C$_1$-C$_6$)alkyl, preferably a methyl, an ethyl, an isopropyl, a tert-butyl, optionally substituted by at least one halogen, preferably a fluorine, or one hydroxy,
            a (C$_1$-C$_6$)alkoxy, preferably a methoxy, optionally substituted by at least one fluorine,
            a halogen, preferably a fluorine or a chlorine,
            a cyano,
            a cycloalkyl, a heterocycloalkyl preferably a morpholine, an aryl, preferably a phenyl, or a heteroaryl, optionally substituted by at least one —OH, halogen, (C$_1$-C$_6$)alkyl, or (C$_1$-C$_6$)alkyloxy, and
            —C(O)R or —S(O$_2$)R with R being a (C$_1$-C$_6$)alkyl, preferably a methyl,
        a heteroaryl, preferably a pyridine, a pyrazine, or a thiazole, optionally substituted by at least one group (B) selected from the group consisting of:
            a halogen, preferably a chlorine, and
            a (C$_1$-C$_6$)alkyl, preferably a methyl, or a (C$_1$-C$_6$)alkoxy, optionally the (C$_1$-C$_6$)alkyl or (C$_1$-C$_6$)alkoxy being substituted by at least one halogen, preferably a fluorine, or one hydroxy,
            a cyano,
                a cycloalkyl, a heterocycloalkyl, an aryl, or a heteroaryl, optionally substituted by at least one —OH, halogen, (C$_1$-C$_6$)alkyl, or (C$_1$-C$_6$)alkyloxy, and
                —C(O)R or —S(O$_2$)R with R being a (C$_1$-C$_6$)alkyl,
        a fused arylheterocycloalkyl, preferably a benzodioxole or an isobenzofurane, and
        a fused arylcycloalkyl, preferably an indane,
    a radical selected in the group consisting of:
        (C$_1$-C$_6$)alkylcycloalkyl, preferably a methylcyclohexyl, and
        a (C$_1$-C$_6$)alkylaryl, preferably a methylphenyl,
            said radical is optionally substituted by at least one halogen, preferably a chlorine, one (C$_1$-C$_6$)alkyl or one (C$_1$-C$_6$)alkoxy, optionally substituted by at least one halogen, and
    a (C$_1$-C$_6$)alkyl, preferably a pentyl; and R$_5$ represents H or a (C$_1$-C$_6$)alkyl, preferably a methyl; or R4 and R5 may form together a heterocycloalkyl, preferably a piperazine, optionally substituted by an aryl, preferably a phenyl optionally substituted by at least one halogen, preferably a chlorine.

In a preferred embodiment,

R$_4$ represents a phenyl substituted by at least:
    one (C$_1$-C$_6$)alkyl, preferably a methyl, and/or
    one halogen, preferably a fluorine or a chlorine, and R$_5$ represents H.

In a further particular embodiment,

R$_3$ represents:
    a radical selected from the group consisting of:
        a (C$_1$-C$_6$)alkyl, preferably an ethyl or a propyl optionally substituted by a dimethyl or a spironocyclopentyl, and a (C$_2$-C$_6$)alkenyl, preferably an ethylene,
        a 5-10 membered ring, saturated or unsaturated, selected from the group consisting of:
            a cyclopentyl or a cyclohexyl,
            a cyclohexanone,
            a phenyl, and
            a bicyclo[2,2,2]octane and a 7-oxabicyclo[2.2.1]heptane, and
        a saturated or unsaturated (C$_1$-C$_6$)alkylheteroaryl, preferably methylimidazole optionally substituted by a (C$_1$-C$_6$)alkyl, preferably a methyl,
    said radicals being optionally substituted by at least one group (A) selected in the group consisting of a —C(O)$_2$R, a —C(O)NRR' with R and R' being H, and a —R—OH with R being a (C$_1$-C$_6$)alkyl, preferably a methylene.

More particularly, said at least one group (A), preferably —C(O)$_2$R with R being H, is in vicinal position with respect to the CO of the —NH—CO—R$_3$ group.

In a further particular embodiment,

R₃ may form with the nitrogen atom of the group —NH—CO—R₃ a moiety having the following formula (A):

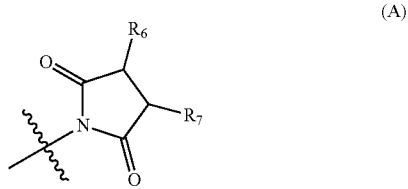

(A)

in which R₆ and R₇ form a cyclohexyl.

In a preferred embodiment, the compound for use of formula (I) is selected from the group consisting of:

Compound 1. 2-[[3-[(3,4-Dimethylphenyl)carbamoyl]-5,6-dihydro-4H-cyclopenta[b]thiophen-2-yl]carbamoyl]cyclohexanecarboxylic acid;

Compound 2. 2-[[3-[(6-Chloro-3-pyridyl)carbamoyl]-5,6-dihydro-4H-cyclopenta[b]thiophen-2-yl]carbamoyl]cyclohexanecarboxylic acid;

Compound 3. 2-[[3-(1,3-Benzodioxol-5-ylcarbamoyl)-5,6-dihydro-4H-cyclopenta[b]thiophen-2-yl]carbamoyl]cyclohexanecarboxylic acid;

Compound 4. 2-[[3-[(4-Fluorophenyl)carbamoyl]-5,6-dihydro-4H-cyclopenta[b]thiophen-2-yl]carbamoyl]cyclohexanecarboxylic acid;

Compound 5. 2-[[3-[(4-Chlorophenyl)methylcarbamoyl]-5,6-dihydro-4H-cyclopenta[b]thiophen-2-yl]carbamoyl]cyclohexanecarboxylic acid;

Compound 6. 2-[[3-[[4-Chloro-3-(trifluoromethyl)phenyl]carbamoyl]-5,6-dihydro-4H-cyclopenta[b]thiophen-2-yl]carbamoyl]cyclohexanecarboxylic acid;

Compound 7. 2-[[3-[(4-Chloro-2-methyl-phenyl)carbamoyl]-5,6-dihydro-4H-cyclopenta[b]thiophen-2-yl]carbamoyl]cyclohexanecarboxylic acid;

Compound 8. 2-[[3-[(Trans-4-methoxycyclohexyl)carbamoyl]-5,6-dihydro-4H-cyclopenta[b]thiophen-2-yl]carbamoyl]cyclohexanecarboxylic acid;

Compound 9. 2-[[3-[[4-(2-Hydroxyethyl)phenyl]carbamoyl]-5,6-dihydro-4H-cyclopenta[b]thiophen-2-yl]carbamoyl]cyclohexanecarboxylic acid;

Compound 10. 2-[[3-[(4-Phenylphenyl)carbamoyl]-5,6-dihydro-4H-cyclopenta[b]thiophen-2-yl]carbamoyl]cyclohexanecarboxylic acid;

Compound 11. 2-[[3-[(3-Chlorophenyl)methylcarbamoyl]-5,6-dihydro-4H-cyclopenta[b]thiophen-2-yl]carbamoyl]cyclohexanecarboxylic acid;

Compound 12. 2-[[3-[(3-Acetylphenyl)carbamoyl]-5,6-dihydro-4H-cyclopenta[b]thiophen-2-yl]carbamoyl]cyclohexanecarboxylic acid;

Compound 13. 2-[[3-[(4-Chloro-3-methyl-phenyl)carbamoyl]-5,6-dihydro-4H-cyclopenta[b]thiophen-2-yl]carbamoyl]cyclohexanecarboxylic acid;

Compound 14. 2-[[3-[(3-chloro-4-methyl-phenyl)carbamoyl]-5,6-dihydro-4H-cyclopenta[b]thiophen-2-yl]carbamoyl]cyclohexanecarboxylic acid;

Compound 15. 2-[[3-[(4-Morpholinophenyl)carbamoyl]-5,6-dihydro-4H-cyclopenta[b]thiophen-2-yl]carbamoyl]cyclohexanecarboxylic acid;

Compound 16. 2-[[3-[(3,4-Difluorophenyl)carbamoyl]-5,6-dihydro-4H-cyclopenta[b]thiophen-2-yl]carbamoyl]cyclohexanecarboxylic acid;

Compound 17. 2-[[3-[(3-Chlorophenyl)carbamoyl]-5,6-dihydro-4H-cyclopenta[b]thiophen-2-yl]carbamoyl]cyclohexanecarboxylic acid;

Compound 18. 2-[[3-[(4,4-Difluorocyclohexyl)carbamoyl]-5,6-dihydro-4H-cyclopenta[b]thiophen-2-yl]carbamoyl]cyclohexanecarboxylic acid;

Compound 19. 2-[[3-[[4-(Hydroxymethyl)phenyl]carbamoyl]-5,6-dihydro-4H-cyclopenta[b]thiophen-2-yl]carbamoyl]cyclohexanecarboxylic acid;

Compound 20. 2-[[3-[[4-(Trifluoromethoxy)phenyl]carbamoyl]-5,6-dihydro-4H-cyclopenta[b]thiophen-2-yl]carbamoyl]cyclohexanecarboxylic acid;

Compound 21. 2-[[3-[(4-tert-Butylphenyl)carbamoyl]-5,6-dihydro-4H-cyclopenta[b]thiophen-2-yl]carbamoyl]cyclohexanecarboxylic acid;

Compound 22. 2-[[3-(pentylcarbamoyl)-5,6-dihydro-4H-cyclopenta[b]thiophen-2-yl]carbamoyl]cyclohexanecarboxylic acid;

Compound 23. 2-[[3-(Indan-1-ylcarbamoyl)-5,6-dihydro-4H-cyclopenta[b]thiophen-2-yl]carbamoyl]cyclohexanecarboxylic acid;

Compound 24. 2-[[3-(Cyclohexylmethylcarbamoyl)-5,6-dihydro-4H-cyclopenta[b]thiophen-2-yl]carbamoyl]cyclohexanecarboxylic acid;

Compound 25. 2-[[3-[(4-Isopropylphenyl)carbamoyl]-5,6-dihydro-4H-cyclopenta[b]thiophen-2-yl]carbamoyl]cyclohexanecarboxylic acid;

Compound 26. 2-[[3-[(5-Chloropyrazin-2-yl)carbamoyl]-5,6-dihydro-4H-cyclopenta[b]thiophen-2-yl]carbamoyl]cyclohexanecarboxylic acid;

Compound 27. 2-[[3-[[4-(Trifluoromethyl)phenyl]carbamoyl]-5,6-dihydro-4H-cyclopenta[b]thiophen-2-yl]carbamoyl]cyclohexanecarboxylic acid;

Compound 28. 2-[[3-[(4-Cyanophenyl)carbamoyl]-5,6-dihydro-4H-cyclopenta[b]thiophen-2-yl]carbamoyl]cyclohexanecarboxylic acid;

Compound 29. 2-[[3-[(5-Chlorothiazol-2-yl)carbamoyl]-5,6-dihydro-4H-cyclopenta[b]thiophen-2-yl]carbamoyl]cyclohexanecarboxylic acid;

Compound 30. 2-[[3-(1,3-Dihydroisobenzofuran-5-ylcarbamoyl)-5,6-dihydro-4H-cyclopenta[b]thiophen-2-yl]carbamoyl]cyclohexanecarboxylic acid;

Compound 31. 2-[[3-[(4-Methylsulfonylphenyl)carbamoyl]-5,6-dihydro-4H-cyclopenta[b]thiophen-2-yl]carbamoyl]cyclohexanecarboxylic acid;

Compound 32. 2-[[3-[[6-(Trifluoromethyl)-3-pyridyl]carbamoyl]-5,6-dihydro-4H-cyclopenta[b]thiophen-2-yl]carbamoyl]cyclohexanecarboxylic acid;

Compound 33. 2-[[3-[(5-Methyl-3-pyridyl)carbamoyl]-5,6-dihydro-4H-cyclopenta[b]thiophen-2-yl]carbamoyl]cyclohexanecarboxylic acid;

Compound 34. 2-[[3-[(4-Chlorophenyl)-methyl-carbamoyl]-5,6-dihydro-4H-cyclopenta[b]thiophen-2-yl]carbamoyl]cyclohexanecarboxylic acid;

Compound 35. 2-[[3-[(4-Methylcyclohexyl)carbamoyl]-5,6-dihydro-4H-cyclopenta[b]thiophen-2-yl]carbamoyl]cyclohexanecarboxylic acid;

Compound 36. 2-[[3-[4-(4-chlorophenyl)piperazine-1-carbonyl]-5,6-dihydro-4H-cyclopenta[b]thiophen-2-yl]carbamoyl]cyclohexanecarboxylic acid;

Compound 37. 2-[[3-[(4-Chlorophenyl)carbamoyl]-5,7-dihydro-4H-thieno[2,3-c]pyran-2-yl]carbamoyl]cyclohexanecarboxylic acid;

Compound 38. 2-[[3-[(4-Chlorophenyl)carbamoyl]-4,6-dihydrothieno[3,4-b]thiophen-2-yl]carbamoyl]cyclohexanecarboxylic acid;

Compound 39. 2-[[3-[(4-Chlorophenyl)carbamoyl]-4-methyl-4,6-dihydrothieno[2,3-c]furan-2-yl]carbamoyl]cyclohexanecarboxylic acid;

Compound 40. 2-[[4-[(4-Chlorophenyl)carbamoyl]-2,3-dihydrothieno[2,3-b]thiophen-5-yl]carbamoyl]cyclohexanecarboxylic acid;

Compound 41. 2-[[3-[(4-Chlorophenyl)carbamoyl]benzothiophen-2-yl]carbamoyl]cyclohexanecarboxylic acid;

Compound 42. 2-[[3-[(4-Chlorophenyl)carbamoyl]thieno[3,4-b]thiophen-2-yl]carbamoyl]cyclohexanecarboxylic acid;

Compound 43. 4-[[3-[(4-Chlorophenyl)carbamoyl]-5,6-dihydro-4H-cyclopenta[b]thiophen-2-yl]amino]-4-oxo-but-2-enoic acid;

Compound 44. 2-[[3-[(4-Chlorophenyl)carbamoyl]-5,6-dihydro-4H-cyclopenta[b]thiophen-2-yl]carbamoyl]benzoic acid;

Compound 45. 2-[1-[2-[[3-[(4-Chlorophenyl)carbamoyl]-5,6-dihydro-4H-cyclopenta[b]thiophen-2-yl]amino]-2-oxoethyl]cyclopentyl]acetic acid;

Compound 46. 2-[[3-[(4-Chlorophenyl)carbamoyl]-5,6-dihydro-4H-cyclopenta[b]thiophen-2-yl]carbamoyl]cyclopentanecarboxylic acid;

Compound 47. 5-[[3-[(4-Chlorophenyl)carbamoyl]-5,6-dihydro-4H-cyclopenta[b]thiophen-2-yl]amino]-3,3-dimethyl-5-oxo-pentanoic acid;

Compound 48. 6-[[3-[(4-Chlorophenyl)carbamoyl]-5,6-dihydro-4H-cyclopenta[b]thiophen-2-yl]carbamoyl]cyclohex-3-ene-1-carboxylic acid;

Compound 49. 2-[[3-[(4-Chlorophenyl)carbamoyl]-5,6-dihydro-4H-cyclopenta[b]thiophen-2-yl]carbamoyl]cyclohexane-trans-carboxylic acid;

Compound 50. 4-[[3-[(4-Chlorophenyl)carbamoyl]-5,6-dihydro-4H-cyclopenta[b]thiophen-2-yl]amino]-4-oxo-butanoic acid;

Compound 51. 2-[[3-[(4-Chlorophenyl)carbamoyl]-5,6-dihydro-4H-cyclopenta[b]thiophen-2-yl]carbamoyl]-7-oxabicyclo[2.2.1]heptane-3-carboxylic acid;

Compound 52. N-(4-Chlorophenyl)-2-(cyclohexanecarbonylamino)-5,6-dihydro-4H-cyclopenta[b]thiophene-3-carboxamide;

Compound 53. N-(4-Chlorophenyl)-2-[(3-oxocyclohexanecarbonyl)amino]-5,6-dihydro-4H-cyclopenta[b]thiophene-3-carboxamide;

Compound 54. N-(4-Chlorophenyl)-2-(1,3-dioxo-3a,4,5,6,7,7a-hexahydroisoindol-2-yl)-5,6-dihydro-4H-cyclopenta[b]thiophene-3-carboxamide;

Compound 55. N2-[3-[(4-Chlorophenyl)carbamoyl]-5,6-dihydro-4H-cyclopenta[b]thiophen-2-yl]cyclohexane-1,2-dicarboxamide;

Compound 56. N-(4-Chlorophenyl)-2-[[2-(hydroxymethyl)cyclohexanecarbonyl]amino]-5,6-dihydro-4H-cyclopenta[b]thiophene-3-carboxamide;

Compound 57. 2-[[3-[(4-Chlorophenyl)carbamoyl]-5,6-dihydro-4H-cyclopenta[b]thiophen-2-yl]carbamoyl]cyclohexane-cis-carboxylic acid;

Compound 58. 2-[[3-(m-Tolylcarbamoyl)-5,6-dihydro-4H-cyclopenta[b]thiophen-2-yl]carbamoyl]cyclohexanecarboxylic acid;

Compound 59. 2-[[3-[(4-Chlorophenyl)carbamoyl]-4-ethyl-5-methyl-2-thienyl]carbamoyl]cyclohexanecarboxylic acid;

Compound 60. 6-[[3-(p-Tolylcarbamoyl)-4,5,6,7-tetrahydrobenzothiophen-2-yl]carbamoyl]cyclohex-3-ene-1-carboxylic acid;

Compound 61. 2-[[3-[(4-Chlorophenyl)carbamoyl]-4,5,6,7-tetrahydrobenzothiophen-2-yl]carbamoyl]cyclohexane-cis-carboxylic acid;

Compound 62. 2-Benzamido-N-(m-tolyl)-5,6-dihydro-4H-cyclopenta[b]thiophene-3-carboxamide;

Compound 63. 2-[[3-(Benzylcarbamoyl)-5,6-dihydro-4H-cyclopenta[b]thiophen-2-yl]carbamoyl]cyclohexanecarboxylic acid;

Compound 64. 2-[[3-[(3-Methoxyphenyl)carbamoyl]-5,6-dihydro-4H-cyclopenta[b]thiophen-2-yl]carbamoyl]cyclohexanecarboxylic acid;

Compound 65. 2-[[3-(Cyclohexylcarbamoyl)-5,6-dihydro-4H-cyclopenta[b]thiophen-2-yl]carbamoyl]cyclohexanecarboxylic acid;

Compound 66. 2-[[3-(p-Tolylcarbamoyl)-5,6-dihydro-4H-cyclopenta[b]thiophen-2-yl]carbamoyl]cyclohexanecarboxylic acid;

Compound 67. 2-[[3-(o-Tolylcarbamoyl)-5,6-dihydro-4H-cyclopenta[b]thiophen-2-yl]carbamoyl]cyclohexanecarboxylic acid;

Compound 68. 6-[[3-(m-Tolylcarbamoyl)-4,5,6,7-tetrahydrobenzothiophen-2-yl]carbamoyl]cyclohex-3-ene-1-carboxylic acid;

Compound 69. 2-[[3-(m-Tolylcarbamoyl)-4,5,6,7-tetrahydrobenzothiophen-2-yl]carbamoyl]cyclohexanecarboxylic acid;

Compound 70. 2-[[3-[(3-Chlorophenyl)carbamoyl]-4-ethyl-5-methyl-2-thienyl]carbamoyl]cyclohexanecarboxylic acid;

Compound 71. 2-[[3-[(4-Chlorophenyl)carbamoyl]-2-thienyl]carbamoyl]bicyclo[2.2.2]octane-3-carboxylic acid;

Compound 72. 2-[[5-Isopropyl-3-(phenylcarbamoyl)-2-thienyl]carbamoyl]cyclohexanecarboxylic acid;

Compound 73. 2-[[4-Ethyl-5-methyl-3-(phenylcarbamoyl)-2-thienyl]carbamoyl]cyclohexanecarboxylic acid;

Compound 74. 2-[[3-(Phenylcarbamoyl)-5,6-dihydro-4H-cyclopenta[b]thiophen-2-yl]carbamoyl]cyclohexanecarboxylic acid;

Compound 75. N-(4-Chlorophenyl)-2-[[2-(2-methylimidazol-1-yl)acetyl]amino]-4,5,6,7-tetrahydrobenzothiophene-3-carboxamide;

Compound 76. 2-[[3-[(4-Methoxyphenyl)carbamoyl]-5,6-dihydro-4H-cyclopenta[b]thiophen-2-yl]carbamoyl]cyclohexanecarboxylic acid;

Compound 77. 2-[[3-[[3-(Trifluoromethyl)phenyl]carbamoyl]-5,6-dihydro-4H-cyclopenta[b]thiophen-2-yl]carbamoyl]cyclohexanecarboxylic acid;

Compound 78. N-(4-chlorophenyl)-2-[(2-pyrazin-2-ylacetyl)amino]-5,6-dihydro-4H-cyclopenta[b]thiophene-3-carboxamide;

Compound 79. 2-[[6-tert-butyl-3-[(4-chlorophenyl)carbamoyl]-4,5,6,7-tetrahydrobenzothiophen-2-yl]carbamoyl]cyclohexanecarboxylic acid;

Compound 80. N-[3-[(4-chlorophenyl)carbamoyl]-5,6-dihydro-4H-cyclopenta[b]thiophen-2-yl]-1-sulfamoyl-piperidine-2-carboxamide;

Compound 81. N-(4-chlorophenyl)-2-[(2-tetrahydropyran-4-ylacetyl)amino]-5,6-dihydro-4H-cyclopenta[b]thiophene-3-carboxamide;

Compound 82. N3-[3-[(4-chlorophenyl)carbamoyl]-5,6-dihydro-4H-cyclopenta[b]thiophen-2-yl]morpholine-3,4-dicarboxamide;

Compound 83. N-[3-[(4-chlorophenyl)carbamoyl]-5,6-dihydro-4H-cyclopenta[b]thiophen-2-yl]-1-sulfamoyl-piperidine-3-carboxamide;

Compound 84. 1-acetyl-N-[3-[(4-chlorophenyl)carbamoyl]-5,6-dihydro-4H-cyclopenta[b]thiophen-2-yl]azetidine-2-carboxamide;

Compound 85. N-(4-chlorophenyl)-2-[[(1S,2R)-2-(methanesulfonamido)cyclohexane carbonyl]amino]-5,6-dihydro-4H-cyclopenta[b]thiophene-3-carboxamide;

Compound 86. N-[3-[(4-chlorophenyl)carbamoyl]-5,6-dihydro-4H-cyclopenta[b]thiophen-2-yl]-4-methylsulfonyl-morpholine-2-carboxamide;

Compound 87. N-[3-[(4-chlorophenyl)carbamoyl]-5,6-dihydro-4H-cyclopenta[b]thiophen-2-yl]-4-sulfamoyl-morpholine-2-carboxamide;

Compound 88. N1-[3-[(4-chlorophenyl)carbamoyl]-5,6-dihydro-4H-cyclopenta[b]-thiophen-2-yl]-N2-methoxy-cyclohexane-1,2-dicarboxamide;

Compound 89. 1-[[3-[(4-chlorophenyl)carbamoyl]-5,6-dihydro-4H-cyclopenta[b]thiophen-2-yl]carbamoyl]piperidine-2-carboxylic acid;

Compound 90. N-(4-chlorophenyl)-2-[[2-(hydroxycarbamoyl) cyclohexanecarbonyl]amino]-5,6-dihydro-4H-cyclopenta[b]thiophene-3-carboxamide;

Compound 91. 2-[[6-tert-butoxycarbonyl-3-[(4-chlorophenyl)carbamoyl]-5,7-dihydro-4H-thieno[2,3-c]pyridin-2-yl]carbamoyl]cyclohexanecarboxylic acid;

Compound 92. N3-[3-[(4-chlorophenyl)carbamoyl]-5,6-dihydro-4H-cyclopenta[b]thiophen-2-yl]piperidine-1,3-dicarboxamide;

Compound 93. N-[3-[(4-chlorophenyl)carbamoyl]-5,6-dihydro-4H-cyclopenta[b]thiophen-2-yl]-4-methylsulfonyl-morpholine-3-carboxamide;

Compound 94. N-[3-[(4-chlorophenyl)carbamoyl]-5,6-dihydro-4H-cyclopenta[b]thiophen-2-yl]oxetane-3-carboxamide;

Compound 95. N-[3-[(4-chlorophenyl)carbamoyl]-5,6-dihydro-4H-cyclopenta[b]thiophen-2-yl]-1-methylsulfonyl-piperidine-3-carboxamide;

Compound 96. N-[3-[(4-chlorophenyl)carbamoyl]-5,6-dihydro-4H-cyclopenta[b]thiophen-2-yl]azetidine-2-carboxamide;

Compound 97. 4-[[3-[(4-chlorophenyl)carbamoyl]-5,6-dihydro-4H-cyclopenta[b]thiophen-2-yl]carbamoyl]cyclohexanecarboxylic acid, isomer A;

Compound 98. 4-[[3-[(4-chlorophenyl)carbamoyl]-5,6-dihydro-4H-cyclopenta[b]thiophen-2-yl]carbamoyl]cyclohexanecarboxylic acid, isomer B;

Compound 99. 3-[[3-[(4-chlorophenyl)carbamoyl]-5,6-dihydro-4H-cyclopenta[b]thiophen-2-yl]carbamoyl]cyclohexanecarboxylic acid;

Compound 100. N-[3-[(4-chlorophenyl)carbamoyl]-5,6-dihydro-4H-cyclopenta[b]thiophen-2-yl]-1-methylsulfonyl-piperidine-2-carboxamide;

Compound 101. N-[3-[(4-chlorophenyl)carbamoyl]-5,6-dihydro-4H-cyclopenta[b]thiophen-2-yl]-2-oxo-piperidine-4-carboxamide;

Compound 102. N-[3-[(4-chlorophenyl)carbamoyl]-5,6-dihydro-4H-cyclopenta[b]thiophen-2-yl]-1-sulfamoyl-azetidine-2-carboxamide;

Compound 103. (N-[3-[(4-chlorophenyl)carbamoyl]-5,6-dihydro-4H-cyclopenta[b]thiophen-2-yl]morpholine-3-carboxamide;

Compound 104. 4-(6-tert-butyl-3-(m-tolylcarbamoyl)-4,5,6,7-tetrahydrobenzo[b]thiophene-2-ylamino)-4-oxobutanoic acid; and Compound 105. 4-(6-tert-butyl-3-(4-methoxyphenylcarbamoyl)-4,5,6,7-tetrahydrobenzo[b]thiophene-2-ylamino)-4-oxobutanoic acid.

The present invention also provides a new compound of formula (I):

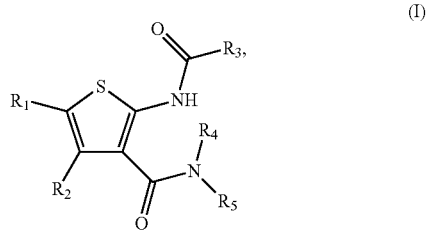

wherein:

$R_1$ and $R_2$ form together a 5-7 membered ring, saturated or unsaturated, said 5-7 membered ring comprises one or more heteroatoms chosen among:

N, optionally substituted by a radical selected in the group consisting of a $(C_1-C_6)$alkyl, a $(C_2-C_6)$alkenyl, a $(C_2-C_6)$alkynyl, a 5-10 membered ring, saturated or unsaturated, selected from the group consisting of cycloalkyl, aryl, heterocycloalkyl, and heteroaryl, a saturated or unsaturated $(C_1-C_6)$alkylcycloalkyl, $(C_1-C_6)$alkylaryl, $(C_1-C_6)$alkylheterocycloalkyl), or $(C_1-C_6)$alkylheteroaryl, and a CO—$(C_1-C_6)$alkyl, a $CO_2$—$(C_1-C_6)$alkyl, a CO—$(C_1-C_6)$alkylaryl, a CO-aryl, a CO-heteroaryl, a $SO_2$-aryl, or a $SO_2$-heteroaryl, said radical is optionally substituted by at least one —OH, halogen, $(C_1-C_6)$alkyl, or $(C_1-C_6)$alkyloxy, O, and S, and said 5-7 membered ring is optionally substituted by:

a $(C_1-C_6)$alkyl, a $(C_2-C_6)$alkenyl, a $(C_2-C_6)$alkynyl, optionally substituted by at least one halogen, or —OH, a 5-10 membered ring, saturated or unsaturated, selected from the group consisting of cycloalkyl, aryl, heterocycloalkyl, and heteroaryl, a saturated or unsaturated $(C_1-C_6)$alkylcycloalkyl, $(C_1-C_6)$alkylaryl, $(C_1-C_6)$alkylheterocycloalkyl), or $(C_1-C_6)$alkylheteroaryl, a halogen, —CN, or —$NO_2$, —C(O)R, —C(O)$_2$R, —C(O)NRR', —CONHOR, —CONHSO$_2$R, —NRR', —N(R)C(O)R', —N(R)NR'R", —N(R)C(O)$_2$R', —N(R)C(O)NR'R", —N(R)S(O)$_2$R', —OR, —SR, —S(O)R, —S(O$_2$)R, —S(O)NRR', or —S(O)$_2$NRR', R, R', and R" being independently H, $(C_1-C_6)$alkyl, cycloalkyl, aryl, heterocycloalkyl, heteroaryl, $(C_1-C_6)$alkylcycloalkyl, $(C_1-C_6)$alkylaryl, $(C_1-C_6)$alkylheterocycloalkyl), $(C_1-C_6)$alkylheteroaryl, or R and R' or R' and R" may form a 5-7 membered ring, optionally interrupted by one or several heteroatoms, said 5-7 membered ring is optionally substituted by at least one —OH, halogen, $(C_1-C_6)$alkyl or $(C_1-C_6)$alkyloxy;

$R_3$ represents:

a radical selected from the group consisting of:
a $(C_1$-$C_6)$alkyl, a $(C_2$-$C_6)$alkenyl, a $(C_2$-$C_6)$alkynyl, a 4-10 membered ring, saturated or unsaturated, selected from the group consisting of a cycloalkyl, a cycloalkanonyl, a heterocycloalkanonyl, an aryl, a heterocycloalkyl, a heteroaryl, and a 5-10 membered bridged carbocyclyl or heterocyclyl, and a saturated or unsaturated $(C_1$-$C_6)$alkylcycloalkyl, $(C_1$-$C_6)$alkylaryl, $(C_1$-$C_6)$alkylheterocycloalkyl, and $(C_1$-$C_6)$alkylheteroaryl, said radicals being optionally substituted by a $(C_1$-$C_6)$alkyl or a $(C_1$-$C_6)$alkoxy, optionally substituted by at least one halogen, preferably fluorine;

a 5-10 membered ring, saturated or unsaturated, selected from the group consisting of a cycloalkyl, a spironocycloalkyl, an aryl, a heterocycloalkyl, and a heteroaryl, or a saturated or unsaturated $(C_1$-$C_6)$alkylcycloalkyl, $(C_1$-$C_6)$alkylaryl, $(C_1$-$C_6)$alkylheterocycloalkyl, or $(C_1$-$C_6)$alkylheteroaryl; and said optionally substituted radical being optionally substituted by at least one group (A) selected in the group consisting of:

—C(O)R, —C(O)$_2$R, —C(O)NRR', —CONHOR, —CONHSO$_2$R, —NRR', —N(R)C(O)R', —N(R)NR'R", —N(R)C(O)$_2$R', —N(R)C(O)NR'R", —N(R)S(O)$_2$R', —R—OH, —OR, —SR, —S(O)R, —S(O$_2$)R, —S(O)NRR', —S(O)$_2$NRR', R, R', and R" are such as defined above, and a tetrazolyl;

a —X—Y unit, in which:

X is O or NH, and

Y is selected from the radical consisting of:

a $(C_1$-$C_6)$alkyl, a $(C_2$-$C_6)$alkenyl, a $(C_2$-$C_6)$alkynyl, a 5-10 membered ring, saturated or unsaturated, selected from the group consisting of a cycloalkyl, a cycloalkanonyl, an aryl, a heterocycloalkyl, a heteroaryl, and a 5-10 membered bridged carbocyclyl or heterocyclyl, and a saturated or unsaturated $(C_1$-$C_6)$alkylcycloalkyl, $(C_1$-$C_6)$alkylaryl, $(C_1$-$C_6)$alkylheterocycloalkyl, $(C_1$-$C_6)$alkylheteroaryl, said radicals being optionally substituted by:

a $(C_1$-$C_6)$alkyl or a $(C_1$-$C_6)$alkoxy, a 5-10 membered ring, saturated or unsaturated, selected from the group consisting of a cycloalkyl, a spironocycloalkyl, an aryl, a heterocycloalkyl, and a heteroaryl, a saturated or unsaturated $(C_1$-$C_6)$alkylcycloalkyl, $(C_1$-$C_6)$alkylaryl, $(C_1$-$C_6)$alkylheterocycloalkyl, or $(C_1$-$C_6)$alkylheteroaryl, and said optionally substituted radical being optionally substituted by at least one group (A) as above defined; or $R_3$ may form with the nitrogen atom of the group —NH—CO—$R_3$ a moiety having the following formula (A):

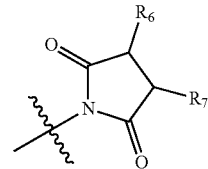

(A)

in which $R_6$ and $R_7$ represent independently H, or a $(C_1$-$C_6)$alkyl or $R_6$ and $R_7$ may form a 5-10 membered ring saturated or unsaturated, selected from the group consisting of a cycloalkyl, an aryl, a heterocycloalkyl, and a heteroaryl, said 5-10 membered ring being optionally substituted by at least one —OH, halogen, $(C_1$-$C_6)$alkyl, or $(C_1$-$C_6)$alkyloxy;

$R_4$ represents a radical selected in the group of:

a 5-14 membered ring, saturated or unsaturated, selected from the group consisting of a cycloalkyl, an aryl, a heterocycloalkyl, a heteroaryl, a fused arylheterocycloalkyl, and a fused arylcycloalkyl, a $(C_1$-$C_6)$alkylcycloalkyl, a $(C_1$-$C_6)$alkylaryl, a $(C_1$-$C_6)$alkylheterocycloalkyl, and a $(C_1$-$C_6)$alkylheteroaryl, and a $(C_1$-$C_6)$alkyl, said radicals being optionally substituted by at least one group (B) selected in the group consisting of:

a $(C_1$-$C_6)$alkyl or a $(C_1$-$C_6)$alkoxy, optionally substituted by at least one OH, one halogen or one —NRR', R, R', and R" are such as defined above, a halogen, —CN, or —NO$_2$, a 5-10 membered ring, saturated or unsaturated, selected from the group consisting of a cycloalkyl, an aryl, a heterocycloalkyl, and a heteroaryl, optionally substituted by at least one OH, one halogen, one $(C_1$-$C_6)$alkyl, one $(C_1$-$C_6)$alkyloxy or one —NRR', R, R', and R" are such as defined above a saturated or unsaturated $(C_1$-$C_6)$alkylcycloalkyl, $(C_1$-$C_6)$alkylaryl, $(C_1$-$C_6)$alkylheterocycloalkyl, or $(C_1$-$C_6)$alkylheteroaryl, optionally substituted by at least one —OH, halogen, $(C_1$-$C_6)$alkyl, or $(C_1$-$C_6)$alkyloxy, —C(O)R, —C(O)$_2$R, —C(O)NRR', —CONHOR, —CONHSO$_2$R, —NRR', —N(R)C(O)R', —N(R)NR'R", —N(R)C(O)$_2$R', —N(R)C(O)NR'R", —N(R)S(O)$_2$R', —OR, —SR, —S(O)R, —S(O$_2$)R, —S(O)NRR', or —S(O)$_2$NRR', R, R', and R" are such as defined above; and $R_5$ represents H, a $(C_1$-$C_6)$alkyl, a $(C_2$-$C_6)$alkenyl, or a $(C_2$-$C_6)$alkynyl; or $R_4$ and $R_5$ may form together a 5-14 membered ring, optionally interrupted by one or several heteroatoms, said 5-14 membered ring is optionally substituted by at least one —OH, halogen, $(C_1$-$C_6)$alkyl, $(C_1$-$C_6)$alkyloxy, cycloalkyl, or a 5-10 membered ring selected in the group of an aryl, a heterocycloalkyl, and a heteroaryl, optionally substituted by at least one —OH, halogen, $(C_1$-$C_6)$alkyl, or $(C_1$-$C_6)$alkyloxy;

and the pharmaceutical salts thereof.

In a preferred embodiment, $R_1$ and $R_2$ form together a 5-7 membered ring, saturated or unsaturated, said 5-7 membered ring comprises one or more heteroatoms chosen among:
O, and
S, and
said 5-7 membered ring is optionally substituted by:
a ($C_1$-$C_6$)alkyl, preferably a methyl;
$R_3$ represents:
a radical selected from the group consisting of:
a ($C_1$-$C_6$)alkyl, preferably an ethyl or a propyl optionally substituted by a dimethyl or a spironocyclopentyl, and a ($C_2$-$C_6$)alkenyl, preferably an ethylene,
a 5-10 membered ring, saturated or unsaturated, selected from the group consisting of:
a cyclopentyl or a cyclohexyl,
a cyclohexanone,
a phenyl, and
a bicyclo[2,2,2]octane and a 7-oxabicyclo[2.2.1]heptane, and
a saturated or unsaturated ($C_1$-$C_6$)alkylheteroaryl, preferably methylimidazole optionally substituted by a ($C_1$-$C_6$)alkyl, preferably a methyl,
said radicals being optionally substituted by at least one group (A) selected in the group consisting of a —C(O)$_2$R with R being H, and —R—OH with R being a ($C_1$-$C_6$)alkyl, preferably a methylene,
$R_4$ represents a radical selected in the group consisting of:
a 5-10 membered ring, saturated or unsaturated, selected from the group consisting of:
a cycloalkyl, preferably a cyclohexyl, optionally substituted by at least one group (B) selected from the group consisting of:
a ($C_1$-$C_6$)alkyl, preferably a methyl, optionally substituted by at least one halogen, or one hydroxy,
a ($C_1$-$C_6$)alkoxy, preferably a methoxy, and
a halogen, preferably a fluorine,
a cyano,
a cycloalkyl, a heterocycloalkyl, an aryl, or a heteroaryl, optionally substituted by at least one —OH, halogen, ($C_1$-$C_6$)alkyl, or ($C_1$-$C_6$)alkyloxy,
—C(O)R or —S(O$_2$)R with R being a ($C_1$-$C_6$)alkyl,
an aryl, preferably a phenyl, optionally substituted by at least one group (B) selected from the group consisting of:
a ($C_1$-$C_6$)alkyl, preferably a methyl, an ethyl, an isopropyl, a tert-butyl, optionally substituted by at least one halogen, preferably a fluorine, or one hydroxy,
a ($C_1$-$C_6$)alkoxy, preferably a methoxy, optionally substituted by at least one fluorine,
a halogen, preferably a fluorine or a chlorine,
a cyano,
a cycloalkyl, a heterocycloalkyl, preferably a morpholine, an aryl, preferably a phenyl, or a heteroaryl, optionally substituted by at least one —OH, halogen, ($C_1$-$C_6$)alkyl, or ($C_1$-$C_6$)alkyloxy,
—C(O)R or —S(O$_2$)R with R being a ($C_1$-$C_6$)alkyl, preferably a methyl,
a heteroaryl, preferably a pyridine, a pyrazine, or a thiazole, optionally substituted by at least one group (B) selected from the group consisting of:
a halogen, preferably a chlorine,
a ($C_1$-$C_6$)alkyl, preferably a methyl, or a ($C_1$-$C_6$)alkoxy, optionally substituted by at least one halogen, preferably a fluorine, or one hydroxy,
a cyano,
a cycloalkyl, a heterocycloalkyl, an aryl, or a heteroaryl, optionally substituted by at least one —OH, halogen, ($C_1$-$C_6$)alkyl, or ($C_1$-$C_6$)alkyloxy, and
—C(O)R or —S(O$_2$)R with R being a ($C_1$-$C_6$)alkyl,
a fused arylheterocycloalkyl, preferably a benzodioxole or an isobenzofurane, and
a fused arylcycloalkyl, preferably an indane,
a radical selected in the group consisting of:
($C_1$-$C_6$)alkylcycloalkyl, preferably a methylcyclohexyl, and
a ($C_1$-$C_6$)alkylaryl, preferably a methylphenyl,
said radical is optionally substituted by at least one halogen, preferably a chlorine, one ($C_1$-$C_6$)alkyl or one ($C_1$-$C_6$)alkoxy, optionally substituted by at least one halogen; and
a ($C_1$-$C_6$)alkyl, preferably a pentyl; and
$R_5$ represents H;
and the pharmaceutical salts thereof.

More particularly, $R_3$ represents a cycloalkyl, preferably a cyclohexyl, substituted by at least one group (A), preferably —C(O)$_2$R with R being H, said at least one group (A) being in vicinal position with respect to the CO of the —NH—CO—$R_3$ group.

In a more preferred embodiment, the compound of formula (I) is selected from the group the group consisting of:
Compound 37. 2-[[3-[(4-Chlorophenyl)carbamoyl]-5,7-dihydro-4H-thieno[2,3-c]pyran-2-yl]carbamoyl]cyclohexanecarboxylic acid;
Compound 38. 2-[[3-[(4-Chlorophenyl)carbamoyl]-4,6-dihydrothieno[3,4-b]thiophen-2-yl]carbamoyl]cyclohexanecarboxylic acid;
Compound 39. 2-[[3-[(4-Chlorophenyl)carbamoyl]-4-methyl-4,6-dihydrothieno[2,3-c]furan-2-yl]carbamoyl]cyclohexanecarboxylic acid;
Compound 40 (2-[[4-[(4-Chlorophenyl)carbamoyl]-2,3-dihydrothieno[2,3-b]thiophen-5-yl]carbamoyl]cyclohexanecarboxylic acid;
Compound 42. 2-[[3-[(4-Chlorophenyl)carbamoyl]thieno[3,4-b]thiophen-2-yl]carbamoyl]cyclohexanecarboxylic acid; and
Compound 99. 3-[[3-[(4-chlorophenyl)carbamoyl]-5,6-dihydro-4H-cyclopenta[b]thiophen-2-yl]carbamoyl]cyclohexanecarboxylic acid.

A further object of the invention is a compound as such of formula (I) for use as a drug.

The present invention further provides a new compound selected from the group consisting of:
Compound 1. 2-[[3-[(3,4-Dimethylphenyl)carbamoyl]-5,6-dihydro-4H-cyclopenta[b]thiophen-2-yl]carbamoyl]cyclohexanecarboxylic acid;
Compound 2. 2-[[3-[(6-Chloro-3-pyridyl)carbamoyl]-5,6-dihydro-4H-cyclopenta[b]thiophen-2-yl]carbamoyl]cyclohexanecarboxylic acid;
Compound 3. 2-[[3-(1,3-Benzodioxol-5-ylcarbamoyl)-5,6-dihydro-4H-cyclopenta[b]thiophen-2-yl]carbamoyl]cyclohexanecarboxylic acid;
Compound 4. 2-[[3-[(4-Fluorophenyl)carbamoyl]-5,6-dihydro-4H-cyclopenta[b]thiophen-2-yl]carbamoyl]cyclohexanecarboxylic acid;

Compound 5. 2-[[3-[(4-Chlorophenyl)methylcarbamoyl]-5,6-dihydro-4H-cyclopenta[b]thiophen-2-yl]carbamoyl]cyclohexanecarboxylic acid;

Compound 6. 2-[[3-[[4-Chloro-3-(trifluoromethyl)phenyl]carbamoyl]-5,6-dihydro-4H-cyclopenta[b]thiophen-2-yl]carbamoyl]cyclohexanecarboxylic acid;

Compound 7. 2-[[3-[(4-Chloro-2-methyl-phenyl)carbamoyl]-5,6-dihydro-4H-cyclopenta[b]thiophen-2-yl]carbamoyl]cyclohexanecarboxylic acid;

Compound 8. 2-[[3-[(Trans-4-methoxycyclohexyl)carbamoyl]-5,6-dihydro-4H-cyclopenta[b]thiophen-2-yl]carbamoyl]cyclohexanecarboxylic acid;

Compound 9. 2-[[3-[[4-(2-Hydroxyethyl)phenyl]carbamoyl]-5,6-dihydro-4H-cyclopenta[b]thiophen-2-yl]carbamoyl]cyclohexanecarboxylic acid;

Compound 10. 2-[[3-[(4-Phenylphenyl)carbamoyl]-5,6-dihydro-4H-cyclopenta[b]thiophen-2-yl]carbamoyl]cyclohexanecarboxylic acid;

Compound 11. 2-[[3-[(3-Chlorophenyl)methylcarbamoyl]-5,6-dihydro-4H-cyclopenta[b]thiophen-2-yl]carbamoyl]cyclohexanecarboxylic acid;

Compound 12. 2-[[3-[(3-Acetylphenyl)carbamoyl]-5,6-dihydro-4H-cyclopenta[b]thiophen-2-yl]carbamoyl]cyclohexanecarboxylic acid;

Compound 13. 2-[[3-[(4-Chloro-3-methyl-phenyl)carbamoyl]-5,6-dihydro-4H-cyclopenta[b]thiophen-2-yl]carbamoyl]cyclohexanecarboxylic acid;

Compound 14. 2-[[3-[(3-Chloro-4-methyl-phenyl)carbamoyl]-5,6-dihydro-4H-cyclopenta[b]thiophen-2-yl]carbamoyl]cyclohexanecarboxylic acid;

Compound 15. 2-[[3-[(4-Morpholinophenyl)carbamoyl]-5,6-dihydro-4H-cyclopenta[b]thiophen-2-yl]carbamoyl]cyclohexanecarboxylic acid;

Compound 16. 2-[[3-[(3,4-Difluorophenyl)carbamoyl]-5,6-dihydro-4H-cyclopenta[b]thiophen-2-yl]carbamoyl]cyclohexanecarboxylic acid;

Compound 17. 2-[[3-[(3-Chlorophenyl)carbamoyl]-5,6-dihydro-4H-cyclopenta[b]thiophen-2-yl]carbamoyl]cyclohexanecarboxylic acid;

Compound 18. 2-[[3-[(4,4-Difluorocyclohexyl)carbamoyl]-5,6-dihydro-4H-cyclopenta[b]thiophen-2-yl]carbamoyl]cyclohexanecarboxylic acid;

Compound 19. 2-[[3-[[4-(Hydroxymethyl)phenyl]carbamoyl]-5,6-dihydro-4H-cyclopenta[b]thiophen-2-yl]carbamoyl]cyclohexanecarboxylic acid;

Compound 20. 2-[[3-[[4-(Trifluoromethoxy)phenyl]carbamoyl]-5,6-dihydro-4H-cyclopenta[b]thiophen-2-yl]carbamoyl]cyclohexanecarboxylic acid;

Compound 21. 2-[[3-[(4-tert-Butylphenyl)carbamoyl]-5,6-dihydro-4H-cyclopenta[b]thiophen-2-yl]carbamoyl]cyclohexanecarboxylic acid;

Compound 22. 2-[[3-(pentylcarbamoyl)-5,6-dihydro-4H-cyclopenta[b]thiophen-2-yl]carbamoyl]cyclohexanecarboxylic acid;

Compound 23. 2-[[3-(Indan-1-ylcarbamoyl)-5,6-dihydro-4H-cyclopenta[b]thiophen-2-yl]carbamoyl]cyclohexanecarboxylic acid;

Compound 24. 2-[[3-(Cyclohexylmethylcarbamoyl)-5,6-dihydro-4H-cyclopenta[b]thiophen-2-yl]carbamoyl]cyclohexanecarboxylic acid;

Compound 25. 2-[[3-[(4-Isopropylphenyl)carbamoyl]-5,6-dihydro-4H-cyclopenta[b]thiophen-2-yl]carbamoyl]cyclohexanecarboxylic acid;

Compound 26. 2-[[3-[(5-Chloropyrazin-2-yl)carbamoyl]-5,6-dihydro-4H-cyclopenta[b]thiophen-2-yl]carbamoyl]cyclohexanecarboxylic acid;

Compound 27. 2-[[3-[[4-(Trifluoromethyl)phenyl]carbamoyl]-5,6-dihydro-4H-cyclopenta[b]thiophen-2-yl]carbamoyl]cyclohexanecarboxylic acid;

Compound 28. 2-[[3-[(4-Cyanophenyl)carbamoyl]-5,6-dihydro-4H-cyclopenta[b]thiophen-2-yl]carbamoyl]cyclohexanecarboxylic acid;

Compound 29. 2-[[3-[(5-Chlorothiazol-2-yl)carbamoyl]-5,6-dihydro-4H-cyclopenta[b]thiophen-2-yl]carbamoyl]cyclohexanecarboxylic acid;

Compound 30. 2-[[3-(1,3-Dihydroisobenzofuran-5-ylcarbamoyl)-5,6-dihydro-4H-cyclopenta[b]thiophen-2-yl]carbamoyl]cyclohexanecarboxylic acid;

Compound 31. 2-[[3-[(4-Methylsulfonylphenyl)carbamoyl]-5,6-dihydro-4H-cyclopenta[b]thiophen-2-yl]carbamoyl]cyclohexanecarboxylic acid;

Compound 32. 2-[[3-[[6-(Trifluoromethyl)-3-pyridyl]carbamoyl]-5,6-dihydro-4H-cyclopenta[b]thiophen-2-yl]carbamoyl]cyclohexanecarboxylic acid;

Compound 33. 2-[[3-[(5-Methyl-3-pyridyl)carbamoyl]-5,6-dihydro-4H-cyclopenta[b]thiophen-2-yl]carbamoyl]cyclohexanecarboxylic acid;

Compound 34. 2-[[3-[(4-Chlorophenyl)-methyl-carbamoyl]-5,6-dihydro-4H-cyclopenta[b]thiophen-2-yl]carbamoyl]cyclohexanecarboxylic acid;

Compound 35. 2-[[3-[(4-Methylcyclohexyl)carbamoyl]-5,6-dihydro-4H-cyclopenta[b]thiophen-2-yl]carbamoyl]cyclohexanecarboxylic acid;

Compound 36. 2-[[3-[4-(4-chlorophenyl)piperazine-1-carbonyl]-5,6-dihydro-4H-cyclopenta[b]thiophen-2-yl]carbamoyl]cyclohexanecarboxylic acid;

Compound 41. 2-[[3-[(4-Chlorophenyl)carbamoyl]benzothiophen-2-yl]carbamoyl]cyclohexane carboxylic acid;

Compound 44. 2-[[3-[(4-Chlorophenyl)carbamoyl]-5,6-dihydro-4H-cyclopenta[b]thiophen-2-yl]carbamoyl]benzoic acid;

Compound 45. 2-[1-[2-[[3-[(4-Chlorophenyl)carbamoyl]-5,6-dihydro-4H-cyclopenta[b]thiophen-2-yl]amino]-2-oxoethyl]cyclopentyl]acetic acid;

Compound 46. 2-[[3-[(4-Chlorophenyl)carbamoyl]-5,6-dihydro-4H-cyclopenta[b]thiophen-2-yl]carbamoyl]cyclopentanecarboxylic acid;

Compound 47. 5-[[3-[(4-Chlorophenyl)carbamoyl]-5,6-dihydro-4H-cyclopenta[b]thiophen-2-yl]amino]-3,3-dimethyl-5-oxo-pentanoic acid;

Compound 49. 2-[[3-[(4-Chlorophenyl)carbamoyl]-5,6-dihydro-4H-cyclopenta[b]thiophen-2-yl]carbamoyl]cyclohexane-trans-carboxylic acid;

Compound 51. 2-[[3-[(4-Chlorophenyl)carbamoyl]-5,6-dihydro-4H-cyclopenta[b]thiophen-2-yl]carbamoyl]-7-oxabicyclo[2.2.1]heptane-3-carboxylic acid;

Compound 52. N-(4-Chlorophenyl)-2-(cyclohexanecarbonylamino)-5,6-dihydro-4H-cyclopenta[b]thiophene-3-carboxamide;

Compound 53. N-(4-Chlorophenyl)-2-[(3-oxocyclohexanecarbonyl)amino]-5,6-dihydro-4H-cyclopenta[b]thiophene-3-carboxamide;

Compound 54. N-(4-Chlorophenyl)-2-(1,3-dioxo-3a,4,5,6,7,7a-hexahydroisoindol-2-yl)-5,6-dihydro-4H-cyclopenta[b]thiophene-3-carboxamide;

Compound 55. N2-[3-[(4-Chlorophenyl)carbamoyl]-5,6-dihydro-4H-cyclopenta[b]thiophen-2-yl]cyclohexane-1,2-dicarboxamide;

Compound 56. N-(4-Chlorophenyl)-2-[[2-(hydroxymethyl)cyclohexanecarbonyl]amino]-5,6-dihydro-4H-cyclopenta[b]thiophene-3-carboxamide;

Compound 57. 2-[[3-[(4-Chlorophenyl)carbamoyl]-5,6-dihydro-4H-cyclopenta[b]thiophen-2-yl]carbamoyl]cyclohexane-cis-carboxylic acid; and Compound 61. 2-[[3-[(4-Chlorophenyl)carbamoyl]-4,5,6,7-tetrahydrobenzothiophen-2-yl]carbamoyl]cyclohexane-cis-carboxylic acid;

and its use as a drug.

The present invention relates to any compound as defined above for the treatment of cancer or a metabolic disease. Preferably, the metabolic disease is selected from the group consisting of diabetes, in particular diabetes type I or diabetes type II, atherosclerosis, obesity, diabetic neuropathies, lysosomal storage diseases, severe insulin resistance, hyperinsulinemia, hyperlipidemia, Rabson-Mendenhall syndrome, leprechaunism, lipoatrophic diabetes, acute and chronic renal insufficiency, end-stage chronic renal failure, glomerulonephritis, interstitial nephritis, pyelonephritis, glomerulosclerosis, lipoatrophic diabetes, hepatic steatosis, nonalcoholic fatty liver disease, Nonalcoholic steatohepatitis (NASH), glucose intolerance, lipodystrophy, coronary heart disease, diabetic retinopathy, diabetic neuropathy, diabetic nephropathy, hypoglycemia, hyperglycemia, beta cell dysfunction or hyperinsulinaemia, Wolfram syndrome, Polycystic ovary syndrome, pyruvate dehydrogenase deficiency, Albright hereditary osteodystrophy, cystinosis, fructose intolerance, Walker-Warburg syndrome, hypobetalipoproteinemia, Alström syndrome, and cirrhosis. Preferably, the cancer is selected from the group consisting of bone cancer, gastrointestinal cancer, liver cancer, pancreatic cancer, gastric cancer, colorectal cancer, esophageal cancer, oro-pharyngeal cancer, laryngeal cancer, salivary gland carcinoma, thyroid cancer, lung cancer, cancer of the head or neck, skin cancer, squamous cell cancer, melanoma, uterine cancer, cervical cancer, endometrial carcinoma, vulvar cancer, ovarian cancer, breast cancer, prostate cancer, cancer of the endocrine system, sarcoma of soft tissue, bladder cancer, kidney cancer, glioblastoma and various types of cancers of the central nervous system, lymphoma and leukemia.

Preferably, the viral infection is an infection by a virus selected from the group consisting of Alphaviridae, Flaviviridae, Hepadnaviridae, Herpesviridae, Orthomyxoviridae, Papovaviridae, Paramyxoviridae, Picornaviridae, Polyomaviridae, Reoviridae, Retroviridae, Rhabdoviridae, and Tobamoviruses. More preferably, the virus is selected from the group consisting of:

Barmah Forest virus, Middelburg virus, Ndumu virus, Bebaru virus, Chikungunya virus, Mayaro virus, O'nyong'nyong virus, Ross River virus, Semliki Forest virus, Sindbis virus, Una virus, Eastern equine encephalitis virus, Tonate virus, Venezuelan equine encephalitis virus, Cabassou virus, Everglades virus, Mosso das Pedras virus, Mucambo virus, Parmana virus, Pixuna virus, Rio Negro virus, Trocara virus, Aura virus, Babanki virus, Kyzylagach virus, Ockelbo virus, Whataroa virus, Sleeping disease virus, Samon pancreatic disease virus, Southern elephant seal virus, and Western equine encephalitis virus; preferably selected from the group consisting of Barmah Forest virus, Chikungunya virus, Mayaro virus, O'nyong'nyong virus, Ross River virus, Semliki Forest virus, Sindbis virus, Una virus, Eastern equine encephalitis virus, Tonate virus, Venezuelan equine encephalitis virus and Western equine encephalitis virus;

dengue virus, Hepatitis C virus, Japanese encephalitis virus, West Nile virus, yellow fever virus, Zika virus, Tick-borne encephalitis virus, Kyasanur forest disease virus, Murray Valley encephalitis virus, and Saint Louis encephalitis virus;

Hepatitis B virus;

Herpes Simplex virus 1 (HSV-1), Herpes Simplex virus 2 (HSV-2), Varicella zoster virus (VZV), Epstein-Barr virus (EBV), Cytomegalovirus (CMV), Roseolovirus (HHV-6A and 6B), HHV-7 and Kaposi's sarcoma-associated herpesvirus (KSHV);

Influenza virus A, Influenza virus B, Influenza virus C, Isavirus, Thogotovirus and Quaranjavirus, preferably selected from the group consisting of Influenza virus A and Influenza virus B, for instance selected from the subtypes consisting of H1N1, H1N2, H2N2, H3N1, H3N2, H3N8, H5N1, H5N2, H5N3, H5N8, H5N9, H7N1, H7N2, H7N3, H7N4, H7N7, H7N9, H9N2, and H10N7;

Papillomavirus (HPC) and Polyomavirus, especially Simian virus 40, Merkel cell polyomavirus, Trichodysplasia spinulosa polyomavirus, BK polyomavirus, JC polyomavirus and Human polyomavirus 7;

Rubulavirus, Morbillivirus, Pneumovirus, Metapneumovirus, Avulavirus, Ferlavirus, Henipavirus, Respirovirus, preferably from the group consisting of the mumps virus, measles virus, human parainfluenza viruses (HPIV), especially HPIV-1, HPIV-2, HPIV-3 or HPIV-4, respiratory syncytial virus (RSV), in particular Human respiratory syncytial virus (HRSV), canine distemper virus, phocine distemper virus, cetacean morbillivirus, Newcastle disease virus, rinderpest virus, Hendra virus and Nipah virus;

Aphthovirus, Aquamavirus, Avihepatovirus, Cardiovirus, Cosavirus, Dicipivirus, Enterovirus, Erbovirus, Hepatovirus, Kobuvirus, Megrivirus, Parechovirus, Piscevirus, Rhinovirus, Salivirus, Sapelovirus, Senecavirus, Techovirus, and Tremovirus, in a particular embodiment, a Rhinovirus, for instance a Rhinovirus A, Rhinovirus B or Rhinovirus C;

Alpharetrovirus; especially Avian leukosis virus and Rous sarcoma virus; Betaretrovirus, especially Mouse mammary tumour virus; Gammaretrovirus, especially Murine leukemia virus and Feline leukemia virus; Deltaretrovirus, especially Bovine leukemia virus and Human T-lymphotropic virus; Epsilonretrovirus, especially Walleye dermal sarcoma virus; Lentivirus, especially Human immunodeficiency virus 1 and Simian, Feline immunodeficiency viruses; Spumavirus, especially Simian foamy virus; and, vesiculovirus, especially vesicular stomatitis virus, lyssavirus, especially rabies virus, Ephemerovirus, novirhabdovirus, cytorhabdovirus and nucleorhabdovirus.

DETAILED DESCRIPTION OF THE INVENTION

The present invention relates to identification of a new class of compounds having an antiviral effect. More precisely, the compounds have been designed for inducing autophagy.

Definitions

According to the present invention, the terms below have the following meanings:

The terms mentioned herein with prefixes such as for example $C_1$-$C_3$, $C_1$-$C_6$ or $C_2$-$C_6$ can also be used with lower numbers of carbon atoms such as $C_1$-$C_2$, $C_1$-$C_5$, or $C_2$-$C_5$. If, for example, the term $C_1$-$C_3$ is used, it means that the corresponding hydrocarbon chain may comprise from 1 to 3 carbon atoms, especially 1, 2 or 3 carbon atoms. If, for example, the term $C_1$-$C_6$ is used, it means that the corresponding hydrocarbon chain may comprise from 1 to 6 carbon atoms, especially 1, 2, 3, 4, 5 or 6 carbon atoms. If, for example, the term $C_2$-$C_6$ is used, it means that the corresponding hydrocarbon chain may comprise from 2 to 6 carbon atoms, especially 2, 3, 4, 5 or 6 carbon atoms.

The term "alkyl" refers to a saturated, linear or branched aliphatic group. The term "($C_1$-$C_3$)alkyl" more specifically means methyl, ethyl, propyl, or isopropyl. The term "($C_1$-$C_6$)alkyl" more specifically means methyl, ethyl, propyl, isopropyl, butyl, isobutyl, tert-butyl, pentyl or hexyl. In a preferred embodiment, the "alkyl" is a methyl, an ethyl, a propyl, an isopropyl, or a tert-butyl, more preferably a methyl.

The term "alkenyl" refers to an unsaturated, linear or branched aliphatic group comprising at least one carbon-carbon double bound. The term "($C_2$-$C_6$)alkenyl more specifically means ethenyl, propenyl, isopropenyl, butenyl, isobutenyl, pentenyl, or hexenyl.

The term "alkynyl" refers to an unsaturated, linear or branched aliphatic group comprising at least one carbon-carbon triple bound. The term "($C_2$-$C_6$)alkynyl more specifically means ethynyl, propynyl, butynyl, pentynyl, isopentynyl, or hexynyl.

The term "alkoxy" or "alkyloxy" corresponds to the alkyl group as above defined bonded to the molecule by an —O— (ether) bond. ($C_1$-$C_3$)alkoxy includes methoxy, ethoxy, propyloxy, and isopropyloxy. ($C_1$-$C_6$)alkoxy includes methoxy, ethoxy, propyloxy, isopropyloxy, butyloxy, isobutyloxy, tert-butyloxy, pentyloxy and hexyloxy. In a preferred embodiment, the "alkoxy" or "alkyloxy" is a methoxy.

The term "thioalkyl" corresponds to the alkyl group as above defined bounded to the molecule by a —S— (thioether) bound. Thio-($C_1$-$C_6$)alkyl group includes thio-methyl, thio-ethyl, thio-propyl, thio-butyl, thio-pentyl and thio-hexyl.

The term "cycloalkyl" corresponds to a saturated or unsaturated mono-, bi- or tri-cyclic alkyl group comprising between 3 and 20 atoms of carbons. It also includes fused, bridged, or spiro-connected cycloalkyl groups. The term "cycloalkyl" includes for instance cyclopropyl, cyclobutyl, cyclopentyl, and cyclohexyl. The term "cycloalkyl" may also refer to a 5-10 membered bridged carbocyclyl such as bicyclo[2,2,1]heptanyl, bicyclo[2,2,2]octanyl, or adamantyl, preferably bicyclo[2,2,2]octanyl. In a preferred embodiment, the "cycloalkyl" is a cyclopentyl or a cyclohexyl.

The term "cycloalkanonyl" corresponds to a cycloalkyl as above defined further substituted by a ketone. Representative cycloalkanonyl groups include for instance cyclopropanone, cyclobutanone, cyclopentanone, and cyclohexanone. In a preferred embodiment, the cycloalkanonyl is a cyclohexanone.

The term "heterocycloalkyl" corresponds to a saturated or unsaturated cycloalkyl group as above defined further comprising at least one heteroatom such as nitrogen, oxygen, or sulphur atom. It also includes fused, bridged, or spiro-connected heterocycloalkyl groups. Representative heterocycloalkyl groups include, but are not limited to 3-dioxolane, benzo[1,3]dioxolyl, pyrazolinyl, pyranyl, thiomorpholinyl, pyrazolidinyl, piperidyl, piperazinyl, 1,4-dioxanyl, imidazolinyl, pyrrolinyl, pyrrolidinyl, piperidinyl, imidazolidinyl, morpholinyl, 1,4-dithianyl, pyrrolidinyl, oxozolinyl, oxazolidinyl, isoxazolinyl, isoxazolidinyl, thiazolinyl, thiazolidinyl, isothiazolinyl, isothiazolidinyl, dihydropyranyl, tetrahydro-2H-pyranyl, tetrahydrofuranyl, and tetrahydrothiophenyl. The term "heterocycloalkyl" may also refer to a 5-10 membered bridged heterocyclyl such as 7-oxabicyclo[2,2,1]heptanyl. In a preferred embodiment, the heterocycloalkyl group is a tetrahydro-2H-pyranyl, a tetrahydro-2H-pyranyl, a tetrahydrothiophenyl, a morpholinyl, or a piperazinyl.

The term "aryl" corresponds to a mono- or bi-cyclic aromatic hydrocarbons having from 6 to 12 carbon atoms. For instance, the term "aryl" includes phenyl, biphenyl, or naphthyl. In a preferred embodiment, the aryl is a phenyl.

The term "heteroaryl" as used herein corresponds to an aromatic, mono- or poly-cyclic group comprising between 5 and 14 atoms and comprising at least one heteroatom such as nitrogen, oxygen or sulphur atom. Examples of such mono- and poly-cyclic heteroaryl group may be: pyridinyl, thiazolyl, thiophenyl, furanyl, pyrrolyl, pyrazolyl, imidazolyl, triazolyl, tetrazolyl, benzofuranyl, thianaphthalenyl, indolyl, indolinyl, quinolinyl, isoquinolinyl, benzimidazolyl, tetrahydroquinolinyl, tetrahydroisoquinolinyl, triazinyl, thianthrenyl, isobenzofuranyl, chromenyl, xanthenyl, phenoxanthinyl, isothiazolyl, isoxazolyl, pyrazinyl, pyridazinyl, indolizinyl, isoindolyl, indazolyl, purinyl, quinolizinyl, phtalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, indolinyl, isoindolinyl, oxazolidinyl, benzotriazolyl, benzisoxazolyl, oxindolyl, benzoxazolinyl, benzothienyl, benzothiazolyl, isatinyl, dihydropyridyl, pyrimidinyl, s-triazinyl, oxazolyl, or thiofuranyl. In a preferred embodiment, the heteroaryl group is a thiophenyl, a pyridinyl, a pyrazinyl, or a thiazolyl.

The terms "fused arylheterocycloalkyl" and "fused arylcycloalkyl" correspond to a bicyclic group in which an aryl as above defined is bounded to the heterocycloalkyl or the cycloalkyl as above defined by at least two carbons. In other terms, the aryl shares a carbon bond with the heterocycloalkyl or the cycloalkyl. A fused arylheterocycloalkyl is for instance a benzodioxole or an isobenzofurane. A fused arylcycloalkyl is for instance an indane.

The term "halogen" corresponds to a fluorine, chlorine, bromine, or iodine atom, preferably a fluorine, chlorine or bromine, and more preferably a chlorine or a fluorine.

The expression "substituted by at least" means that the radical is substituted by one or several groups of the list.

As used herein, the terms "treatment", "treat" or "treating" refer to any act intended to ameliorate the health status of patients such as therapy, prevention, prophylaxis and retardation of a disease, in particular a viral infection. In certain embodiments, such terms refer to the amelioration or eradication of the disease, or symptoms associated with it. In other embodiments, this term refers to minimizing the spread or worsening of the disease, resulting from the administration of one or more therapeutic agents to a subject with such a disease.

As used herein, the terms "subject", "individual" or "patient" are interchangeable and refer to an animal, preferably to a mammal, even more preferably to a human, including adult, child, newborn and human at the prenatal stage. However, the term "subject" can also refer to non-human animals, in particular mammals such as dogs, cats, horses, cows, pigs, sheep and non-human primates, among others.

The terms "quantity," "amount," and "dose" are used interchangeably herein and may refer to an absolute quantification of a molecule.

As used herein, the terms "active principle", "active ingredient" and "active pharmaceutical ingredient" are equivalent and refers to a component of a pharmaceutical composition having a therapeutic effect.

As used herein, the term "therapeutic effect" refers to an effect induced by an active ingredient, or a pharmaceutical composition according to the invention, capable to prevent or to delay the appearance of a disease, such as a viral infection or a cancer, or to cure or to attenuate the effects of a disease.

As used herein, the term "effective amount" refers to a quantity of an active ingredient or of a pharmaceutical composition which prevents, removes or reduces the deleterious effects of the disease. It is obvious that the quantity to be administered can be adapted by the man skilled in the art according to the subject to be treated, to the nature of the disease, etc. In particular, doses and regimen of administration may be function of the nature, of the stage and of the severity of the disease to be treated, as well as of the weight, the age and the global health of the subject to be treated, as well as of the judgment of the doctor.

As used herein, the term "excipient or pharmaceutically acceptable carrier" refers to any ingredient except active ingredients that is present in a pharmaceutical composition. Its addition may be aimed to confer a particular consistency or other physical or gustative properties to the final product. An excipient or pharmaceutically acceptable carrier must be devoid of any interaction, in particular chemical, with the active ingredients.

As used herein, the term "viral infection" refers to the invasion of an organism's body tissues by disease-causing viruses, their multiplication, and the reaction of host tissues to these viruses.

The terms "viral agent", "viral pathogen" and "disease-causing virus", as used herein, are equivalent and refer to viruses that cause infection.

As used herein, the terms "antiviral", "antiviral molecule", "antiviral drug" or "antiviral agent" are equivalent and refer to a molecule used in the treatment and prevention of viral infections. Antiviral drugs do not destroy their target viruses, instead they inhibit their development. Antiviral drugs may target any stage of the viral life cycle, in particular attachment to a host cell, release of viral genes and possibly enzymes into the host cell, replication of viral components using host-cell machinery, assembly of viral components into complete viral particles, or release of viral particles to infect new host cells.

As used herein, the terms "autophagy-inducing agent", "autophagy-inducing molecule" or "autophagy-inducing drug" are equivalent and refer to a molecule capable to promote or increase autophagy when administered to a subject, a tissue or a cell.

As used herein, the terms "autophagy", "autophagocytosis", or "self-eating" are equivalent and refer to a cellular self-degradative process which promote proteolytic degradation of cytosolic components at the lysosome. Degraded cytosolic components comprise misfolded or aggregated proteins, damaged organelles or intracellular pathogens. Autophagy is also important for balancing sources of energy at critical times in development and in response to nutrient stress, as well as for antigen presentation. The term "autophagy" according to the invention encompasses the three well defined types of autophagy: macro-autophagy, micro-autophagy, and chaperone-mediated autophagy (cf. Glick D et al, 2010, J. Pathol, 221(1): 3-12).

The term "cancer" or "tumor", as used herein, refers to the presence of cells possessing characteristics typical of cancer-causing cells, such as uncontrolled proliferation, and/or immortality, and/or metastatic potential, and/or rapid growth and/or proliferation rate, and/or certain characteristic morphological features. This term refers to any type of malignancy (primary or metastases) in any type of subject. In particular, the term encompasses prostate cancer at any stage of progression.

A used herein, the terms "apoptosis-inducing agent" "apoptosis-inducing molecule" or "apoptosis-inducing drug" are equivalent and refer to a molecule capable to induce apoptosis when administered to a subject, a tissue or a cell.

As used herein, the terms "apoptosis", or "programmed cell-death" are equivalent and refers to a cell death process during which cell shrinks and condenses, cytoskeleton collapses, nuclear envelope disassembles, nuclear DNA breaks up into fragments, and cell surface is altered, displaying properties that cause the dying cell to be rapidly phagocytosed, either by a neighboring cell or by a macrophage before any leakage of its contents occurs. Apoptosis not only avoids damaging the neighbor cells as in cell necrosis but also allows the organic components of the dead cell to be recycled by the cell that ingests it.

Compounds

Compounds for Therapeutic Application According to the Invention

As illustrated by examples, the inventors have demonstrated an antiviral effect for the compounds of formula (I). In addition, the compounds of formula (I) also have an autophagy-inducing effect. They also can be useful for treating cancer.

Accordingly, the present invention relates a compound for use according to the present invention, especially as an antiviral drug, said compound having the formula (I):

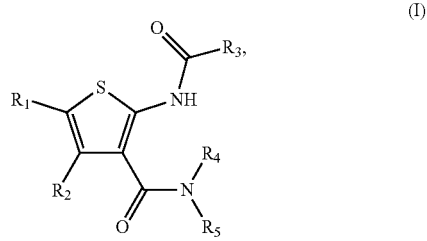

wherein:
$R_1$ and $R_2$ represent independently:
  H;
  a $(C_1-C_6)$alkyl; or
  $R_1$ and $R_2$ may form together a 5-7 membered ring, saturated or unsaturated,
    said 5-7 membered ring optionally comprises one or more heteroatoms chosen among:
      N, optionally substituted by a radical selected in the group consisting of
        a $(C_1-C_6)$alkyl, a $(C_2-C_6)$alkenyl, a $(C_2-C_6)$alkynyl,
      a 5-10 membered ring, saturated or unsaturated, selected from the group consisting of cycloalkyl, aryl, heterocycloalkyl, and heteroaryl, a saturated or unsaturated $(C_1-C_6)$alkylcycloalkyl, $(C_1-C_6)$alkylaryl, $(C_1-C_6)$alkylheterocycloalkyl), or $(C_1-C_6)$alkylheteroaryl, and
a CO—$(C_1-C_6)$alkyl, a $CO_2$—$(C_1-C_6)$alkyl, a CO—$(C_1-C_6)$alkylaryl, a CO-aryl, a CO-heteroaryl, a $SO_2$-aryl, or a $SO_2$-heteroaryl,
said radical is optionally substituted by at least one —OH, halogen, $(C_1-C_6)$alkyl, or $(C_1-C_6)$alkyloxy,
O, and
S, and
said 5-7 membered ring is optionally substituted by:
a $(C_1-C_6)$alkyl, a $(C_1-C_6)$alkyloxy, a $(C_2-C_6)$alkenyl, a $(C_2-C_6)$alkynyl, optionally substituted by at least one halogen, or —OH,
a 5-10 membered ring, saturated or unsaturated, selected from the group consisting of cycloalkyl, aryl, heterocycloalkyl, and heteroaryl, optionally substituted by at least one —OH, halogen, $(C_1-C_6)$alkyl, or $(C_1-C_6)$alkyloxy,
a saturated or unsaturated $(C_1-C_6)$alkylcycloalkyl, $(C_1-C_6)$alkylaryl, $(C_1-C_6)$alkylheterocycloalkyl), or $(C_1-C_6)$alkylheteroaryl, optionally substituted by at least one —OH, halogen, $(C_1-C_6)$alkyl, or $(C_1-C_6)$alkyloxy,
a halogen, —CN, or —$NO_2$,
—C(O)R, —C(O)$_2$R, —C(O)NRR', —CONHOR, —CONHSO$_2$R, —NRR', —N(R)C(O)R', —N(R)NR'R", —N(R)C(O)$_2$R', —N(R)C(O)NR'R", —N(R)S(O)$_2$R', —OR, —SR, —S(O)R, —S(O$_2$)R, —S(O)NRR', or —S(O)$_2$NRR', R, R', and R" being independently H, $(C_1-C_6)$alkyl, cycloalkyl, aryl, heterocycloalkyl, heteroaryl, $(C_1-C_6)$alkylcycloalkyl, $(C_1-C_6)$alkylaryl, $(C_1-C_6)$alkylheterocycloalkyl), $(C_1-C_6)$alkylheteroaryl, or R and R' or R' and R" may form a 5-7 membered ring, optionally interrupted by one or several heteroatoms, said 5-7 membered ring is optionally substituted by at least one —OH, halogen, $(C_1-C_6)$alkyl, or $(C_1-C_6)$alkyloxy;
$R_3$ represents:
a radical selected from the group consisting of:
a $(C_1-C_6)$alkyl, a $(C_2-C_6)$alkenyl, a $(C_2-C_6)$alkynyl,
a 4-10 or 5-10 membered ring, saturated or unsaturated, selected from the group consisting of a cycloalkyl, a cycloalkanonyl, a heterocycloalkanonyl, an aryl, a heterocycloalkyl, a heteroaryl, a 5-10 membered bridged carbocyclyl or heterocyclyl, and
a saturated or unsaturated $(C_1-C_6)$alkylcycloalkyl, $(C_1-C_6)$alkylaryl, $(C_1-C_6)$alkylheterocycloalkyl, and $(C_1-C_6)$alkylheteroaryl,
said radicals being optionally substituted by:
a $(C_1-C_6)$alkyl or a $(C_1-C_6)$alkoxy, optionally substituted by at least one halogen, preferably a fluorine,
a 5-10 membered ring, saturated or unsaturated, selected from the group consisting of a cycloalkyl, a spironocycloalkyl, an aryl, a heterocycloalkyl, and a heteroaryl, or
a saturated or unsaturated $(C_1-C_6)$alkylcycloalkyl, $(C_1-C_6)$alkylaryl, $(C_1-C_6)$alkylheterocycloalkyl, or $(C_1-C_6)$alkylheteroaryl; and
said optionally substituted radical being optionally substituted by at least one group (A) selected in the group consisting of:

—C(O)R, —C(O)$_2$R, —C(O)NRR', —CONHOR, —CONHSO$_2$R, —NRR', —N(R)C(O)R', —N(R)NR'R", —N(R)C(O)$_2$R', —N(R)C(O)NR'R", —N(R)S(O)$_2$R', —R—OH, —OR, —SR, —S(O)R, —S(O$_2$)R, —S(O)NRR', —S(O)$_2$NRR', R, R', and R" are such as above defined, and a tetrazolyl;
a —X—Y unit, in which:
X is O or NH, and
Y is selected from the radical consisting of:
a $(C_1-C_6)$alkyl, a $(C_2-C_6)$alkenyl, a $(C_2-C_6)$alkynyl,
a 5-10 membered ring, saturated or unsaturated, selected from the group consisting of a cycloalkyl, a cycloalkanonyl, an aryl, a heterocycloalkyl, a heteroaryl, and a 5-10 membered bridged carbocyclyl or heterocyclyl, and
a saturated or unsaturated $(C_1-C_6)$alkylcycloalkyl, $(C_1-C_6)$alkylaryl, $(C_1-C_6)$alkylheterocycloalkyl, $(C_1-C_6)$alkylheteroaryl,
said radicals being optionally substituted by:
a $(C_1-C_6)$alkyl or a $(C_1-C_6)$alkoxy,
a 5-10 membered ring, saturated or unsaturated, selected from the group consisting of a cycloalkyl, a spironocycloalkyl, an aryl, a heterocycloalkyl, and a heteroaryl, or
a saturated or unsaturated $(C_1-C_6)$alkylcycloalkyl, $(C_1-C_6)$alkylaryl, $(C_1-C_6)$alkylheterocycloalkyl, or $(C_1-C_6)$alkylheteroaryl, and
said optionally substituted radical being optionally substituted by at least one group (A) as above defined; or
$R_3$ may form with the nitrogen atom of the group —NH—CO—$R_3$ a moiety having the following formula (A):

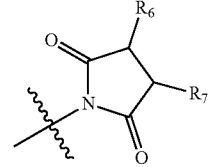

(A)

in which $R_6$ and $R_7$ represent independently H, or a $(C_1-C_6)$alkyl or $R_6$ and $R_7$ may form a 5-10 membered ring saturated or unsaturated, selected from the group consisting of a cycloalkyl, an aryl, a heterocycloalkyl, and a heteroaryl, said 5-10 membered ring being optionally substituted by at least one —OH, halogen, $(C_1-C_6)$alkyl, or $(C_1-C_6)$alkyloxy;
$R_4$ represents a radical selected in the group of:
a 5-14 membered ring, saturated or unsaturated, selected from the group consisting of a cycloalkyl, an aryl, a heterocycloalkyl, a heteroaryl, a fused arylheterocycloalkyl, and a fused arylcycloalkyl,
a $(C_1-C_6)$alkylcycloalkyl, a $(C_1-C_6)$alkylaryl, a $(C_1-C_6)$alkylheterocycloalkyl, and a $(C_1-C_6)$alkylheteroaryl, and
a $(C_1-C_6)$alkyl,
said radicals being optionally substituted by at least one group (B) selected in the group consisting of:
a $(C_1-C_6)$alkyl or a $(C_1-C_6)$alkoxy, optionally substituted by at least one OH, one halogen or one —NRR', R, R', and R" are such as defined above, a halogen, —CN, or —NO$_2$,
a 5-10 membered ring, saturated or unsaturated, selected from the group consisting of a cycloalkyl, an aryl, a heterocycloalkyl, and a heteroaryl, optionally substituted by at least one —OH, one halogen, one (C$_1$-C$_6$)alkyl, one (C$_1$-C$_6$)alkyloxy or one —NRR', R, R', and R" are such as defined above,
a saturated or unsaturated (C$_1$-C$_6$)alkylcycloalkyl, (C$_1$-C$_6$)alkylaryl, (C$_1$-C$_6$)alkylheterocycloalkyl, or (C$_1$-C$_6$)alkylheteroaryl, optionally substituted by at least one —OH, halogen, (C$_1$-C$_6$)alkyl, or (C$_1$-C$_6$)alkyloxy,
—C(O)R, —C(O)$_2$R, —C(O)NRR', —CONHOR, —CONHSO$_2$R, —NRR', —N(R)C(O)R', —N(R)NR'R", —N(R)C(O)$_2$R', —N(R)C(O)NR'R", —N(R)S(O)$_2$R', —OR, —SR, —S(O)R, —S(O)$_2$R, —S(O)NRR', or —S(O)$_2$NRR', R, R', and R" are such as defined above; and R$_5$ represents H, a (C$_1$-C$_6$)alkyl, a (C$_2$-C$_6$)alkenyl, or a (C$_2$-C$_6$)alkynyl; or R$_4$ and R$_5$ may form together a 5-14 membered ring, optionally interrupted by one or several heteroatoms, said 5-14 membered ring is optionally substituted by at least one —OH, halogen, (C$_1$-C$_6$)alkyl, (C$_1$-C$_6$)alkyloxy, cycloalkyl, or a 5-10 membered ring selected in the group of an aryl, a heterocycloalkyl, and a heteroaryl, optionally substituted by at least one —OH, halogen, (C$_1$-C$_6$)alkyl, or (C$_1$-C$_6$)alkyloxy;

and the pharmaceutical salts thereof.

In a particular embodiment, R$_1$ and R$_2$ form together a 5- or 6-membered ring, saturated or unsaturated, selected in the group consisting of a cycloalkyl and an aryl,
said 5- or 6-membered ring optionally comprises one O or one S, and
said 5- or 6-membered ring is optionally substituted by a (C$_1$-C$_6$)alkyl.

Preferably, R$_1$ and R$_2$ form together a cyclopentyl, a cyclohexyl, a tetrahydro-2H-pyran, a tetrahydrofuran optionally substituted by a (C$_1$-C$_6$)alkyl, preferably a methyl, a thiophene, a tetrahydro-thiophene, or a phenyl, preferably a cyclopentyl.

In a particular embodiment,
R$_4$ represents a radical selected in the group consisting of:
a 5-10 membered ring, saturated or unsaturated, selected from the group consisting of:
a cycloalkyl, preferably a cyclohexyl, optionally substituted by at least one group (B) selected from the group consisting of:
a (C$_1$-C$_6$)alkyl, preferably a methyl, optionally substituted by at least one halogen, or one hydroxy,
a (C$_1$-C$_6$)alkoxy, preferably a methoxy,
a halogen, preferably a fluorine,
a cyano,
a cycloalkyl, a heterocycloalkyl, an aryl, or a heteroaryl, optionally substituted by at least one —OH, halogen, (C$_1$-C$_6$)alkyl, or (C$_1$-C$_6$)alkyloxy, and
—C(O)R or —S(O$_2$)R with R being a (C$_1$-C$_6$)alkyl,
an aryl, preferably a phenyl, optionally substituted by at least one group (B) selected from the group consisting of:
a (C$_1$-C$_6$)alkyl, preferably a methyl, an ethyl, an isopropyl, a tert-butyl, optionally substituted by at least one halogen, preferably a fluorine, or one hydroxy,
a (C$_1$-C$_6$)alkoxy, preferably a methoxy, optionally substituted by at least one fluorine,
a halogen, preferably a fluorine or a chlorine,
a cyano,
a cycloalkyl, a heterocycloalkyl, preferably a morpholine, an aryl, preferably a phenyl, or a heteroaryl, optionally substituted by at least one —OH, halogen, (C$_1$-C$_6$)alkyl, or (C$_1$-C$_6$)alkyloxy, and
—C(O)R or —S(O$_2$)R with R being a (C$_1$-C$_6$)alkyl, preferably a methyl,
a heteroaryl, preferably a pyridine, a pyrazine, or a thiazole, optionally substituted by at least one group (B) selected from the group consisting of:
a halogen, preferably a chlorine, and
a (C$_1$-C$_6$)alkyl, preferably a methyl, or a (C$_1$-C$_6$)alkoxy, optionally substituted by at least one halogen, preferably a fluorine, or one hydroxy,
a cyano,
a cycloalkyl, a heterocycloalkyl, an aryl, or a heteroaryl, optionally substituted by at least one —OH, halogen, (C$_1$-C$_6$)alkyl, or (C$_1$-C$_6$)alkyloxy, and
—C(O)R or —S(O$_2$)R with R being a (C$_1$-C$_6$)alkyl,
a fused arylheterocycloalkyl, preferably a benzodioxole or an isobenzofurane, and
a fused arylcycloalkyl, preferably an indane,
a radical selected in the group consisting of:
(C$_1$-C$_6$)alkylcycloalkyl, preferably a methylcyclohexyl, and
a (C$_1$-C$_6$)alkylaryl, preferably a methylphenyl,
said radical being optionally substituted by at least one halogen, preferably a chlorine, one (C$_1$-C$_6$)alkyl or one (C$_1$-C$_6$)alkoxy, optionally substituted by at least one halogen, and
a (C$_1$-C$_6$)alkyl, preferably a pentyl; and R$_5$ represents H or a (C$_1$-C$_6$)alkyl, preferably a methyl; or
R$_4$ and R$_5$ may form together a heterocycloalkyl, preferably a piperazine, optionally substituted by an aryl, preferably a phenyl optionally substituted by at least one halogen, preferably a chlorine.

In a preferred embodiment, the at least one group (B) is selected from the group consisting of a (C$_1$-C$_6$)alkyl or a (C$_1$-C$_6$)alkoxy optionally substituted by at least one halogen or one hydroxy, a halogen, a cyano, —C(O)R and —S(O$_2$)R with R being a (C$_1$-C$_6$)alkyl. More preferably, the at least one group (B) is selected from the group consisting of a (C$_1$-C$_6$)alkyl and a halogen.

In an even more preferred embodiment, R$_4$ represents a phenyl substituted by at least:
one (C$_1$-C$_6$)alkyl, preferably a methyl, and/or
one halogen, preferably a fluorine or a chlorine, and
R$_5$ represents H.

In a particular embodiment,
R$_3$ represents:
a radical selected from the group consisting of:
a (C$_1$-C$_6$)alkyl, preferably an ethyl or a propyl optionally substituted by a dimethyl or a spironocyclopentyl, and a (C$_2$-C$_6$)alkenyl, preferably an ethylene, a 5-10 membered ring, saturated or unsaturated, selected from the group consisting of:
a cyclopentyl or a cyclohexyl,
a cyclohexanone,
a phenyl, and
a bicyclo[2,2,2]octane and a 7-oxabicyclo[2.2.1]heptane, and
a saturated or unsaturated $(C_1-C_6)$alkylheteroaryl, preferably methylimidazole optionally substituted by a $(C_1-C_6)$alkyl, preferably a methyl,
said radicals being optionally substituted by at least one group (A) selected in the group consisting of a —$C(O)_2R$, a —$C(O)NRR'$ with R and R' being H, and a —R—OH with R being a $(C_1-C_6)$alkyl, preferably a methylene.

In a further particular embodiment, $R_3$ represents a —X—Y unit, in which:
X is O or NH, and
Y is selected from the radical consisting of:
a $(C_1-C_6)$alkyl, a $(C_2-C_6)$alkenyl, a $(C_2-C_6)$alkynyl,
a 5-10 membered ring, saturated or unsaturated, selected from the group consisting of a cycloalkyl, a cycloalkanonyl, an aryl, a heterocycloalkyl, a heteroaryl, and a 5-10 membered bridged carbocyclyl or heterocyclyl, and
a saturated or unsaturated $(C_1-C_6)$alkylcycloalkyl, $(C_1-C_6)$alkylaryl, $(C_1-C_6)$alkylheterocycloalkyl, $(C_1-C_6)$alkylheteroaryl,
said radicals being optionally substituted by:
a $(C_1-C_6)$alkyl or a $(C_1-C_6)$alkoxy,
a 5-10 membered ring, saturated or unsaturated, selected from the group consisting of a cycloalkyl, a spironocycloalkyl, an aryl, a heterocycloalkyl, and a heteroaryl, or
a saturated or unsaturated $(C_1-C_6)$alkylcycloalkyl, $(C_1-C_6)$alkylaryl, $(C_1-C_6)$alkylheterocycloalkyl, or $(C_1-C_6)$alkylheteroaryl, and
said optionally substituted radical being optionally substituted by at least one group (A) as above defined.

According to this embodiment, the compounds have the following formula (IA):

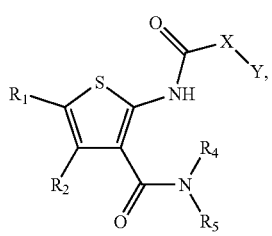

(IA)

in which, $R_1$, $R_2$, $R_4$, $R_5$, X and Y are such as above defined.

In a preferred embodiment,
X is O or NH, preferably NH, and
Y is a radical selected in the group consisting of:
a $(C_1-C_6)$alkyl, a $(C_2-C_6)$alkenyl, a $(C_2-C_6)$alkynyl,
a 5-10 membered ring, saturated or unsaturated, selected from the group consisting of a cycloalkyl, a cycloalkanonyl, an aryl, and a 5-10 membered bridged carbocyclyl or heterocyclyl, and a saturated or unsaturated $(C_1-C_6)$alkylcycloalkyl, $(C_1-C_6)$alkylaryl, said radicals being optionally substituted by:
a $(C_1-C_6)$alkyl or a $(C_1-C_6)$alkoxy,
a 5-10 membered ring, saturated or unsaturated, selected from the group consisting of a cycloalkyl, a spironocycloalkyl, and an aryl, or
a saturated or unsaturated $(C_1-C_6)$alkylcycloalkyl, or $(C_1-C_6)$alkylaryl, and
said optionally substituted radical being optionally substituted by at least one group (A) as above defined.

In a further particular embodiment, $R_3$ may form with the nitrogen atom of the group —NH—CO—$R_3$ a moiety having the following formula (A):

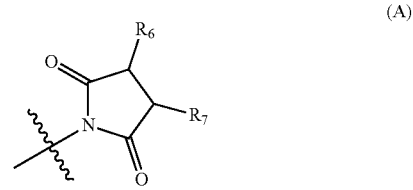

(A)

in which $R_6$ and $R_7$ represent independently H, or a $(C_1-C_6)$alkyl or $R_6$ and $R_7$ may form a 5-10 membered ring saturated or unsaturated, selected from the group consisting of a cycloalkyl, an aryl, a heterocycloalkyl, and a heteroaryl, said 5-10 membered ring being optionally substituted by at least one —OH, halogen, $(C_1-C_6)$alkyl, or $(C_1-C_6)$alkyloxy.

According to this embodiment, the compounds have the following formula (IB):

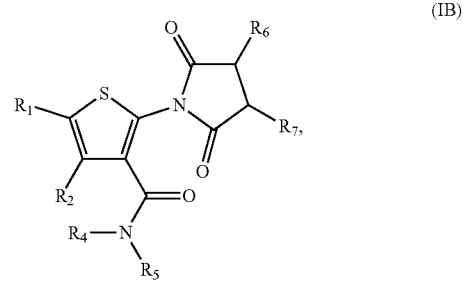

(IB)

in which, $R_1$, $R_2$, $R_4$, $R_5$, $R_6$, and $R_7$ are such as above defined.

In a preferred embodiment, $R_6$ and $R_7$ form a cycloalkyl, preferably a cyclohexyl.

In a further particular embodiment, the compounds have the following formula (IC):

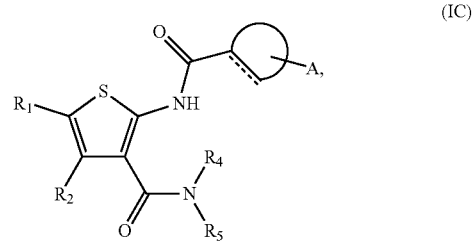

(IC)

in which, $R_1$, $R_2$, $R_4$, $R_5$, are such as above defined, and A is selected in the group consisting of: a tetrazolyl, C(O)R, —C(O)$_2$R, —C(O)NRR', —CONHOR, —CONHSO$_2$R, —NRR', —N(R)C(O)R', —N(R)NR'R", —N(R)C(O)$_2$R', —N(R)C(O)NR'R", —N(R)S(O)$_2$R', —R—OH, —OR, —SR, —S(O)R, —S(O)$_2$R, —S(O)NRR', —S(O)$_2$NRR', with R, R', and R" being independently H, ($C_1$-$C_6$)alkyl, cycloalkyl, aryl, heterocycloalkyl, heteroaryl, ($C_1$-$C_6$)alkylcycloalkyl, ($C_1$-$C_6$)alkylaryl, ($C_1$-$C_6$)alkylheterocycloalkyl), ($C_1$-$C_6$)alkylheteroaryl, or R and R' or R' and R" may form a 5-7 membered ring, optionally interrupted by one or several heteroatoms, said 5-7 membered ring is optionally substituted by at least one —OH, halogen, ($C_1$-$C_6$)alkyl, or ($C_1$-$C_6$)alkyloxy.

In a preferred embodiment, the at least one group (A) as above defined is in vicinal position with respect to the CO of the —NH—CO—$R_3$ group. According to this preferred embodiment, the compounds have the following formula (ID):

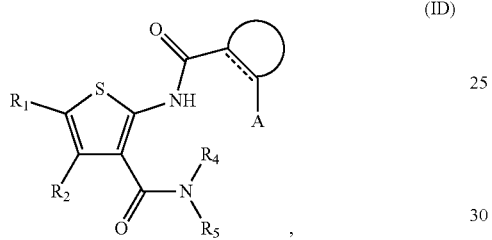

in which, $R_1$, $R_2$, $R_4$, $R_5$, and A are such as above defined. Preferably, the at least one group (A) is selected in the group consisting of: —C(O)$_2$R, —C(O)NRR' with R and R' representing H, and —R—OH with R being a ($C_1$-$C_6$)alkyl, preferably a methyl.

In a more preferred embodiment, the compound for use as an antiviral drug are of formula (I) in which:
$R_1$ and $R_2$ represent independently:
  H;
  a ($C_1$-$C_6$)alkyl; or
  $R_1$ and $R_2$ may form together a 5-7 membered ring, saturated or unsaturated, preferably a cyclopentyl, a cyclohexyl, or an aryl,
    said 5-7 membered ring optionally comprises one or more heteroatoms chosen among:
      O, and
      S, and
    said 5-7 membered ring is optionally substituted by a ($C_1$-$C_6$)alkyl;
$R_3$ represents:
  a radical selected from the group consisting of:
    a ($C_1$-$C_6$)alkyl, a ($C_2$-$C_6$)alkenyl,
    a 5-10 membered ring, saturated or unsaturated, selected from the group consisting of a cycloalkyl, preferably a cyclopentyl or a cyclohexyl, a cycloalkanonyl, an aryl, preferably a phenyl, a 5-10 membered bridged carbocyclyl or heterocyclyl, and
    a saturated or unsaturated ($C_1$-$C_6$)alkylheteroaryl, said radicals being optionally substituted by:
      a ($C_1$-$C_6$)alkyl, preferably a methyl, or
      a spironocycloalkyl,
    said optionally substituted radical being optionally substituted by at least one group (A) selected in the group consisting of: —C(O)$_2$R, —C(O)NRR', with R and R' being H, and —R—OH with R being a ($C_1$-$C_6$)alkyl, preferably a methylene; or
$R_3$ may form with the nitrogen atom of the group —NH—CO—$R_3$ a moiety having the following formula (A):

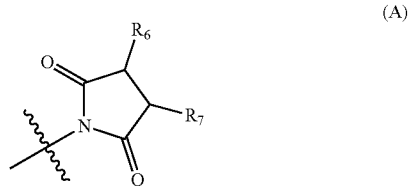

in which $R_6$ and $R_7$ may form a cycloalkyl, preferably a cyclohexyl;
$R_4$ represents a radical selected in the group
  a 5-14 membered ring, saturated or unsaturated, selected from the group consisting of a cycloalkyl, preferably a cyclohexyl, an aryl, preferably a phenyl, a heteroaryl, preferably a pyridinyl, a pyrimidinyl, a thiazolyl, a fused arylheterocycloalkyl, preferably a benzodioxole or an isobenzofurane, and a fused arylcycloalkyl, preferably an indane,
  a ($C_1$-$C_6$)alkylcycloalkyl, preferably a methylcyclohexyl, and a ($C_1$-$C_6$)alkylaryl, preferably a methylphenyl,
  said radicals being optionally substituted by at least one group (B) selected in the group consisting of:
    a ($C_1$-$C_6$)alkyl, preferably a methyl, an ethyl, an isopropyl, or a tert-butyl, or a ($C_1$-$C_6$)alkoxy, preferably a methoxy,
      optionally substituted by at least one OH, one halogen, preferably a chlorine or a fluorine,
    a halogen, preferably a chlorine or a fluorine,
    —CN,
    a 5-10 membered ring, saturated or unsaturated, selected from the group consisting of an aryl, preferably a phenyl, and a heterocycloalkyl, preferably a morpholine,
    —C(O)R, —C(O)$_2$R, or —S(O$_2$)R, with R being H or a methyl; and
$R_5$ represents a H or a ($C_1$-$C_6$)alkyl, preferably a methyl; or
$R_4$ and $R_5$ may form together a pyrazinyl, optionally substituted by at least one 4-chloro-phenyl.

In a further preferred embodiment, the compounds for use as an antiviral drug are selected from the group consisting of:
Compound 1. 2-[[3-[(3,4-Dimethylphenyl)carbamoyl]-5,6-dihydro-4H-cyclopenta[b]thiophen-2-yl]carbamoyl]cyclohexanecarboxylic acid;
Compound 2. 2-[[3-[(6-Chloro-3-pyridyl)carbamoyl]-5,6-dihydro-4H-cyclopenta[b]thiophen-2-yl]carbamoyl]cyclohexanecarboxylic acid;
Compound 3. 2-[[3-(1,3-Benzodioxol-5-ylcarbamoyl)-5,6-dihydro-4H-cyclopenta[b]thiophen-2-yl]carbamoyl]cyclohexanecarboxylic acid;
Compound 4. 2-[[3-[(4-Fluorophenyl)carbamoyl]-5,6-dihydro-4H-cyclopenta[b]thiophen-2-yl]carbamoyl]cyclohexanecarboxylic acid;
Compound 5. 2-[[3-[(4-Chlorophenyl)methylcarbamoyl]-5,6-dihydro-4H-cyclopenta[b]thiophen-2-yl]carbamoyl]cyclohexanecarboxylic acid;

Compound 6. 2-[[3-[[4-Chloro-3-(trifluoromethyl)phenyl]carbamoyl]-5,6-dihydro-4H-cyclopenta[b]thiophen-2-yl]carbamoyl]cyclohexanecarboxylic acid;

Compound 7. 2-[[3-[(4-Chloro-2-methyl-phenyl)carbamoyl]-5,6-dihydro-4H-cyclopenta[b]thiophen-2-yl]carbamoyl]cyclohexanecarboxylic acid;

Compound 8. 2-[[3-[(Trans-4-methoxycyclohexyl)carbamoyl]-5,6-dihydro-4H-cyclopenta[b]thiophen-2-yl]carbamoyl]cyclohexanecarboxylic acid;

Compound 9. 2-[[3-[[4-(2-Hydroxyethyl)phenyl]carbamoyl]-5,6-dihydro-4H-cyclopenta[b]thiophen-2-yl]carbamoyl]cyclohexanecarboxylic acid;

Compound 10. 2-[[3-[(4-Phenylphenyl)carbamoyl]-5,6-dihydro-4H-cyclopenta[b]thiophen-2-yl]carbamoyl]cyclohexanecarboxylic acid;

Compound 11. 2-[[3-[(3-Chlorophenyl)methylcarbamoyl]-5,6-dihydro-4H-cyclopenta[b]thiophen-2-yl]carbamoyl]cyclohexanecarboxylic acid;

Compound 12. 2-[[3-[(3-Acetylphenyl)carbamoyl]-5,6-dihydro-4H-cyclopenta[b]thiophen-2-yl]carbamoyl]cyclohexanecarboxylic acid;

Compound 13. 2-[[3-[(4-Chloro-3-methyl-phenyl)carbamoyl]-5,6-dihydro-4H-cyclopenta[b]thiophen-2-yl]carbamoyl]cyclohexanecarboxylic acid;

Compound 14. 2-[[3-[(3-chloro-4-methyl-phenyl)carbamoyl]-5,6-dihydro-4H-cyclopenta[b]thiophen-2-yl]carbamoyl]cyclohexanecarboxylic acid;

Compound 15. 2-[[3-[(4-Morpholinophenyl)carbamoyl]-5,6-dihydro-4H-cyclopenta[b]thiophen-2-yl]carbamoyl]cyclohexanecarboxylic acid;

Compound 16. 2-[[3-[(3,4-Difluorophenyl)carbamoyl]-5,6-dihydro-4H-cyclopenta[b]thiophen-2-yl]carbamoyl]cyclohexanecarboxylic acid;

Compound 17. 2-[[3-[(3-Chlorophenyl)carbamoyl]-5,6-dihydro-4H-cyclopenta[b]thiophen-2-yl]carbamoyl]cyclohexanecarboxylic acid;

Compound 18. 2-[[3-[(4,4-Difluorocyclohexyl)carbamoyl]-5,6-dihydro-4H-cyclopenta[b]thiophen-2-yl]carbamoyl]cyclohexanecarboxylic acid;

Compound 19. 2-[[3-[[4-(Hydroxymethyl)phenyl]carbamoyl]-5,6-dihydro-4H-cyclopenta[b]thiophen-2-yl]carbamoyl]cyclohexanecarboxylic acid;

Compound 20. 2-[[3-[[4-(Trifluoromethoxy)phenyl]carbamoyl]-5,6-dihydro-4H-cyclopenta[b]thiophen-2-yl]carbamoyl]cyclohexanecarboxylic acid;

Compound 21. 2-[[3-[(4-tert-Butylphenyl)carbamoyl]-5,6-dihydro-4H-cyclopenta[b]thiophen-2-yl]carbamoyl]cyclohexanecarboxylic acid;

Compound 22. 2-[[3-(pentylcarbamoyl)-5,6-dihydro-4H-cyclopenta[b]thiophen-2-yl]carbamoyl]cyclohexanecarboxylic acid;

Compound 23. 2-[[3-(Indan-1-ylcarbamoyl)-5,6-dihydro-4H-cyclopenta[b]thiophen-2-yl]carbamoyl]cyclohexanecarboxylic acid;

Compound 24. 2-[[3-(Cyclohexylmethylcarbamoyl)-5,6-dihydro-4H-cyclopenta[b]thiophen-2-yl]carbamoyl]cyclohexanecarboxylic acid;

Compound 25. 2-[[3-[(4-Isopropylphenyl)carbamoyl]-5,6-dihydro-4H-cyclopenta[b]thiophen-2-yl]carbamoyl]cyclohexanecarboxylic acid;

Compound 26. 2-[[3-[(5-Chloropyrazin-2-yl)carbamoyl]-5,6-dihydro-4H-cyclopenta[b]thiophen-2-yl]carbamoyl]cyclohexanecarboxylic acid;

Compound 27. 2-[[3-[[4-(Trifluoromethyl)phenyl]carbamoyl]-5,6-dihydro-4H-cyclopenta[b]thiophen-2-yl]carbamoyl]cyclohexanecarboxylic acid;

Compound 28. 2-[[3-[(4-Cyanophenyl)carbamoyl]-5,6-dihydro-4H-cyclopenta[b]thiophen-2-yl]carbamoyl]cyclohexanecarboxylic acid;

Compound 29. 2-[[3-[(5-Chlorothiazol-2-yl)carbamoyl]-5,6-dihydro-4H-cyclopenta[b]thiophen-2-yl]carbamoyl]cyclohexanecarboxylic acid;

Compound 30. 2-[[3-(1,3-Dihydroisobenzofuran-5-ylcarbamoyl)-5,6-dihydro-4H-cyclopenta[b]thiophen-2-yl]carbamoyl]cyclohexanecarboxylic acid;

Compound 31. 2-[[3-[(4-Methylsulfonylphenyl)carbamoyl]-5,6-dihydro-4H-cyclopenta[b]thiophen-2-yl]carbamoyl]cyclohexanecarboxylic acid;

Compound 32. 2-[[3-[[6-(Trifluoromethyl)-3-pyridyl]carbamoyl]-5,6-dihydro-4H-cyclopenta[b]thiophen-2-yl]carbamoyl]cyclohexanecarboxylic acid;

Compound 33. 2-[[3-[(5-Methyl-3-pyridyl)carbamoyl]-5,6-dihydro-4H-cyclopenta[b]thiophen-2-yl]carbamoyl]cyclohexanecarboxylic acid;

Compound 34. 2-[[3-[(4-Chlorophenyl)-methyl-carbamoyl]-5,6-dihydro-4H-cyclopenta[b]thiophen-2-yl]carbamoyl]cyclohexanecarboxylic acid;

Compound 35. 2-[[3-[(4-Methylcyclohexyl)carbamoyl]-5,6-dihydro-4H-cyclopenta[b]thiophen-2-yl]carbamoyl]cyclohexanecarboxylic acid;

Compound 36. 2-[[3-[4-(4-chlorophenyl)piperazine-1-carbonyl]-5,6-dihydro-4H-cyclopenta[b]thiophen-2-yl]carbamoyl]cyclohexanecarboxylic acid;

Compound 37. 2-[[3-[(4-Chlorophenyl)carbamoyl]-5,7-dihydro-4H-thieno[2,3-c]pyran-2-yl]carbamoyl]cyclohexanecarboxylic acid;

Compound 38. 2-[[3-[(4-Chlorophenyl)carbamoyl]-4,6-dihydrothieno[3,4-b]thiophen-2-yl]carbamoyl]cyclohexanecarboxylic acid;

Compound 39. 2-[[3-[(4-Chlorophenyl)carbamoyl]-4-methyl-4,6-dihydrothieno[2,3-c]furan-2-yl]carbamoyl]cyclohexanecarboxylic acid;

Compound 40 (2-[[4-[(4-Chlorophenyl)carbamoyl]-2,3-dihydrothieno[2,3-b]thiophen-5-yl]carbamoyl]cyclohexanecarboxylic acid;

Compound 41. 2-[[3-[(4-Chlorophenyl)carbamoyl]benzothiophen-2-yl]carbamoyl]cyclohexane carboxylic acid;

Compound 42. 2-[[3-[(4-Chlorophenyl)carbamoyl]thieno[3,4-b]thiophen-2-yl]carbamoyl]cyclohexanecarboxylic acid;

Compound 43. 4-[[3-[(4-Chlorophenyl)carbamoyl]-5,6-dihydro-4H-cyclopenta[b]thiophen-2-yl]amino]-4-oxo-but-2-enoic acid;

Compound 44. Example #44. 2-[[3-[(4-Chlorophenyl)carbamoyl]-5,6-dihydro-4H-cyclopenta[b]thiophen-2-yl]carbamoyl]benzoic acid;

Compound 45. 2-[1-[2-[[3-[(4-Chlorophenyl)carbamoyl]-5,6-dihydro-4H-cyclopenta[b]thiophen-2-yl]amino]-2-oxoethyl]cyclopentyl]acetic acid;

Compound 46. 2-[[3-[(4-Chlorophenyl)carbamoyl]-5,6-dihydro-4H-cyclopenta[b]thiophen-2-yl]carbamoyl]cyclopentanecarboxylic acid;

Compound 47. 5-[[3-[(4-Chlorophenyl)carbamoyl]-5,6-dihydro-4H-cyclopenta[b]thiophen-2-yl]amino]-3,3-dimethyl-5-oxo-pentanoic acid;

Compound 48. 6-[[3-[(4-Chlorophenyl)carbamoyl]-5,6-dihydro-4H-cyclopenta[b]thiophen-2-yl]carbamoyl]cyclohex-3-ene-1-carboxylic acid;

Compound 49. 2-[[3-[(4-Chlorophenyl)carbamoyl]-5,6-dihydro-4H-cyclopenta[b]thiophen-2-yl]carbamoyl]cyclohexane-trans-carboxylic acid;

Compound 50. 4-[[3-[(4-Chlorophenyl)carbamoyl]-5,6-dihydro-4H-cyclopenta[b]thiophen-2-yl]amino]-4-oxo-butanoic acid;

Compound 51. 2-[[3-[(4-Chlorophenyl)carbamoyl]-5,6-dihydro-4H-cyclopenta[b]thiophen-2-yl]carbamoyl]-7-oxabicyclo[2.2.1]heptane-3-carboxylic acid;

Compound 52. N-(4-Chlorophenyl)-2-(cyclohexanecarbonylamino)-5,6-dihydro-4H-cyclopenta[b]thiophene-3-carboxamide;

Compound 53. N-(4-Chlorophenyl)-2-[(3-oxocyclohexanecarbonyl)amino]-5,6-dihydro-4H-cyclopenta[b]thiophene-3-carboxamide;

Compound 54. N-(4-Chlorophenyl)-2-(1,3-dioxo-3a,4,5,6,7,7a-hexahydroisoindol-2-yl)-5,6-dihydro-4H-cyclopenta[b]thiophene-3-carboxamide;

Compound 55. N2-3-[(4-Chlorophenyl)carbamoyl]-5,6-dihydro-4H-cyclopenta[b]thiophen-2-yl]cyclohexane-1,2-dicarboxamide;

Compound 56. N-(4-Chlorophenyl)-2-[[2-(hydroxymethyl)cyclohexanecarbonyl]amino]-5,6-dihydro-4H-cyclopenta[b]thiophene-3-carboxamide;

Compound 57. 2-[[3-[(4-Chlorophenyl)carbamoyl]-5,6-dihydro-4H-cyclopenta[b]thiophen-2-yl]carbamoyl]cyclohexane-cis-carboxylic acid;

Compound 58. 2-[[3-(m-Tolylcarbamoyl)-5,6-dihydro-4H-cyclopenta[b]thiophen-2-yl]carbamoyl]cyclohexanecarboxylic acid;

Compound 59. 2-[[3-[(4-Chlorophenyl)carbamoyl]-4-ethyl-5-methyl-2-thienyl]carbamoyl]cyclohexanecarboxylic acid;

Compound 60. 6-[[3-(p-Tolylcarbamoyl)-4,5,6,7-tetrahydrobenzothiophen-2-yl]carbamoyl]cyclohex-3-ene-1-carboxylic acid;

Compound 61. 2-[[3-[(4-Chlorophenyl)carbamoyl]-4,5,6,7-tetrahydrobenzothiophen-2-yl]carbamoyl]cyclohexane-cis-carboxylic acid;

Compound 62. 2-Benzamido-N-(m-tolyl)-5,6-dihydro-4H-cyclopenta[b]thiophene-3-carboxamide;

Compound 63. 2-[[3-(Benzylcarbamoyl)-5,6-dihydro-4H-cyclopenta[b]thiophen-2-yl]carbamoyl]cyclohexanecarboxylic acid;

Compound 64. 2-[[3-[(3-Methoxyphenyl)carbamoyl]-5,6-dihydro-4H-cyclopenta[b]thiophen-2-yl]carbamoyl]cyclohexanecarboxylic acid;

Compound 65. 2-[[3-(Cyclohexylcarbamoyl)-5,6-dihydro-4H-cyclopenta[b]thiophen-2-yl]carbamoyl]cyclohexanecarboxylic acid;

Compound 66. 2-[[3-(p-Tolylcarbamoyl)-5,6-dihydro-4H-cyclopenta[b]thiophen-2-yl]carbamoyl]cyclohexanecarboxylic acid;

Compound 67. 2-[[3-(o-Tolylcarbamoyl)-5,6-dihydro-4H-cyclopenta[b]thiophen-2-yl]carbamoyl]cyclohexanecarboxylic acid;

Compound 68. 6-[[3-(m-Tolylcarbamoyl)-4,5,6,7-tetrahydrobenzothiophen-2-yl]carbamoyl]cyclohex-3-ene-1-carboxylic acid;

Compound 69. 2-[[3-(m-Tolylcarbamoyl)-4,5,6,7-tetrahydrobenzothiophen-2-yl]carbamoyl]cyclohexanecarboxylic acid;

Compound 70. 2-[[3-[(3-Chlorophenyl)carbamoyl]-4-ethyl-5-methyl-2-thienyl]carbamoyl]cyclohexanecarboxylic acid;

Compound 71. 2-[[3-[(4-Chlorophenyl)carbamoyl]-2-thienyl]carbamoyl]bicyclo[2.2.2]octane-3-carboxylic acid;

Compound 72. 2-[[5-Isopropyl-3-(phenylcarbamoyl)-2-thienyl]carbamoyl]cyclohexanecarboxylic acid;

Compound 73. 2-[[4-Ethyl-5-methyl-3-(phenylcarbamoyl)-2-thienyl]carbamoyl]cyclohexanecarboxylic acid;

Compound 74. 2-[[3-(Phenylcarbamoyl)-5,6-dihydro-4H-cyclopenta[b]thiophen-2-yl]carbamoyl]cyclohexanecarboxylic acid;

Compound 75. N-(4-Chlorophenyl)-2-[[2-(2-methylimidazol-1-yl)acetyl]amino]-4,5,6,7-tetrahydrobenzothiophene-3-carboxamide;

Compound 76. 2-[[3-[(4-Methoxyphenyl)carbamoyl]-5,6-dihydro-4H-cyclopenta[b]thiophen-2-yl]carbamoyl]cyclohexanecarboxylic acid;

Compound 77. 2-[[3-[[3-(Trifluoromethyl)phenyl]carbamoyl]-5,6-dihydro-4H-cyclopenta[b]thiophen-2-yl]carbamoyl]cyclohexanecarboxylic acid;

Compound 78. N-(4-chlorophenyl)-2-[(2-pyrazin-2-ylacetyl)amino]-5,6-dihydro-4H-cyclopenta[b]thiophene-3-carboxamide;

Compound 79. 2-[[6-tert-butyl-3-[(4-chlorophenyl)carbamoyl]-4,5,6,7-tetrahydrobenzothiophen-2-yl]carbamoyl]cyclohexanecarboxylic acid;

Compound 80. N-[3-[(4-chlorophenyl)carbamoyl]-5,6-dihydro-4H-cyclopenta[b]thiophen-2-yl]-1-sulfamoyl-piperidine-2-carboxamide;

Compound 81. N-(4-chlorophenyl)-2-[(2-tetrahydropyran-4-ylacetyl)amino]-5,6-dihydro-4H-cyclopenta[b]thiophene-3-carboxamide;

Compound 82. N3-[3-[(4-chlorophenyl)carbamoyl]-5,6-dihydro-4H-cyclopenta[b]thiophen-2-yl]morpholine-3,4-dicarboxamide;

Compound 83. N-[3-[(4-chlorophenyl)carbamoyl]-5,6-dihydro-4H-cyclopenta[b]thiophen-2-yl]-1-sulfamoyl-piperidine-3-carboxamide;

Compound 84. 1-acetyl-N-[3-[(4-chlorophenyl)carbamoyl]-5,6-dihydro-4H-cyclopenta[b]thiophen-2-yl]azetidine-2-carboxamide;

Compound 85. N-(4-chlorophenyl)-2-[[(1S,2R)-2-(methanesulfonamido)cyclohexane carbonyl]amino]-5,6-dihydro-4H-cyclopenta[b]thiophene-3-carboxamide;

Compound 86. N-[3-[(4-chlorophenyl)carbamoyl]-5,6-dihydro-4H-cyclopenta[b]thiophen-2-yl]-4-methylsulfonyl-morpholine-2-carboxamide;

Compound 87. N-[3-[(4-chlorophenyl)carbamoyl]-5,6-dihydro-4H-cyclopenta[b]thiophen-2-yl]-4-sulfamoyl-morpholine-2-carboxamide;

Compound 88. N1-[3-[(4-chlorophenyl)carbamoyl]-5,6-dihydro-4H-cyclopenta[b]-thiophen-2-yl]-N2-methoxy-cyclohexane-1,2-dicarboxamide;

Compound 89. 1-[[3-[(4-chlorophenyl)carbamoyl]-5,6-dihydro-4H-cyclopenta[b]thiophen-2-yl]carbamoyl]piperidine-2-carboxylic acid;

Compound 90. N-(4-chlorophenyl)-2-[[2-(hydroxycarbamoyl) cyclohexanecarbonyl]amino]-5,6-dihydro-4H-cyclopenta[b]thiophene-3-carboxamide;

Compound 91. 2-[[6-tert-butoxycarbonyl-3-[(4-chlorophenyl)carbamoyl]-5,7-dihydro-4H-thieno[2,3-c]pyridin-2-yl]carbamoyl]cyclohexanecarboxylic acid;

Compound 92. N3-[3-[(4-chlorophenyl)carbamoyl]-5,6-dihydro-4H-cyclopenta[b]thiophen-2-yl]piperidine-1,3-dicarboxamide;

Compound 93. N-[3-[(4-chlorophenyl)carbamoyl]-5,6-dihydro-4H-cyclopenta[b]thiophen-2-yl]-4-methylsulfonyl-morpholine-3-carboxamide;

Compound 94. N-[3-[(4-chlorophenyl)carbamoyl]-5,6-dihydro-4H-cyclopenta[b]thiophen-2-yl]oxetane-3-carboxamide;

Compound 95. N-[3-[(4-chlorophenyl)carbamoyl]-5,6-dihydro-4H-cyclopenta[b]thiophen-2-yl]-1-methylsulfonyl-piperidine-3-carboxamide;

Compound 96. N-[3-[(4-chlorophenyl)carbamoyl]-5,6-dihydro-4H-cyclopenta[b]thiophen-2-yl]azetidine-2-carboxamide;

Compound 97. 4-[[3-[(4-chlorophenyl)carbamoyl]-5,6-dihydro-4H-cyclopenta[b]thiophen-2-yl]carbamoyl]cyclohexanecarboxylic acid, isomer A;

Compound 98. 4-[[3-[(4-chlorophenyl)carbamoyl]-5,6-dihydro-4H-cyclopenta[b]thiophen-2-yl]carbamoyl]cyclohexanecarboxylic acid, isomer B;

Compound 99. 3-[[3-[(4-chlorophenyl)carbamoyl]-5,6-dihydro-4H-cyclopenta[b]thiophen-2-yl]carbamoyl]cyclohexanecarboxylic acid;

Compound 100. N-[3-[(4-chlorophenyl)carbamoyl]-5,6-dihydro-4H-cyclopenta[b]thiophen-2-yl]-1-methylsulfonyl-piperidine-2-carboxamide;

Compound 101. N-[3-[(4-chlorophenyl)carbamoyl]-5,6-dihydro-4H-cyclopenta[b]thiophen-2-yl]-2-oxo-piperidine-4-carboxamide;

Compound 102. N-[3-[(4-chlorophenyl)carbamoyl]-5,6-dihydro-4H-cyclopenta[b]thiophen-2-yl]-1-sulfamoyl-azetidine-2-carboxamide;

Compound 103. N-[3-[(4-chlorophenyl)carbamoyl]-5,6-dihydro-4H-cyclopenta[b]thiophen-2-yl]morpholine-3-carboxamide;

Compound 104. 4-(6-tert-butyl-3-(m-tolylcarbamoyl)-4,5,6,7-tetrahydrobenzo[b]thiophene-2-ylamino)-4-oxobutanoic acid; and Compound 105. 4-(6-tert-butyl-3-(4-methoxyphenylcarbamoyl)-4,5,6,7-tetrahydrobenzo[b]thiophene-2-ylamino)-4-oxobutanoic acid.

In a further more preferred embodiment, the compounds for use as an antiviral drug are selected from the group consisting of:

Compound 1. 2-[[3-[(3,4-Dimethylphenyl)carbamoyl]-5,6-dihydro-4H-cyclopenta[b]thiophen-2-yl]carbamoyl]cyclohexanecarboxylic acid;

Compound 6. 2-[[3-[[4-Chloro-3-(trifluoromethyl)phenyl]carbamoyl]-5,6-dihydro-4H-cyclopenta[b]thiophen-2-yl]carbamoyl]cyclohexanecarboxylic acid;

Compound 10. 2-[[3-[(4-Phenylphenyl)carbamoyl]-5,6-dihydro-4H-cyclopenta[b]thiophen-2-yl]carbamoyl]cyclohexanecarboxylic acid;

Compound 11. 2-[[3-[(3-Chlorophenyl)methylcarbamoyl]-5,6-dihydro-4H-cyclopenta[b]thiophen-2-yl]carbamoyl] cyclohexanecarboxylic acid;

Compound 13. 2-[[3-[(4-Chloro-3-methyl-phenyl)carbamoyl]-5,6-dihydro-4H-cyclopenta[b]thiophen-2-yl]carbamoyl]cyclohexanecarboxylic acid;

Compound 14. 2-[[3-[(3-chloro-4-methyl-phenyl)carbamoyl]-5,6-dihydro-4H-cyclopenta[b]thiophen-2-yl]carbamoyl]cyclohexanecarboxylic acid;

Compound 17. 2-[[3-[(3-Chlorophenyl)-5,6-dihydro-4H-cyclopenta[b]thiophen-2-yl]carbamoyl]cyclohexanecarboxylic acid;

Compound 20. 2-[[3-[[4-(Trifluoromethoxy)phenyl]carbamoyl]-5,6-dihydro-4H-cyclopenta[b]thiophen-2-yl]carbamoyl]cyclohexanecarboxylic acid;

Compound 21. 2-[[3-[(4-tert-Butylphenyl)carbamoyl]-5,6-dihydro-4H-cyclopenta[b]thiophen-2-yl]carbamoyl]cyclohexanecarboxylic acid;

Compound 23. 2-[[3-(Indan-1-ylcarbamoyl)-5,6-dihydro-4H-cyclopenta[b]thiophen-2-yl]carbamoyl]cyclohexanecarboxylic acid;

Compound 25. 2-[[3-[(4-Isopropylphenyl)carbamoyl]-5,6-dihydro-4H-cyclopenta[b]thiophen-2-yl]carbamoyl]cyclohexanecarboxylic acid;

Compound 29. 2-[[3-[(5-Chlorothiazol-2-yl)carbamoyl]-5,6-dihydro-4H-cyclopenta[b]thiophen-2-yl]carbamoyl]cyclohexanecarboxylic acid;

Compound 38. 2-[[3-[(4-Chlorophenyl)carbamoyl]-4,6-dihydrothieno[3,4-b]thiophen-2-yl]carbamoyl]cyclohexanecarboxylic acid;

Compound 40. 2-[[4-[(4-Chlorophenyl)carbamoyl]-2,3-dihydrothieno[2,3-b]thiophen-5-yl]carbamoyl] cyclohexanecarboxylic acid;

Compound 41. 2-[[3-[(4-Chlorophenyl)carbamoyl]benzothiophen-2-yl]carbamoyl]cyclohexane carboxylic acid;

Compound 42. 2-[[3-[(4-Chlorophenyl)carbamoyl]thieno[3,4-b]thiophen-2-yl]carbamoyl] cyclohexanecarboxylic acid;

Compound 45. 2-[1-[2-[[3-[(4-Chlorophenyl)carbamoyl]-5,6-dihydro-4H-cyclopenta[b]thiophen-2-yl]amino]-2-oxo-ethyl]cyclopentyl]acetic acid;

Compound 54. N-(4-Chlorophenyl)-2-(1,3-dioxo-3a,4,5,6,7,7a-hexahydroisoindol-2-yl)-5,6-dihydro-4H-cyclopenta[b]thiophene-3-carboxamide;

Compound 57. 2-[[3-[(4-Chlorophenyl)carbamoyl]-5,6-dihydro-4H-cyclopenta[b]thiophen-2-yl]carbamoyl]cyclohexane-cis-carboxylic acid;

Compound 61. 2-[[3-[(4-Chlorophenyl)carbamoyl]-4,5,6,7-tetrahydrobenzothiophen-2-yl]carbamoyl]cyclohexane-cis-carboxylic acid;

Compound 72. 2-[[5-Isopropyl-3-(phenylcarbamoyl)-2-thienyl]carbamoyl]cyclohexanecarboxylic acid; and Compound 77. 2-[[3-[[3-(Trifluoromethyl)phenyl]carbamoyl]-5,6-dihydro-4H-cyclopenta[b]thiophen-2-yl]carbamoyl]cyclohexanecarboxylic acid.

New Compounds of the Invention

The inventors have also provided new compounds and the pharmaceutical salts thereof of formula (I):

in which:

$R_1$ and $R_2$ form together a 5-7 membered ring, saturated or unsaturated, said 5-7 membered ring comprises one or more heteroatoms chosen among:

—N, optionally substituted by a radical selected in the group consisting of a ($C_1$-$C_6$)alkyl, a ($C_2$-$C_6$)alkenyl, a ($C_2$-$C_6$)alkynyl, a 5-10 membered ring, saturated or unsaturated, selected from the group consisting of cycloalkyl, aryl, heterocycloalkyl, and heteroaryl, a saturated or unsaturated ($C_1$-$C_6$)alkylcycloalkyl, ($C_1$-$C_6$)alkylaryl, ($C_1$-$C_6$)alkylheterocycloalkyl), or ($C_1$-$C_6$)alkylheteroaryl, and a CO—($C_1$-$C_6$)alkyl, a $CO_2$—($C_1$-$C_6$)alkyl, a CO—($C_1$-$C_6$)alkylaryl, a CO-aryl, a CO-heteroaryl, a $SO_2$-aryl, or a $SO_2$-heteroaryl,
said radical is optionally substituted by at least one —OH, halogen, ($C_1$-$C_6$)alkyl, or ($C_1$-$C_6$)alkyloxy,
O, and
S, and
said 5-7 membered ring is optionally substituted by:
a ($C_1$-$C_6$)alkyl, a ($C_2$-$C_6$)alkenyl, a ($C_2$-$C_6$)alkynyl, optionally substituted by at least one halogen, or —OH,
a 5-10 membered ring, saturated or unsaturated, selected from the group consisting of cycloalkyl, aryl, heterocycloalkyl, and heteroaryl,
a saturated or unsaturated ($C_1$-$C_6$)alkylcycloalkyl, ($C_1$-$C_6$)alkylaryl, ($C_1$-$C_6$)alkylheterocycloalkyl), or ($C_1$-$C_6$)alkylheteroaryl,
a halogen, —CN, or —$NO_2$,
—C(O)R, —C(O)$_2$R, —C(O)NRR', —CONHOR, —CONHSO$_2$R, —NRR', —N(R)C(O)R', —N(R)NR'R", —N(R)C(O)$_2$R', —N(R)C(O)NR'R", —N(R)S(O)$_2$R', —OR, —SR, —S(O)R, —S(O$_2$)R, —S(O)NRR', or —S(O)$_2$NRR', R, R', and R" being independently H, ($C_1$-$C_6$) alkyl, cycloalkyl, aryl, heterocycloalkyl, heteroaryl, ($C_1$-$C_6$)alkylcycloalkyl, ($C_1$-$C_6$)alkylaryl, ($C_1$-$C_6$)alkylheterocycloalkyl), ($C_1$-$C_6$) alkylheteroaryl, or R and R' or R' and R" may form a 5-7 membered ring, optionally interrupted by one or several heteroatoms, said 5-7 membered ring is optionally substituted by at least one —OH, halogen, ($C_1$-$C_6$)alkyl or ($C_1$-$C_6$)alkyloxy;
$R_3$ represents:
a radical selected from the group consisting of:
a ($C_1$-$C_6$)alkyl, a ($C_2$-$C_6$)alkenyl, a ($C_2$-$C_6$)alkynyl,
a 4-10 or 5-10 membered ring, saturated or unsaturated, selected from the group consisting of a cycloalkyl, a cycloalkanonyl, a heterocycloalkanonyl, an aryl, a heterocycloalkyl, a heteroaryl, and a 5-10 membered bridged carbocyclyl or heterocyclyl, and
a saturated or unsaturated ($C_1$-$C_6$)alkylcycloalkyl, ($C_1$-$C_6$)alkylaryl, ($C_1$-$C_6$)alkylheterocycloalkyl, and ($C_1$-$C_6$)alkylheteroaryl,
said radicals being optionally substituted by
a ($C_1$-$C_6$)alkyl or a ($C_1$-$C_6$)alkoxy, optionally substituted by at least one halogen, preferably fluorine,
a 5-10 membered ring, saturated or unsaturated, selected from the group consisting of a cycloalkyl, a spironocycloalkyl, an aryl, a heterocycloalkyl, and a heteroaryl, or
a saturated or unsaturated ($C_1$-$C_6$)alkylcycloalkyl, ($C_1$-$C_6$)alkylaryl, ($C_1$-$C_6$)alkylheterocycloalkyl, or ($C_1$-$C_6$)alkylheteroaryl; and
said optionally substituted radical being optionally substituted by at least one group (A) selected in the group consisting of:
—C(O)R, —C(O)$_2$R, —C(O)NRR', —CONHOR, —CONHSO$_2$R, —NRR', —N(R)C(O)R', —N(R)NR'R", —N(R)C(O)$_2$R', —N(R)C(O)NR'R", —N(R)S(O)$_2$R', —R, —OH, —OR, —SR, —S(O)R, —S(O$_2$)R, —S(O)NRR', —S(O)$_2$NRR', R, R', and R" are such as defined above, and a tetrazolyl;

a —X—Y unit, in which:
X is O or NH, and
Y is selected from the radical consisting of:
a ($C_1$-$C_6$)alkyl, a ($C_2$-$C_6$)alkenyl, a ($C_2$-$C_6$)alkynyl,
a 5-10 membered ring, saturated or unsaturated, selected from the group consisting of a cycloalkyl, a cycloalkanonyl, an aryl, a heterocycloalkyl, a heteroaryl, and a 5-10 membered bridged carbocyclyl or heterocyclyl, and
a saturated or unsaturated ($C_1$-$C_6$)alkylcycloalkyl, ($C_1$-$C_6$)alkylaryl, ($C_1$-$C_6$)alkylheterocycloalkyl, ($C_1$-$C_6$)alkylheteroaryl,
said radicals being optionally substituted by:
a ($C_1$-$C_6$)alkyl or a ($C_1$-$C_6$)alkoxy,
a 5-10 membered ring, saturated or unsaturated, selected from the group consisting of a cycloalkyl, a spironocycloalkyl, an aryl, a heterocycloalkyl, and a heteroaryl,
a saturated or unsaturated ($C_1$-$C_6$)alkylcycloalkyl, ($C_1$-$C_6$)alkylaryl, ($C_1$-$C_6$)alkylheterocycloalkyl, or ($C_1$-$C_6$)alkylheteroaryl, and
said optionally substituted radical being optionally substituted by at least one group (A) as above defined; or
$R_3$ may form with the nitrogen atom of the group —NH—CO—$R_3$ a moiety having the following formula (A):

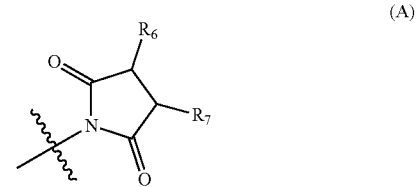

(A)

in which $R_6$ and $R_7$ represent independently H, or a ($C_1$-$C_6$)alkyl or $R_6$ and $R_7$ may form a 5-10 membered ring saturated or unsaturated, selected from the group consisting of a cycloalkyl, an aryl, a heterocycloalkyl, and a heteroaryl, said 5-10 membered ring being optionally substituted by at least one —OH, halogen, ($C_1$-$C_6$)alkyl, or ($C_1$-$C_6$)alkyloxy;
$R_4$ represents a radical selected in the group
a 5-14 membered ring, saturated or unsaturated, selected from the group consisting of a cycloalkyl, an aryl, a heterocycloalkyl, a heteroaryl, a fused arylheterocycloalkyl, and a fused arylcycloalkyl,
a ($C_1$-$C_6$)alkylcycloalkyl, a ($C_1$-$C_6$)alkylaryl, a ($C_1$-$C_6$) alkylheterocycloalkyl, and a ($C_1$-$C_6$)alkylheteroaryl, and
a ($C_1$-$C_6$)alkyl,
said radicals being optionally substituted by at least one group (B) selected in the group consisting of:
a ($C_1$-$C_6$)alkyl or a ($C_1$-$C_6$)alkoxy, optionally substituted by at least one OH, one halogen or one —NRR', R, R', and R" are such as defined above,
a halogen, —CN, or —$NO_2$,
a 5-10 membered ring, saturated or unsaturated, selected from the group consisting of a cycloalkyl, an aryl, a heterocycloalkyl, and a heteroaryl, optionally substituted by at least one OH, one halogen, one ($C_1$-$C_6$)alkyl, one ($C_1$-$C_6$)alkyloxy or one —NRR', R, R', and R" are such as defined above,
a saturated or unsaturated ($C_1$-$C_6$)alkylcycloalkyl, ($C_1$-$C_6$)alkylaryl, ($C_1$-$C_6$)alkylheterocycloalkyl, or ($C_1$-$C_6$)alkylheteroaryl, optionally substituted by at least one —OH, halogen, ($C_1$-$C_6$)alkyl, or ($C_1$-$C_6$)alkyloxy,
—C(O)R, —C(O)$_2$R, —C(O)NRR', —CONHOR, —CONHSO$_2$R, —NRR', —N(R)C(O)R', —N(R)NR'R", —N(R)C(O)$_2$R', —N(R)C(O)NR'R", —N(R)S(O)$_2$R', —OR, —SR, —S(O)R, —S(O$_2$)R, —S(O)NRR', or —S(O)$_2$NRR', R, R', and R" are such as defined above; and $R_5$ represents H, a ($C_1$-$C_6$)alkyl, a ($C_2$-$C_6$)alkenyl, or a ($C_2$-$C_6$)alkynyl; or $R_4$ and $R_5$ may form together a 5-14 membered ring, optionally interrupted by one or several heteroatoms, said 5-14 membered ring is optionally substituted by at least one —OH, halogen, ($C_1$-$C_6$)alkyl, ($C_1$-$C_6$)alkyloxy, cycloalkyl, or a 5-10 membered ring selected in the group of an aryl, a heterocycloalkyl, and a heteroaryl, optionally substituted by at least one —OH, halogen, ($C_1$-$C_6$)alkyl, or ($C_1$-$C_6$)alkyloxy.

In a particular embodiment, the new compounds as such are of formula (I) in which:

$R_1$ and $R_2$ form together a 5-7 membered ring, saturated or unsaturated,
said 5-7 membered ring comprises one or more heteroatoms chosen among:
O, and
S, and
said 5-7 membered ring is optionally substituted by:
a ($C_1$-$C_6$)alkyl, preferably a methyl;

$R_3$ represents:
a radical selected from the group consisting of:
a ($C_1$-$C_6$)alkyl, preferably an ethyl or a propyl optionally substituted by a dimethyl or a spironocyclopentyl, and a ($C_2$-$C_6$)alkenyl, preferably an ethylene,
a 5-10 membered ring, saturated or unsaturated, selected from the group consisting of:
a cyclopentyl or a cyclohexyl,
a cyclohexanone,
a phenyl, and
a bicyclo[2,2,2]octane and a 7-oxabicyclo[2.2.1]heptane, and
a saturated or unsaturated ($C_1$-$C_6$)alkylheteroaryl, preferably methylimidazole optionally substituted by a ($C_1$-$C_6$)alkyl, preferably a methyl,
said radicals being optionally substituted by at least one group (A) selected in the group consisting of a —C(O)$_2$R with R being H, and —R—OH with R being a ($C_1$-$C_6$)alkyl, preferably a methylene.

$R_4$ represents a radical selected in the group consisting of:
a 5-10 membered ring, saturated or unsaturated, selected from the group consisting of:
a cycloalkyl, preferably a cyclohexyl, optionally substituted by at least one group (B) selected from the group consisting of:
a ($C_1$-$C_6$)alkyl, preferably a methyl, optionally substituted by at least one halogen, or one hydroxy,
a ($C_1$-$C_6$)alkoxy, preferably a methoxy, and a halogen, preferably a fluorine,
a cyano,
a cycloalkyl, a heterocycloalkyl, an aryl, or a heteroaryl, optionally substituted by at least one —OH, halogen, ($C_1$-$C_6$)alkyl, or ($C_1$-$C_6$)alkyloxy,
—C(O)R or —S(O$_2$)R with R being a ($C_1$-$C_6$)alkyl,
an aryl, preferably a phenyl, optionally substituted by at least one group (B) selected from the group consisting of:
a ($C_1$-$C_6$)alkyl, preferably a methyl, an ethyl, an isopropyl, a tert-butyl, optionally substituted by at least one halogen, preferably a fluorine, or one hydroxy,
a ($C_1$-$C_6$)alkoxy, preferably a methoxy, optionally substituted by at least one fluorine,
a halogen, preferably a fluorine or a chlorine,
a cyano,
a cycloalkyl, a heterocycloalkyl, preferably a morpholine, an aryl, preferably a phenyl, or a heteroaryl, optionally substituted by at least one —OH, halogen, ($C_1$-$C_6$)alkyl, or ($C_1$-$C_6$)alkyloxy,
—C(O)R or —S(O$_2$)R with R being a ($C_1$-$C_6$)alkyl, preferably a methyl,
a heteroaryl, preferably a pyridine, a pyrazine, or a thiazole, optionally substituted by at least one group (B) selected from the group consisting of:
a halogen, preferably a chlorine,
a ($C_1$-$C_6$)alkyl, preferably a methyl, or a ($C_1$-$C_6$)alkoxy, optionally substituted by at least one halogen, preferably a fluorine, or one hydroxy,
a cyano,
a cycloalkyl, a heterocycloalkyl, an aryl, or a heteroaryl, optionally substituted by at least one —OH, halogen, ($C_1$-$C_6$)alkyl, or ($C_1$-$C_6$)alkyloxy, and
—C(O)R or —S(O$_2$)R with R being a ($C_1$-$C_6$)alkyl,
a fused arylheterocycloalkyl, preferably a benzodioxole or an isobenzofurane, and
a fused arylcycloalkyl, preferably an indane, and
a radical selected in the group consisting of:
($C_1$-$C_6$)alkylcycloalkyl, preferably a methylcyclohexyl, and
a ($C_1$-$C_6$)alkylaryl, preferably a methylphenyl,
said radical is optionally substituted by at least one halogen, preferably a chlorine, one ($C_1$-$C_6$)alkyl or one ($C_1$-$C_6$)alkoxy, optionally substituted by at least one halogen; and
a ($C_1$-$C_6$)alkyl, preferably a pentyl; and $R_5$ represents H.

In a preferred embodiment, the new compounds as such are of formula (I) in which:
$R_1$ and $R_2$ form together a 5-7 membered ring, saturated or unsaturated,
said 5-7 membered ring comprises one or more heteroatoms chosen among:
O, and
S, and
said 5-7 membered ring is optionally substituted by:
a ($C_1$-$C_6$)alkyl, preferably a methyl;
$R_3$ represents a cyclohexyl, substituted by at least one group (A) being a —C(O)$_2$R with R being H,
$R_4$ represents a phenyl, substituted by at least one group (B) being a halogen, preferably a chlorine; and
$R_5$ represents H.

In a further preferred embodiment, $R_1$ and $R_2$ form together a tetrahydro-2H-pyran, a tetrahydrofuran optionally substituted by a $(C_1-C_6)$alkyl, preferably a methyl, a tetrahydro-thiophene, a thiophene, or a phenyl.

In a further preferred embodiment, $R_3$ represents a cycloalkyl, preferably a cyclohexyl, substituted by at least one group (A), preferably —C(O)$_2$R with R being H, said at least one group (A) is in vicinal position with respect to the CO of the —NH—CO—$R_3$ group.

In a more preferred embodiment, the new compounds as such are selected in the group consisting of:

Compound 37. 2-[[3-[(4-Chlorophenyl)carbamoyl]-5,7-dihydro-4H-thieno[2,3-c]pyran-2-yl]carbamoyl]cyclohexanecarboxylic acid;

Compound 38. 2-[[3-[(4-Chlorophenyl)carbamoyl]-4,6-dihydrothieno[3,4-b]thiophen-2-yl]carbamoyl]cyclohexanecarboxylic acid;

Compound 39. 2-[[3-[(4-Chlorophenyl)carbamoyl]-4-methyl-4,6-dihydrothieno[2,3-c]furan-2-yl]carbamoyl] cyclohexanecarboxylic acid;

Compound 40. 2-[[4-[(4-Chlorophenyl)carbamoyl]-2,3-dihydrothieno[2,3-b]thiophen-5-yl]carbamoyl] cyclohexanecarboxylic acid; and Compound 42. 2-[[3-[(4-Chlorophenyl)carbamoyl]thieno[3,4-b]thiophen-2-yl]carbamoyl] cyclohexanecarboxylic acid; and Compound 99. 3-[[3-[(4-chlorophenyl)carbamoyl]-5,6-dihydro-4H-cyclopenta[b]thiophen-2-yl]carbamoyl]cyclohexanecarboxylic acid.

The inventors have further provided new compounds and the pharmaceutical salts thereof selected in the group consisting of:

Compound 1. 2-[[3-[(3,4-Dimethylphenyl)carbamoyl]-5,6-dihydro-4H-cyclopenta[b]thiophen-2-yl]carbamoyl]cyclohexanecarboxylic acid;

Compound 2. 2-[[3-[(6-Chloro-3-pyridyl)carbamoyl]-5,6-dihydro-4H-cyclopenta[b]thiophen-2-yl]carbamoyl]cyclohexanecarboxylic acid;

Compound 3. 2-[[3-(1,3-Benzodioxol-5-ylcarbamoyl)-5,6-dihydro-4H-cyclopenta[b]thiophen-2-yl]carbamoyl]cyclohexanecarboxylic acid;

Compound 4. 2-[[3-[(4-Fluorophenyl)carbamoyl]-5,6-dihydro-4H-cyclopenta[b]thiophen-2-yl]carbamoyl]cyclohexanecarboxylic acid;

Compound 5. 2-[[3-[(4-Chlorophenyl)methylcarbamoyl]-5,6-dihydro-4H-cyclopenta[b]thiophen-2-yl]carbamoyl]cyclohexanecarboxylic acid;

Compound 6. 2-[[3-[[4-Chloro-3-(trifluoromethyl)phenyl]carbamoyl]-5,6-dihydro-4H-cyclopenta[b]thiophen-2-yl]carbamoyl]cyclohexanecarboxylic acid;

Compound 7. 2-[[3-[(4-Chloro-2-methyl-phenyl)carbamoyl]-5,6-dihydro-4H-cyclopenta[b]thiophen-2-yl]carbamoyl]cyclohexanecarboxylic acid;

Compound 8. 2-[[3-[(Trans-4-methoxycyclohexyl)carbamoyl]-5,6-dihydro-4H-cyclopenta[b]thiophen-2-yl]carbamoyl]cyclohexanecarboxylic acid;

Compound 9. 2-[[3-[[4-(2-Hydroxyethyl)phenyl]carbamoyl]-5,6-dihydro-4H-cyclopenta[b]thiophen-2-yl]carbamoyl]cyclohexanecarboxylic acid;

Compound 10. 2-[[3-[(4-Phenylphenyl)carbamoyl]-5,6-dihydro-4H-cyclopenta[b]thiophen-2-yl]carbamoyl]cyclohexanecarboxylic acid;

Compound 11. 2-[[3-[(3-Chlorophenyl)methylcarbamoyl]-5,6-dihydro-4H-cyclopenta[b]thiophen-2-yl]carbamoyl]cyclohexanecarboxylic acid;

Compound 12. 2-[[3-[(3-Acetylphenyl)carbamoyl]-5,6-dihydro-4H-cyclopenta[b]thiophen-2-yl]carbamoyl]cyclohexanecarboxylic acid;

Compound 13. 2-[[3-[(4-Chloro-3-methyl-phenyl)carbamoyl]-5,6-dihydro-4H-cyclopenta[b]thiophen-2-yl]carbamoyl]cyclohexanecarboxylic acid;

Compound 14. 2-[[3-[(3-chloro-4-methyl-phenyl)carbamoyl]-5,6-dihydro-4H-cyclopenta[b]thiophen-2-yl]carbamoyl]cyclohexanecarboxylic acid;

Compound 15. 2-[[3-[(4-Morpholinophenyl)carbamoyl]-5,6-dihydro-4H-cyclopenta[b]thiophen-2-yl]carbamoyl]cyclohexanecarboxylic acid;

Compound 16. 2-[[3-[(3,4-Difluorophenyl)carbamoyl]-5,6-dihydro-4H-cyclopenta[b]thiophen-2-yl]carbamoyl]cyclohexanecarboxylic acid;

Compound 17. 2-[[3-[(3-Chlorophenyl)carbamoyl]-5,6-dihydro-4H-cyclopenta[b]thiophen-2-yl]carbamoyl]cyclohexanecarboxylic acid;

Compound 18. 2-[[3-[(4,4-Difluorocyclohexyl)carbamoyl]-5,6-dihydro-4H-cyclopenta[b]thiophen-2-yl]carbamoyl] cyclohexanecarboxylic acid;

Compound 19. 2-[[3-[[4-(Hydroxymethyl)phenyl]carbamoyl]-5,6-dihydro-4H-cyclopenta[b]thiophen-2-yl]carbamoyl]cyclohexanecarboxylic acid;

Compound 20. 2-[[3-[[4-(Trifluoromethoxy)phenyl]carbamoyl]-5,6-dihydro-4H-cyclopenta[b]thiophen-2-yl]carbamoyl]cyclohexanecarboxylic acid;

Compound 21. 2-[[3-[(4-tert-Butylphenyl)carbamoyl]-5,6-dihydro-4H-cyclopenta[b]thiophen-2-yl]carbamoyl]cyclohexanecarboxylic acid;

Compound 22. 2-[[3-(pentylcarbamoyl)-5,6-dihydro-4H-cyclopenta[b]thiophen-2-yl]carbamoyl]cyclohexanecarboxylic acid;

Compound 23. 2-[[3-(Indan-1-ylcarbamoyl)-5,6-dihydro-4H-cyclopenta[b]thiophen-2-yl]carbamoyl]cyclohexanecarboxylic acid;

Compound 24. 2-[[3-(Cyclohexylmethylcarbamoyl)-5,6-dihydro-4H-cyclopenta[b]thiophen-2-yl]carbamoyl]cyclohexanecarboxylic acid;

Compound 25. 2-[[3-[(4-Isopropylphenyl)carbamoyl]-5,6-dihydro-4H-cyclopenta[b]thiophen-2-yl]carbamoyl]cyclohexanecarboxylic acid;

Compound 26. 2-[[3-[(5-Chloropyrazin-2-yl)carbamoyl]-5,6-dihydro-4H-cyclopenta[b]thiophen-2-yl]carbamoyl]cyclohexanecarboxylic acid;

Compound 27. 2-[[3-[[4-(Trifluoromethyl)phenyl]carbamoyl]-5,6-dihydro-4H-cyclopenta[b] thiophen-2-yl]carbamoyl]cyclohexanecarboxylic acid;

Compound 28. 2-[[3-[(4-Cyanophenyl)carbamoyl]-5,6-dihydro-4H-cyclopenta[b]thiophen-2-yl]carbamoyl]cyclohexanecarboxylic acid;

Compound 29. 2-[[3-[(5-Chlorothiazol-2-yl)carbamoyl]-5,6-dihydro-4H-cyclopenta[b]thiophen-2-yl]carbamoyl]cyclohexanecarboxylic acid;

Compound 30. 2-[[3-(1,3-Dihydroisobenzofuran-5-ylcarbamoyl)-5,6-dihydro-4H-cyclopenta[b]thiophen-2-yl]carbamoyl]cyclohexanecarboxylic acid;

Compound 31. 2-[[3-[(4-Methylsulfonylphenyl)carbamoyl]-5,6-dihydro-4H-cyclopenta[b]thiophen-2-yl]carbamoyl]cyclohexanecarboxylic acid;

Compound 32. 2-[[3-[[6-(Trifluoromethyl)-3-pyridyl]carbamoyl]-5,6-dihydro-4H-cyclopenta[b]thiophen-2-yl]carbamoyl]cyclohexanecarboxylic acid;

Compound 33. 2-[[3-[(5-Methyl-3-pyridyl)carbamoyl]-5,6-dihydro-4H-cyclopenta[b]thiophen-2-yl]carbamoyl]cyclohexanecarboxylic acid;

Compound 34. 2-[[3-[(4-Chlorophenyl)-methyl-carbamoyl]-5,6-dihydro-4H-cyclopenta[b]thiophen-2-yl]carbamoyl]cyclohexanecarboxylic acid;

Compound 35. 2-[[3-[(4-Methylcyclohexyl)carbamoyl]-5,6-dihydro-4H-cyclopenta[b]thiophen-2-yl]carbamoyl]cyclohexanecarboxylic acid;

Compound 36. 2-[[3-[4-(4-chlorophenyl)piperazine-1-carbonyl]-5,6-dihydro-4H-cyclopenta[b]thiophen-2-yl]carbamoyl]cyclohexanecarboxylic acid;

Compound 41. 2-[[3-[(4-Chlorophenyl)carbamoyl]benzothiophen-2-yl]carbamoyl]cyclohexane carboxylic acid;

Compound 44. 2-[[3-[(4-Chlorophenyl)carbamoyl]-5,6-dihydro-4H-cyclopenta[b]thiophen-2-yl]carbamoyl]benzoic acid;

Compound 45. 2-[1-[2-[[3-[(4-Chlorophenyl)carbamoyl]-5,6-dihydro-4H-cyclopenta[b]thiophen-2-yl]amino]-2-oxoethyl]cyclopentyl]acetic acid;

Compound 46. 2-[[3-[(4-Chlorophenyl)carbamoyl]-5,6-dihydro-4H-cyclopenta[b]thiophen-2-yl]carbamoyl]cyclopentanecarboxylic acid;

Compound 47. 5-[[3-[(4-Chlorophenyl)carbamoyl]-5,6-dihydro-4H-cyclopenta[b]thiophen-2-yl]amino]-3,3-dimethyl-5-oxo-pentanoic acid;

Compound 49. 2-[[3-[(4-Chlorophenyl)carbamoyl]-5,6-dihydro-4H-cyclopenta[b]thiophen-2-yl]carbamoyl]cyclohexane-trans-carboxylic acid;

Compound 51. 2-[[3-[(4-Chlorophenyl)carbamoyl]-5,6-dihydro-4H-cyclopenta[b]thiophen-2-yl]carbamoyl]-7-oxabicyclo[2.2.1]heptane-3-carboxylic acid;

Compound 52. N-(4-Chlorophenyl)-2-(cyclohexanecarbonylamino)-5,6-dihydro-4H-cyclopenta[b] thiophene-3-carboxamide;

Compound 53. N-(4-Chlorophenyl)-2-[(3-oxocyclohexanecarbonyl)amino]-5,6-dihydro-4H-cyclopenta[b]thiophene-3-carboxamide;

Compound 54. N-(4-Chlorophenyl)-2-(1,3-dioxo-3a,4,5,6,7,7a-hexahydroisoindol-2-yl)-5,6-dihydro-4H-cyclopenta[b]thiophene-3-carboxamide;

Compound 55. N2-[3-[(4-Chlorophenyl)carbamoyl]-5,6-dihydro-4H-cyclopenta[b]thiophen-2-yl]cyclohexane-1,2-dicarboxamide;

Compound 56. N-(4-Chlorophenyl)-2-[[2-(hydroxymethyl)cyclohexanecarbonyl]amino]-5,6-dihydro-4H-cyclopenta[b]thiophene-3-carboxamide;

Compound 57. 2-[[3-[(4-Chlorophenyl)carbamoyl]-5,6-dihydro-4H-cyclopenta[b]thiophen-2-yl]carbamoyl]cyclohexane-cis-carboxylic acid; and Compound 61. 2-[[3-[(4-Chlorophenyl)carbamoyl]-4,5,6,7-tetrahydrobenzothiophen-2-yl]carbamoyl]cyclohexane-cis-carboxylic acid.

Therapeutic Uses of the Compounds

The present invention relates to a pharmaceutical or veterinary composition comprising a new compound according to the invention. Preferably, the pharmaceutical composition further comprises a pharmaceutically or veterinary acceptable carrier or excipient. The invention further relates to a method for treating a disease in a subject, wherein a therapeutically effective amount of a new compound according to the invention, is administered to said subject in need thereof. The present invention relates to the use of a new compound according to the invention as a drug. The invention also relates to the use of a new compound according to the invention, for the manufacture of a medicine.

In addition, the present invention relates to a method for treating an infectious disease, preferably a viral disease, in a subject, wherein a therapeutically effective amount of a compound according to the invention, is administered to said subject suffering of an infectious disease, preferably a viral disease. The present invention relates to the use of the compounds according to the invention as an anti-infectious agent, preferably an antiviral agent. The invention also relates to the use of the compounds according to the invention, for the manufacture of a medicine for the treatment of an infectious disease, preferably a viral infection. The invention relates to a compound according to the invention for use in the treatment of an infectious disease, preferably a viral infection.

The present invention further relates to a method for treating a cancer in a subject, wherein a therapeutically effective amount of a compound according to the invention is administered to said subject suffering of a cancer, the compound having a pro-apoptotic effect or inducing autophagy. The present invention relates to the use of the compounds according to the invention as an antitumor agent, preferably a cytotoxic agent, a pro-apoptotic agent or an agent inducing autophagy. The invention also relates to the use of the compounds according to the invention, for the manufacture of a medicine for the treatment of a cancer. The invention relates to a compound according to the invention for use in the treatment of a cancer.

The present invention further relates to a method for treating a disease in a subject, wherein a therapeutically effective amount of a compound according to the invention is administered to said subject, the compound inducing autophagy. The present invention relates to the use of the compounds according to the invention as an agent inducing autophagy. The invention also relates to the use of the compounds according to the invention, for the manufacture of a medicine for inducing autophagy. The invention relates to a compound according to the invention for use in the induction of autophagy. The induction of autophagy is useful for the treatment of a disease selected from the group consisting of cancer, infectious diseases, neurodegenerative diseases, inflammatory diseases, autoimmune diseases, aging, muscle diseases, liver diseases, and metabolic diseases. The induction of autophagy is useful for the treatment of a disease associated with a defect or a decrease of autophagy.

The present invention also relates to a phytosanitary composition comprising a compound according to the invention, preferably a new compound according to the invention. It also relates to the use of a compound according to the invention, preferably a new compound according to the invention, as a phytosanitary agent. Thereby, the compound according to the invention. It further relates to a method for treating a plant against infection, especially infection by a virus, comprising contacting the plant with an efficient amount of a compound according to the invention, preferably a new compound according to the invention.

The present invention further relates to a method for treating a metabolic disorder or disease in a subject, wherein a therapeutically effective amount of a compound according to the invention is administered to said subject suffering of a metabolic disorder or disease. The invention also relates to the use of the compounds according to the invention, for the manufacture of a medicine for the treatment of a metabolic disorder or disease. The invention relates to a compound according to the invention for use in the treatment of a metabolic disorder or disease.

Antiviral Agents

The present invention relates to the use of a compound according to the invention as an antiviral agent. The present invention also relates to a compound of the present invention for use in the treatment of viral infections, the use of a compound of the present invention for the manufacture of a medicine for the treatment of viral infections, and to a method for treating a viral infection in a subject, comprising administering a therapeutically effective amount of a compound according to the invention to the subject.

The present invention also relates to the use of a compound of the present invention as a research tool, especially for studying viral infections. It further relates to a method for blocking viral infection in a cell, a tissue or a subject.

The viral agent can be a DNA virus or a RNA virus. The viral agent can be selected from the group consisting of Alphaviridae, Flaviviridae, Hepadnaviridae, Herpesviridae, Orthomyxoviridae, Papovaviridae, Paramyxoviridae, Picornaviridae, Polyomaviridae, Reoviridae, Retroviridae, Rhabdoviridae, and Tobamoviruses.

In one embodiment, the Alphaviridae is selected from the group consisting of Barmah Forest virus, Middelburg virus, Ndumu virus, Bebaru virus, Chikungunya virus, Mayaro virus, O'nyong'nyong virus, Ross River virus, Semliki Forest virus, Sindbis virus, Una virus, Eastern equine encephalitis virus, Tonate virus, Venezuelan equine encephalitis virus, Cabassou virus, Everglades virus, Mosso das Pedras virus, Mucambo virus, Parmana virus, Pixuna virus, Rio Negro virus, Trocara virus, Aura virus, Babanki virus, Kyzylagach virus, Ockelbo virus, Whataroa virus, Sleeping disease virus, Samon pancreatic disease virus, Southern elephant seal virus, and Western equine encephalitis virus; preferably selected from the group consisting of Barmah Forest virus, Chikungunya virus, Mayaro virus, O'nyong'nyong virus, Ross River virus, Semliki Forest virus, Sindbis virus, Una virus, Eastern equine encephalitis virus, Tonate virus, Venezuelan equine encephalitis virus and Western equine encephalitis virus.

In one embodiment, the Flaviviridae is selected from the group consisting of dengue virus, Hepatitis C virus, Japanese encephalitis virus, West Nile virus, yellow fever virus, Zika virus, Tick-borne encephalitis virus, Kyasanur forest disease virus, Murray Valley encephalitis virus, and Saint Louis encephalitis virus.

In one embodiment, the Hepadnaviridae is selected from the group consisting of Hepatitis B virus.

In one embodiment, the Herpesviridae is selected from the group consisting of Herpes Simplex virus 1 (HSV-1), Herpes Simplex virus 2 (HSV-2), Varicella zoster virus (VZV), Epstein-Barr virus (EBV), Cytomegalovirus (CMV), Roseolovirus (HHV-6A and 6B), HHV-7 and Kaposi's sarcoma-associated herpesvirus (KSHV).

In one embodiment, the Orthomyxoviridae is selected from the group consisting of Influenza virus A, Influenza virus B, Influenza virus C, Isavirus, Thogotovirus and Quaranjavirus, preferably selected from the group consisting of Influenza virus A and Influenza virus B. In one embodiment, the Influenza virus A is selected from the subtypes consisting of H1N1, H1N2, H2N2, H3N1, H3N2, H3N8, H5N1, H5N2, H5N3, H5N8, H5N9, H7N1, H7N2, H7N3, H7N4, H7N7, H7N9, H9N2, and H10N7.

In one embodiment, the Papovaviridae is selected from the group consisting of Papillomavirus (HPC) and Polyomavirus, especially Simian virus 40, Merkel cell polyomavirus, Trichodysplasia spinulosa polyomavirus, BK polyomavirus, JC polyomavirus and Human polyomavirus 7.

In one embodiment, the Paramyxoviridae is selected from the group consisting of Rubulavirus, Morbillivirus, Pneumovirus, Metapneumovirus, Avulavirus, Ferlavirus, Henipavirus, Respirovirus, preferably from the group consisting of the mumps virus, measles virus, human parainfluenza viruses (HPIV), especially HPIV-1, HPIV-2, HPIV-3 or HPIV-4, respiratory syncytial virus (RSV), in particular Human respiratory syncytial virus (HRSV), canine distemper virus, phocine distemper virus, cetacean morbillivirus, Newcastle disease virus, rinderpest virus, Hendra virus and Nipah virus.

In one embodiment, the Picornaviridae is selected from the group consisting of Aphthovirus, Aquamavirus, Avihepatovirus, Cardiovirus, Cosavirus, Dicipivirus, Enterovirus, Erbovirus, Hepatovirus, Kobuvirus, Megrivirus, Parechovirus, Piscevirus, Salivirus, Sapelovirus, Senecavirus, Techovirus, and Tremovirus.

In one embodiment, the Retroviridae is selected from the group consisting of Alpharetrovirus; especially Avian leukosis virus and Rous sarcoma virus; Betaretrovirus, especially Mouse mammary tumour virus; Gammaretrovirus, especially Murine leukemia virus and Feline leukemia virus; Deltaretrovirus, especially Bovine leukemia virus and Human T-lymphotropic virus; Epsilonretrovirus, especially Walleye dermal sarcoma virus; Lentivirus, especially Human immunodeficiency virus 1 and Simian, Feline immunodeficiency viruses; Spumavirus, especially Simian foamy virus.

In one embodiment, the Rhabdoviridae is selected from the group consisting of vesiculovirus, especially vesicular stomatitis virus, lyssavirus, especially rabies virus, Ephemerovirus, novirhabdovirus, cytorhabdovirus and nucleorhabdovirus.

In one preferred embodiment, the viral agent according to the invention is selected from the group consisting in Herpesviridae such as Varicella zoster virus (VZV), Epstein-Barr (EB) virus, Herpes simplex virus of type 1 (HSV-1), Kaposi sarcoma herpesvirus (KSHV), murine 7-HV68 virus (γ-MHV68), or human cytomegalovirus (HCMV); Hepadnaviridae such as Hepatitis virus B (HBV); Papovaviridae such as Human papillomavirus type 16 (HPV16); Parvoviridae such as Human parvovirus B19; Polyomaviridae such as Simian virus 40; Retroviridae such has Human immunodeficiency virus 1 (HIV-1), or Simian immunodeficiency virus type 1 (SIV 1); Orthomyxoviridae such as Influenza A virus; Flaviviridae such as Dengue virus, or Hepatitis C virus; Picornaviridae such as Poliovirus, Coxsakievirus B3 (CVB3), or Coxsakievirus B4 (CVB4); Reoviridae such as Rotavirus; Alphaviridae such as Sindbis virus; Tobamoviruses such as Tabacco mosaic virus; Rhabdoviridae such as vesicular stomatitis virus. More preferably, the viral agent according to the invention is an influenza virus. Still preferably, the viral agent according to the invention is an influenza virus A or B, even more preferably an influenza virus A.

In a preferred embodiment, the viral agent according to the invention is a virus that modulates autophagy as part of its life cycle, preferably a virus that inhibits autophagy as part of its life cycle.

In another preferred embodiment, the viral agent according to the invention presents an antiviral resistance to classic antiviral drugs. The terms "antiviral resistance", "antiviral agent resistance" or "antiviral drug resistance", as used herein, are equivalent and refer to the ability of viruses to resist the effects of an antiviral agent previously used to treat them. Antiviral resistance can be defined by a decreased susceptibility to a drug through either a minimally effective, or completely ineffective, treatment response to prevent associated illnesses from a particular virus.

Autophagy-Inducing Agents

The compounds of the present invention are able to induce autophagy. Accordingly, the present invention relates to the use of a compound of the present invention as an autophagy-inducing agent. The present invention also relates to a compound of the present invention for use for augmenting or promoting autophagy, the use of a compound of the present invention for the manufacture of a medicine for augmenting or promoting autophagy, and to a method for augmenting or promoting autophagy in a subject, comprising administering an effective amount of a compound of the present invention to the subject.

The present invention also relates to the use of a compound of the present invention as a research tool, especially for studying autophagy. It further relates to a method for augmenting or promoting autophagy in a cell, a tissue or a subject.

Defects in autophagy have been linked to a wide range of medical illnesses including cancer, infectious diseases, neurodegenerative diseases, inflammatory diseases, autoimmune diseases, aging, muscle diseases, liver diseases, and metabolic diseases (Levine et al, 2015, J Clin Invest, 125, 14-24). Therefore, an autophagy inducing agent may prevent or treat these clinical conditions.

Accordingly, the present invention relates to a compound of the present invention for use for preventing or treating a disease or disorder associated with autophagy, especially autophagy defect or decrease. It relates also to the use of a compound of the present invention for the manufacture of a medicine for preventing or treating a disease or disorder associated with autophagy, especially autophagy defect or decrease. It finally relates to a method for preventing or treating a disease or disorder associated with autophagy, especially autophagy defect or decrease, in a subject comprising administering a therapeutic amount of a compound of the present invention to the subject.

In one aspect, the disease or disorder associated with autophagy, especially autophagy defect or decrease, is a disease or disorder that can be prevented, reduced or treated by increasing autophagy, especially with an autophagy-inducing agent. For instance, the disease or disorder associated with autophagy can be cancer, infectious diseases, neurodegenerative diseases, inflammatory diseases, autoimmune diseases, liver diseases, aging, muscle diseases, or metabolic diseases.

In one aspect, the cancer can be a solid tumor or a hematopoietic cancer. For instance, the cancer can be selected from the group consisting of bone cancer, gastro-intestinal cancer, liver cancer, pancreatic cancer, gastric cancer, colorectal cancer, esophageal cancer, oro-pharyngeal cancer, laryngeal cancer, salivary gland carcinoma, thyroid cancer, lung cancer, cancer of the head or neck, skin cancer, squamous cell cancer, melanoma, uterine cancer, cervical cancer, endometrial carcinoma, vulvar cancer, ovarian cancer, breast cancer, prostate cancer, cancer of the endocrine system, sarcoma of soft tissue, bladder cancer, kidney cancer, glioblastoma and various types of cancers of the central nervous system, lymphoma and leukemia. In a preferred embodiment, the cancer is a breast cancer, in particular a triple-negative breast cancer, prostate cancer and ovarian cancer.

In this aspect, the compound of the present invention can be combined with radiotherapy, immunotherapy, hormonotherapy, or chemotherapy, all well-known by the person skilled in the field.

In one aspect, the infectious diseases can be selected from the group consisting of a bacterial infection, in particular intracellular bacterial infections and mycobacterial infections, a fungal infection, and a viral infection, in particular a chronic viral infection.

In one aspect, the neurodegenerative disease is selected from the group consisting of Adrenal Leukodystrophy, Alexander's disease, Alper's disease, Alzheimer's disease, Amyotrophic lateral sclerosis, ataxia telangiectasia, Batten disease, bovine spongiform encephalopathy, Canavan disease, cerebral palsy, corticobasal degeneration, Creutzfeldt-Jakob disease, familial fatal insomnia, frontotemporal lobar degeneration, Huntington's disease, HIV-associated dementia, Kennedy's disease, Krabbe's disease, Lewy body dementia, neuroborreliosis, Machado-Joseph disease, multiple system atrophy, multiple sclerosis, narcolepsy, Niemann Pick disease, Parkinson's disease, Pelizaeus-Merzbacher disease, Pick's disease, primary lateral sclerosis, prion diseases, progressive supranuclear palsy, Refsum's disease, Sandhoff disease, Schilder's disease, subacute combined degeneration of spinal cord secondary to pernicious anaemia, Spielmeyer-Vogt-Sjogren-Batten disease, spinocerebellar ataxia, spinal muscular atrophy, Steele-Richardson-Olszewski disease, Tabes dorsalis and toxic encephalopathy. In a particular aspect, the neurodegenerative disease is selected from the group consisting of Parkinson's disease, Alzheimer's disease, Huntington's disease, and Creutzfeldt-Jakob's disease.

In one aspect, the muscle disease can be selected from the group consisting of cardiomyopathy, Pompe disease, muscular dystrophy, and myotonic dystrophy.

In one aspect, the inflammatory disease or disorder can be selected from the group consisting of Crohn disease, inflammatory bowel disease, asthma, chronic obtrusive pulmonary disease (COPD), systemic lupus erythematosus, cystic fibrosis, psoriasis, infectious arthritis, and multiple sclerosis.

In one aspect, the metabolic disease or disorder can be selected from the group consisting of diabetes, in particular diabetes type I or diabetes type II, atherosclerosis, obesity, diabetic neuropathies, lysosomal storage diseases, severe insulin resistance, hyperinsulinemia, hyperlipidemia, Rabson-Mendenhall syndrome, leprechaunism, lipoatrophic diabetes, acute and chronic renal insufficiency, end-stage chronic renal failure, glomerulonephritis, interstitial nephritis, pyelonephritis, glomerulosclerosis, and lipoatrophic diabetes, hepatic steatosis, nonalcoholic fatty liver disease, Nonalcoholic steatohepatitis (NASH), glucose intolerance, lipodystrophy, coronary heart disease, diabetic retinopathy, diabetic neuropathy, diabetic nephropathy, hypoglycemia, hyperglycemia, beta cell dysfunction or hyperinsulinaemia, Wolfram syndrome, Polycystic ovary syndrome, pyruvate dehydrogenase deficiency, Albright hereditary osteodystrophy, cystinosis, fructose intolerance, Walker-Warburg syndrome, hypobetalipoproteinemia, Alström syndrome, and cirrhosis.

In another aspect, the metabolic disease or disorder can be selected from the group consisting of activator deficiency/GM2 gangliosidosis, alpha-mannosidosis, aspartylglucoaminuria, cholesteryl ester storage disease, chronic hexosaminidase A deficiency, cystinosis, Danon disease, Fabry disease, Farber disease, fucosidosis, galactosialidosis, Gaucher Disease (Types I, II and III), GM1 Ganliosidosis, including infantile, late infantile/juvenile and adult/chronic), Hunter syndrome (MPS II), Mucolipidosis II, Infantile Free Sialic Acid Storage Disease (ISSD), Juvenile Hexosaminidase A Deficiency, Krabbe disease, Lysosomal acid lipase deficiency, Metachromatic Leukodystrophy, Hurler syndrome, Scheie syndrome, Hurler-Scheie syndrome, Sanfilippo syndrome, Morquio Type A and B, Maroteaux-Lamy, Sly syndrome, mucolipidosis, multiple sulfate deficiency, Niemann-Pick disease, Neuronal ceroid lipofuscinoses, CLN6 disease, Jansky-Bielschowsky disease, pycnodysostosis, Sandhoff disease, Schindler disease, and Tay-Sachs or Wolman disease.

The disease or disorder associated with autophagy can be a chronic inflammatory disease, a metabolic syndrome, an inflammation-associated metabolic disorder, a liver disease, a renal disease, a cardiovascular disease, a muscle degeneration and atrophy, symptoms of aging (including the amelioration or the delay in onset or severity or frequency of aging-related symptoms and chronic conditions including muscle atrophy, frailty, metabolic disorders, low grade inflammation, atherosclerosis and associated conditions such as cardiac and neurological both central and peripheral manifestations including stroke, age-associated dementia and sporadic form of Alzheimer's disease, pre-cancerous states, and psychiatric conditions including depression), spinal cord injury, infectious disease and developmental disease.

Apoptosis-Inducing Agents

The compounds of the present invention are able to induce apoptosis. Accordingly, the present invention relates to the use of a compound of the present invention as an apoptosis-inducing agent.

The present invention also relates to a compound of the present invention for use for preventing or treating a disease or disorder associated with apoptosis. It relates also to the use of a compound of the present invention for the manufacture of a medicine for preventing or treating a disease or disorder associated with apoptosis. It finally relates to a method for preventing or treating a disease or disorder associated with apoptosis in a subject comprising administering a therapeutic amount of a compound of the present invention to the subject.

The present invention also relates to the use of a compound of the present invention as a research tool, especially for studying apoptosis. It further relates to a method for augmenting or promoting apoptosis in a cell, a tissue or a subject.

In one aspect, the disease or disorder associated with apoptosis is a disease or disorder that can be prevented, reduced or treated by increasing apoptosis, especially with an apoptosis-inducing agent. For instance, the disease or disorder associated with apoptosis is cancer. Therefore, the compounds of the present invention can be used for treating cancer.

In a particular aspect, the present invention relates to the use of a compound of the present invention as an antitumor drug. It also relates to a compound of the present invention for use in the treatment of cancer. It relates to the use of a compound of the present invention for the manufacture of a medicine for the treatment of cancer. It finally relates to a method for treating a cancer in a subject comprising administering a therapeutic amount of a compound of the present invention to the subject.

Preferably, the cancer is as described above for the autophagy part.

Pharmaceutical Composition

The present invention also relates to a pharmaceutical composition comprising a compound of the present invention, preferably a new compound of the present invention. The composition further comprises at least one pharmaceutically acceptable carrier or excipient.

In a particular embodiment, the pharmaceutical composition according to the invention further comprises at least another active ingredient, preferably selected from the group consisting in an antiviral agent, an anti-cancerous agent, an anti-apoptotic agent, an anti-autophagy agent, an autophagy inducing agent, an antibiotic, an antiparasitic agent, an antifungal agent, or a molecule aimed to treat neurodegenerative diseases, inflammatory diseases, autoimmune diseases, liver diseases, aging, muscle diseases, or metabolic diseases. Preferably, the other active ingredient is an antiviral agent. More preferably, the other active ingredient is an antiviral agent against an influenza virus, preferably an influenza A virus.

In a particular embodiment, the pharmaceutical composition according to the invention further comprises an antiviral agent, for instance and non-exhaustively, an agent selected from the group consisting of neuraminidase inhibitors, M2 inhibitors, RNA polymerase inhibitors, interferons (immune system modulators interferon alpha-2a and PEGylated interferon alpha-2a (Pegasys) and interferon alpha-2b (ViraferonPeg ou Introna)), antiviral vaccine, antigenic polypeptides or neutralizing antibodies directed to a viral antigenic polypeptide.

The invention also concerns the pharmaceutical composition of the invention for use in the treatment of a disease. The invention also relates to the use of a pharmaceutical composition according to the invention for the manufacture of a medicine for treating a disease in a subject. The invention further relates to a method for treating a disease in a subject, wherein a therapeutically effective amount of a pharmaceutical composition according to the invention is administered to said subject suffering from said disease.

Preferably, the disease is selected from the group consisting of cancer, infectious diseases, neurodegenerative diseases, inflammatory diseases, autoimmune diseases, aging, muscle diseases, liver diseases, and metabolic diseases. In a preferred embodiment, the disease is selected from the group consisting of cancer and infectious diseases, in particular viral infection. In a very specific embodiment, the disease is an infection by influenza virus, preferable influenza A virus.

Subject, Regimen and Administration

The subject according to the invention is an animal, preferably a mammal, even more preferably a human. However, the term "subject" can also refer to non-human animals, in particular mammals such as dogs, cats, horses, cows, pigs, sheep, donkeys, rabbits, ferrets, gerbils, hamsters, chinchillas, rats, mice, guinea pigs and non-human primates, among others, that are in need of treatment.

The human subject according to the invention may be a human at the prenatal stage, a new-born, a child, an infant, an adolescent or an adult, in particular an adult of at least 40 years old, preferably an adult of at least 50 years old, still more preferably an adult of at least 60 years old, even more preferably an adult of at least 70 years old.

In a preferred embodiment, the subject has been diagnosed with a disease. Preferably, the subject has been diagnosed with a disease selected from the group consisting in viral infection, diseases or disorders associated with autophagy, in particular a defect or decrease of autophagy, such as cancer, infectious diseases, neurodegenerative diseases, inflammatory diseases, autoimmune diseases, aging, muscle diseases, liver diseases, and metabolic diseases, and diseases or disorders associated with apoptosis such as cancer.

In a particular embodiment, the subject presents an antiviral resistance.

Diagnostic method of these diseases are well known by the man skilled in the art.

The compound according to the invention or the pharmaceutical composition according to the invention may be administered by any conventional route of administration. In particular, the compound or the pharmaceutical composition of the invention can be administered by a topical, enteral, oral, parenteral, intranasal, intravenous, intra-arterial, intramuscular, intratumoral, subcutaneous or intraocular administration and the like.

In particular, the compound according to the invention or the pharmaceutical composition according to the invention can be formulated for a topical, enteral, oral, parenteral, intranasal, intravenous, intra-arterial, intramuscular, intratumoral, subcutaneous or intraocular administration and the like.

Preferably, the compound according to the invention or the pharmaceutical composition according to the invention is administered by enteral or parenteral route of administration. When administered parenterally, the compound according to the invention or the pharmaceutical composition according to the invention is preferably administered by intravenous route of administration. When administered enterally, the compound according to the invention or the pharmaceutical composition according to the invention is preferably administered by oral route of administration.

The pharmaceutical composition comprising the molecule is formulated in accordance with standard pharmaceutical practice (Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

For oral administration, the composition can be formulated into conventional oral dosage forms such as tablets, capsules, powders, granules and liquid preparations such as syrups, elixirs, and concentrated drops. Nontoxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials, are also necessary. For example, starch, gelatine, sugars such as lactose or dextrose, and natural or synthetic gums can be used as binders. Disintegrants are also necessary in the tablets to facilitate break-up of the tablet. Disintegrants include starches, clays, celluloses, algins, gums and crosslinked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

For transdermal administration, the composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Pharmaceutical compositions according to the invention may be formulated to release the active drug substantially immediately upon administration or at any predetermined time or time period after administration.

Preferably, the treatment with the compound according to the invention or the pharmaceutical composition according to the invention start no longer than a month, preferably no longer than a week, after the diagnosis of the disease. In a most preferred embodiment, the treatment starts the day of the diagnosis.

The compound according to the invention or the pharmaceutical composition according to the invention may be administered as a single dose or in multiple doses.

Preferably, the treatment is administered regularly, preferably between every day and every month, more preferably between every day and every two weeks, more preferably between every day and every week, even more preferably the treatment is administered every day. In a particular embodiment, the treatment is administered several times a day, preferably 2 or 3 times a day, even more preferably 3 times a day.

The duration of treatment with the compound according to the invention or the pharmaceutical composition according to the invention is preferably comprised between 1 day and 20 weeks, more preferably between 1 day and 10 weeks, still more preferably between 1 day and 4 weeks, even more preferably between 1 day and 2 weeks. In a particular embodiment, the duration of the treatment is of about 1 week. Alternatively, the treatment may last as long as the disease persists.

The amount of compound according to the invention or of pharmaceutical composition according to the invention to be administered has to be determined by standard procedure well known by those of ordinary skills in the art. Physiological data of the patient (e.g. age, size, and weight) and the routes of administration have to be taken into account to determine the appropriate dosage, so as a therapeutically effective amount will be administered to the patient.

In a preferred embodiment, the total compound dose for each administration of the compound according to the invention or of the pharmaceutical composition according to the invention is comprised between 0.00001 and 1 g, preferably between 0.01 and 10 mg.

The form of the pharmaceutical compositions, the route of administration and the dose of administration of the compound according to the invention, or the pharmaceutical composition according to the invention can be adjusted by the man skilled in the art according to the type and severity of the disease, and to the patient, in particular its age, weight, sex, and general physical condition.

Kit and Use of a Kit

The present invention also relates to the combined use of a compound of the present invention with at least another active ingredient, preferably selected from the group consisting in an antiviral agent, an anti-cancerous agent, an anti-apoptotic agent, an anti-autophagy agent, an autophagy inducing agent, an antibiotic, an antiparasitic agent, an antifungal agent, or a molecule aimed to treat neurodegenerative diseases, inflammatory diseases, autoimmune diseases, liver diseases, aging, muscle diseases, or metabolic diseases for the treatment of a disease selected from the group consisting of cancer, infectious diseases, in particular viral diseases, neurodegenerative diseases, inflammatory diseases, autoimmune diseases, aging, muscle diseases, liver diseases, and metabolic diseases.

The present invention also relates to a product comprising a compound of the present invention, and another active ingredient, as a combined preparation for simultaneous, separate or sequential use, in particular for use for the treatment of a disease selected from the group consisting of cancer, infectious diseases, in particular viral diseases, neurodegenerative diseases, inflammatory diseases, autoimmune diseases, aging, muscle diseases, liver diseases, and metabolic diseases. Preferably, the other active ingredient is selected from the group consisting in an antiviral agent, an anti-cancerous agent, an anti-apoptotic agent, an anti-autophagy agent, an autophagy inducing agent, an antibiotic, an antiparasitic agent, an antifungal agent, or a molecule aimed to treat neurodegenerative diseases, inflammatory diseases, autoimmune diseases, liver diseases, aging, muscle diseases, or metabolic diseases. Preferably, the other active ingredient is an antiviral.

Preferably, the subject is a human.

All the references cited in this application, including scientific articles and summaries, published patent applications, granted patents or any other reference, are entirely incorporated herein by reference, which includes all the results, tables, figures and texts of theses references.

Although having different meanings, the terms "comprising", "having", "consisting in" and "containing" can be replaced one for the other in the entire application.

Further aspects and advantages of the present invention will be described in the following examples, which should be regarded as illustrative and not limiting.

EXAMPLES

Chemistry

Abbreviations

AcOH Acetic acid
Aq Aqueous
br s Broad singlet
CDCl$_3$ Deuterated chloroform
Conc Concentrated
d Doublet
DAD Diode Array Detector
DCM Dichloromethane (methylene chloride)
dd Doublet of doublets
ddd Doublet of doublets of doublets
DIEA N,N-Diisopropylethylamine
DMAP 4-Dimethylaminopyridine
DMF N,N-Dimethylformamide
DMSO Dimethyl sulfoxide
dt Doublet of triplets
EDCI N-(3-Dimethylaminopropyl)-N'-ethylcarbodiimide hydrochloride
ESI Electrospray Ionization
EtOAc Ethyl acetate
Et$_2$O Diethyl ether
Et$_3$N Triethylamine
EtOH Ethanol
g Gram(s)
h Hour(s)
HATU O-(7-Azabenzotriazol-1-yl)-N,N,N',N'-tetramethyluronium hexafluorophosphate
HCl Hydrochloric acid
HPLC High-pressure liquid chromatography
i-PrOH Isopropanol
KOH Potassium hydroxide
LC/MS Liquid chromatography/mass spectrometry
m Multiplet
M Molar
MeCN Acetonitrile
MeOH Methyl alcohol
MgSO$_4$ Magnesium sulfate
min Minute(s)
mmol Millimole
MHz MegaHertz
MS Mass spectrometry
N Normal
NaHCO$_3$ Sodium bicarbonate
NH$_4$Cl Ammonium chloride
NMR Nuclear magnetic resonance
p para
PDA Photodiode Array
pH $-\log[H^+]$
ppm Parts per million
q Quadruplet
quin Quintuplet
RP-HPLC Reverse-phase high-pressure liquid chromatography
R$_t$ Retention time
rt Room temperature
s Singlet
t Triplet
td Triplet of doublets
TFA Trifluoroacetic acid
tert-Tertiary
THF Tetrahydrofuran General Synthetic Schemes Compounds of the invention may be prepared using the synthetic transformations illustrated in Schemes I-VII. Starting materials are commercially available or may be prepared by the procedures described herein, by literature procedures, or by procedures that would be well known to one skilled in the art of organic chemistry. Unless stated, all aqueous solutions are saturated.

Methods for preparing 2-[[3-carbamoyl-5,6-dihydro-4H-cyclopenta[b]thiophen-2-yl]carbamoyl]cyclohexanecarboxylic acid compounds of the invention are illustrated in Schemes I-II. In Scheme I, step a, commercially available amines are reacted with cyanoacetic acid 1 using conditions described in Preparation #1, Step A, or by methods known to one skilled in the art (for example, *Organic Letters*, 2011, 13(23), 6280-6283) to give cyanoacetamide 2. In Scheme I, step b, cyanoacetamide 2 can undergo a 3-component reaction (so called Gewald reaction as described in *Ber.* 1966, 99, 94-100) with sulfur and cyclopentanone using conditions such as those described in Preparation #1, Step B, or by methods known to one skilled in the art (for example *American Journal of Organic Chemistry*, 2012, 2(2), 32-40) to provide the 2-aminothiophene-3-carboxamide based compounds 3. 2-Aminothiophenes 3 may react with cyclic anhydride as described in Scheme I, step c using conditions such as those described in Example #1, or by methods known to one skilled in the art (*Org. Biomol. Chem.*, 2014, 12(12), 1942-1956) to give 2-[[3-carbamoyl-5,6-dihydro-4H-cyclopenta[b]thiophen-2-yl]carbamoyl]cyclohexanecarboxylic acid derivatives 4.

Scheme I

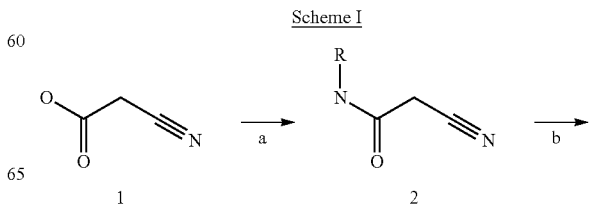

-continued

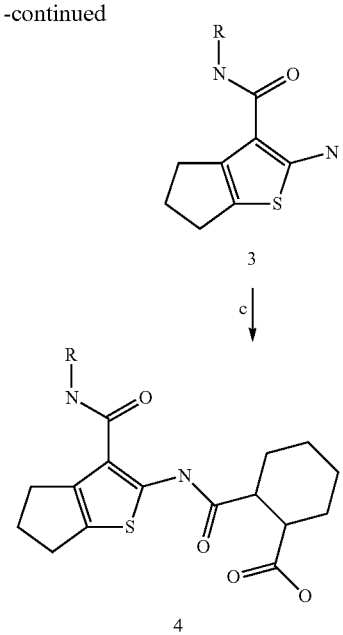

The carboxamide group on position 3 of the 5,6-dihydro-4H-cyclopenta[b]thiophene derivatives can be built later in the synthesis as described in Scheme II. tert-Butyl 2-amino-5,6-dihydro-4H-cyclopenta[b]thiophene-3-carboxylate compound 5 (*Journal of Medicinal Chemistry*, 2005, 48(26), 8270-8288) in Scheme II, step a can be reacted with cyclic anhydride using conditions such as those described in Preparation #8, or by methods known to one skilled in the art (for example, *Org. Biomol. Chem.*, 2014, 12(12), 1942-1956) to give the cyclohexanecarboxylic acid 6. Intramolecular protection by forming the succinimide derivative 7 can be achieved as described in Preparation #9, Step A, or by methods known to one skilled in the art (for example, *Bioorganic & Medicinal Chemistry Letters*, 2009, 19(17), 4967-4970). Deprotection of tert-butyl ester 7 can be performed using conditions such as those described in Greene, T. W. and Wuts. P. G. M "Protective Groups in Organic Synthesis, 3$^{rd}$ Edition, 1999, Wiley-Interscience". Hence tert-butyl group can be removed from a protected carboxylic acid (Scheme II, step c) to yield the unprotected carboxylic acid 8 (Preparation #9, Step B) and the deprotected compound 8 may then be reacted further (Scheme II, step d) to build the carboxamide moiety as described in Example #14, or by methods known to one skilled in the art (for example, *Med Chem Comm*, 2014, 5(2), 142-146). Release of the carboxylic acid moiety belonging to the cyclohexyl group can be achieved during the basic hydrolytic workup after the amide coupling leading to carboxylic acid 9 as described in Example #14 for example, or by methods known to one skilled in the art (for example, PCT Int. Appl. 2003, WO 2003062241). Alternatively the protection of the carboxylic acid function of cyclohexyl moiety can be protected by a methyl ester group (Scheme II, step e) as described in Preparation #10 step A, or by methods known to one skilled in the art (for example *Bioorganic & Medicinal Chemistry Letters*, 2016, 26(3), 965-968) to give cyclohexanecarboxylic methyl ester 10. Deprotection of tert-butyl ester 10 can be performed using conditions such as those described in Greene, T. W. and Wuts. P. G. M "Protective Groups in Organic Synthesis, 3$^{rd}$ Edition, 1999, Wiley-Interscience". Hence tert-butyl group can be removed from a protected carboxylic acid (Scheme II, step f) to yield the unprotected carboxylic acid 11 (Preparation #10, Step B) and the deprotected compound 11 may then be reacted further to build the carboxamide moiety (Scheme II, step g) leading to the amides as described in Example #22, or by methods known to one skilled in the art (for example, *MedChemComm.*, 2014, 5(2), 142-146). Release of the carboxylic acid moiety belonging to the cyclohexyl group can be achieved during the basic hydrolytic workup after the amide coupling leading to carboxylic acids 9 as described in Example #22 for example, or by methods known to one skilled in the art (for example, *ChemMedChem.*, 2011, 6(1), 131-140).

Scheme II

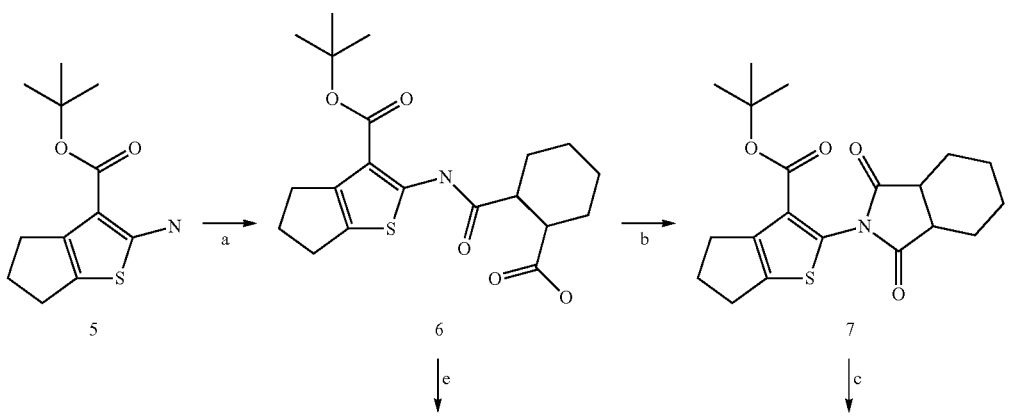

In Scheme III, step a, N-(4-chlorophenyl)-2-cyano-acetamide is reacted with various saturated carbocyclic or heterocyclic ketones and sulfur in a 3-component reaction using conditions such as those described in Preparation #11 for example, or by methods known to one skilled in the art (for example, PCT Int. Appl. 2009, WO 2009009550). 2-Aminothiophene derivatives 13 may react with cyclic anhydride as described in Scheme III, step b using conditions such as those described in Example #10, or by methods known to one skilled in the art (for example, *Org. Biomol. Chem.*, 2014, 12, 1942-1956) to give cyclohexanecarboxylic acid derivatives 14.

In Scheme IV, step a, derivatization of 2-amino-N-(4-chlorophenyl)-5,6-dihydro-4H-cyclopenta[b]thiophene-3-carboxamide 15 (prepared such as described by *Indian Journal of Heterocyclic Chemistry* 2003, 13(2), 185-186) to give carboxamides 16 can be achieved by reaction with anhydrides using conditions such as those described in Example #44, by reactions with acid chlorides using conditions such as those described in Example #51, by reactions with carboxylic acid and coupling agents such as those described in Example #52 or by methods known to one skilled in the art (for example, *International Journal of Chemical Sciences,* 2007, 5(3), 1284-1290).

Scheme IV

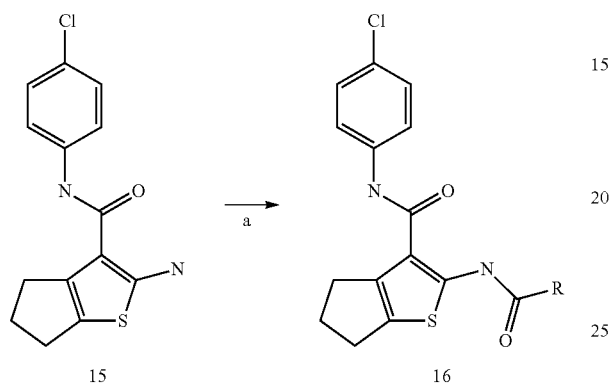

In Scheme V, step a, cyclization of 2-[[3-[(4-chlorophenyl)carbamoyl]-5,6-dihydro-4H-cyclopenta[b]thiophen-2-yl]carbamoyl]cyclohexane-cis-carboxylic acid 17 (prepared as in Example #47) provides succinimide 18 as described in Example #53 or using methods known to one skilled in the art (for example, *Bioorganic & Medicinal Chemistry Letters,* 2009, 19(17), 4967-4970). Aminolysis of succinimide 18 to carboxamide 19 (Scheme V, step b) may be accomplished using methods such as those described in Example #54 or using methods known to one skilled in the art (for example, *European Journal of Medicinal Chemistry,* 2015, 98, 49-53). Alternatively 2-[[3-[(4-chlorophenyl)carbamoyl]-5,6-dihydro-4H-cyclopenta[b]thiophen-2-yl]carbamoyl]cyclohexane-cis-carboxylic acid 17 can be reduced using conditions such as those described in Example #55 or by methods known to one skilled in the art (for example, *Journal of Medicinal Chemistry,* 2006, 49(3), 1066-1079) to give alcohol 20 (Scheme V, step c).

Scheme V

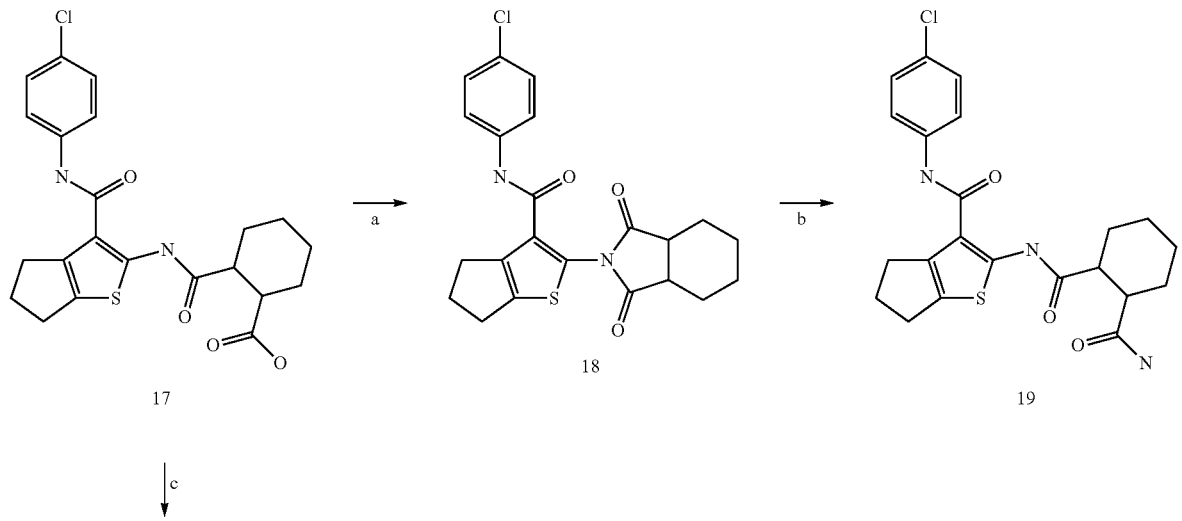

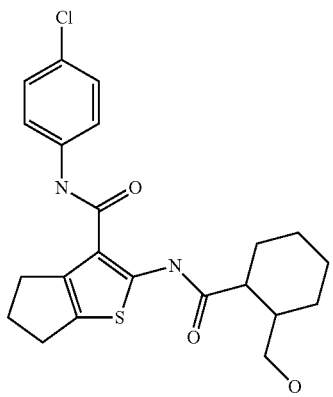

20

In Scheme VI, aromatization of 2-[[3-[(4-chlorophenyl)carbamoyl]-4,5,6,7-tetrahydrobenzothiophen-2-yl]carbamoyl]cyclohexane-cis-carboxylic acid 21 (prepared as in Example #11) can be achieved after protection of the carboxylic acid by a methyl ester group (Scheme VI, step a) as described in Example #56 step A, or by methods known to one skilled in the art (for example *Bioorganic & Medicinal Chemistry Letters,* 2016, 26(3), 965-968) to give cyclohexanecarboxylic methyl ester 22. Oxidation of 4,5,6,7-tetrahydrobenzothiophene 22 can be performed using conditions such as those described in Example #56 step B, or by methods known to one skilled in the art (for example PCT Int. Appl. 2005, WO 2005044008) to give benzothiophene 23 (Scheme VI, step b). Deprotection of methyl ester 23 can be performed using conditions such as those described in Greene, T. W. and Wuts. P. G. M "Protective Groups in Organic Synthesis, $3^{rd}$ Edition, 1999, Wiley-Interscience". Hence methyl ester group can be removed from a protected carboxylic acid to yield the unprotected carboxylic acid 24 using methods such as those described in Example #56 step C (Scheme VI, step c) or by methods known to one skilled in the art (for example, *ChemMedChem.,* 2011, 6(1), 131-140).

Scheme VI

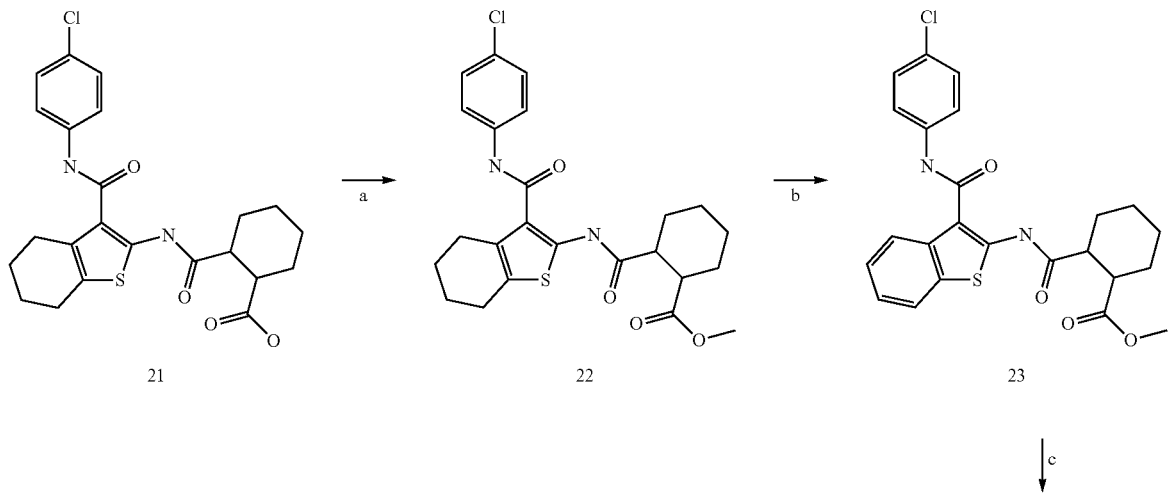

-continued

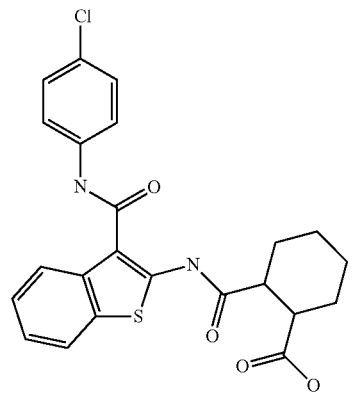

24

Methods for preparing thieno[3,4-b]thiophene compounds of the invention are illustrated in Scheme VII. In Scheme VII, step a, heterobicyclic system 26 formation can be achieved using a 3-component reaction (so called Gewald reaction) with sulfur and tetrahydrothiophen-3-one 25 using conditions such as those described in Example #57, Step A, or by methods known to one skilled in the art (PCT Int. Appl. 2008, WO 2008063667) to provide the 4,6-dihydrothieno [3,4-b]thiophene 26. Derivatization of the amine function with 1,2-cyclohexane dicarboxylic anhydride to yield carboxylic acid 27 can be performed using conditions described in Example #57, Step B for example, or by methods known to one skilled in the art (for example, *Org. Biomol. Chem.*, 2014, 12(12), 1942-1956). In Scheme VII, step c, Intramolecular protection by forming the succinimide derivative 28 can be achieved as described in Example #57, Step C, or by methods known to one skilled in the art (for example, *Bioorganic & Medicinal Chemistry Letters*, 2009, 19(17), 4967-4970). 4,6-Dihydrothieno[3,4-b]thiophene 28 can then be oxidized to thieno[3,4-b]thiophene 29 using conditions such as those described in Example #57, Step D, or by methods known to one skilled in the art (for example, *Macromolecules*, 2013, 46(22), 8873-8881). Deprotection of tert-butyl ester 29 can be performed using conditions such as those described in Greene, T. W. and Wuts. P. G. M "Protective Groups in Organic Synthesis, $3^{rd}$ Edition, 1999, Wiley-Interscience". Hence tert-butyl group can be removed from a protected carboxylic acid to yield the unprotected carboxylic acid 30 (Example #57, Step E) and the deprotected compound 30 may then be reacted further (Scheme VII, step f) to build the carboxamide moiety as described in Example #57, Step F, or by methods known to one skilled in the art (for example, *Med Chem Comm*, 2014, 5(2), 142-146). In scheme VII, step g, release of the carboxylic acid moiety belonging to the cyclohexyl group can be performed on succinimide 31 as described in Example #57, Step G, or by methods known to one skilled in the art (for example, PCT Int. Appl. 2003, WO 2003062241) providing the carboxylic acid 32.

Scheme VII

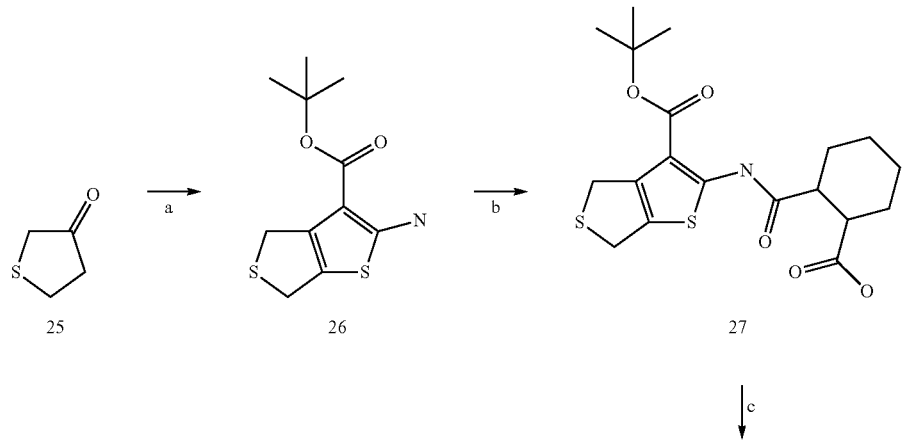

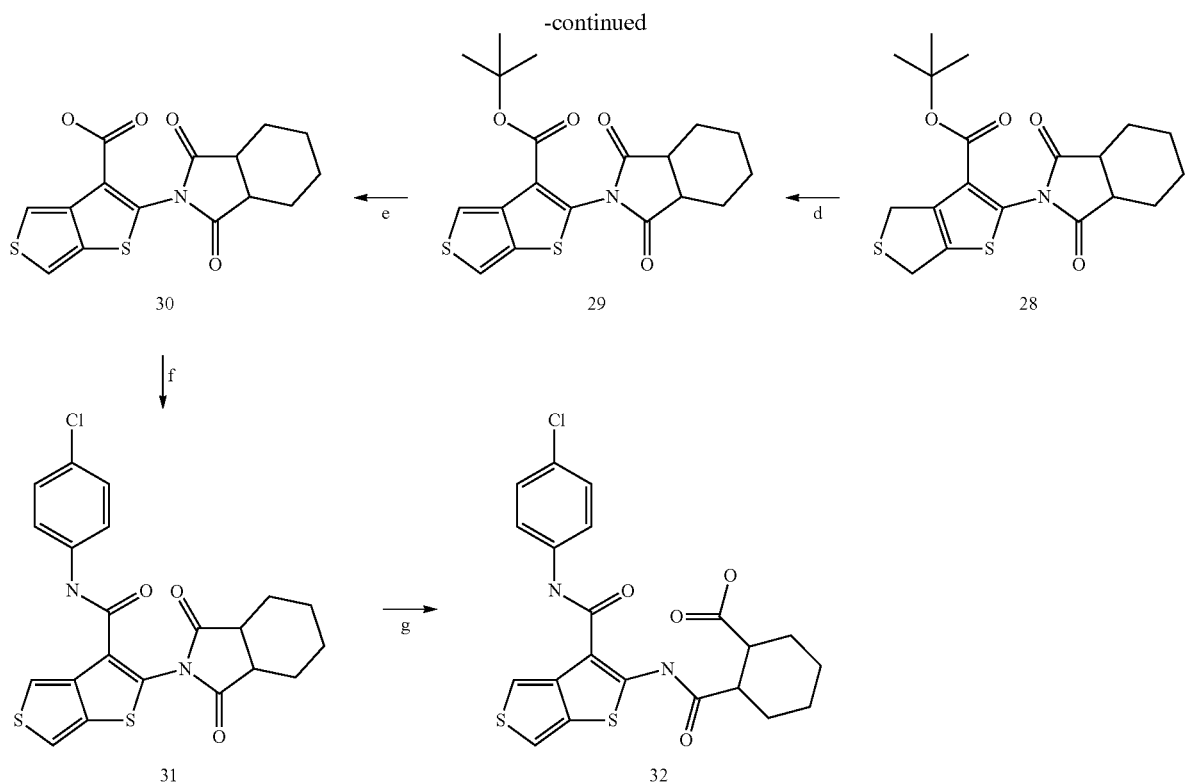

Analytical Methods

Analytical data is included within the procedures below, in the illustrations of the general procedures, or in the tables of examples. Unless otherwise stated, all H NcR data were collected on a Bruker DPX 300 Hz equipped with 5 mm BB(O)F GRADZ probe, Bruker AVII 400 MHz equipped with 5 mm BB(O)F GRADZ probe, Bruker AVII 500 MHz equipped with 5 mm BBI GRADZ probe, Bruker Avance 400 MHz equipped with 5 mm QNP probe or Bruker Avance III 400 MHz, 5 mm BBFO Plus probe instruments and chemical shifts are quoted in parts per million (ppm).

LC/MS was performed on oPLC Agilent 1100 series instrument with a PDA detector from 1100 series coupled to Waters ZQ mass spectrometer, UPLC Acquity Waters with a PDA Acquity detector and a SQ Acquity mass spectrometer, a Shimadzu UFLC-XR system coupled to a LCMS-IT-TOF mass spectrometer Acquity UPLC (binary pump/PDA detector) coupled to Waters ZQ Mass Spectrometer or Acquity i-Class (quaternary pump/PDA detector) coupled to Quattro Micro Mass Spectrometer. LC/MS data is referenced to LC/MS conditions using the method number provided in Table 1.

TABLE 1

LC/MS analysis methods

| Method | Conditions |
| --- | --- |
| A | LC/MS analysis condition: Column: KINETEX XB-C18 core-shell, 30 × 3 mm, 2.6 μm, Temperature 45° C., Mobile phase: MeCN (0.1% AcOH) in water (0.1% AcOH), from 10% to 100% within 3.15 min; Flow rate: 1.4 ml/min; Wavelength: 210-260 nm DAD. |
| B | LC/MS analysis condition: Column: ACQUITY UPLC BEH C18, 50 × 2.1 mm, 1.7 μm, Temperature 45° C., Mobile phase: MeCN (0.1% AcOH) in water (0.1% AcOH), from 5% to 95% within 2.50 min; Flow rate: 0.8 ml/min; Wavelength: 210-260 nm DAD. |
| C | LC/MS analysis condition: Column: XBRIDGE-C18, 50 × 2.1 mm, 2.6 μm, Temperature 45° C., Mobile phase: MeCN (0.05% HCOOH) in water (0.1% HCOOH), from 5% to 95% within 4.9 min; Flow rate: 0.45 ml/min; Wavelength: 210-260 nm DAD. |
| D | LC/MS analysis condition: Column: ACQUITY UPLC BEH C18 1.7 μm, 100 × 2.1 mm, maintained at 40° C.. Mobile phase: MeCN (0.1% formic acid) in water (0.1% formic acid), from 5% to 95% within 6 min; Flow rate: 0.4 ml/min; Wavelength: 200-500 nm DAD. ZQ Mass Spectrometer. |
| E | LC/MS analysis condition: Column: ACQUITY UPLC BEH C18 1.7 μm, 100 × 2.1 mm, maintained at 40° C.. Mobile phase: MeCN (0.1% formic acid) in water (0.1% formic acid), from 5% to 95% within 6 min; Flow rate: 0.4 ml/min; Wavelength: 200-500 nm DAD. Quattro Micro Mass Spectrometer. |

Purification Methods

For the general procedures, intermediate and final compounds may be purified by any technique or combination of techniques known to one skilled in the art. Some examples that are not limiting include flash chromatography with a solid phase (i.e. silica gel, alumina, etc.) and a solvent (or combination of solvents, i.e. heptane, EtOAc, DCM, MeOH, MeCN, water, etc.) that elutes the desired compounds; RP-HPLC purification performed on Waters system including a 2525 binary Pump, a ZQ Mass spectrometer, two 515 pumps, a PDA detector and a 2767 Autosampler, managed by FMasslynX/fractionlynx or Agilent Technologies 1260 Infinity purification system and Agilent 6120 series Single Quadrupole Mass Spectrometer (see Table 2 for some non-limiting conditions); recrystalization from an appropriate solvent (i.e. MeOH, EtOH, i-PrOH, EtOAc, toluene, etc.) or combination of solvents (i.e. EtOAc/heptane, EtOAc/MeOH, etc.); precipitation from a combination of solvents (i.e. DMF/water, DMSO/DCM, EtOAc/heptane, etc.); trituration with an appropriate solvent (i.e. EtOAc, DCM, MeCN, MeOH, EtOH, i-PrOH, n-PrOH, etc.); extractions by dissolving a compound in a liquid and washing with an appropriately immiscible liquid (i.e. DCM/water, EtOAc/water, DCM/saturated $NaHCO_3$, EtOAc/saturated $NaHCO_3$, DCM/10% aqueous HCl, EtOAc/10% aqueous HCl, etc.); distillation (i.e. simple, fractional, Kugelrohr, etc.). Descriptions of these techniques can be found in the following references: Gordon, A. J. and Ford, R. A. "The Chemist's Companion", 1972; Palleros, D. R. "Experimental Organic Chemistry", 2000; Still, W. C., Kahn and M. Mitra, A. *J. Org. Chem.* 1978, 43, 2923; Yan, B. "Analysis and Purification Methods in Combinatorial Chemistry" 2003; Harwood, L. M., Moody, C. J. and Percy, J. M. "Experimental Organic Chemistry: Standard and Microscale, $2^{nd}$ Edition", 1999.

TABLE 2

RP-HPLC purification methods

| Method | Conditions |
|---|---|
| 1 | RP- HPLC purification condition: Column: KINETEX XB-C18 21.2 × 150 mm, 5 µm, Mobile phase: MeCN in water (0.1% HCOOH); Flow rate: 25 ml/min; Wavelength: 210-260 nm DAD. Sample injected in DMSO/MeCN, 12 min non-linear gradient from 10% to 100% MeCN. |
| 2 | RP- HPLC purification condition: Column: SUNFIRE 19 × 150 mm, 5 µm, Mobile phase: MeCN in water (0.1% HCOOH), Flow rate: 25 ml/min; Wavelength: 210-260 nm DAD. Sample injected in DMSO/MeCN, 12 min non-linear gradient from 10% to 100% MeCN. |
| 3 | RP- HPLC purification condition: Column XSELECT CSH Prep C18 19 × 250 mm, 5 µm, Mobile phase: MeCN in water (0.1% HCOOH), Flow rate: 20 ml/min; Wavelength: 210-260 nm DAD. Sample injected in DMSO (+ optional formic acid and water), 22 min non-linear gradient from 10% to 95% MeCN, centered around a specific focused gradient. |
| 4 | RP- HPLC purification condition: Column XBridge Prep C18 19 × 250 mm, 5 µm, Mobile phase: MeCN in water (0.1% aqueous ammonia), Flow rate: 20 ml/min; Wavelength: 210-260 nm DAD. Sample injected in DMSO (+optional formic acid and water), 22 min non-linear gradient from 10% to 95% MeCN, centered around a specific focused gradient. |

PREPARATIONS AND EXAMPLES

All starting materials are commercially available from Sigma-Aldrich (including Fluka and Discovery CPR) or Acros unless otherwise noted after the chemical name. Reagent/reactant names given are as named on the commercial bottle or as generated by IUPAC conventions, Accelrys Draw 4.0 or ChemDraw 16.0. None of the specific conditions and reagents noted herein is to be construed as limiting the scope of the invention and are provided for illustrative purposes only.

Example #1. 2-[[3-[[4-Chloro-3-(trifluoromethyl)phenyl]carbamoyl]-5,6-dihydro-4H-cyclopenta[b]thiophen-2-yl]carbamoyl]cyclohexanecarboxylic acid (Compound 6)

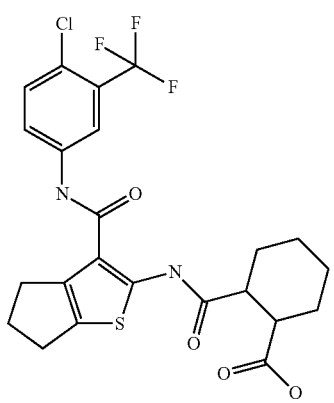 [SMILES: O=C(Nc1ccc(Cl)c(C(F)(F)F)c1)c1c(NC(=O)C2CCCCC2C(=O)O)sc2c1CCC2]

2-Amino-N-[4-chloro-3-(trifluoromethyl)phenyl]-5,6-dihydro-4H-cyclopenta[b]thiophene-3-carboxamide (Preparation #1, Step B, 70 mg, 0.19 mmol) was dissolved in THF (1.00 ml) then cis-1,2-cyclohexane dicarboxylic anhydride (60 mg, 0.39 mmol) was added and the mixture was stirred at 75° C. overnight. The mixture was cooled to rt then concentrated in vacuo to provide a red-brown paste. The residue was purified by column chromatography on silica gel (eluting with 10-25% EtOAc in cyclohexane) to give 2-[[3-[[4-chloro-3-(trifluoromethyl)phenyl]carbamoyl]-5,6-dihydro-4H-cyclopenta[b]thiophen-2-yl]carbamoyl]cyclohexanecarboxylic acid (0.064 g, 64%) as a pink solid. $^1$H NMR (DMSO-$d_6$, 400 MHz): δ=12.11 (br s, 1H), 11.14 (br s, 1H), 9.51 (br s, 1H), 8.19 (d, J=2.6 Hz, 1H), 7.97 (dd, J=8.8, 2.6 Hz, 1H), 7.71 (d, J=8.8 Hz, 1H), 2.95-3.08 (m, 2H), 2.91 (m, 1H), 2.80-2.86 (m, 3H), 2.38 (quin, J=7.2 Hz, 2H), 1.99-2.08 (m, 1H), 1.88-1.96 (m, 1H), 1.77-1.85 (m, 1H), 1.65-1.73 (m, 1H), 1.49-1.58 (m, 1H), 1.32-1.45 ppm (m, 3H). LC/MS (Table 1, Method B) R$_t$=2.09 min; MS m/z: 513 [M−H]$^-$.

Example #2. 2-[[3-[(6-Chloro-3-pyridyl)carbamoyl]-5,6-dihydro-4H-cyclopenta[b]thiophen-2-yl]carbamoyl]cyclohexanecarboxylic acid (Compound 2)

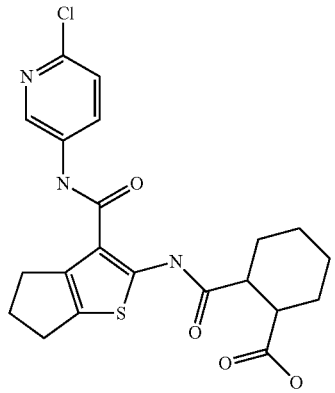

2-Amino-N-(6-chloro-3-pyridyl)-5,6-dihydro-4H-cyclopenta[b]thiophene-3-carboxamide (Preparation #2, 75 mg, 0.26 mmol) was dissolved in THF (1.00 ml) then cis-1,2-cyclohexane dicarboxylic anhydride (79 mg, 0.51 mmol) was added and the mixture was stirred at 75° C. overnight. The mixture was cooled to rt then concentrated in vacuo to provide a brown paste. The mixture was taken up in EtOAc (0.50 ml) to provide a solid which was filtered and washed three times with a minimum of EtOAc. The solid was dried under vacuum to give 2-[[3-[(6-chloro-3-pyridyl)carbamoyl]-5,6-dihydro-4H-cyclopenta[b]thiophen-2-yl]carbamoyl]cyclohexanecarboxylic acid (0.054 g, 47%) as a white solid. $^1$H NMR (DMSO-$d_6$, 400 MHz): δ=12.12 (br s, 1H), 11.23 (br s, 1H), 9.38 (br s, 1H), 8.65 (d, J=2.6 Hz, 1H), 8.15 (dd, J=8.6, 2.6 Hz, 1H), 7.52 (d, J=8.6 Hz, 1H), 2.94-3.07 (m, 2H), 2.79-2.92 (m, 4H), 2.38 (quin, J=7.2 Hz, 2H), 1.98-2.08 (m, 1H), 1.87-1.95 (m, 1H), 1.76-1.86 (m, 1H), 1.63-1.74 (m, 1H), 1.49-1.61 (m, 1H), 1.30-1.47 ppm (m, 3H). LC/MS (Table 1, Method B) R$_t$=1.73 min; MS m/z: 446 [M−H]$^-$.

The following compounds were prepared using the same procedure with the appropriate starting material.

Example #3. 2-[[3-[(5-Chloropyrazin-2-yl)carbamoyl]-5,6-dihydro-4H-cyclopenta[b]thiophen-2-yl]carbamoyl]cyclohexanecarboxylic acid (Compound 26)

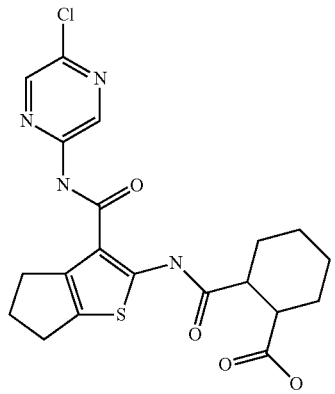

The title compound was synthesized according to the procedure described in Example 2 using Preparation #3 as a starting material (yield 51%). $^1$H NMR (DMSO-d$_6$, 400 MHz): δ=12.14 (br s, 1H), 11.22 (br s, 1H), 9.73 (br s, 1H), 9.18 (s, 1H), 8.60 (s, 1H), 3.01 (m, 2H), 2.92 (m, 1H), 2.77-2.89 (m, 3H), 2.38 (quin, J=7.0 Hz, 2H), 1.90-2.08 (m, 2H), 1.80-1.89 (m, 1H), 1.64-1.75 (m, 1H), 1.49-1.61 (m, 1H), 1.32-1.47 ppm (m, 3H). LC/MS (Table 1, Method B) R$_t$=1.86 min; MS m/z: 447 [M–H]$^-$.

Example #4. 2-[[3-[(4-Chloro-2-methyl-phenyl)carbamoyl]-5,6-dihydro-4H-cyclopenta[b]thiophen-2-yl]carbamoyl]cyclohexanecarboxylic acid (Compound 7)

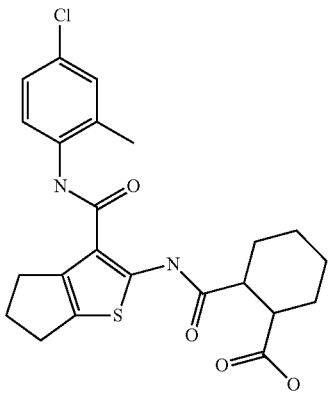

The title compound was synthesized according to the procedure described in Example 2 using Preparation #4 as a starting material (yield 53%). $^1$H NMR (DMSO-d$_6$, 400 MHz): δ=12.13 (br s, 1H), 11.71 (br s, 1H), 8.50 (br s, 1H), 7.68 (d, J=8.6 Hz, 1H), 7.38 (d, J=2.4 Hz, 1H), 7.30 (dd, J=8.6, 2.4 Hz, 1H), 3.04-3.13 (m, 2H), 2.87-2.94 (m, 1H), 2.80-2.87 (m, 3H), 2.41 (quin, J=7.3 Hz, 2H), 2.26 (s, 3H), 1.99-2.08 (m, 1H), 1.78-1.95 (m, 2H), 1.63-1.75 (m, 1H), 1.52-1.62 (m, 1H), 1.29-1.48 ppm (m, 3H). LC/MS (Table 1, Method B) R$_t$=2.00 min; MS m/z: 459 [M–H]$^-$.

Example #5. 2-[[3-[(3-Chlorophenyl)carbamoyl]-5,6-dihydro-4H-cyclopenta[b]thiophen-2-yl]carbamoyl]cyclohexanecarboxylic acid (Compound 17)

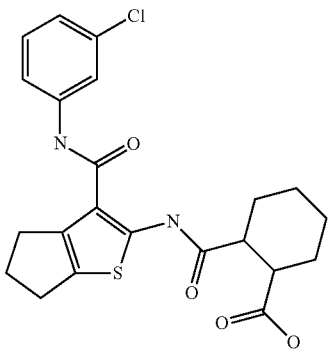 [SMILES: O=C(Nc1cccc(Cl)c1)c1c(NC(=O)C2CCCCC2C(=O)O)sc2c1CCC2]

The title compound was synthesized according to the procedure described in Example 2 using 2-amino-N-(3-chlorophenyl)-5,6-dihydro-4H-cyclopenta[b]thiophene-3-carboxamide (International Journal of chemical Sciences (2007), 5(3), 1284-1290) as a starting material (yield 82%). $^1$H NMR (DMSO-d$_6$, 400 MHz): δ=12.13 (br s, 1H), 11.25 (br s, 1H), 9.23 (br s, 1H), 7.82 (t, J=2.0 Hz, 1H), 7.58 (br d, J=8.1 Hz, 1H), 7.38 (t, J=8.1 Hz, 1H), 7.17 (dd, J=8.1, 2.0 Hz, 1H), 3.01 (m, 2H), 2.78-2.93 (m, 4H), 2.38 (quin, J=7.1 Hz, 2H), 1.98-2.07 (m, 1H), 1.88-1.97 (m, 1H), 1.78-1.87 (m, 1H), 1.64-1.74 (m, 1H), 1.50-1.62 (m, 1H), 1.33-1.47 ppm (m, 3H). LC/MS (Table 1, Method B) R$_t$=1.98 min; MS m/z: 445 [M–H]$^-$.

Example #6. 2-[[3-[(5-Chlorothiazol-2-yl)carbamoyl]-5,6-dihydro-4H-cyclopenta[b]thiophen-2-yl]carbamoyl]cyclohexanecarboxylic acid (Compound 29)

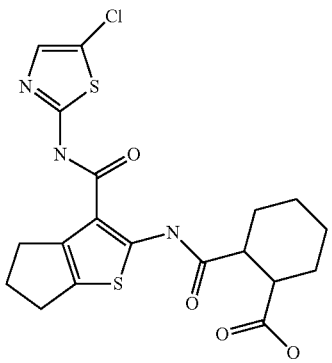 [SMILES: O=C(Nc1ncc(Cl)s1)c1c(NC(=O)C2CCCCC2C(=O)O)sc2c1CCC2]

The title compound was synthesized according to the procedure described in Example 2 using Preparation #7 as a starting material (yield 78%). $^1$H NMR (DMSO-d$_6$, 400 MHz): δ=10.93-12.89 (br s, 3H), 7.61 (s, 1H), 2.93-3.02 (m, 3H), 2.76-2.85 (m, 3H), 2.34 (quin, J=7.0 Hz, 2H), 1.92-2.08 (m, 2H), 1.79-1.88 (m, 1H), 1.67-1.77 (m, 1H), 1.49-1.61 (m, 1H), 1.36-1.48 ppm (m, 3H). LC/MS (Table 1, Method B) R$_t$=1.90 min; MS m/z: 452 [M–H]$^-$.

Example #7. 2-[[3-[[4-(Trifluoromethyl)phenyl]carbamoyl]-5,6-dihydro-4H-cyclopenta[b]thiophen-2-yl]carbamoyl]cyclohexanecarboxylic acid (Compound 27)

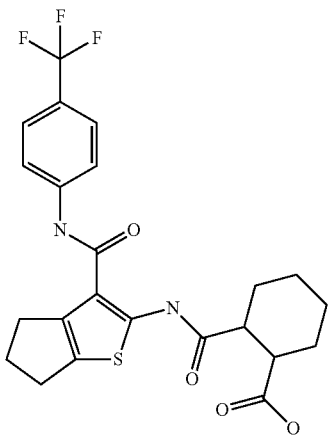 [SMILES: O=C(Nc1ccc(C(F)(F)F)cc1)c1c(NC(=O)C2CCCCC2C(=O)O)sc2c1CCC2]

2-Amino-N-[4-(trifluoromethyl)phenyl]-5,6-dihydro-4H-cyclopenta[b]thiophene-3-carboxamide (Preparation #5, 18 mg, 0.055 mmol) was dissolved in THF (0.36 ml) then cis-1,2-cyclohexane dicarboxylic anhydride (17 mg, 0.11 mmol) was added and the mixture was stirred at 75° C. overnight. Cis-1,2-cyclohexane dicarboxylic anhydride (8.5 mg, 0.055 mmol) was added again and the reaction was further heated for 4 h at 75° C. The reaction went to completion after a new addition of cis-1,2-cyclohexane dicarboxylic anhydride (8.5 mg, 0.055 mmol) and 1 h heating at 75° C. The mixture was cooled to rt then concentrated in vacuo to provide a gum which was solubilized in 2 mL of EtOAc. Few drops of MeCN were added allowing crystallization upon trituration. The expected product was filtered off and washed with MeCN. The solid was dried under vacuum and purified by RP-HPLC (Table 2, Method 1) to give 2-[[3-[[4-(trifluoromethyl)phenyl]carbamoyl]-5,6-dihydro-4H-cyclopenta[b]thiophen-2-yl]carbamoyl]cyclohexanecarboxylic acid (0.012 g, 45%) as a white solid. $^1$H NMR (DMSO-$d_6$, 400 MHz): δ=12.13 (br s, 1H), 11.23 (br s, 1H), 9.45 (br s, 1H), 7.87 (d, J=8.6 Hz, 2H), 7.72 (d, J=8.6 Hz, 2H), 3.01 (m, 2H), 2.79-2.89 (m, 4H), 2.38 (quin, J=6.6 Hz, 2H), 1.99-2.07 (m, 1H), 1.89-1.92 (m, 1H), 1.83-1.87 (m, 1H), 1.63-1.75 (m, 1H), 1.57 (m, 1H), 1.41 ppm (m, 3H). LC/MS (Table 1, Method B) $R_t$=2.01 min; MS m/z: 481 [M+H]$^+$.

Example #8. 2-[[3-[(4-Cyanophenyl)carbamoyl]-5,6-dihydro-4H-cyclopenta[b]thiophen-2-yl]carbamoyl]cyclohexanecarboxylic acid (Compound 28)

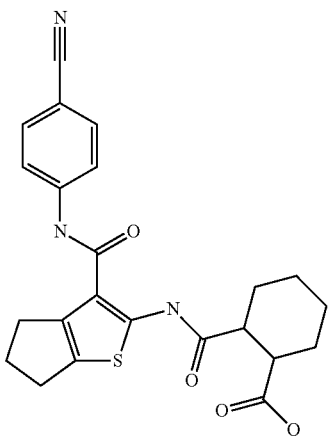 [SMILES: N#Cc1ccc(NC(=O)c2c(NC(=O)C3CCCCC3C(=O)O)sc3c2CCC3)cc1]

2-Amino-N-(4-cyanophenyl)-5,6-dihydro-4H-cyclopenta[b]thiophene-3-carboxamide (Preparation #6, 180 mg, 0.64 mmol) was dissolved in THF (1.8 ml) then cis-1,2-cyclohexane dicarboxylic anhydride (196 mg, 1.27 mmol) was added and the mixture was stirred at 75° C. for 1.5 h until disappearance of starting material. The mixture was cooled to rt then concentrated in vacuo to provide a beige solid which was filtered and washed with MeCN and EtOAc. The solid was dried under vacuum to give 2-[[3-[(4-cyanophenyl)carbamoyl]-5,6-dihydro-4H-cyclopenta[b]thiophen-2-yl]carbamoyl]cyclohexanecarboxylic acid (0.163 g, 58%) as a beige solid. $^1$H NMR (DMSO-$d_6$, 400 MHz): δ=12.13 (br s, 1H), 11.17 (br s, 1H), 9.55 (br s, 1H), 7.85 (d, J=6.6 Hz, 2H), 7.82 (d, J=6.6 Hz, 2H), 2.93-3.06 (m, 2H), 2.79-2.93 (m, 4H), 2.38 (quin, J=7.3 Hz, 2H), 2.02 (m, 1H), 1.89-1.97 (m, 1H), 1.83 (m, 1H), 1.64-1.73 (m, 1H), 1.55 (m, 1H), 1.40 ppm (m, 3H). LC/MS (Table 1, Method B) $R_t$=1.74 min; MS m/z: 436 [M+H]$^+$.

Example #9. 2-[[3-[(4-Chlorophenyl)carbamoyl]-4-methyl-4,6-dihydrothieno[2,3-c]furan-2-yl]carbamoyl]cyclohexanecarboxylic acid (Compound 39)

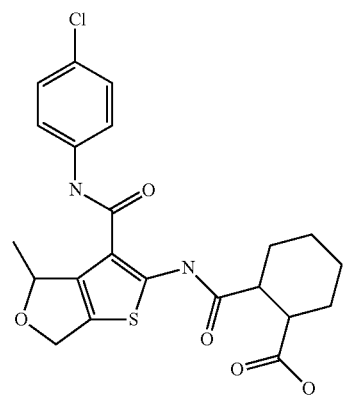 [SMILES: CC1OCc2sc(NC(=O)C3CCCCC3C(=O)O)c(C(=O)Nc3ccc(Cl)cc3)c21]

2-Amino-N-(4-chlorophenyl)-4-methyl-4,6-dihydrothieno[2,3-c]furan-3-carboxamide (Preparation #11, 98 mg, 0.32 mmol) was dissolved in 1,4-dioxane (1.5 ml) in a 5 ml microwave vial then cis-1,2-cyclohexane dicarboxylic anhydride (73 mg, 0.48 mmol) was added. The vial was sealed and the mixture was stirred at 140° C. under microwave irradiation for 1 h. Cyclohexane dicarboxylic anhydride (73 mg, 0.48 mmol) was added again and the mixture was stirred at 140° C. under microwave irradiation for another 1 h. This was repeated a third time until disappearance of starting material. The mixture was cooled to rt then concentrated in vacuo. The solid was purified by RP-HPLC (Table 2, Method 2). Upon collection and evaporation of solvents the residual solid was freeze-dried with water then the resulting solid was dried at 50° C. under vacuo to give 2-[[3-[(4-chlorophenyl)carbamoyl]-4-methyl-4,6-dihydrothieno[2,3-c]furan-2-yl]carbamoyl]cyclohexanecarboxylic acid (0.027 g, 18%) as an off-white solid. $^1$H NMR (DMSO-$d_6$, 400 MHz): δ=12.13 (br s, 1H), 11.01 (br s, 1H), 9.71 (br s, 1H), 7.66 (dd, J=9.0, 2.2 Hz, 2H), 7.41 (d, J=9.0 Hz, 2H), 5.55-5.76 (m, 1H), 4.98 (dd, J=11.0, 4.6 Hz, 1H), 4.92 (dd, J=11.0, 2.4 Hz, 1H), 2.75-2.99 (m, 2H), 1.93-2.09 (m, 2H), 1.75-1.84 (m, 1H), 1.63-1.74 (m, 1H), 1.46-1.59 (m, 1H), 1.33-1.46 (m, 3H), 1.24 ppm (d, J=6.2 Hz, 3H). LC/MS (Table 1, Method B) $R_t$=1.78 min; MS m/z: 461 [M−H]$^-$.

Example #10. 2-[[3-[(4-Chlorophenyl)carbamoyl]-5,7-dihydro-4H-thieno[2,3-c]pyran-2-yl]carbamoyl]cyclohexanecarboxylic acid (Compound 37)

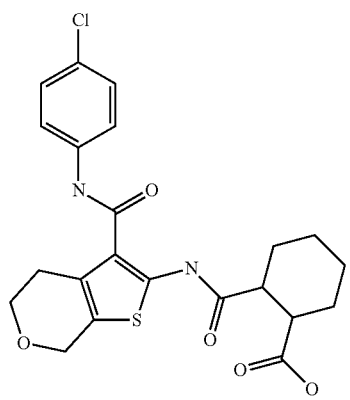 [SMILES: O=C(Nc1ccc(Cl)cc1)c1c(NC(=O)C2CCCCC2C(=O)O)sc2c1CCOC2]

2-Amino-N-(4-chlorophenyl)-5,7-dihydro-4H-thieno[2,3-c]pyran-3-carboxamide (PCT Int. Appl. 2005, WO 2005023818), (45 mg, 0.15 mmol) was dissolved in THF (2 ml) then cis-1,2-cyclohexane dicarboxylic anhydride (26 mg, 0.17 mmol) was added and the mixture was stirred under reflux overnight. The reaction was not completed and cis-1,2-cyclohexane dicarboxylic anhydride (26 mg, 0.17 mmol) was added again upon cooling to room temperature. The mixture was stirred for further 24 h until disappearance of starting material. The mixture was cooled to rt then concentrated in vacuo to provide a solid which was filtered and washed with EtOAc then a large amount of water. The solid was dried under vacuum to give 2-[[3-[(4-chlorophenyl)carbamoyl]-5,7-dihydro-4H-thieno[2,3-c]pyran-2-yl]carbamoyl]cyclohexanecarboxylic acid (0.021 g, 31%) as a white solid. $^1$H NMR (DMSO-$d_6$, 500 MHz): δ=12.08 (br s, 1H), 10.85 (br s, 1H), 9.74 (br s, 1H), 7.70 (d, J=8.6 Hz, 2H), 7.40 (d, J=8.6 Hz, 2H), 4.66 (br s, 2H), 3.84 (m, 2H), 2.81-2.98 (m, 2H), 2.77 (m, 2H), 1.97-2.08 (m, 1H), 1.86-1.97 (m, 1H), 1.64-1.80 (m, 2H), 1.41-1.55 (m, 2H), 1.31-1.41 ppm (m, 2H). LC/MS (Table 1, Method B) $R_t$=1.74 min; MS m/z: 461 [M–H]$^-$.

Example #11. 2-[[3-[(4-Chlorophenyl)carbamoyl]-4,5,6,7-tetrahydrobenzothiophen-2-yl]carbamoyl]cyclohexane-cis-carboxylic acid (Compound 61)

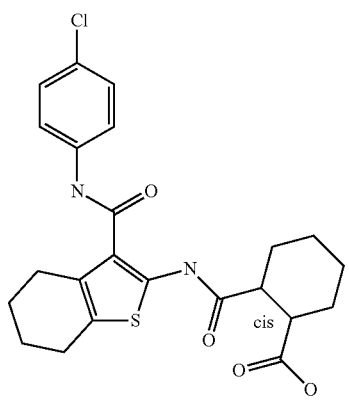 [SMILES: O=C(Nc1ccc(Cl)cc1)c1c(NC(=O)C2CCCCC2C(=O)O)sc2c1CCCC2]

2-Amino-N-(4-chlorophenyl)-4,5,6,7-tetrahydrobenzothiophene-3-carboxamide (*European Journal of Medicinal Chemistry*, 2010, 45(9), 4365-4369), (4.15 g, 13.5 mmol) was dissolved in THF (85 ml) then cis-1,2-cyclohexane dicarboxylic anhydride (4.17 g, 27 mmol) was added and the mixture was stirred under reflux overnight. The mixture was cooled to rt then concentrated in vacuo to provide 4.86 g of a beige solid which was recrystallized from THF/Et$_2$O to give 2-[[3-[(4-chlorophenyl)carbamoyl]-4,5,6,7-tetrahydrobenzothiophen-2-yl]carbamoyl]cyclohexane-cis-carboxylic acid (2.92 g, 47%) as a white solid. $^1$H NMR (DMSO-$d_6$, 300 MHz): δ=12.05 (s, 1H), 10.71 (br s, 1H), 9.75 (s, 1H), 7.70 (d, J=8.9 Hz, 2H), 7.39 (d, J=8.9 Hz, 2H), 2.92 (m, 1H), 2.54-2.78 (m, 5H), 1.84-2.11 (m, 2H), 1.61-1.83 (m, 6H), 1.27-1.56 ppm (m, 4H). LC/MS (Table 1, Method A) $R_t$=2.55 min; MS m/z: 461 [M+H]$^+$.

Example #12. 2-[[4-[(4-Chlorophenyl)carbamoyl]-2,3-dihydrothieno[2,3-b]thiophen-5-yl]carbamoyl]cyclohexanecarboxylic acid (Compound 40)

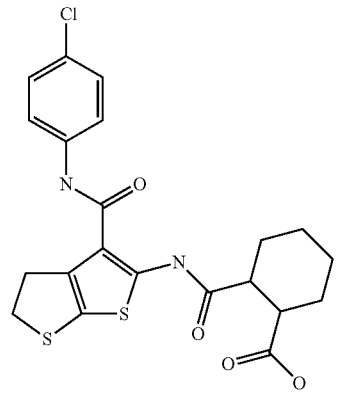 [SMILES: O=C(Nc1ccc(Cl)cc1)c1c(NC(=O)C2CCCCC2C(=O)O)sc2c1CCS2]

5-Amino-N-(4-chlorophenyl)-2,3-dihydrothieno[2,3-b]thiophene-4-carboxamide (Preparation #12, Compound A, 65 mg, 0.21 mmol) was dissolved in THF (1.3 ml) then cis-1,2-cyclohexane dicarboxylic anhydride (65 mg, 0.42 mmol) was added. The mixture was stirred at rt for 3 days. The mixture was cooled to rt then concentrated in vacuo to provide a black paste. The solid was purified by RP-HPLC (Table 2, Method 2) to provide 2-[[4-[(4-chlorophenyl)carbamoyl]-2,3-dihydrothieno[2,3-b]thiophen-5-yl]carbamoyl]cyclohexane carboxylic acid (0.060 g, 62%) as a yellow solid. $^1$H NMR (DMSO-$d_6$, 400 MHz): δ=12.12 (br s, 1H), 11.03 (s, 1H), 9.60 (s, 1H), 7.68 (d, J=9.0 Hz, 2H), 7.41 (d, J=9.0 Hz, 2H), 3.77 (t, J=7.9 Hz, 2H), 3.26 (m, 2H), 2.90 (m, 1H), 2.76-2.85 (m, 1H), 1.96-2.06 (m, 1H), 1.87-1.95 (m, 1H), 1.75-1.82 (m, 1H), 1.65-1.72 (m, 1H), 1.48-1.56 (m, 1H), 1.37-1.44 ppm (m, 3H). LC/MS (Table 1, Method B) $R_t$=1.89 min; MS m/z: 463 [M–H]$^-$.

Example #13. 2-[[3-[(4-Chlorophenyl)carbamoyl]-4,6-dihydrothieno[3,4-b]thiophen-2-yl]carbamoyl]cyclohexanecarboxylic acid (Compound 38)

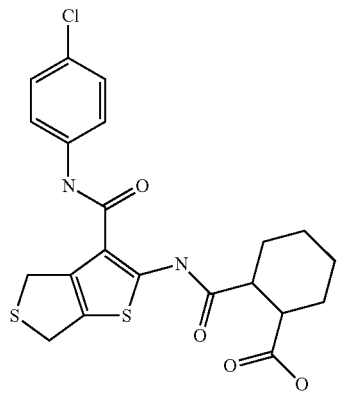 [SMILES: O=C(Nc1ccc(Cl)cc1)c1c(NC(=O)C2CCCCC2C(=O)O)sc2c1CSC2]

2-Amino-N-(4-chlorophenyl)-4,6-dihydrothieno[3,4-b]thiophene-3-carboxamide (Preparation #12, Compound B, 56 mg, 0.18 mmol) was dissolved in THF (1.1 ml) then cis-1,2-cyclohexane dicarboxylic anhydride (56 mg, 0.36 mmol) was added. The mixture was stirred under reflux for 48 h. The mixture was cooled to rt then concentrated in vacuo to provide a black paste. The residue was triturated in EtOAc (0.50 ml) to provide a solid which was filtered and washed three times with a minimum of EtOAc. The solid was dried under vacuum to give 2-[[3-[(4-chlorophenyl) carbamoyl]-4,6-dihydrothieno[3,4-b]thiophen-2-yl]carbamoyl]cyclohexanecarboxylic acid (0.044 g, 51%) as a grey solid. $^1$H NMR (DMSO-d$_6$, 300 MHz): δ=12.14 (br s, 1H), 11.08 (br s, 1H), 9.58 (br s, 1H), 7.68 (d, J=8.9 Hz, 2H), 7.41 (d, J=8.9 Hz, 2H), 4.33 (dt, J=13.0, 3.3 Hz, 1H), 4.29 (dt, J=13.0, 3.6 Hz, 1H), 4.14 (t, J=3.3 Hz, 2H), 2.87-2.95 (m, 1H), 2.79-2.87 (m, 1H), 1.96-2.09 (m, 1H), 1.86-1.96 (m, 1H), 1.74-1.85 (m, 1H), 1.62-1.74 (m, 1H), 1.47-1.60 (m, 1H), 1.30-1.46 ppm (m, 3H). LC/MS (Table 1, Method A) R$_t$=2.44 min; MS m/z: 465 [M+H]$^+$.

Example #14. 2-[[3-(pentylcarbamoyl)-5,6-dihydro-4H-cyclopenta[b]thiophen-2-yl]carbamoyl]cyclohexanecarboxylic acid (Compound 22)

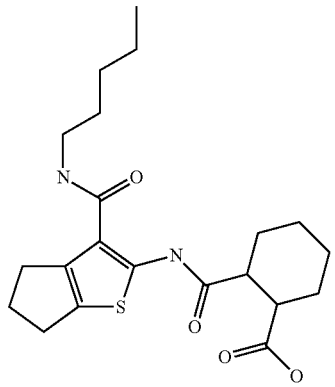 [SMILES: CCCCCNC(=O)c1c(NC(=O)C2CCCCC2C(=O)O)sc2c1CCC2]

tert-Butyl 2-(1,3-dioxo-3a,4,5,6,7,7a-hexahydroisoindol-2-yl)-5,6-dihydro-4H-cyclopenta[b]thiophene-3-carboxylate (Preparation #9, 60 mg, 0.19 mmol) was dissolved in DMF (600 μl) then Et$_3$N (32 μl, 0.23 mmol) and HATU (86 mg, 0.23 mmol) were added at rt. The reaction mixture was stirred at this temperature for 15 min before adding n-pentylamine (20 mg, 0.23 mmol). The reaction mixture was heated to 50° C. and stirred at this temperature overnight. To this reaction mixture was added Aq LiOH 1M (1.5 ml, 1.5 mmol) and the reaction was stirred at rt for 2 h. The solvent were then removed under reduced pressure. The residue was taken up in DCM (2 ml) and washed with Aq HCl 1N (2 ml 3×). The organic layer was dried by passing through a teflon membrane based cartridge and concentrated to provide a crude sample which was purified by RP-HPLC (Table 2, Method 2) to give 2-[[3-(pentylcarbamoyl)-5,6-dihydro-4H-cyclopenta[b]thiophen-2-yl]carbamoyl]cyclohexanecarboxylic acid (50 mg, 64%) as a white powder. $^1$H NMR (DMSO-d$_6$, 400 MHz): δ=12.14 (br s, 2H), 7.12 (br s, 1H), 3.20-3.30 (m, 2H), 2.84-2.98 (m, 3H), 2.78 (m, 3H), 2.35 (quin, J=7.1 Hz, 2H), 1.97-2.10 (m, 1H), 1.79-1.95 (m, 2H), 1.63-1.74 (m, 1H), 1.48-1.62 (m, 3H), 1.20-1.47 (m, 7H), 0.88 ppm (t, J=7.1 Hz, 3H). LC/MS (Table 1, Method B) R$_t$=1.90 min; MS m/z: 407 [M+H]$^+$.

The following compounds were prepared using the same procedure with the appropriate starting material.

Example #16. 2-[[3-(1,3-Dihydroisobenzofuran-5-ylcarbamoyl)-5,6-dihydro-4H-cyclopenta[b]thiophen-2-yl]carbamoyl]cyclohexanecarboxylic acid (Compound 30)

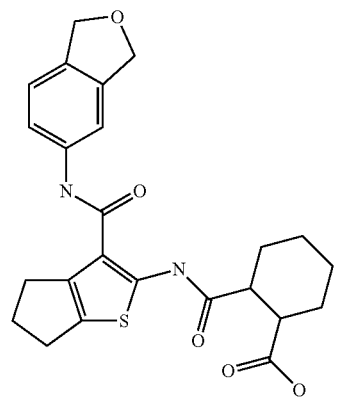 [SMILES: O=C(Nc1ccc2c(c1)COC2)c1c(NC(=O)C2CCCCC2C(=O)O)sc2c1CCC2]

The title compound was synthesized according to the procedure described in Example 14 using Preparation #9 as a starting material (yield 36%, 50 mg). $^1$H NMR (DMSO-d$_6$, 400 MHz): δ=12.12 (br s, 1H), 11.43 (br s, 1H), 9.08 (br s, 1H), 7.66 (br s, 1H), 7.49 (dd, J=8.0, 1.9 Hz, 1H), 7.28 (d, J=8.0 Hz, 1H), 4.95-5.02 (m, 4H), 3.02 (m, 2H), 2.77-2.91 (m, 4H), 2.38 (quin, J=7.5 Hz, 2H), 1.97-2.07 (m, 1H), 1.88-1.97 (m, 1H), 1.78-1.87 (m, 1H), 1.64-1.73 (m, 1H), 1.52-1.60 (m, 1H), 1.33-1.46 ppm (m, 3H). LC/MS (Table 1, Method B) R$_t$=1.70 min; MS m/z: 455 [M+H]$^+$.

Example #17. 2-[[3-[(4-Methylsulfonylphenyl)carbamoyl]-5,6-dihydro-4H-cyclopenta[b]thiophen-2-yl]carbamoyl]cyclohexanecarboxylic acid (Compound 31)

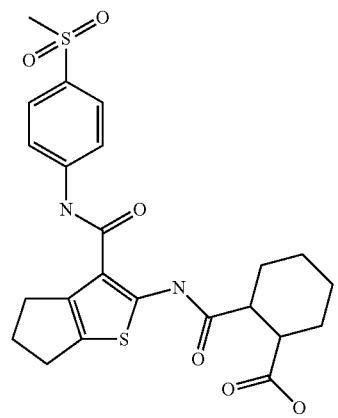 [SMILES: CS(=O)(=O)c1ccc(NC(=O)c2c(NC(=O)C3CCCCC3C(=O)O)sc3c2CCC3)cc1]

The title compound was synthesized according to the procedure described in Example 14 using Preparation #9 as a starting material (yield 7%, 7 mg). $^1$H NMR (DMSO-d$_6$, 400 MHz): δ=12.11 (br s, 1H), 11.21 (br s, 1H), 9.55 (br s, 1H), 7.89 (br s, 4H), 3.17 (s, 3H), 2.73-3.09 (m, 6H), 2.27-2.42 (m, 2H), 2.01-2.11 (m, 1H), 1.78-1.99 (m, 2H), 1.52-1.74 (m, 2H), 1.42 ppm (br s, 3H). LC/MS (Table 1, Method B) R$_t$=1.56 min; MS m/z: 491 [M+H]$^+$.

Example #18. 2-[[3-[[6-(Trifluoromethyl)-3-pyridyl]carbamoyl]-5,6-dihydro-4H-cyclopenta[b]thiophen-2-yl]carbamoyl]cyclohexanecarboxylic acid (Compound 32)

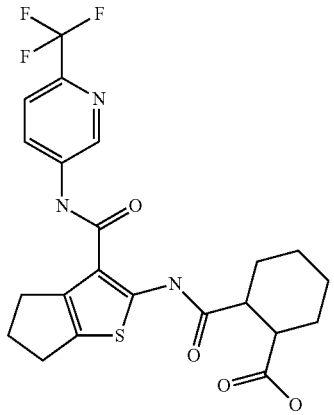 [SMILES: O=C(Nc1ccc(C(F)(F)F)nc1)c1c(NC(=O)C2CCCCC2C(=O)O)sc2c1CCC2]

The title compound was synthesized according to the procedure described in Example 14 using Preparation #9 as a starting material (yield 9%, 13 mg). $^1$H NMR (DMSO-d$_6$, 400 MHz): δ=12.14 (br s, 1H), 11.18 (br s, 1H), 9.70 (br s, 1H), 8.94 (d, J=2.2 Hz, 1H), 8.39 (dd, J=8.4, 2.2 Hz, 1H), 7.91 (d, J=8.4 Hz, 1H), 3.01 (m, 2H), 2.90 (dt, J=8.4, 4.2 Hz, 1H), 2.79-2.87 (m, 3H), 2.38 (quin, J=7.3 Hz, 2H), 1.98-2.07 (m, 1H), 1.88-1.98 (m, 1H), 1.77-1.87 (m, 1H), 1.64-1.74 (m, 1H), 1.50-1.61 (m, 1H), 1.34-1.45 ppm (m, 3H). LC/MS (Table 1, Method B) R$_t$=1.83 min; MS m/z: 482 [M+H]$^+$.

Example #19. 2-[[3-[(5-Methyl-3-pyridyl)carbamoyl]-5,6-dihydro-4H-cyclopenta[b]thiophen-2-yl]carbamoyl]cyclohexanecarboxylic acid (Compound 33)

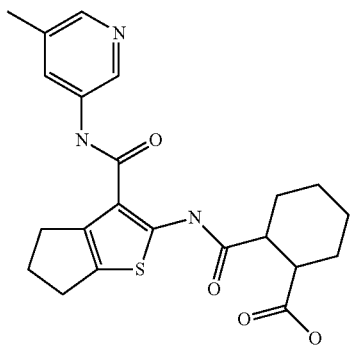 [SMILES: Cc1cncc(NC(=O)c2c(NC(=O)C3CCCCC3C(=O)O)sc3c2CCC3)c1]

The title compound was synthesized according to the procedure described in Example 14 using Preparation #9 as a starting material (yield 13%, 17 mg). $^1$H NMR (DMSO-d$_6$, 400 MHz): δ=12.14 (br s, 1H), 11.31 (br s, 1H), 9.17 (br s, 1H), 8.61 (d, J=2.2 Hz, 1H), 8.17 (br s, 1H), 7.92 (br s, 1H), 3.02 (m, 2H), 2.77-2.92 (m, 4H), 2.39 (quin, J=7.0 Hz, 2H), 2.32 (s, 3H), 1.98-2.09 (m, 1H), 1.87-1.97 (m, 1H), 1.77-1.87 (m, 1H), 1.63-1.74 (m, 1H), 1.51-1.62 (m, 1H), 1.40 ppm (m, 3H). LC/MS (Table 1, Method B) R$_t$=1.44 min; MS m/z: 428 [M+H]$^+$.

Example #20. 2-[[3-[4-(4-chlorophenyl)piperazine-1-carbonyl]-5,6-dihydro-4H-cyclopenta[b]thiophen-2-yl]carbamoyl]cyclohexanecarboxylic acid (Compound 36)

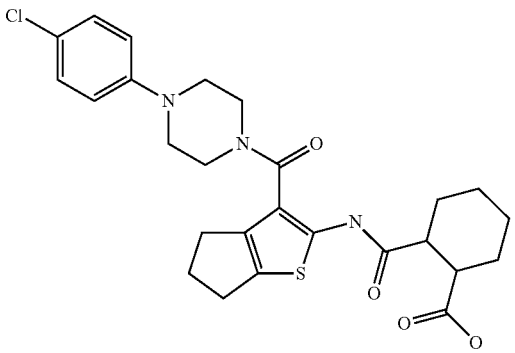 [SMILES: O=C(O)C1CCCCC1C(=O)Nc1sc2c(c1C(=O)N1CCN(c3ccc(Cl)cc3)CC1)CCC2]

The title compound was synthesized according to the procedure described in Example 14 using Preparation #9 as a starting material (yield 15%, 23 mg). $^1$H NMR (DMSO-d$_6$, 400 MHz): δ=12.05 (br s, 1H), 10.63 (br s, 1H), 7.24 (d, J=9.1 Hz, 2H), 6.96 (d, J=9.1 Hz, 2H), 3.57 (m, 4H), 3.16 (m, 4H), 2.95 (m, 1H), 2.80 (br t, J=7.0 Hz, 2H), 2.56-2.64 (m, 3H), 2.31 (quin, J=7.0 Hz, 2H), 1.96-2.06 (m, 1H), 1.84-1.96 (m, 1H), 1.51-1.71 (m, 3H), 1.25-1.45 ppm (m, 3H). LC/MS (Table 1, Method B) R$_t$=1.85 min; MS m/z: 516 [M+H]$^-$.

Example #21. 2-[[3-[(4-Chlorophenyl)-methyl-carbamoyl]-5,6-dihydro-4H-cyclopenta[b]thiophen-2-yl]carbamoyl]cyclohexanecarboxylic acid (Compound 34)

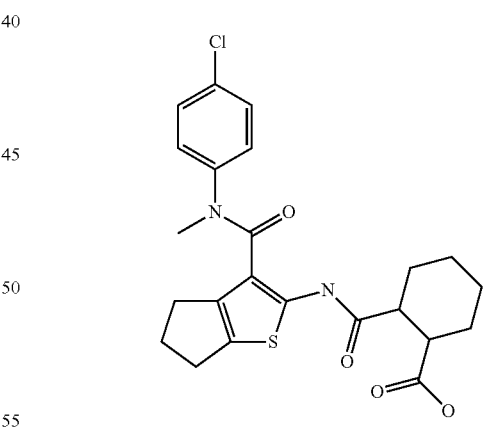

tert-Butyl 2-(1,3-dioxo-3a,4,5,6,7,7a-hexahydroisoindol-2-yl)-5,6-dihydro-4H-cyclopenta[b]thiophene-3-carboxylate (Preparation #9, 250 mg, 0.78 mmol) was dissolved in DMF (2.50 ml) then Et$_3$N (158 μl, 1.17 mmol), 4-chloro-N-methylaniline (133 mg, 0.94 mmol) and HATU (357 mg, 0.94 mmol) were added at rt and the reaction mixture was heated to 50-60° C. and stirred at this temperature overnight. 4-Chloro-N-methylaniline (133 mg, 0.94 mmol) and Et$_3$N (158 μl, 1.17 mmol) were added again and the reaction mixture was further stirred at this temperature one more night. To this reaction mixture was added a solution of LiOH, H$_2$O (164 mg, 3.91 mmol) in water (1 ml) and the reaction was stirred at 30° C. for 1 h. HCl 1N (25 ml) was poured in the reaction mixture and the product was extracted with EtOAc. The organic layers were then dried over MgSO$_4$, filtered and concentrated in vacuo to provide a crude sample which was purified by RP-HPLC (Table 2, Method 1) to give 2-[[3-[(4-chlorophenyl)-methyl-carbamoyl]-5,6-dihydro-4H-cyclopenta[b]thiophen-2-yl]carbamoyl]cyclohexanecarboxylic acid (10 mg, 3%) as a white powder. $^1$H NMR (DMSO-d$_6$, 500 MHz): δ=12.05 (br s, 1H), 10.58 (br s, 1H), 7.32 (d, J=8.8 Hz, 2H), 7.20 (d, J=8.8 Hz, 2H), 3.34 (s, 3H), 2.91-3.00 (m, 1H), 2.61-2.69 (m, 3H), 2.17-2.30 (m, 2H), 2.08-2.17 (m, 2H), 1.97-2.06 (m, 1H), 1.89-1.97 (m, 1H), 1.64-1.76 (m, 2H), 1.52-1.62 (m, 1H), 1.27-1.44 ppm (m, 3H). LC/MS (Table 1, Method B) R$_t$=1.76 min; MS m/z: 459 [M–H]$^-$.

Example #22. 2-[[3-[(3,4-Dimethylphenyl)carbamoyl]-5,6-dihydro-4H-cyclopenta[b]thiophen-2-yl]carbamoyl]cyclohexanecarboxylic acid (Compound 1)

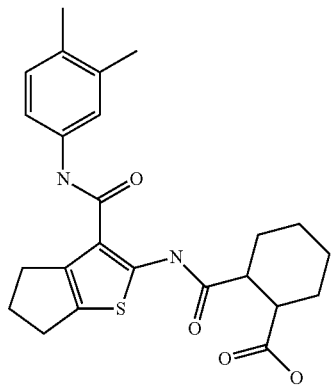 [SMILES: Cc1ccc(NC(=O)c2c(NC(=O)C3CCCCC3C(=O)O)sc3c2CCC3)cc1C]

2-[(2-Methoxycarbonylcyclohexanecarbonyl)amino]-5,6-dihydro-4H-cyclopenta[b]thiophene-3-carboxylic acid (Preparation #10, 95 mg, 0.27 mmol) was dissolved in DMF (1.25 ml) then N-methylmorpholine (33 µl, 0.30 mmol) and HATU (114 mg, 0.30 mmol) were added at rt. The reaction mixture was stirred at this temperature for 20 min before adding 3,4-dimethylaniline (36 mg, 0.30 mmol). The reaction mixture was heated to 50° C. and stirred at this temperature overnight. To this reaction mixture was added Aq LiOH 1M (1.35 ml, 1.35 mmol) and the reaction was stirred at rt for 2 h. The solvents were then removed under reduced pressure. The residue was taken up in DCM (2 ml) and washed with Aq HCl 1N (2 ml). The phases were separated and the aqueous layer was extracted with DCM (2 ml). The organic layers were combined, dried by passing through a teflon membrane based cartridge and concentrated to provide a crude sample which was purified by column chromatography on silica gel (eluting with 10-40% EtOAc in cyclohexane) to give 2-[[3-[(3,4-dimethylphenyl)carbamoyl]-5,6-dihydro-4H-cyclopenta[b]thiophen-2-yl]carbamoyl]cyclohexanecarboxylic acid (39 mg, 33%) as a white powder. $^1$H NMR (DMSO-d$_6$, 400 MHz): δ=12.13 (br s, 1H), 11.50 (br s, 1H), 8.83 (br s, 1H), 7.36-7.43 (m, 2H), 7.10 (d, J=8.8 Hz, 1H), 2.95-3.09 (m, 2H), 2.85-2.92 (m, 2H), 2.82 (br t, J=7.1 Hz, 2H), 2.38 (quin, J=7.1 Hz, 2H), 2.22 (s, 3H), 2.19 (s, 3H), 1.98-2.09 (m, 1H), 1.79-1.96 (m, 2H), 1.52-1.75 (m, 2H), 1.32-1.47 ppm (m, 3H). LC/MS (Table 1, Method B) R$_t$=1.96 min; MS m/z: 439 [M–H]$^-$.

Example #23. 2-[[3-(1,3-Benzodioxol-5-ylcarbamoyl)-5,6-dihydro-4H-cyclopenta[b]thiophen-2-yl]carbamoyl]cyclohexanecarboxylic acid (Compound 3)

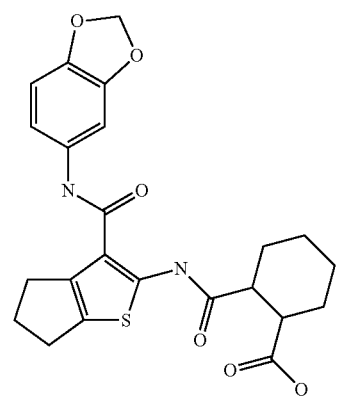 [SMILES: O=C(Nc1ccc2c(c1)OCO2)c1c(NC(=O)C2CCCCC2C(=O)O)sc2c1CCC2]

2-[(2-Methoxycarbonylcyclohexanecarbonyl)amino]-5,6-dihydro-4H-cyclopenta[b]thiophene-3-carboxylic acid (Preparation #10, 95 mg, 0.27 mmol) and N-methylmorpholine (26 µl, 0.24 mmol) were dissolved in DMF (325 µl) then 20 µl of a solution 1:1 of N-methylmorpholine (10 µl, 0.09 mmol) in DMF and 600 µL of a solution of HATU (114 mg, 0.30 mmol) in DMF were added at rt to this solution. The resulting solution was then added onto 1,3-benzodioxol-5-amine (61.7 mg, 0.45 mmol) and the reaction mixture was heated to 50° C. and stirred at this temperature overnight. To this reaction mixture was added Aq LiOH 1M (1.35 ml, 1.35 mmol) and the reaction was stirred at rt for 3 h. The solvents were then removed under reduced pressure. The residue was taken up in DCM (2 ml) and washed with Aq HCl 1N (2 ml). The phases were separated and the aqueous layer was extracted with DCM (2 ml). The organic layers were combined, dried by passing through a teflon membrane based cartridge and concentrated to provide a crude sample which was purified by RP-HPLC (Table 2, Method 1) to give 2-[[3-(1,3-benzodioxol-5-ylcarbamoyl)-5,6-dihydro-4H-cyclopenta[b]thiophen-2-yl]carbamoyl]cyclohexanecarboxylic acid (47 mg, 38%). $^1$H NMR (DMSO-d$_6$, 500 MHz): δ=12.13 (br s, 1H), 11.43 (br s, 1H), 8.91 (br s, 1H), 7.29 (d, J=1.9 Hz, 1H), 7.06 (dd, J=8.4, 1.9 Hz, 1H), 6.90 (d, J=8.4 Hz, 1H), 6.01 (s, 2H), 2.94-3.07 (m, 2H) 2.84-2.91 (m, 2H) 2.82 (br t, J=7.2 Hz, 2H), 2.38 (quin, J=7.2 Hz, 2H), 1.98-2.06 (m, 1H), 1.87-1.96 (m, 1H), 1.84 (m, 1H), 1.68 (m, 1H), 1.57 (m, 1H), 1.31-1.47 ppm (m, 3H). LC/MS (Table 1, Method B) R$_t$=1.76 min; MS m/z: 457 [M+H]$^+$.

The following compounds were prepared using the same procedure with the appropriate starting material.

Example #24. 2-[[3-[(4-Fluorophenyl)carbamoyl]-5,6-dihydro-4H-cyclopenta[b]thiophen-2-yl]carbamoyl]cyclohexanecarboxylic acid (Compound 4)

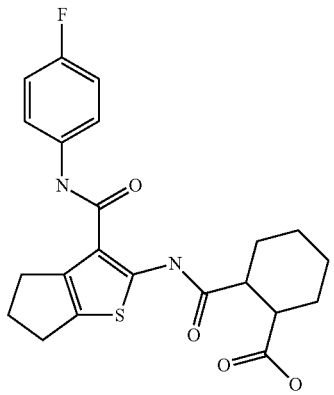 [SMILES: O=C(Nc1ccc(F)cc1)c1c(NC(=O)C2CCCCC2C(=O)O)sc2c1CCC2]

The title compound was synthesized according to the procedure described in Example 23 using Preparation #10 as a starting material (yield 35%, 41 mg). $^1$H NMR (DMSO-$d_6$, 500 MHz): δ=12.14 (br s, 1H), 11.39 (br s, 1H), 9.08 (br s, 1H), 7.66 (dd, J=9.0, 5.0 Hz, 2H), 7.20 (t, J=9.0 Hz, 2H), 3.02 (m, 2H), 2.84-2.91 (m, 2H) 2.83 (br t, J=7.2 Hz, 2H), 2.38 (quin, J=7.2 Hz, 2H), 1.98-2.06 (m, 1H), 1.88-1.96 (m, 1H), 1.77-1.87 (m, 1H), 1.68 (m, 1H), 1.56 (m, 1H), 1.32-1.47 ppm (m, 3H). LC/MS (Table 1, Method B) $R_t$=1.83 min; MS m/z: 431 [M+H]$^+$.

Example #25. 2-[[3-[(4-Methylcyclohexyl)carbamoyl]-5,6-dihydro-4H-cyclopenta[b]thiophen-2-yl]carbamoyl]cyclohexanecarboxylic acid (Compound 35)

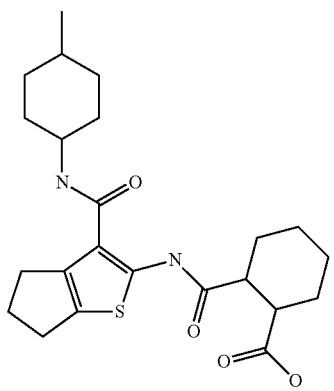 [SMILES: CC1CCC(NC(=O)c2c(NC(=O)C3CCCCC3C(=O)O)sc3c2CCC3)CC1]

The title compound was synthesized as a mixture of cis/trans 4-methylcyclohexylamide according to the procedure described in Example 23 using Preparation #10 as a starting material (yield 41%, 48 mg). $^1$H NMR (DMSO-$d_6$, 400 MHz): δ=12.01 (br s, 2H), 6.69 (br s, 1H), 3.91-4.08 (m, 0.6H), 3.68 (ddt, J=11.6, 7.7, 3.8 Hz, 0.4H), 2.85-3.04 (m, 3H), 2.72-2.84 (m, 3H), 2.27-2.45 (m, 2H), 1.97-2.10 (m, 1H), 1.80-1.96 (m, 3H), 1.63-1.79 (m, 3H), 1.48-1.63 (m, 4H), 1.28-1.47 (m, 4H), 1.12-1.28 (m, 1.2H), 0.96-1.11 (m, 0.8H), 0.92 (d, J=6.5 Hz, 1.8H), 0.88 ppm (d, J=6.5 Hz, 1.2H). LC/MS (Table 1, Method B) $R_t$=2.03 min; MS m/z: 431 [M−H]$^−$.

Example #26. 2-[[3-[(4-Chlorophenyl)methylcarbamoyl]-5,6-dihydro-4H-cyclopenta[b]thiophen-2-yl]carbamoyl]cyclohexanecarboxylic acid (Compound 5)

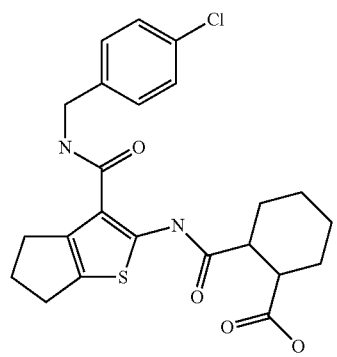 [SMILES: O=C(NCc1ccc(Cl)cc1)c1c(NC(=O)C2CCCCC2C(=O)O)sc2c1CCC2]

The title compound was synthesized according to the procedure described in Example 23 using Preparation #10 as a starting material (yield 36%, 45 mg). $^1$H NMR (DMSO-$d_6$, 500 MHz): δ=12.12 (br s, 1H), 11.98 (br s, 1H), 7.67 (br s, 1H), 7.39 (d, J=8.4 Hz, 2H), 7.34 (d, J=8.4 Hz, 2H), 4.48 (d, J=6.1 Hz, 2H), 2.96 (td, J=6.7, 4.8 Hz, 2H), 2.89 (br d, J=4.8 Hz, 1H), 2.79 (br t, J=7.2 Hz, 3H), 2.37 (quin, J=7.2 Hz, 2H), 2.01 (td, J=6.6, 2.6 Hz, 1H), 1.79-1.94 (m, 2H), 1.67 (m, 1H), 1.55 (m, 1H), 1.31-1.48 ppm (m, 3H). LC/MS (Table 1, Method B) $R_t$=1.88 min; MS m/z: 461 [M+H]$^+$.

Example #27. 2-[[3-[(4,4-Difluorocyclohexyl)carbamoyl]-5,6-dihydro-4H-cyclopenta[b]thiophen-2-yl]carbamoyl]cyclohexanecarboxylic acid (Compound 18)

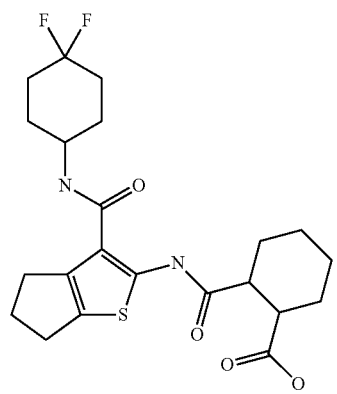 [SMILES: O=C(NC1CCC(F)(F)CC1)c1c(NC(=O)C2CCCCC2C(=O)O)sc2c1CCC2]

The title compound was synthesized according to the procedure described in Example 23 using Preparation #10 as a starting material (yield 31%, 38 mg). $^1$H NMR (DMSO-$d_6$, 400 MHz): δ=12.11 (br s, 1H), 11.84 (br s, 1H), 6.87 (br s, 1H), 3.88-4.08 (m, 1H), 2.86-3.00 (m, 3H), 2.78 (br t, J=6.8 Hz, 3H), 2.35 (quin, J=7.3 Hz, 2H), 1.96-2.13 (m, 4H), 1.79-1.96 (m, 5H), 1.51-1.77 (m, 4H), 1.23-1.50 ppm (m, 3H). LC/MS (Table 1, Method B) $R_t$=1.78 min; MS m/z: 455 [M+H]$^-$.

Example #28. 2-[[3-[(Trans-4-methoxycyclohexyl)carbamoyl]-5,6-dihydro-4H-cyclopenta[b]thiophen-2-yl]carbamoyl]cyclohexanecarboxylic acid (Compound 8)

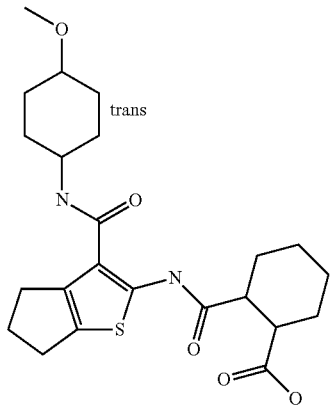 [SMILES: COC1CCC(NC(=O)c2c(NC(=O)C3CCCCC3C(=O)O)sc3c2CCC3)CC1]

The title compound was synthesized according to the procedure described in Example 23 using Preparation #10 as a starting material (yield 13%, 16 mg). $^1$H NMR (DMSO-d$_6$, 400 MHz): δ=12.11 (br s, 1H), 11.91 (br s, 1H), 6.70 (br s, 1H), 3.64-3.85 (m, 1H), 3.24 (s, 3H), 3.02-3.17 (m, 1H), 2.85-2.97 (m, 3H), 2.78 (br t, J=6.6 Hz, 3H), 2.35 (quin, J=7.3 Hz, 2H), 1.99 (m, 3H), 1.79-1.93 (m, 4H), 1.53-1.72 (m, 2H), 1.31-1.50 (m, 5H), 1.23 ppm (m, 2H). LC/MS (Table 1, Method B) $R_t$=1.67 min; MS m/z: 449 [M+H]$^+$.

Example #29. 2-[[3-[(4-tert-Butylphenyl)carbamoyl]-5,6-dihydro-4H-cyclopenta[b]thiophen-2-yl]carbamoyl]cyclohexanecarboxylic acid (Compound 21)

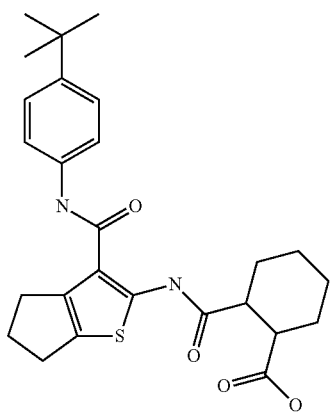 [SMILES: CC(C)(C)c1ccc(NC(=O)c2c(NC(=O)C3CCCCC3C(=O)O)sc3c2CCC3)cc1]

The title compound was synthesized according to the procedure described in Example 23 using Preparation #10 as a starting material (yield 53%, 67 mg). $^1$H NMR (DMSO-d$_6$, 400 MHz): δ=12.13 (br s, 1H), 11.47 (br s, 1H), 8.92 (br s, 1H), 7.54 (d, J=8.6 Hz, 2H), 7.37 (d, J=8.6 Hz, 2H), 2.96-3.09 (m, 2H), 2.75-2.93 (m, 4H), 2.39 (quin, J=7.0 Hz, 2H), 1.97-2.12 (m, 1H), 1.88-1.97 (m, 1H), 1.78-1.87 (m, 1H), 1.51-1.77 (m, 2H), 1.32-1.48 (m, 3H), 1.28 ppm (s, 9H). LC/MS (Table 1, Method B) $R_t$=2.16 min; MS m/z: 467 [M−H]$^-$.

Example #30. 2-[[3-[[4-(2-Hydroxyethyl)phenyl]carbamoyl]-5,6-dihydro-4H-cyclopenta[b]thiophen-2-yl]carbamoyl]cyclohexanecarboxylic acid (Compound 9)

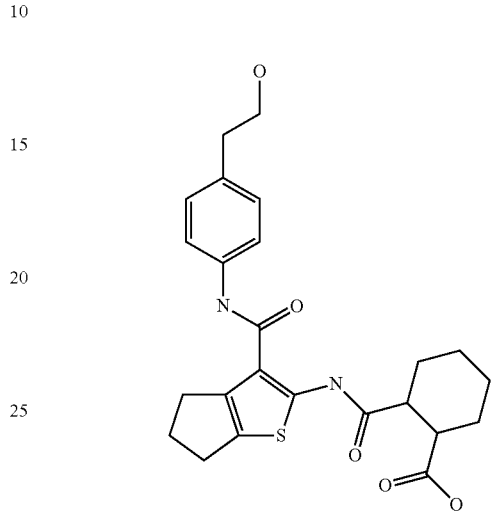

The title compound was synthesized according to the procedure described in Example 23 using Preparation #10 as a starting material (yield 39%, 48 mg). $^1$H NMR (DMSO-d$_6$, 400 MHz): δ=12.12 (br s, 1H), 11.46 (br s, 1H), 8.92 (br s, 1H), 7.53 (d, J=8.6 Hz, 2H), 7.19 (d, J=8.6 Hz, 2H), 4.61 (t, J=5.3 Hz, 1H), 3.58 (td, J=7.2, 5.3 Hz, 2H), 2.95-3.10 (m, 2H), 2.76-2.94 (m, 4H), 2.70 (t, J=7.2 Hz, 2H), 2.38 (quin, J=7.3 Hz, 2H), 1.97-2.12 (m, 1H), 1.79-1.96 (m, 2H), 1.62-1.75 (m, 1H), 1.50-1.61 (m, 1H), 1.29-1.48 ppm (m, 3H). LC/MS (Table 1, Method B) $R_t$=1.55 min; MS m/z: 457 [M+H]$^+$.

Example #31. 2-[[3-[(4-Phenylphenyl)carbamoyl]-5,6-dihydro-4H-cyclopenta[b]thiophen-2-yl]carbamoyl]cyclohexanecarboxylic acid (Compound 10)

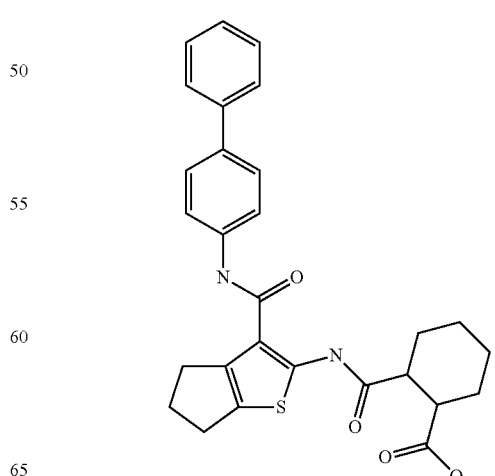

The title compound was synthesized according to the procedure described in Example 23 using Preparation #10 as a starting material (yield 29%, 38 mg). $^1$H NMR (DMSO-$d_6$, 400 MHz): δ=12.14 (br s, 1H), 11.42 (br s, 1H), 9.13 (br s, J=2.0 Hz, 1H), 7.75 (d, J=9.5 Hz, 2H), 7.64-7.70 (m, 4H), 7.46 (td, J=7.6, 1.1 Hz, 2H), 7.35 (tt, J=7.6, 2.0 Hz, 1H), 3.05 (m, 2H), 2.86-2.92 (m, 2H), 2.84 (br t, J=7.3 Hz, 2H), 2.40 (quin, J=7.3 Hz, 2H), 1.99-2.10 (m, 1H), 1.89-1.98 (m, 1H), 1.80-1.89 (m, 1H), 1.64-1.75 (m, 1H), 1.51-1.63 (m, 1H), 1.29-1.48 ppm (m, 3H). LC/MS (Table 1, Method B) $R_t$=2.10 min; MS m/z: 489 [M+H]$^+$.

Example #32. 2-[[3-(Indan-1-ylcarbamoyl)-5,6-dihydro-4H-cyclopenta[b]thiophen-2-yl]carbamoyl]cyclohexanecarboxylic acid (Compound 23)

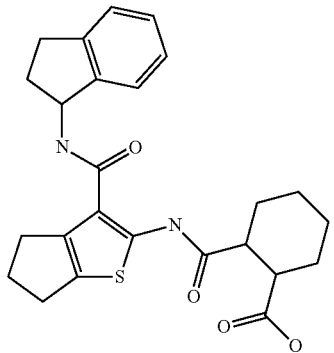 [SMILES: O=C(NC1CCc2ccccc21)c1c(NC(=O)C2CCCCC2C(=O)O)sc2c1CCC2]

The title compound was synthesized according to the procedure described in Example 23 using Preparation #10 as a starting material (yield 26%, 32 mg). $^1$H NMR (DMSO-$d_6$, 400 MHz): δ=12.13 (s, 1H), 11.90 (br s, 1H), 7.14-7.33 (m, 5H), 5.50 (q, J=8.1 Hz, 1H), 2.81-3.03 (m, 6H), 2.78 (br t, J=7.3 Hz, 2H), 2.43-2.48 (m, 1H), 2.32 (quin, J=7.3 Hz, 2H), 1.83-2.09 (m, 4H), 1.65-1.77 (m, 1H), 1.54-1.64 (m, 1H), 1.30-1.50 ppm (m, 3H). LC/MS (Table 1, Method B) $R_t$=1.94 min; MS m/z: 453 [M+H]$^+$.

Example #33. 2-[[3-[(3-Chlorophenyl)methylcarbamoyl]-5,6-dihydro-4H-cyclopenta[b]thiophen-2-yl]carbamoyl]cyclohexanecarboxylic acid (Compound 11)

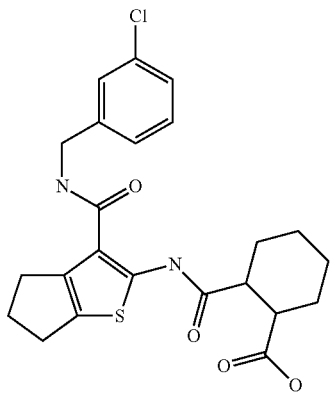 [SMILES: O=C(NCc1cccc(Cl)c1)c1c(NC(=O)C2CCCCC2C(=O)O)sc2c1CCC2]

The title compound was synthesized according to the procedure described in Example 23 using Preparation #10 as a starting material (yield 35%, 44 mg). $^1$H NMR (DMSO-$d_6$, 400 MHz): δ=12.10 (br s, 1H), 11.95 (br s, 1H), 7.70 (br s, 1H), 7.34-7.39 (m, 2H), 7.27-7.32 (m, 2H), 4.49 (d, J=5.9 Hz, 2H), 2.97 (br t, J=7.3 Hz, 2H), 2.88 (q, J=4.6 Hz, 1H), 2.80 (br t, J=7.3 Hz, 3H), 2.38 (quin, J=7.3 Hz, 2H), 1.96-2.06 (m, 1H), 1.79-1.94 (m, 2H), 1.61-1.74 (m, 1H), 1.51-1.60 (m, 1H), 1.30-1.49 ppm (m, 3H). LC/MS (Table 1, Method B) $R_t$=1.87 min; MS m/z: 461 [M+H]$^+$.

Example #34. 2-[[3-[[4-(Hydroxymethyl)phenyl]carbamoyl]-5,6-dihydro-4H-cyclopenta[b]thiophen-2-yl]carbamoyl]cyclohexanecarboxylic acid (Compound 19)

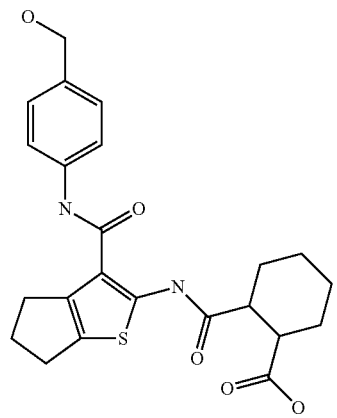 [SMILES: O=C(Nc1ccc(CO)cc1)c1c(NC(=O)C2CCCCC2C(=O)O)sc2c1CCC2]

The title compound was synthesized according to the procedure described in Example 23 using Preparation #10 as a starting material (yield 18%, 22 mg). $^1$H NMR (DMSO-$d_6$, 400 MHz): δ=12.13 (br s, 1H), 11.45 (br s, 1H), 8.96 (br s, 1H), 7.60 (d, J=8.6 Hz, 2H), 7.29 (d, J=8.6 Hz, 2H), 5.13 (t, J=5.6 Hz, 1H), 4.46 (d, J=5.6 Hz, 2H), 3.03 (m, 2H), 2.85-2.91 (m, 2H), 2.83 (br t, J=7.3 Hz, 2H), 2.39 (quin, J=7.3 Hz, 2H), 1.98-2.07 (m, 1H), 1.88-1.97 (m, 1H), 1.79-1.88 (m, 1H), 1.63-1.74 (m, 1H), 1.53-1.61 (m, 1H), 1.32-1.46 ppm (m, 3H). LC/MS (Table 1, Method B) $R_t$=1.49 min; MS m/z: 443 [M+H]$^+$.

Example #35. 2-[[3-[(3-Acetylphenyl)carbamoyl]-5,6-dihydro-4H-cyclopenta[b]thiophen-2-yl]carbamoyl]cyclohexanecarboxylic acid (Compound 12)

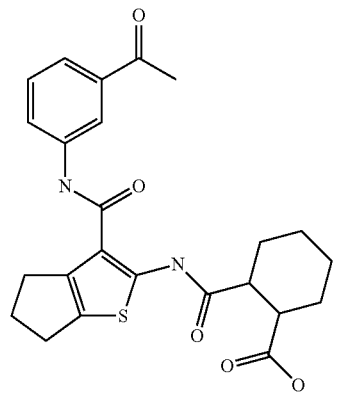 [SMILES: CC(=O)c1cccc(NC(=O)c2c(NC(=O)C3CCCCC3C(=O)O)sc3c2CCC3)c1]

The title compound was synthesized according to the procedure described in Example 23 using Preparation #10 as a starting material (yield 12%, 15 mg). $^1$H NMR (DMSO-d$_6$, 400 MHz): δ=12.12 (br s, 1H), 11.31 (br s, 1H), 9.24 (br s, 1H), 8.20 (t, J=2.0 Hz, 1H), 7.93 (ddd, J=7.7, 2.0, 1.0 Hz, 1H), 7.73 (br d, J=7.7 Hz, 1H), 7.52 (t, J=7.7 Hz, 1H), 3.04 (m, 2H), 2.78-2.93 (m, 4H), 2.59 (s, 3H), 2.39 (quin, J=7.0 Hz, 2H), 1.98-2.07 (m, 1H), 1.88-1.97 (m, 1H), 1.77-1.87 (m, 1H), 1.63-1.75 (m, 1H), 1.50-1.62 (m, 1H), 1.28-1.48 ppm (m, 3H). LC/MS (Table 1, Method B) R$_t$=1.71 min; MS m/z: 455 [M+H]$^+$.

Example #36. 2-[[3-[(4-Chloro-3-methyl-phenyl)carbamoyl]-5,6-dihydro-4H-cyclopenta[b]thiophen-2-yl]carbamoyl]cyclohexanecarboxylic acid (Compound 13)

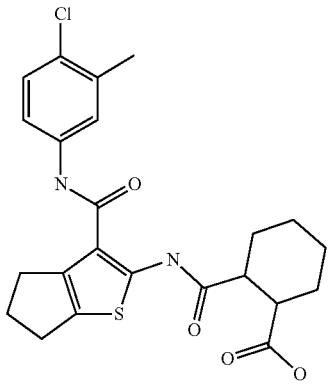

The title compound was synthesized according to the procedure described in Example 23 using Preparation #10 as a starting material (yield 18%, 23 mg). $^1$H NMR (DMSO-d$_6$, 400 MHz): δ=12.13 (br s, 1H), 11.34 (br s, 1H), 9.06 (br s, 1H), 7.62 (d, J=2.4 Hz, 1H), 7.54 (dd, J=8.7, 2.4 Hz, 1H), 7.38 (d, J=8.7 Hz, 1H), 3.01 (m, 2H), 2.85-2.92 (m, 2H), 2.82 (br t, J=7.3 Hz, 2H), 2.38 (quin, J=7.3 Hz, 2H), 2.33 (s, 3H), 1.97-2.07 (m, 1H), 1.87-1.96 (m, 1H), 1.77-1.87 (m, 1H), 1.64-1.74 (m, 1H), 1.51-1.61 (m, 1H), 1.32-1.48 ppm (m, 3H). LC/MS (Table 1, Method B) R$_t$=2.06 min; MS m/z: 461 [M+H]$^+$.

Example #37. 2-[[3-[(3-chloro-4-methyl-phenyl)carbamoyl]-5,6-dihydro-4H-cyclopenta[b]thiophen-2-yl]carbamoyl]cyclohexanecarboxylic acid (Compound 14)

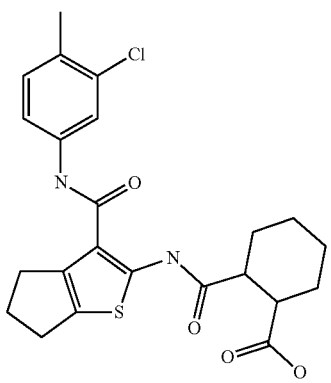

The title compound was synthesized according to the procedure described in Example 23 using Preparation #10 as a starting material (yield 14%, 18 mg). $^1$H NMR (DMSO-d$_6$, 400 MHz): δ=12.13 (br s, 1H), 11.30 (br s, 1H), 9.10 (br s, 1H), 7.80 (d, J=2.2 Hz, 1H), 7.49 (dd, J=8.1, 2.2 Hz, 1H), 7.32 (d, J=8.1 Hz, 1H), 3.01 (m, 2H), 2.79-2.92 (m, 4H), 2.38 (quin, J=7.2 Hz, 2H), 2.30 (s, 3H), 1.97-2.07 (m, 1H), 1.88-1.97 (m, 1H), 1.78-1.87 (m, 1H), 1.65-1.74 (m, 1H), 1.51-1.62 (m, 1H), 1.33-1.47 ppm (m, 3H). LC/MS (Table 1, Method B) R$_t$=2.07 min; MS m/z: 461 [M+H]$^+$.

Example #38. 2-[[3-[(4-Morpholinophenyl)carbamoyl]-5,6-dihydro-4H-cyclopenta[b]thiophen-2-yl]carbamoyl]cyclohexanecarboxylic acid (Compound 15)

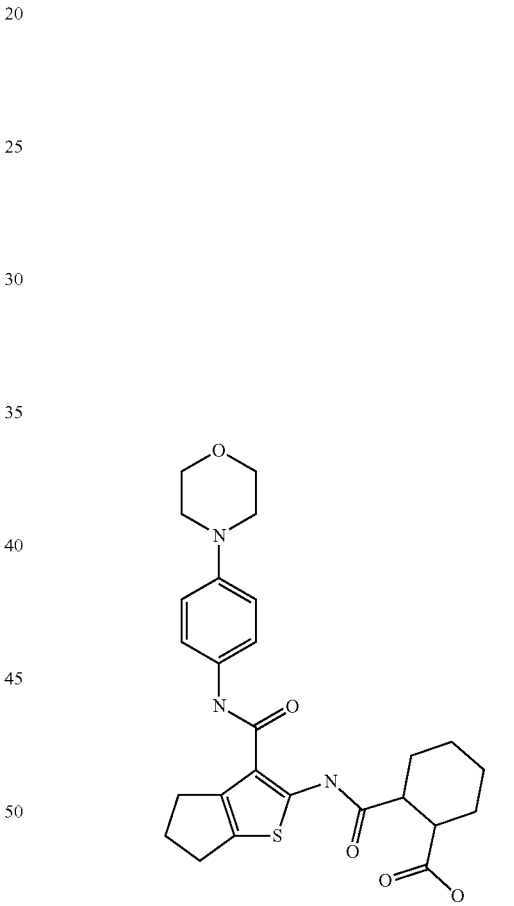

The title compound was synthesized according to the procedure described in Example 23 using Preparation #10 as a starting material (yield 36%, 49 mg). $^1$H NMR (DMSO-d$_6$, 400 MHz): δ=12.12 (br s, 1H), 11.56 (br s, 1H), 8.77 (br s, 1H), 7.50 (d, J=9.1 Hz, 2H), 6.94 (d, J=9.1 Hz, 2H), 3.74 (m, 4H), 3.07 (m, 4H), 2.99-3.04 (m, 2H), 2.76-2.93 (m, 4H), 2.38 (quin, J=7.5 Hz, 2H), 1.98-2.07 (m, 1H), 1.79-1.97 (m, 2H), 1.63-1.74 (m, 1H), 1.52-1.62 (m, 1H), 1.31-1.49 ppm (m, 3H). LC/MS (Table 1, Method B) R$_t$=1.70 min; MS m/z: 498 [M+H]$^+$.

Example #39. 2-[[3-[(3,4-Difluorophenyl)carbamoyl]-5,6-dihydro-4H-cyclopenta[b]thiophen-2-yl]carbamoyl]cyclohexanecarboxylic acid (Compound 16)

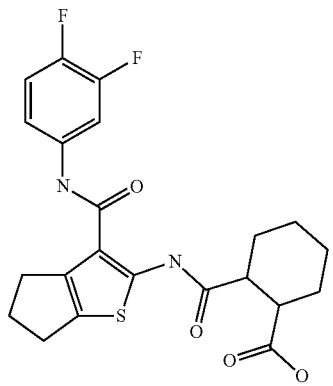

The title compound was synthesized according to the procedure described in Example 23 using Preparation #10 as a starting material (yield 7%, 9 mg). $^1$H NMR (DMSO-d$_6$, 400 MHz): δ=12.12 (br s, 1H), 11.24 (br s, 1H), 9.26 (br s, 1H), 7.75-7.84 (m, 1H), 7.40-7.46 (m, 2H), 3.00 (m, 2H), 2.77-2.93 (m, 4H), 2.38 (quin, J=7.3 Hz, 2H), 1.98-2.07 (m, 1H), 1.88-1.97 (m, 1H), 1.77-1.87 (m, 1H), 1.62-1.74 (m, 1H), 1.51-1.61 (m, 1H), 1.30-1.47 ppm (m, 3H). LC/MS (Table 1, Method B) R$_t$=1.88 min; MS m/z: 449 [M+H]$^+$.

Example #40. 2-[[3-[[4-(Trifluoromethoxy)phenyl]carbamoyl]-5,6-dihydro-4H-cyclopenta[b]thiophen-2-yl]carbamoyl]cyclohexanecarboxylic acid (Compound 20)

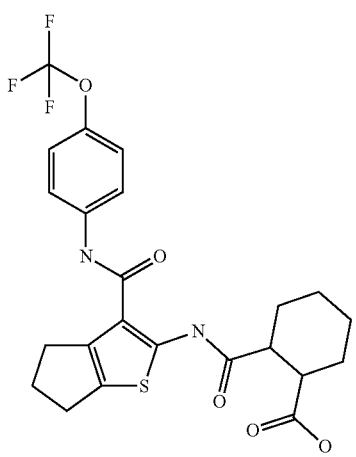

The title compound was synthesized according to the procedure described in Example 23 using Preparation #10 as a starting material (yield 13%, 18 mg). $^1$H NMR (DMSO-d$_6$, 400 MHz): δ=12.13 (br s, 1H), 11.31 (br s, 1H), 9.24 (br s, 1H), 7.76 (d, J=9.1 Hz, 2H), 7.37 (d, J=9.1 Hz, 2H), 3.01 (m, 2H), 2.78-2.90 (m, 4H), 2.38 (quin, J=7.2 Hz, 2H), 1.98-2.07 (m, 1H), 1.87-1.97 (m, 1H), 1.78-1.87 (m, 1H), 1.63-1.73 (m, 1H), 1.51-1.61 (m, 1H), 1.31-1.49 ppm (m, 3H). LC/MS (Table 1, Method B) R$_t$=2.02 min; MS m/z: 497 [M+H]$^+$.

Example #41. 2-[[3-(Cyclohexylmethylcarbamoyl)-5,6-dihydro-4H-cyclopenta[b]thiophen-2-yl]carbamoyl]cyclohexanecarboxylic acid (Compound 24)

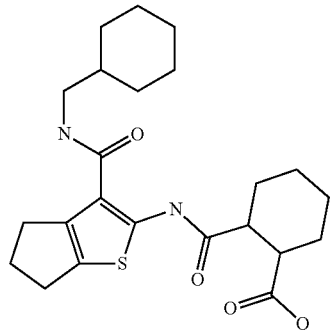

The title compound was synthesized according to the procedure described in Example 23 using Preparation #10 as a starting material (yield 29%, 34 mg). $^1$H NMR (DMSO-d$_6$, 400 MHz): δ=12.10 (br s, 1H), 12.02 (s, 1H), 7.03 (br t, J=6.1 Hz, 1H), 3.13 (br t, J=6.8 Hz, 2H), 2.92 (m, 3H), 2.78 (br t, J=6.8 Hz, 3H), 2.36 (quin, J=6.8 Hz, 2H), 1.97-2.08 (m, 1H), 1.79-1.96 (m, 2H), 1.50-1.76 (m, 8H), 1.30-1.48 (m, 3H), 1.08-1.26 (m, 3H), 0.84-0.99 ppm (m, 2H). LC/MS (Table 1, Method B) R$_t$=2.02 min; MS m/z: 433 [M+H]$^+$.

Example #42. 2-[[3-[(4-Isopropylphenyl)carbamoyl]-5,6-dihydro-4H-cyclopenta[b]thiophen-2-yl]carbamoyl]cyclohexanecarboxylic acid (Compound 25)

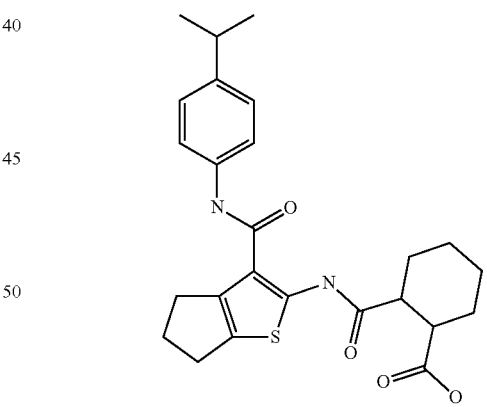

The title compound was synthesized according to the procedure described in Example 23 using Preparation #10 as a starting material (yield 27%, 33 mg). 1H NMR (DMSO-d$_6$, 400 MHz): δ=12.13 (br s, 1H), 11.47 (s, 1H), 8.91 (s, 1H), 7.54 (d, J=8.4 Hz, 2H), 7.22 (d, J=8.4 Hz, 2H), 3.03 (m, 2H), 2.78-2.92 (m, 5H), 2.39 (quin, J=7.3 Hz, 2H), 1.98-2.08 (m, 1H), 1.88-1.96 (m, 1H), 1.78-1.88 (m, 1H), 1.63-1.75 (m, 1H), 1.52-1.63 (m, 1H), 1.33-1.48 (m, 3H), 1.20 ppm (d, J=6.8 Hz, 6H). LC/MS (Table 1, Method B) R$_t$=2.10 min; MS m/z: 455 [M+H]$^+$.

Example #43. 2-[[3-[(4-Methoxyphenyl)carbamoyl]-5,6-dihydro-4H-cyclopenta[b]thiophen-2-yl]carbamoyl]cyclohexanecarboxylic acid (Compound 76)

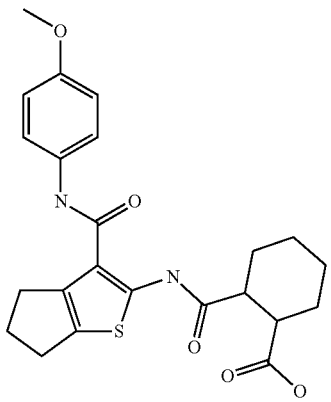

The title compound was synthesized according to the procedure described in Example 23 using Preparation #10 as a starting material (yield 33%, 39 mg). $^1$H NMR (DMSO-d$_6$, 500 MHz): δ=12.22 (br s, 1H), 11.60 (br s, 1H), 8.94 (br s, 1H), 7.62 (d, J=9.1 Hz, 2H), 7.02 (d, J=9.1 Hz, 2H), 3.83 (s, 3H), 3.11 (q, J=7.3 Hz, 2H), 2.87-3.01 (m, 4H), 2.47 (quin, J=7.2 Hz, 2H), 2.06-2.15 (m, 1H), 1.96-2.05 (m, 1H), 1.89-1.95 (m, 1H), 1.73-1.82 (m, 1H), 1.61-1.69 (m, 1H), 1.41-1.55 ppm (m, 3H). LC/MS (Table 1, Method B) R$_t$=1.78 min; MS m/z: 443 [M+H]$^+$.

Example #44. 2-[[3-[(4-Chlorophenyl)carbamoyl]-5,6-dihydro-4H-cyclopenta[b]thiophen-2-yl]carbamoyl]benzoic acid (Compound 44)

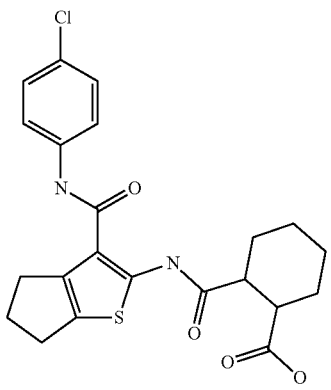

2-Amino-N-(4-chlorophenyl)-5,6-dihydro-4H-cyclopenta[b]thiophene-3-carboxamide (*Indian Journal of Heterocyclic Chemistry*, 2003, 13(2), 185-186), (100 mg, 0.34 mmol) was dissolved in THF (2.00 ml) phthalic anhydride (101 mg, 0.68 mmol) was added. The mixture was stirred under reflux overnight. The mixture was cooled to rt then concentrated in vacuo to provide a brown solid. The residue was washed several times with MeCN and dried under vacuum to give 2-[[3-[(4-chlorophenyl)carbamoyl]-5,6-dihydro-4H-cyclopenta[b]thiophen-2-yl]carbamoyl]benzoic acid (88 mg, 58%) as a beige powder. $^1$H NMR (DMSO-d$_6$, 400 MHz): δ=13.18 (br s, 1H), 11.51 (br s, 1H), 9.39 (br s, 1H), 7.87 (d, J=7.9 Hz, 1H), 7.67 (d, J=9.0 Hz, 2H), 7.60-7.72 (m, 3H), 7.38 (d, J=9.0 Hz, 2H), 3.00 (br t, J=7.1 Hz, 2H), 2.88 (br t, J=7.1 Hz, 2H), 2.40 ppm (quin J=7.1 Hz, 2H). LC/MS (Table 1, Method B) R$_t$=1.88 min; MS m/z: 439 [M−H]$^-$.

The following compounds were prepared using the same procedure with the appropriate starting material.

Example #45. 2-[[3-[(4-Chlorophenyl)carbamoyl]-5,6-dihydro-4H-cyclopenta[b]thiophen-2-yl]carbamoyl]cyclopentanecarboxylic acid (Compound 46)

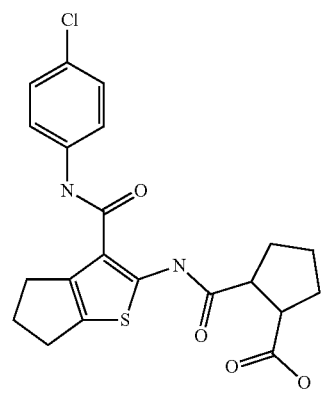

The title compound was synthesized according to the procedure described in Example #44 using 2-amino-N-(4-chlorophenyl)-5,6-dihydro-4H-cyclopenta[b]thiophene-3-carboxamide (*Indian Journal of Heterocyclic Chemistry*, 2003, 13(2), 185-186) and 4,5,6,6a-tetrahydro-3aH-cyclopenta[c]furan-1,3-dione as starting materials (yield 74%, 112 mg). $^1$H NMR (DMSO-d$_6$, 400 MHz): δ=12.00 (br s, 1H), 11.15 (br s, 1H), 9.23 (br s, 1H), 7.70 (d, J=9.0 Hz, 2H), 7.41 (d, J=9.0 Hz, 2H), 3.20 (q, J=7.5 Hz, 1H), 3.03 (q J=7.5 Hz, 1H), 2.99 (br t, J=7.2 Hz, 2H), 2.82 (br t, J=7.2 Hz, 2H), 2.38 (quin, J=7.2 Hz, 2H), 1.86-2.02 (m, 4H), 1.74-1.85 (m, 1H), 1.54-1.67 ppm (m, 1H). LC/MS (Table 1, Method A) R$_t$=2.20 min; MS m/z: 433 [M+H]$^+$.

Example #46. 5-[[3-[(4-Chlorophenyl)carbamoyl]-5,6-dihydro-4H-cyclopenta[b]thiophen-2-yl]amino]-3,3-dimethyl-5-oxo-pentanoic acid (Compound 47)

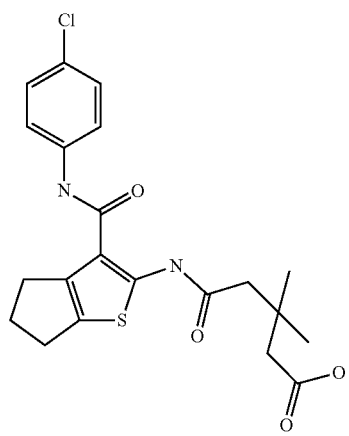

The title compound was synthesized according to the procedure described in Example #44 using 2-amino-N-(4-chlorophenyl)-5,6-dihydro-4H-cyclopenta[b]thiophene-3-carboxamide (*Indian Journal of Heterocyclic Chemistry*, 2003, 13(2), 185-186) and 4,4-dimethyltetrahydropyran-2,6-dione as starting materials (yield 59%, 88 mg). $^1$H NMR (DMSO-$d_6$, 400 MHz): δ=12.06 (br s, 1H), 10.99 (br s, 1H), 9.41 (br s, 1H), 7.70 (d, J=8.8 Hz, 2H), 7.40 (d, J=8.8 Hz, 2H), 2.95 (br t, J=6.8 Hz, 2H), 2.82 (br t, J=6.8 Hz, 2H), 2.50 (br s, 2H), 2.37 (quin, J=6.8 Hz, 2H), 2.29 (br s, 2H), 1.07 ppm (s, 6H). LC/MS (Table 1, Method B) $R_t$=1.90 min; MS m/z: 435 [M+H]$^+$.

Example #47. 2-[[3-[(4-Chlorophenyl)carbamoyl]-5,6-dihydro-4H-cyclopenta[b]thiophen-2-yl]carbamoyl]cyclohexane-cis-carboxylic acid (Compound 57)

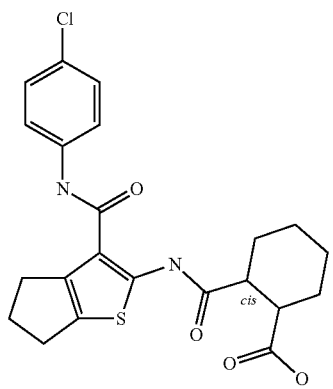

2-Amino-N-(4-chlorophenyl)-5,6-dihydro-4H-cyclopenta[b]thiophene-3-carboxamide (*Indian Journal of Heterocyclic Chemistry*, 2003, 13(2), 185-186), (480 mg, 1.64 mmol) was dissolved in a microwave vial with THF (9.60 ml) then cis-1,2-cyclohexane dicarboxylic anhydride (505 mg, 3.28 mmol) was added. The mixture was heated at 100° C. under microwave with 5 run of 1 h and monitoring the disappearance of the starting material. The mixture was cooled to rt then concentrated in vacuo to provide a brown solid. The residue was purified by column chromatography on silica gel (eluting with 0-20% EtOAc in cyclohexane) to give a product which was triturated in Et$_2$O. This residue was filtered, washed with Et$_2$O and dried under vacuum then freeze-dried to provide 2-[[3-[(4-chlorophenyl)carbamoyl]-5,6-dihydro-4H-cyclopenta[b]thiophen-2-yl]carbamoyl]cyclohexane-cis-carboxylic acid (478 mg, 65%) as a beige powder. $^1$H NMR (DMSO-$d_6$, 400 MHz): δ=12.14 (br s, 1H), 11.34 (br s, 1H), 9.20 (br s, 1H), 7.69 (d, J=9.0 Hz, 2H), 7.41 (d, J=9.0 Hz, 2H), 3.01 (m, 2H), 2.75-2.92 (m, 4H), 2.38 (quin, J=7.2 Hz, 2H), 1.97-2.11 (m, 1H), 1.86-1.96 (m, 1H), 1.77-1.87 (m, 1H), 1.64-1.75 (m, 1H), 1.56 (m, 1H), 1.25-1.50 ppm (m, 3H). LC/MS (Table 1, Method C) $R_t$=4.32 min; MS m/z: 447 [M+H]$^+$.

Example #48. 2-[[3-[(4-Chlorophenyl)carbamoyl]-5,6-dihydro-4H-cyclopenta[b]thiophen-2-yl]carbamoyl]cyclohexane-trans-carboxylic acid (Compound 49)

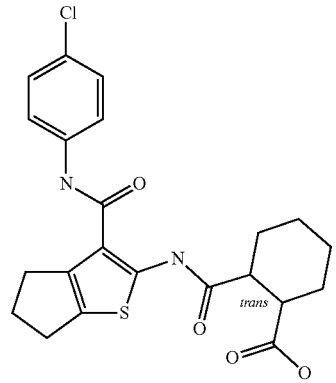

2-Amino-N-(4-chlorophenyl)-5,6-dihydro-4H-cyclopenta[b]thiophene-3-carboxamide (*Indian Journal of Heterocyclic Chemistry*, 2003, 13(2), 185-186), (100 mg, 0.34 mmol) was dissolved in a round bottomed flask with THF (2.00 ml) then trans-1,2-cyclohexane dicarboxylic anhydride (105 mg, 0.68 mmol) was added. The mixture was stirred under reflux for 24 h. The mixture was cooled to rt then concentrated in vacuo to provide a brown solid. The residue was washed several times with MeCN then EtOAc and EtOH. The solid product was resuspended in DMF (1.00 ml) and water (20 ml) was added to precipitate the pure product which was collected by filtration, washed with water and dried under vacuum to give 2-[[3-[(4-chlorophenyl)carbamoyl]-5,6-dihydro-4H-cyclopenta[b]thiophen-2-yl]carbamoyl]cyclohexane-trans-carboxylic acid (95 mg, 62%) as a beige powder. $^1$H NMR (CDCl$_3$, 500 MHz): δ=11.90 (s, 1H), 7.60 (s, 1H), 7.51 (d, J=8.8 Hz, 2H), 7.34 (d, J=8.8 Hz, 2H), 3.02 (br t, J=7.0 Hz, 2H), 2.90 (br t, J=7.0 Hz, 2H), 2.79 (td, Jaa=11.4 Hz, Jae=3.6 Hz, 1H), 2.67 (td, Jaa=11.4 Hz, Jae=3.6 Hz, 1H), 2.55 (quin, J=7.0 Hz, 2H), 2.15-2.22 (m, 1H), 2.04-2.10 (m, 1H), 1.81-1.86 (m, 2H), 1.48-1.61 (m, 1H), 1.25-1.48 ppm (m, 3H). LC/MS (Table 1, Method B) $R_t$=1.96 min; MS m/z: 447 [M+H]$^+$.

Example #49. 2-[1-[2-[[3-[(4-Chlorophenyl)carbamoyl]-5,6-dihydro-4H-cyclopenta[b]thiophen-2-yl]amino]-2-oxo-ethyl]cyclopentyl]acetic acid (Compound 45)

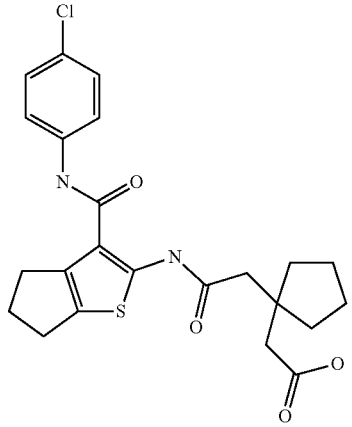

2-Amino-N-(4-chlorophenyl)-5,6-dihydro-4H-cyclopenta[b]thiophene-3-carboxamide (*Indian Journal of Heterocyclic Chemistry*, 2003, 13(2), 185-186), (100 mg, 0.34 mmol) was dissolved with THF (2.00 ml) then 3,3-tetramethyleneglutaric anhydride (115 mg, 0.68 mmol) was added. The mixture was stirred under reflux overnight, 5 days at room temperature then 3,3-tetramethyleneglutaric anhydride (115 mg, 0.68 mmol) was added again and the reaction mixture was heated 24 h under reflux to obtain full consumption of the starting amine. The mixture was cooled to rt then concentrated in vacuo to provide a brown solid. The residue was washed several times with MeCN and EtOAc to give 2-[1-[2-[[3-[(4-chlorophenyl)carbamoyl]-5,6-dihydro-4H-cyclopenta[b]thiophen-2-yl]amino]-2-oxo-ethyl] cyclopentyl]acetic acid (61 mg, 38%) as a beige powder. $^1$H NMR (DMSO-$d_6$, 400 MHz): δ=12.06 (br s, 1H), 10.99 (br s, 1H), 9.35 (br s, 1H), 7.70 (d, J=8.8 Hz, 2H), 7.40 (d, J=8.8 Hz, 2H), 2.96 (br t, J=6.8 Hz, 2H), 2.83 (br t, J=6.8 Hz, 2H), 2.62 (br s, 2H), 2.30-2.45 (m, 4H), 1.48-1.69 ppm (m, 8H). LC/MS (Table 1, Method B) $R_t$=2.02 min; MS m/z: 461 [M+H]$^+$.

Example #50. 2-[[3-[(4-Chlorophenyl)carbamoyl]-5,6-dihydro-4H-cyclopenta[b]thiophen-2-yl]carbamoyl]-7-oxabicyclo[2.2.1]heptane-3-carboxylic acid (Compound 51)

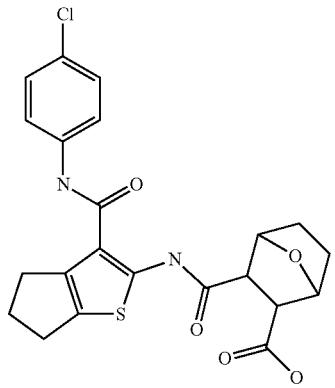

Step A. N-(4-Chlorophenyl)-2-(exo-3,6-epoxyhexahydrophthalimid-1-yl)-5,6-dihydro-4H-cyclopenta[b]thiophene-3-carboxamide

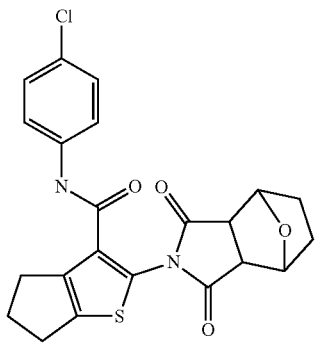 [SMILES: O=C(Nc1ccc(Cl)cc1)c1c(N2C(=O)C3C4CCC(O4)C3C2=O)sc2c1CCC2]

2-Amino-N-(4-chlorophenyl)-5,6-dihydro-4H-cyclopenta[b]thiophene-3-carboxamide (*Indian Journal of Heterocyclic Chemistry*, 2003, 13(2), 185-186), (100 mg, 0.34 mmol) was dissolved with THF (2.00 ml) then norcantharidine (57 mg, 0.34 mmol) was added. The mixture was stirred under reflux overnight. The mixture was cooled to rt then concentrated in vacuo to provide a brown solid. The residue was washed several times with MeCN. The solid was purified by RP-HPLC (Table 2, Method 2) to provide N-(4-chlorophenyl)-2-(exo-3,6-epoxyhexahydrophthalimid-1-yl)-5,6-dihydro-4H-cyclopenta[b]thiophene-3-carboxamide (0.072 g, 48%) as a brown solid. $^1$H NMR (DMSO-$d_6$, 300 MHz): δ=10.00 (s, 1H), 7.63 (d, J=8.9 Hz, 2H), 7.35 (d, J=8.9 Hz, 2H), 4.74 (s, 2H), 3.21 (s, 2H), 2.90 (m, 4H), 2.37 (quin, J=7.1 Hz, 2H), 1.64 ppm (s, 4H). LC/MS (Table 1, Method A) $R_t$=2.10 min; MS m/z: 443 [M+H]$^+$.

Step B. 2-[[3-[(4-Chlorophenyl)carbamoyl]-5,6-dihydro-4H-cyclopenta[b]thiophen-2-yl]carbamoyl]-7-oxabicyclo[2.2.1]heptane-3-carboxylic acid

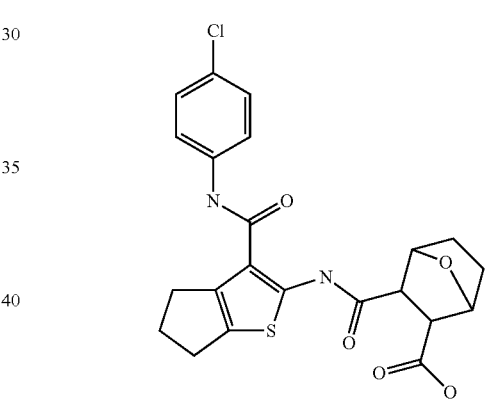

A solution of KOH (31 mg; 0.55 mmol) in water (140 µl) was added at rt onto N-(4-chlorophenyl)-2-(exo-3,6-epoxyhexahydrophthalimid-1-yl)-5,6-dihydro-4H-cyclopenta[b]thiophene-3-carboxamide (Example #50, Step A, 70 mg, 0.16 mmol) previously dissolved in THF (2.85 ml). The reaction mixture was further stirred at rt overnight. The mixture was then concentrated under reduced pressure and the residue was dissolved in EtOAc and acidified with HCl 1M. The aqueous layer was extracted two times with AcOEt and the combined organic layers were dried over MgSO$_4$, filtered and concentrated in vacuo to furnish a white gum which was freeze dried after taking up with EtOH and water providing 2-[[3-[(4-chlorophenyl)carbamoyl]-5,6-dihydro-4H-cyclopenta[b]thiophen-2-yl]carbamoyl]-7-oxabicyclo[2.2.1]heptane-3-carboxylic acid (0.034 g, 47%) as a white powder. $^1$H NMR (DMSO-$d_6$/D$_2$O, 500 MHz): δ=7.47 (d, J=8.9 Hz, 2H), 7.34 (d, J=8.9 Hz, 2H), 4.83 (d, J=4.1 Hz, 1H), 4.65 (d, J=4.1 Hz, 1H), 3.06 (br s, 2H), 2.87 (br t, J=7.1 Hz, 2H), 2.74 (br t, J=7.1 Hz, 2H), 2.33 (quin, J=7.1 Hz, 2H), 1.45-1.68 ppm (m, 4H). LC/MS (Table 1, Method B) $R_t$=1.67 min; MS m/z: 461 [M+H]$^+$.

Example #51. N-(4-Chlorophenyl)-2-(cyclohexanecarbonylamino)-5,6-dihydro-4H-cyclopenta[b]thiophene-3-carboxamide (Compound 52)

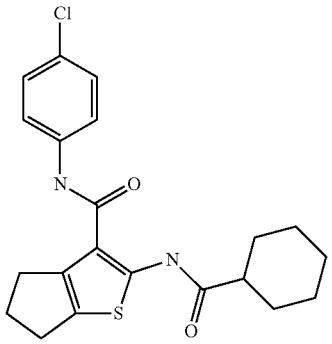 [SMILES: O=C(Nc1ccc(Cl)cc1)c1c(NC(=O)C2CCCCC2)sc2c1CCC2]

2-Amino-N-(4-chlorophenyl)-5,6-dihydro-4H-cyclopenta[b]thiophene-3-carboxamide (*Indian Journal of Heterocyclic Chemistry*, 2003, 13(2), 185-186), (100 mg, 0.34 mmol) and Et$_3$N (95 µl; 0.68 mmol) in THF (1.00 ml) were stirred for 15 min before adding a solution made of cyclohexane carbonyl chloride (53 mg; 0.36 mmol) in THF (1.00 ml) dropwise. The mixture was stirred at rt for 90 min. A new portion of cyclohexane carbonyl chloride (25 mg; 0.17 mmol) was added and the reaction was further pursued at rt for 1 h. Water (20 ml) and few drop of NaOH 1M were poured in the mixture and the product was extracted with EtOAc (2×25 ml). Organics layers were combined, washed with brine, dried over MgSO$_4$ and concentrated to provide 150 mg of crude compound. The residue was purified by column chromatography on silica gel (eluting with 0-10% EtOAc in cyclohexane) to give N-(4-chlorophenyl)-2-(cyclohexanecarbonylamino)-5,6-dihydro-4H-cyclopenta[b]thiophene-3-carboxamide (125 mg, 91%) as a beige powder. $^1$H NMR (DMSO-d$_6$, 500 MHz): δ=11.12 (br s, 1H), 9.28 (br s, 1H), 7.69 (d, J=8.8 Hz, 2H), 7.41 (d, J=8.8 Hz, 2H), 2.98 (br t, J=7.0 Hz, 2H), 2.82 (br t, J=7.0 Hz, 2H), 2.45 (tt, J=11.0, 3.0 Hz, 1H), 2.37 (quin, J=7.0 Hz, 2H), 1.86 (br d, J=11.0 Hz, 2H), 1.73 (dt, J=12.3, 2.9 Hz, 2H), 1.59-1.66 (m, 1H), 1.11-1.45 ppm (m, 5H). LC/MS (Table 1, Method A) R$_t$=2.68 min; MS m/z: 403 [M+H]$^+$.

Example #52. N-(4-Chlorophenyl)-2-[(3-oxocyclohexanecarbonyl)amino]-5,6-dihydro-4H-cyclopenta[b]thiophene-3-carboxamide (Compound 53)

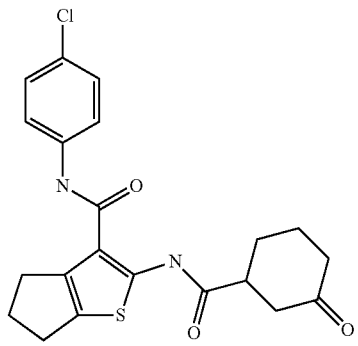 [SMILES: O=C1CCCC(C(=O)Nc2sc3c(c2C(=O)Nc2ccc(Cl)cc2)CCC3)C1]

2-Amino-N-(4-chlorophenyl)-5,6-dihydro-4H-cyclopenta[b]thiophene-3-carboxamide (*Indian Journal of Heterocyclic Chemistry*, 2003, 13(2), 185-186), (100 mg, 0.34 mmol), 3-oxo-1-cyclohexanecarboxylic acid (73 mg; 0.51 mmol) and EDCI (98 mg; 0.51 mmol) were solubilized in DMF (1.00 ml) and stirred at rt overnight. 3-Oxo-1-cyclohexanecarboxylic acid (73 mg; 0.51 mmol) and EDCI (98 mg; 0.51 mmol) were added again and the reaction mixture was further stirred at rt for 24 h. The reaction mixture was diluted with water and extracted with EtOAc (3×). Organics layers were combined and washed with HCl 1M (2×) and brine, dried over MgSO$_4$, filtered and concentrated to give 180 mg of crude product. The residue was first purified by column chromatography on silica gel (eluting with 0-30% EtOAc in cyclohexane) to give 45 mg of an impure product which was repurified by RP-HPLC (Table 2, Method 1) to provide N-(4-chlorophenyl)-2-[(3-oxocyclohexanecarbonyl)amino]-5,6-dihydro-4H-cyclopenta[b]thiophene-3-carboxamide (28 mg, 20%) as a white powder. $^1$H NMR (DMSO-d$_6$, 400 MHz): δ=11.06 (s, 1H), 9.44 (s, 1H), 7.71 (d, J=9.0 Hz, 2H), 7.40 (d, J=9.0 Hz, 2H), 2.99-3.11 (m, 1H), 2.92-2.97 (m, 2H), 2.83 (br t, J=7.3 Hz, 2H), 2.51-2.60 (m, 1H), 2.29-2.44 (m, 4H), 2.15-2.27 (m, 1H), 1.90-2.05 (m, 2H), 1.62-1.85 ppm (m, 2H). LC/MS (Table 1, Method B) R$_t$=1.87 min; MS m/z: 417 [M+H]$^+$.

Example #53. N-(4-Chlorophenyl)-2-(1,3-dioxo-3a,4,5,6,7,7a-hexahydroisoindol-2-yl)-5,6-dihydro-4H-cyclopenta[b]thiophene-3-carboxamide (Compound 54)

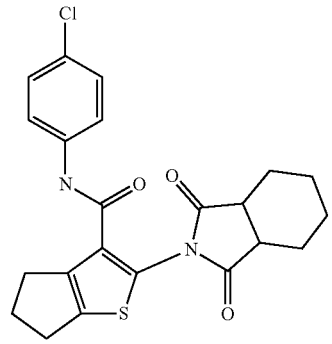 [SMILES: O=C(Nc1ccc(Cl)cc1)c1c(N2C(=O)C3CCCCC3C2=O)sc2c1CCC2]

2-[[3-[(4-Chlorophenyl)carbamoyl]-5,6-dihydro-4H-cyclopenta[b]thiophen-2-yl]carbamoyl] cyclohexane-cis-carboxylic acid (Example #47, 150 mg, 0.34 mmol), was dissolved in DMF (3.00 ml) then HATU (166 mg, 0.44 mmol) and N-methylmorpholine (55 µl, 0.50 mmol) were added at rt. The mixture was stirred at rt overnight. To this mixture was added 20 ml of Aq NaHCO$_3$ to give a white suspension which was filtered, washed with water, Aq HCl 1M then water (3×) and dried in vacuo to give N-(4-chlorophenyl)-2-(1,3-dioxo-3a,4,5,6,7,7a-hexahydroisoindol-2-yl)-5,6-dihydro-4H-cyclopenta[b]thiophene-3-carboxamide (136 mg, 93%) as a white powder. $^1$H NMR (DMSO-d$_6$, 300 MHz): δ=10.15 (s, 1H), 7.65 (d, J=8.9 Hz, 2H), 7.37 (d, J=8.9 Hz, 2H), 3.08 (m, 2H), 2.83-2.98 (m, 4H), 2.37 (quin, J=7.1 Hz, 2H), 1.72 (br s, 4H), 1.20-1.46 ppm (m, 4H). LC/MS (Table 1, Method A) R$_t$=2.43 min; MS m/z: 429 [M+H]$^+$.

Example #54. N2-[3-[(4-Chlorophenyl)carbamoyl]-5,6-dihydro-4H-cyclopenta[b]thiophen-2-yl]cyclohexane-1,2-dicarboxamide (Compound 55)

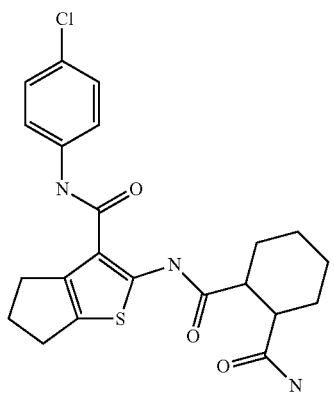 [SMILES: NC(=O)C1CCCCC1C(=O)Nc1sc2c(c1C(=O)Nc1ccc(Cl)cc1)CCC2]

N-(4-Chlorophenyl)-2-(1,3-dioxo-3a,4,5,6,7,7a-hexahydroisoindol-2-yl)-5,6-dihydro-4H-cyclopenta[b]thiophene-3-carboxamide (Example #53, 50 mg, 0.12 mmol) and ammonia 7N in MeOH (200 µl, 1.40 mmol) were stirred together in a sealed tube for 1 h at room temperature. The reaction was not complete and ammonia 7N in MeOH (800 µl, 5.60 mmol) was added again and the reaction mixture was further stirred at rt overnight. Upon completion of the reaction, the solvents were removed under reduced pressure to provide the clean title compound N2-[3-[(4-chlorophenyl)carbamoyl]-5,6-dihydro-4H-cyclopenta[b]thiophen-2-yl]cyclohexane-1,2-dicarboxamide (50 mg, 92%) as a yellow powder. $^1$H NMR (DMSO-$d_6$, 400 MHz): δ=11.30 (s, 1H), 9.11 (s, 1H), 7.69 (d, J=8.8 Hz, 2H), 7.41 (d, J=8.8 Hz, 2H), 7.20 (br s, 1H), 6.70 (br s, 1H), 3.01 (t, J=7.0 Hz, 2H), 2.77-2.89 (m, 3H), 2.67 (m, 1H), 2.38 (quin, J=7.0 Hz, 2H), 1.97-2.16 (m, 2H), 1.73-1.83 (m, 1H), 1.57-1.72 (m, 2H), 1.26-1.47 ppm (m, 3H). LC/MS (Table 1, Method B) $R_t$=1.84 min; MS m/z: 446 [M+H]$^+$.

Example #55. N-(4-Chlorophenyl)-2-[[2-(hydroxymethyl)cyclohexanecarbonyl]amino]-5,6-dihydro-4H-cyclopenta[b]thiophene-3-carboxamide (Compound 56)

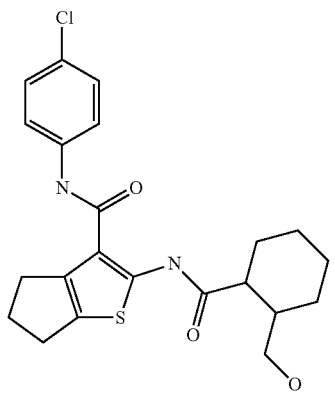 [SMILES: O=C(Nc1ccc(Cl)cc1)c1c(NC(=O)C2CCCCC2CO)sc2c1CCC2]

2-[[3-[(4-Chlorophenyl)carbamoyl]-5,6-dihydro-4H-cyclopenta[b]thiophen-2-yl]carbamoyl]cyclohexane-cis-carboxylic acid (Example #47, 141 mg, 0.32 mmol) was dissolved in THF (7.00 ml). Borane dimethyl sulfide complex (BMS) 2M in THF (1.20 ml, 2.40 mmol) was added and the yellow mixture was stirred at rt for 90 min. The reaction mixture was then quenched with a slow addition of MeOH (7.00 ml) and the mixture was stirred at rt for 1 h before removing the solvent under reduced pressure. The residue was first purified by column chromatography on silica gel (eluting with 0-30% EtOAc in cyclohexane) to give 80 mg of an impure product which was repurified by RP-HPLC (Table 2, Method 2) to provide N-(4-chlorophenyl)-2-[[2-(hydroxymethyl)cyclohexanecarbonyl]amino]-5,6-dihydro-4H-cyclopenta[b]thiophene-3-carboxamide (60 mg, 44%) as a white powder. $^1$H NMR (DMSO-$d_6$, 400 MHz): δ=11.14 (s, 1H), 9.22 (s, 1H), 7.69 (d, J=9.0 Hz, 2H), 7.40 (d, J=9.0 Hz, 2H), 4.47 (t, J=5.0 Hz, 1H), 3.35-3.47 (m, 1H), 3.17-3.29 (m, 1H), 2.99 (br t, J=7.0 Hz, 2H), 2.82 (m, 3H), 2.38 (quin, J=7.0 Hz, 2H), 1.89-1.99 (m, 1H), 1.66-1.80 (m, 3H), 1.48-1.63 (m, 2H), 1.27-1.46 ppm (m, 3H). LC/MS (Table 1, Method B) $R_t$=2.01 min; MS m/z: 431 [M–H]$^-$.

Example #56. 2-[[3-[(4-Chlorophenyl)carbamoyl]benzothiophen-2-yl]carbamoyl]cyclohexane carboxylic acid (Compound 41)

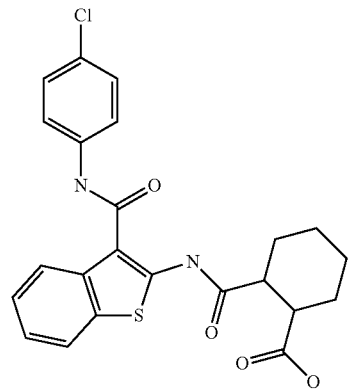 [SMILES: O=C(Nc1ccc(Cl)cc1)c1c(NC(=O)C2CCCCC2C(=O)O)sc2ccccc12]

Step A. Methyl 2-[[3-[(4-chlorophenyl)carbamoyl]-4,5,6,7-tetrahydrobenzothiophen-2-yl]carbamoyl]cyclohexanecarboxylate

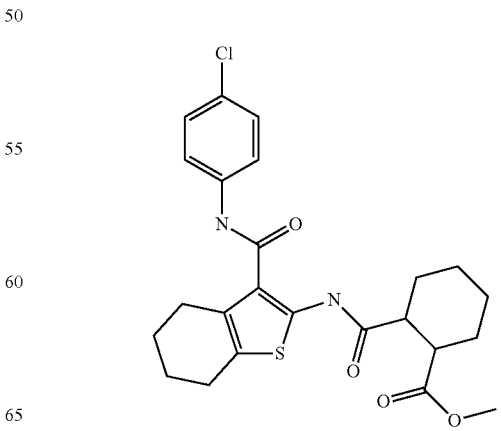

2-[[3-[(4-Chlorophenyl)carbamoyl]-4,5,6,7-tetrahydrobenzothiophen-2-yl]carbamoyl]cyclohexane-cis-carboxylic acid (Example #11, 2.92 g, 6.32 mmol) was dissolved in a mixture of $Et_2O$ (40 ml) and MeOH (10 ml) then trimethylsilyl diazomethane 2M in hexanes (9.50 ml, 19 mmol) was carefully added dropwise at 0° C. during 15 min. The pale yellow reaction mixture was allowed to warm to rt and was further stirred at rt for 3h. MeOH (10 ml) and trimethylsilyl diazomethane 2M in hexanes (9.50 ml, 19 mmol) were added again at 0° C. and the reaction was stopped after 2 more hours once complete conversion was observed. The reaction mixture was cooled to 0° C. and 12 ml of formic acid was cautiously added dropwise with formation of a precipitate. Both precipitate and filtrate were dissolved in DCM and this organic phase was washed with water, Aq $NaHCO_3$ (2×), then brine. The organic layer was dried over $MgSO_4$ and evaporated to provide methyl 2-[[3-[(4-chlorophenyl)carbamoyl]-4,5,6,7-tetrahydrobenzothiophen-2-yl]carbamoyl]cyclohexanecarboxylate (2.50 g; 83%) as a white solid. $^1$H NMR (DMSO-$d_6$, 300 MHz): δ=10.68 (s, 1H), 9.80 (s, 1H), 7.71 (d, J=8.9 Hz, 2H), 7.39 (d, J=8.9 Hz, 2H), 3.52 (s, 3H), 2.95-3.05 (m, 1H), 2.76-2.85 (m, 1H), 2.54-2.75 (m, 4H), 1.85-2.04 (m, 2H), 1.62-1.83 (m, 6H), 1.42-1.59 (m, 2H), 1.28-1.41 ppm (m, 2H). LC/MS (Table 1, Method A) $R_t$=2.81 min; MS m/z: 475 [M+H]$^-$.

Step B. Methyl 2-[[3-[(4-chlorophenyl)carbamoyl]benzothiophen-2-yl]carbamoyl]cyclohexane carboxylate

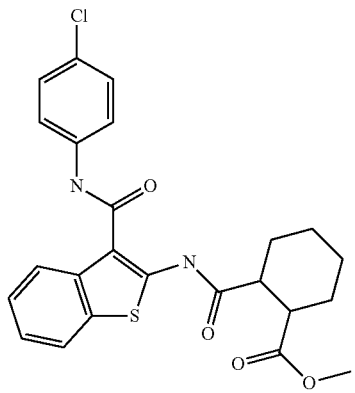 [SMILES: COC(=O)C1CCCCC1C(=O)Nc1sc2ccccc2c1C(=O)Nc1ccc(Cl)cc1]

Methyl 2-[[3-[(4-chlorophenyl)carbamoyl]-4,5,6,7-tetrahydrobenzothiophen-2-yl]carbamoyl] cyclohexanecarboxylate (Example #56, Step A, 1.85 g, 3.89 mmol) was dissolved in fluorobenzene (110 ml) and this yellow solution was heated to 90° C. To this solution was added 2,3-dichloro-5,6-dicyano-1,4-benzoquinone (1.32 g, 5.83 mmol) and the heating was pursued at 90° C. Some 2,3-dichloro-5,6-dicyano-1,4-benzoquinone (260 mg, 1.15 mmol) was added again after 1 h and a third portion of 2,3-dichloro-5,6-dicyano-1,4-benzoquinone (260 mg, 1.15 mmol) was added again after 2 h. The reaction is left stirred at 90° C. for 15 minutes more and stopped after completion. The mixture was diluted with EtOAc (300 ml) and washed with Aq $NaHCO_3$ (2×200 ml). Product was extracted with EtOAc (2×200 ml) and combined organic layers were washed again with water and brine then dried over $MgSO_4$, filtered and concentrated in vacuo to give 1.6 g of a dark brown solid. This residue was triturated in DCM to provide a first crop of desired product as an insoluble off white powder (0.39 g, 21%) after washing with DCM and $Et_2O$. The filtrate was concentrated and purified by column chromatography on silica gel (eluting with 5-20% EtOAc in cyclohexane) to give a second crop of methyl 2-[[3-[(4-chlorophenyl)carbamoyl]benzothiophen-2-yl]carbamoyl]cyclohexanecarboxylate (0.93 g; 51%) as an off-white solid. $^1$H NMR (DMSO-$d_6$, 300 MHz): δ=11.19 (s, 1H), 10.43 (s, 1H), 7.93 (d, J=7.9 Hz, 1H), 7.86 (d, J=7.9 Hz, 1H), 7.79 (d, J=8.9 Hz, 2H), 7.39-7.49 (m, 3H), 7.33 (td, J=7.9, 0.9 Hz, 1H), 3.56 (s, 3H), 3.03-3.15 (m, 1H), 2.86-2.97 (m, 1H), 1.92-2.08 (m, 2H), 1.69-1.89 (m, 2H), 1.32-1.61 ppm (m, 4H). LC/MS (Table 1, Method A) $R_t$=2.85 min; MS m/z: 471 [M+H]$^+$.

Step C. 2-[[3-[(4-Chlorophenyl)carbamoyl]benzothiophen-2-yl]carbamoyl]cyclohexanecarboxylic acid (Compound 41)

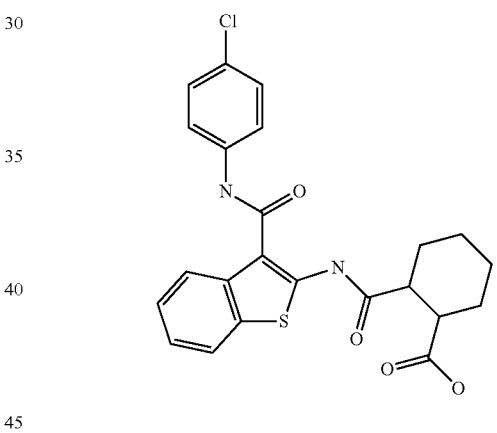

Methyl 2-[[3-[(4-chlorophenyl)carbamoyl]benzothiophen-2-yl]carbamoyl]cyclohexanecarboxylate (Example #56, Step B, 1.32 g, 2.80 mmol) was solubilized in a mixture of THF (10 ml) and water (10 ml) before addition of lithium hydroxide monohydrate (258 mg, 6.16 mmol) at room temperature. The reaction mixture was then stirred 3 h at 70° C. THF was evaporated under reduced pressure and the aqueous residue was diluted with water. The medium was adjusted to pH 1 with conc HCl forming a precipitate. This precipitate was filtered and washed with water (3× until pH 6-7) an dried under vacuum at 35° C. overnight to give 2-[[3-[(4-chlorophenyl)carbamoyl]benzothiophen-2-yl]carbamoyl] cyclohexane carboxylic acid (1.14 g, 86%) as a white solid. $^1$H NMR (DMSO-$d_6$, 500 MHz): δ=12.16 (br s, 1H), 11.21 (s, 1H), 10.40 (s, 1H), 7.93 (d, J=7.9 Hz, 1H), 7.86 (d, J=7.9 Hz, 1H), 7.78 (d, J=8.9 Hz, 2H), 7.43 (m, 3H), 7.32 (m, 1H), 2.98-3.07 (m, 1H), 2.77-2.86 (m, 1H), 2.01-2.10 (m, 1H), 1.93-2.01 (m, 1H), 1.76-1.86 (m, 1H), 1.68-1.76 (m, 1H), 1.30-1.60 ppm (m, 4H). LC/MS (Table 1, Method C) $R_t$=4.51 min; MS m/z: 455 [M–H]$^-$.

Example #57. 2-[[3-[(4-Chlorophenyl)carbamoyl]thieno[3,4-b]thiophen-2-yl]carbamoyl]cyclohexanecarboxylic acid (Compound 42)

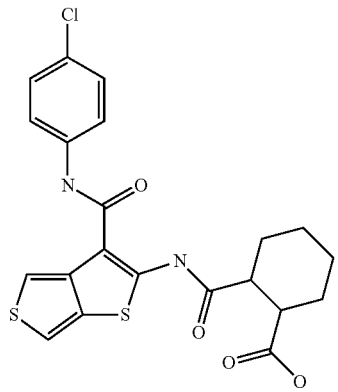 [SMILES: O=C(Nc1ccc(Cl)cc1)c1c(NC(=O)C2CCCCC2C(=O)O)sc2cscc12]

Step A. tert-Butyl 2-amino-4,6-dihydrothieno[3,4-b]thiophene-3-carboxylate and tert-butyl 5-amino-2,3-dihydrothieno[2,3-b]thiophene-4-carboxylate

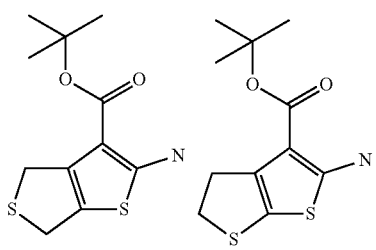

tert-Butyl cyanoacetate (13.3 g, 94.5 mmol) and tetrahydrothiophen-3-one (9.55 g, 93.5 mmol) were dissolved in ethanol (150 ml) then sulfur (3 g, 93.5 mmol) and morpholine (24.5 ml, 280 mmol) were added and the mixture was stirred at 50° C. overnight. The mixture was cooled to rt then concentrated in vacuo. The residue was dissolved with DCM (500 ml), washed with Aq NH$_4$Cl and extracted with DCM (2×). The combined organic phase was dried with MgSO$_4$ and concentrated in vacuo to provide 26 g of a black paste. The residue was purified by column chromatography on silica gel (eluting with 0-5% EtOAc in cyclohexane) to give Compound C: tert-butyl 2-amino-4,6-dihydrothieno[3,4-b]thiophene-3-carboxylate (3.46 g, 14%) as a yellow oil. $^1$H NMR (CDCl$_3$, 300 MHz): δ=5.58 (br s, 1H), 4.12 (dd, J=4.0, 3.2 Hz, 2H), 3.99 (dd, J=4.0, 3.2 Hz, 2H), 1.53 ppm (s, 9H). LC/MS (Table 1, Method A) R$_t$=2.29 min; MS m/z: 258 [M+H] and Compound D: tert-butyl 5-amino-2,3-dihydrothieno[2,3-b]thiophene-4-carboxylate (4.29 g, 16%) as a yellow oil. $^1$H NMR (CDCl$_3$, 300 MHz): δ=5.44 (br s, 1H), 3.56-3.80 (m, 2H), 3.06-3.30 (m, 2H), 1.54 ppm (s, 9H). LC/MS (Table 1, Method A) R$_t$=2.29 min; MS m/z: 256 [M−H]$^−$.

Step B. 2-[(3-tert-Butoxycarbonyl-4,6-dihydrothieno[3,4-b]thiophen-2-yl)carbamoyl] cyclohexane-cis-carboxylic acid

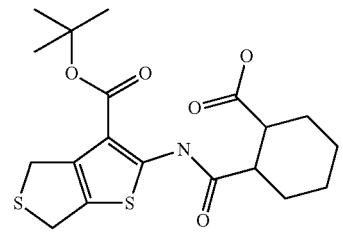 [SMILES: CC(C)(C)OC(=O)c1c(NC(=O)C2CCCCC2C(=O)O)sc2c1CSC2]

tert-Butyl 2-amino-4,6-dihydrothieno[3,4-b]thiophene-3-carboxylate (Compound C: Example #57, Step A, 3.45 g, 13.4 mmol) was dissolved in THF (20 ml) then cis-1,2-cyclohexane dicarboxylic anhydride (4.13 g, 26.8 mmol) was added. The mixture was stirred under reflux overnight. The mixture was cooled to rt then concentrated in vacuo to provide a white solid. The residue was taken up in EtOAc, filtered and washed three times with a minimum of EtOAc. The solid was dried under vacuum to give 2-[(3-tert-butoxycarbonyl-4,6-dihydrothieno[3,4-b]thiophen-2-yl)carbamoyl]cyclohexanecarboxylic acid (3.97 g, 72%) as a white powder. $^1$H NMR (DMSO-d$_6$, 400 MHz): δ=12.23 (br s, 1H), 11.04 (s, 1H), 4.14 (dd, J=5.0, 2.5 Hz, 2H), 4.09 (dd, J=5.0, 2.5 Hz, 2H), 2.92 (m, 2H), 1.97-2.11 (m, 1H), 1.82-1.96 (m, 2H), 1.69 (m, 1H), 1.56-1.64 (m, 1H), 1.54 (s, 9H), 1.31-1.50 ppm (m, 3H). LC/MS (Table 1, Method A) R$_t$=2.53 min; MS m/z: 412 [M+H]$^+$.

Step C. tert-Butyl 2-(1,3-dioxo-3a,4,5,6,7,7a-hexahydroisoindol-2-yl)-4,6-dihydrothieno[3,4-b]thiophene-3-carboxylate

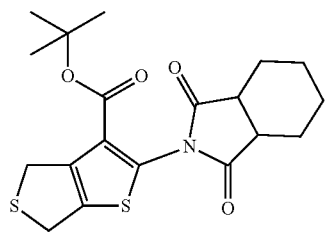 [SMILES: CC(C)(C)OC(=O)c1c(N2C(=O)C3CCCCC3C2=O)sc2c1CSC2]

2-[(3-tert-Butoxycarbonyl-4,6-dihydrothieno[3,4-b]thiophen-2-yl)carbamoyl]cyclohexanecarboxylic acid (Example #57, Step B, 3.97 g, 9.64 mmol) was dissolved in DMF (80 ml) then HATU (4.77 g, 12.54 mmol) and N-methylmorpholine (1.46 g, 14.43 mmol) were added. The mixture was stirred at rt for 2 h. The mixture was quenched with NaHCO$_3$ (200 ml) allowing the product to precipitate. This solid was filtered and washed several time with water and dried under vacuum to give tert-butyl 2-(1,3-dioxo-3a,4,5,6,7,7a-hexahydroisoindol-2-yl)-4,6-dihydrothieno[3,4-b]thiophene-3-carboxylate (3.38 g, 89%) as a white solid. $^1$H NMR (DMSO-d$_6$, 300 MHz): δ=4.22 (d, J=4.3 Hz, 2H), 4.19 (d, J=4.3 Hz, 2H), 3.13 (br t, J=4.6 Hz, 2H), 1.75-1.85 (m, 4H), 1.45 (s, 9H), 1.36-1.43 ppm (m, 4H). LC/MS (Table 1, Method A) R$_t$=2.45 min; MS m/z: 394 [M+H]$^+$.

Step D. tert-Butyl 2-(1,3-dioxo-3a,4,5,6,7,7a-hexahydroisoindol-2-yl)thieno[3,4-b]thiophene-3-carboxylic acid

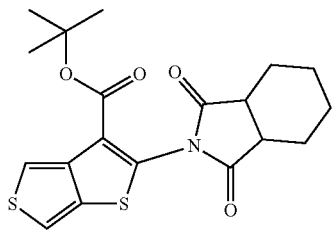 [SMILES: CC(C)(C)OC(=O)c1c(N2C(=O)C3CCCCC3C2=O)sc2cscc12]

tert-Butyl 2-(1,3-dioxo-3a,4,5,6,7,7a-hexahydroisoindol-2-yl)-4,6-dihydrothieno[3,4-b]thiophene-3-carboxylate (Example #57, Step C, 890 mg, 2.26 mmol) was dissolved in Fluorobenzene (30 ml) at rt then 2,3-dichloro-5,6-dicyano-1,4-benzoquinone (770 mg; 3.39 mmol) was added and the resulting brown mixture was stirred at rt for 1 h. The mixture was diluted with EtOAc (100 ml) washed with Aq NaHCO$_3$ (100 ml) and extracted with DCM (2×100 ml). The combined organic phase was dried with MgSO$_4$ and concentrated in vacuo to provide 1.12 g of a brown paste. The residue was purified by column chromatography on silica gel (eluting with 0-10% EtOAc in cyclohexane) to give tert-butyl 2-(1,3-dioxo-3a,4,5,6,7,7a-hexahydroisoindol-2-yl)thieno[3,4-b]thiophene-3-carboxylic acid (772 mg, 87%) as a white solid. $^1$H NMR (DMSO-d$_6$, 300 MHz): δ=7.92 (d, J=2.9 Hz, 1H), 7.86 (d, J=2.9 Hz, 1H), 3.18 (br t, J=5.4 Hz, 2H), 1.82 (m, 4H), 1.53 (s, 9H), 1.43 ppm (m, 4H). LC/MS (Table 1, Method A) R$_t$=2.50 min; MS m/z: 392 [M+H]$^+$.

Step E. 2-(1,3-Dioxo-3a,4,5,6,7,7a-hexahydroisoindol-2-yl)thieno[3,4-b]thiophene-3-carboxylic acid

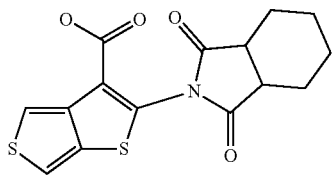 [SMILES: O=C(O)c1c(N2C(=O)C3CCCCC3C2=O)sc2cscc12]

tert-Butyl 2-(1,3-dioxo-3a,4,5,6,7,7a-hexahydroisoindol-2-yl)thieno[3,4-b]thiophene-3-carboxylic acid (Example #57, Step D, 480 mg, 1.23 mmol) was placed in a flame dried 100 mL round bottom flask and dissolved with HCl 4M in 1,4-Dioxane (42 ml, 168 mmol). The colorless mixture was heated at 100° C. for 3 h, cooled down and evaporated then kept in a desiccator under vacuum at rt overnight. The reaction was completed after dissolved again with HCl 4M in 1,4-Dioxane (25 ml, 100 mmol) and heated for 1 h further at 100° C. The mixture was concentrated under vacuum at 60° C. for 1 h to give 2-(1,3-dioxo-3a,4,5,6,7,7a-hexahydroisoindol-2-yl)thieno[3,4-b]thiophene-3-carboxylic acid (412 mg, 100%) as a brown powder. $^1$H NMR (DMSO-d$_6$, 300 MHz): δ=13.34 (br s, 1H), 7.99 (d, J=2.9 Hz, 1H), 7.84 (d, J=2.9 Hz, 1H), 3.17 (m, 2H), 1.75-1.80 (m, 4H), 1.37-1.45 ppm (m, 4H). LC/MS (Table 1, Method A) R$_t$=1.80 min; MS m/z: 336 [M+H]$^+$.

Step F. N-(4-Chlorophenyl)-2-(1,3-dioxo-3a,4,5,6,7,7a-hexahydroisoindol-2-yl)thieno[3,4-b]thiophene-3-carboxamide

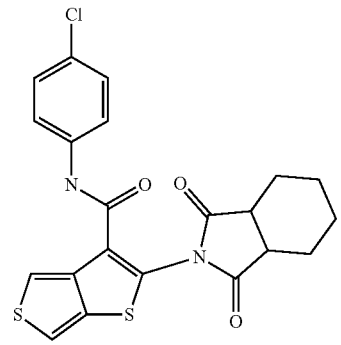 [SMILES: O=C(Nc1ccc(Cl)cc1)c1c(N2C(=O)C3CCCCC3C2=O)sc2cscc12]

2-(1,3-Dioxo-3a,4,5,6,7,7a-hexahydroisoindol-2-yl)thieno[3,4-b]thiophene-3-carboxylic acid (Example #57, Step E, 412 mg, 1.23 mmol) was dissolved in DMF (4.50 ml) then HATU (514 mg, 1.35 mmol), 4-chloroaniline (251 mg, 1.97 mmol) and N-methylmorpholine (149 mg, 1.47 mmol) were added at rt. The mixture was heated at 50° C. and stirred overnight at this temperature. The mixture was cooled to rt and 100 ml of HCl 1M were added to give a white suspension. It was extracted three times with EtOAc (50 ml). The combined organic layers were washed with 50 ml of brine, dried over MgSO$_4$, filtered and concentrated in vacuo to give 1.60 g of a brown solid. The residue was purified by column chromatography on silica gel (eluting with 0-20% EtOAc in cyclohexane) to give 425 mg of expected product still contaminated with residual 4-chloroaniline. The mixture was dissolved in DCM (20 ml) and stirred with polystyrene based isocyanate resin (400 mg; 0.61 mmol) overnight at rt. The resin was filtered off and washed with DCM. The organic phase was concentrated in vacuo to provide N-(4-chlorophenyl)-2-(1,3-dioxo-3a,4,5,6,7,7a-hexahydroisoindol-2-yl)thieno[3,4-b]thiophene-3-carboxamide (388 mg, 71%) as an orange powder. $^1$H NMR (DMSO-d$_6$, 300 MHz): δ=10.44 (s, 1H), 7.85 (d, J=2.8 Hz, 1H), 7.81 (d, J=2.8 Hz, 1H), 7.68 (d, J=8.6 Hz, 2H), 7.39 (d, J=8.6 Hz, 2H), 3.12 (br t, J=4.7 Hz, 2H), 1.65-1.77 (m, 4H), 1.20-1.40 ppm (m, 4H). LC/MS (Table 1, Method A) R$_t$=2.37 min; MS m/z: 445 [M+H]$^+$.

Step G. 2-[[3-[(4-Chlorophenyl)carbamoyl]thieno[3,4-b]thiophen-2-yl]carbamoyl]cyclohexanecarboxylic acid

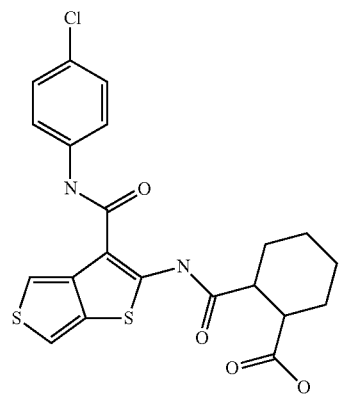 [SMILES: O=C(Nc1ccc(Cl)cc1)c1c(NC(=O)C2CCCCC2C(=O)O)sc2cscc12]

N-(4-Chlorophenyl)-2-(1,3-dioxo-3a,4,5,6,7,7a-hexahydroisoindol-2-yl)thieno[3,4-b]thiophene-3-carboxamide (Example #57, Step F, 577 mg, 1.30 mmol) was dissolved in THF (20 ml) and water (10 ml). To this solution was added LiOH·H$_2$O (272 mg, 6.48 mmol) and the mixture was stirred at rt for 1 h. THF was evaporated and the aqueous residue was diluted with 20 ml of water and acidified with HCl 1M until pH 1. The precipitate was filtered, washed three times with water until neutral pH an dried under vacuum to give 2-[[3-[(4-chlorophenyl)carbamoyl]thieno[3,4-b]thiophen-2-yl]carbamoyl]cyclohexanecarboxylic acid (580 mg, 97%) as a pink powder.

Preparation #1. 2-Amino-N-[4-chloro-3-(trifluoromethyl)phenyl]-5,6-dihydro-4H-cyclopenta[b]thiophene-3-carboxamide

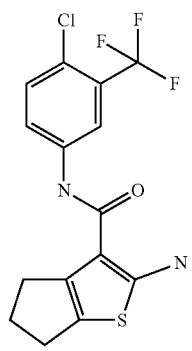 [SMILES: Nc1sc2c(c1C(=O)Nc1ccc(Cl)c(C(F)(F)F)c1)CCC2]

Step A. N-[4-Chloro-3-(trifluoromethyl)phenyl]-2-cyano-acetamide

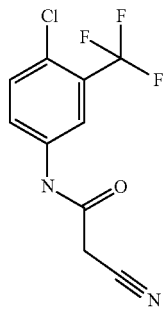 [SMILES: N#CCC(=O)Nc1ccc(Cl)c(C(F)(F)F)c1]

Cyanoacetic acid (283 mg; 3.3 mmol) was dissolved in DCM (6.00 ml) and two drops of DMF followed by oxalyl chloride (430 µl; 5.00 mmol) were successively added (gas release). The colorless mixture was stirred for 1 h at rt then concentrated in vacuo to give a black oil. 4-Chloro-3-(trifluoromethyl)aniline (0.37 ml; 3.00 mmol) and DIEA (660 µl; 4.00 mmol) were added at rt to the black residue previously taken up in 6 mL of DCM. The black mixture was stirred at rt overnight. The reaction was diluted with 20 mL of DCM, quenched by the addition of Aq NaHCO$_3$ and extracted with DCM. The combined organic phase was dried with MgSO$_4$ and concentrated in vacuo. The residue was purified by column chromatography on silica gel (eluting with 25-50% EtOAc in cyclohexane) to give N-[4-chloro-3-(trifluoromethyl)phenyl]-2-cyano-acetamide (0.229 g, 26%) as a pale yellow solid. $^1$H NMR (DMSO-d$_6$, 300 MHz): δ=10.74 (s, 1H), 8.11 (d, J=2.5 Hz, 1H), 7.79 (dd, J=8.6, 2.5 Hz, 1H), 7.70 (d, J=8.6 Hz, 1H), 3.96 ppm (s, 2H). LC/MS (Table 1, Method A) R$_t$=1.93 min; MS m/z: 261 [M−H]$^-$.

Step B. 2-Amino-N-[4-chloro-3-(trifluoromethyl)phenyl]-5,6-dihydro-4H-cyclopenta[b]thiophene-3-carboxamide

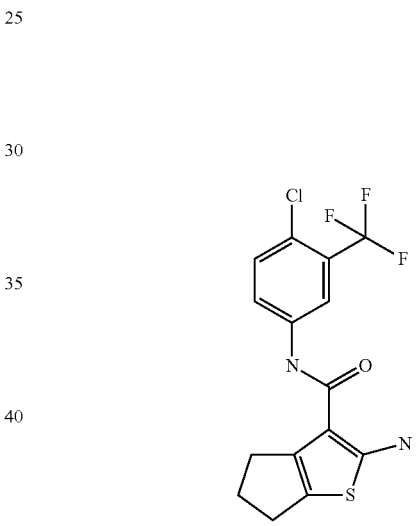

N-[4-Chloro-3-(trifluoromethyl)phenyl]-2-cyano-acetamide (Preparation #1, Step A, 225 mg, 0.86 mmol) was dissolved in Ethanol (3.00 ml) then cyclopentanone (72 mg, 0.86 mmol), sulfur (30 mg, 0.94 mmol) and morpholine (225 µl, 2.57 mmol) were added and the mixture was stirred at 50° C. overnight. The mixture was cooled to rt then concentrated in vacuo. The residue was dissolved with 25 mL of DCM, washed with 25 ml of Aq NH$_4$Cl and extracted with DCM (2×15 ml). The combined organic phase was dried with MgSO$_4$ and concentrated in vacuo to provide a brown solid. The residue was purified by column chromatography on silica gel (eluting with 10-20%0 EtOAc in cyclohexane) to give 2-amino-N-[4-chloro-3-(trifluoromethyl)phenyl]-5,6-dihydro-4H-cyclopenta[b]thiophene-3-carboxamide (0.073 g, 220%) as an orange oil. $^1$H NMR (DMSO-d$_6$, 300 MHz): δ=7.97 (s, 1H), 7.85 (d, J=8.6 Hz, 1H), 7.31 (d, J=2.6 Hz, 1H), 7.23 (dd, J=8.6, 2.6 Hz, 1H), 7.19 (s, 2H), 2.96 (t, J=7.1 Hz, 2H), 2.68 (t, J=7.1 Hz, 2H), 2.34 (quin, J=7.1 Hz, 2H). LC/MS (Table 1, Method A) R$_t$=2.59 mi; MS m/z: 361 [M+H]$^+$.

TABLE 3

The following compounds were prepared using the same procedure with the appropriate starting material.

| Compound | Structure | Starting material | Rt (min) | m/z ESI+ or ESI− |
|---|---|---|---|---|
| Preparation #2 | (6-chloropyridin-3-yl carboxamide of 2-amino-5,6-dihydro-4H-cyclopenta[b]thiophene-3-carboxamide) | 2-cyano-N-(6-chloropyridin-3-yl)acetamide | 2.03 (Table 1, Method A) | 294 [M + H]+ |
| Preparation #3 | (5-chloropyrazin-2-yl analog) | 2-cyano-N-(5-chloropyrazin-2-yl)acetamide | 2.22 (Table 1, Method A) | 295 [M + H]+ |
| Preparation #4 | (4-chloro-2-methylphenyl analog) | 2-cyano-N-(4-chloro-2-methylphenyl)acetamide | 2.43 (Table 1, Method A) | 307 [M + H]+ |
| Preparation #5 | (4-(trifluoromethyl)phenyl analog) | 2-cyano-N-(4-(trifluoromethyl)phenyl)acetamide | 2.47 (Table 1, Method A) | 327 [M + H]+ |

TABLE 3-continued

The following compounds were prepared using the same procedure with the appropriate starting material.

| Compound | Structure | Starting material | Rt (min) | m/z ESI+ or ESI− |
|---|---|---|---|---|
| Preparation #6 | 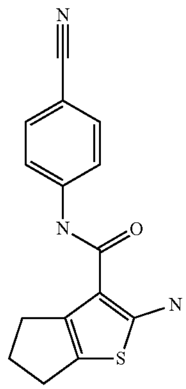 [SMILES: N#Cc1ccc(NC(=O)c2c(N)sc3c2CCC3)cc1] | | 2.14 (Table 1, Method A) | 284 [M + H]+ |
| Preparation #7 | 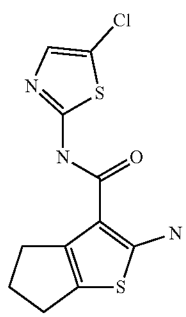 [SMILES: Nc1sc2c(c1C(=O)Nc1ncc(Cl)s1)CCC2] | | 2.24 (Table 1, Method A) | 300 [M + H]+ |

Preparation #8. 2-[(3-tert-Butoxycarbonyl-5,6-dihydro-4H-cyclopenta[b]thiophen-2-yl)carbamoyl]cyclohexanecarboxylic acid

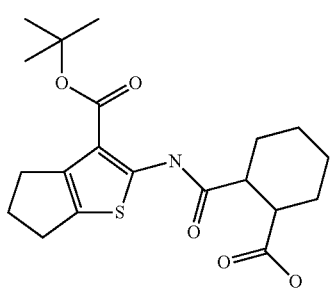 [SMILES: CC(C)(C)OC(=O)c1c(NC(=O)C2CCCCC2C(=O)O)sc2c1CCC2]

tert-Butyl 2-amino-5,6-dihydro-4H-cyclopenta[b]thiophene-3-carboxylate (*Journal of Medicinal Chemistry*, 2005, 48(26), 8270-8288), (2.60 g, 10.86 mmol) was dissolved in THF (40 ml) then cis-1,2-cyclohexane dicarboxylic anhydride (3.35 g, 21.73 mmol) was added. The mixture was stirred under reflux overnight. The mixture was cooled to rt then concentrated in vacuo to provide a white solid. The residue was resuspended in MeCN, filtered and washed three times with MeCN. The solid was dried under vacuum to give 2-[(3-tert-butoxycarbonyl-5,6-dihydro-4H-cyclopenta[b]thiophen-2-yl)carbamoyl]cyclohexanecarboxylic acid (4.08 g, 95%) as a white powder. $^1$H NMR (DMSO-$d_6$, 300 MHz): δ=12.20 (br s, 1H), 11.02 (s, 1H), 2.85-2.96 (m, 2H), 2.71-2.85 (m, 4H), 2.35 (quin, J=7.4 Hz, 2H), 1.96-2.12 (m, 1H), 1.81-1.96 (m, 2H), 1.57-1.76 (m, 2H), 1.53 (s, 9H), 1.29-1.48 ppm (m, 3H). LC/MS (Table 1, Method A) $R_t$=2.64 min; MS m/z: 394 [M+H]+.

Preparation #9. 2-(1,3-Dioxo-3a,4,5,6,7,7a-hexahydroisoindol-2-yl)-5,6-dihydro-4H-cyclopenta[b]thiophene-3-carboxylic acid

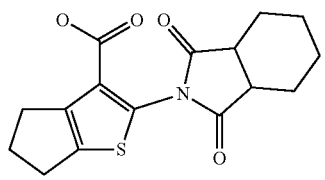 [SMILES: O=C(O)c1c(N2C(=O)C3CCCCC3C2=O)sc2c1CCC2]

Step A. tert-Butyl 2-(1,3-dioxo-3a,4,5,6,7,7a-hexahydroisoindol-2-yl)-5,6-dihydro-4H-cyclopenta[b]thiophene-3-carboxylate

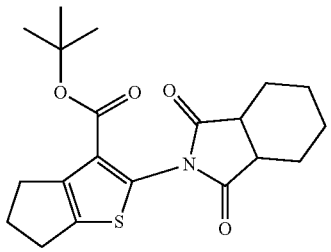 [SMILES: CC(C)(C)OC(=O)c1c(N2C(=O)C3CCCCC3C2=O)sc2c1CCC2]

2-[(3-tert-Butoxycarbonyl-5,6-dihydro-4H-cyclopenta[b]thiophen-2-yl)carbamoyl]cyclohexanecarboxylic acid (Preparation #8, 4.08 g, 10.37 mmol) was suspended in DCM (60 ml) then Et₃N (6.74 ml, 46.7 mmol) and HATU (3.94 g, 10.37 mmol) were added at rt. The reaction mixture was further stirred at this temperature overnight. The mixture was then diluted with DCM and washed with water. Residual product was extracted from aqueous layer with DCM and combined organic layers were then dried over MgSO₄, filtered and concentrated in vacuo. The crude product was purified by column chromatography on silica gel (eluting with 5-15% EtOAc in cyclohexane) to give tert-butyl 2-(1,3-dioxo-3a,4,5,6,7,7a-hexahydroisoindol-2-yl)-5,6-dihydro-4H-cyclopenta[b]thiophene-3-carboxylate (3.14 g, 81%) as a white solid. $^1$H NMR (DMSO-$d_6$, 300 MHz): δ=3.11 (m, 2H), 2.79-2.96 (m, 4H), 2.33 (quin, J=6.9 Hz, 2H), 1.80 (m, 4H), 1.44 (s, 9H), 1.37-1.43 ppm (m, 4H). LC/MS (Table 1, Method A) $R_t$=2.54 min; MS m/z: 376 [M+H]$^+$.

Step B. 2-(1,3-Dioxo-3a,4,5,6,7,7a-hexahydroisoindol-2-yl)-5,6-dihydro-4H-cyclopenta[b]thiophene-3-carboxylic acid

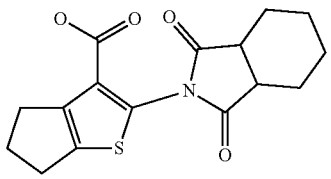 [SMILES: O=C(O)c1c(N2C(=O)C3CCCCC3C2=O)sc2c1CCC2]

To tert-butyl 2-(1,3-dioxo-3a,4,5,6,7,7a-hexahydroisoindol-2-yl)-5,6-dihydro-4H-cyclopenta[b]thiophene-3-carboxylate (Preparation #9, Step A, 3.14 g, 8.36 mmol) was added a mixture of TFA (6.3 ml) in DCM (25 ml) and the reaction mixture was stirred for 6 h at rt to achieve full conversion. The reaction mixture was concentrated under reduced pressure. Some Et₂O was added and the mixture was sonicated to afford a milky suspension. This suspension could not be filtered and was concentrated to dryness to afford a white powder. This powder was taken up two more times in Et₂O and concentrated to provide 2-(1,3-Dioxo-3a,4,5,6,7,7a-hexahydroisoindol-2-yl)-5,6-dihydro-4H-cyclopenta[b]thiophene-3-carboxylic acid (2.44 g, 91%) as a white powder. $^1$H NMR (DMSO-$d_6$, 300 MHz): δ=12.88 (br s, 1H), 3.10 (m, 2H), 2.89 (q, J=7.3 Hz, 4H), 2.33 (quin, J=7.3 Hz, 2H), 1.78 (m, 4H), 1.31-1.54 ppm (m, 4H). LC/MS (Table 1, Method A) $R_t$=1.84 min; MS m/z: 320 [M+H]$^+$.

Preparation #10. 2-[(2-Methoxycarbonylcyclohexanecarbonyl)amino]-5,6-dihydro-4H-cyclopenta[b]thiophene-3-carboxylic acid

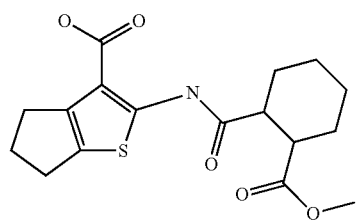 [SMILES: COC(=O)C1CCCCC1C(=O)Nc1sc2c(c1C(=O)O)CCC2]

Step A. tert-Butyl 2-[(2-methoxycarbonylcyclohexanecarbonyl)amino]-5,6-dihydro-4H-cyclopenta[b]thiophene-3-carboxylate

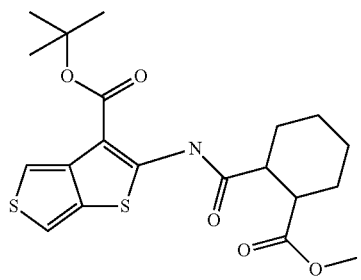 [SMILES: COC(=O)C1CCCCC1C(=O)Nc1sc2cscc2c1C(=O)OC(C)(C)C]

2-[(3-tert-Butoxycarbonyl-5,6-dihydro-4H-cyclopenta[b]thiophen-2-yl)carbamoyl]cyclohexanecarboxylic acid (Preparation #8, 29.7 g, 75.5 mmol) was suspended in a mixture of Et₂O (300 ml) and MeOH (30 ml) to provide a white heterogeneous mixture. Trimethylsilyl diazomethane 2M in hexanes (113 ml, 226 mmol) was carefully added dropwise during 50 min. The pale yellow reaction mixture was stirred at rt for 3 h. MeOH (30 ml) were added again and the reaction was stopped after 1 more hour once complete conversion was observed. The reaction mixture was cooled to 0° C. and 25 ml of formic acid was cautiously added dropwise with formation of a precipitate. To the reaction mixture was poured water (200 ml) and the product was extracted with DCM (300 ml×2). This organic phase was washed with Aq K₂CO₃ (200 ml), then brine. The organic layer was dried over MgSO4 and evaporated to provide an off-white powder which was purified by column chromatography on silica gel (eluting with 0-5% EtOAc in cyclohexane) to give tert-butyl 2-[(2-methoxycarbonylcyclohexanecarbonyl)amino]-5,6-dihydro-4H-cyclopenta[b]thiophene-3-carboxylate (23.6 g; 69%) as a white solid. LC/MS (Table 1, Method A) Rt=2.55 min; MS m/z: 408 [M+H]$_+$.

Step B. 2-[(2-Methoxycarbonylcyclohexanecarbonyl)amino]-5,6-dihydro-4H-cyclopenta[b]thiophene-3-carboxylic acid

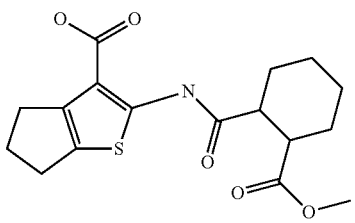 [SMILES: COC(=O)C1CCCCC1C(=O)Nc1sc2c(c1C(=O)O)CCC2]

To tert-butyl 2-[(2-methoxycarbonylcyclohexanecarbonyl)amino]-5,6-dihydro-4H-cyclopenta[b]thiophene-3-carboxylate (Preparation #10, Step A, 15.0 g, 36.8 mmol) was dissolved in DCM (300 ml) and TFA (150 ml) was subsequently added at rt. The reaction mixture was stirred for 3 h at rt then concentrated under reduced pressure. The residue was taken up three times in Et$_2$O and concentrated to provide 2-[(2-methoxycarbonylcyclohexanecarbonyl)amino]-5,6-dihydro-4H-cyclopenta[b]thiophene-3-carboxylic acid (12.0 g, 100%) as a pale blue powder. $^1$H NMR (DMSO-d$_6$, 300 MHz): δ=13.00 (br s, 1H), 11.25 (br s, 1H), 3.55 (s, 3H), 2.91-3.05 (m, 2H), 2.68-2.87 (m, 4H), 2.30 (quin, J=7.3 Hz, 2H), 1.80-2.10 (m, 3H), 1.66-1.79 (m, 1H), 1.50-1.65 (m, 1H), 1.29-1.48 ppm (m, 3H). LC/MS (Table 1, Method A) R$_t$=1.38 min; MS m/z: 352 [M+H]$^+$.

Preparation #11. 2-Amino-N-(4-chlorophenyl)-4-methyl-4,6-dihydrothieno[2,3-c]furan-3-carboxamide

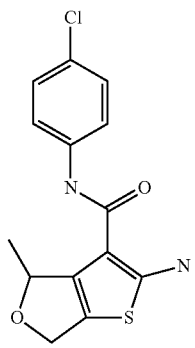 [SMILES: CC1OCc2sc(N)c(C(=O)Nc3ccc(Cl)cc3)c21]

N-(4-Chlorophenyl)-2-cyano-acetamide (*Organic & Biomolecular Chemistry*, 2015, 13(27), 7487-7499), (250 mg, 1.28 mmol) was dissolved in ethanol (4.00 ml) then 2-methyltetrahydrofuran-3-one (130 mg, 1.30 mmol), sulfur (45 mg, 1.41 mmol) and morpholine (335 µl, 3.85 mmol) were added and the mixture was stirred at 50° C. overnight. The mixture was cooled to rt then concentrated in vacuo. The residue was dissolved with DCM, washed with Aq NH$_4$Cl and extracted with DCM (2×). The combined organic phase was dried with MgSO$_4$ and concentrated in vacuo to provide an orange foam. The residue was purified by column chromatography on silica gel (eluting with 0-50% EtOAc in cyclohexane) to give 2-amino-N-(4-chlorophenyl)-4-methyl-4,6-dihydrothieno[2,3-c]furan-3-carboxamide (0.098 g, 23%) as an orange oil. $^1$H NMR (DMSO-d$_6$, 300 MHz): δ=9.01 (s, 1H), 7.60 (dd, J=6.7, 2.2 Hz, 2H), 7.35 (dd, J=6.7, 2.2 Hz, 2H), 6.99 (s, 2H), 5.58 (ddd, J=5.6, 4.3, 2.0 Hz, 1H), 4.85 (dd, J=10.7, 4.3 Hz, 1H), 4.78 (dd, J=10.7, 2.0 Hz, 1H) 1.21 (d, J=5.6 Hz, 3H). LC/MS (Table 1, Method A) R$_t$=2.02 min; MS m/z: 308 [M+H]$^+$.

Preparation #12. 5-Amino-N-(4-chlorophenyl)-2,3-dihydrothieno[2,3-b]thiophene-4-carboxamide and 2-amino-N-(4-chlorophenyl)-4,6-dihydrothieno[3,4-b]thiophene-3-carboxamide

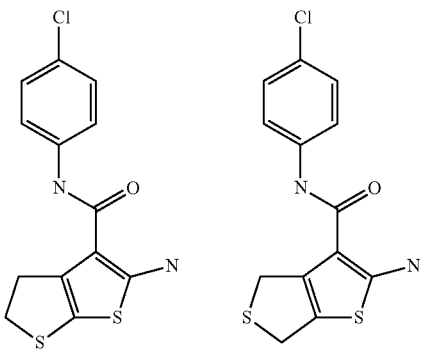 [SMILES: Nc1sc2c(c1C(=O)Nc1ccc(Cl)cc1)CCS2 ; Nc1sc2c(c1C(=O)Nc1ccc(Cl)cc1)CSC2]

N-(4-Chlorophenyl)-2-cyano-acetamide (*Organic & Biomolecular Chemistry*, 2015, 13(27), 7487-7499), (500 mg, 2.57 mmol) was dissolved in ethanol (8.00 ml) then tetrahydrothiophen-3-one (220 µl, 2.57 mmol), sulfur (91 mg, 2.84 mmol) and morpholine (675 µl, 7.72 mmol) were added and the mixture was stirred at 50° C. overnight. The mixture was cooled to rt then concentrated in vacuo. The residue was dissolved with DCM, washed with Aq NH$_4$Cl and extracted with DCM (2×). The combined organic phase was dried with MgSO$_4$ and concentrated in vacuo to provide 930 mg of a black paste. The residue was purified by column chromatography on silica gel (eluting with 0-20% EtOAc in cyclohexane) to give Compound A: 5-amino-N-(4-chlorophenyl)-2,3-dihydrothieno[2,3-b]thiophene-4-carboxamide (0.089 g, 9%) as an amorphous black solid. $^1$H NMR (CDCl$_3$, 300 MHz): δ=7.83 (br s, 1H), 7.48 (d, J=8.9 Hz, 2H), 7.30 (d, J=8.9 Hz, 2H), 5.70 (br s, 2H), 3.79 (t, J=8.0 Hz, 2H), 3.30 ppm (t, J=8.0 Hz, 2H). LC/MS (Table 1, Method A) R$_t$=2.23 min; MS m/z: 311 [M+H]$^+$ and Compound B: 2-amino-N-(4-chlorophenyl)-4,6-dihydrothieno[3,4-b]thiophene-3-carboxamide (0.059 g, 7%) as an amorphous brown solid. $^1$H NMR (CDCl$_3$, 300 MHz): δ=7.56 (br s, 1H), 7.46 (d, J=8.9 Hz, 2H), 7.29 (d, J=8.9 Hz, 2H), 5.94 (br s, 2H), 4.27 (m, 2H), 4.07 ppm (m, 2H). LC/MS (Table 1, Method A) R$_t$=2.23 min; MS m/z: 311 [M+H]$^+$.

Supply of Commercial Compounds

Some compounds, already described in literature have been prepared: Compound 43, Compound 48, Compound 50, and Compound 76. Other compounds have been purchased through commercial suppliers such as Vitas-M Laboratory Ltd; Enamine or Princeton BioMolecular Research Inc.

Compound 58: Vitas-M Laboratory, Ltd., Ref #
Compound 59: Vitas-M Laboratory, Ltd., Ref #
Compound 60: Vitas-M Laboratory, Ltd., Ref #
Compound 62: Vitas-M Laboratory, Ltd., Ref #STK097973
Compound 63: Vitas-M Laboratory, Ltd., Ref #STK470711

Compound 64: Vitas-M Laboratory, Ltd., Ref #STK470961
Compound 65: Vitas-M Laboratory, Ltd., Ref #STK471010
Compound 66: Vitas-M Laboratory, Ltd., Ref #STK470994
Compound 67: Princeton BioMolecular Research, Inc., Ref #OSSL-225782
Compound 68: Vitas-M Laboratory, Ltd., Ref #STK471002
Compound 69: Vitas-M Laboratory, Ltd., Ref #STK470996
Compound 70: Vitas-M Laboratory, Ltd., Ref #STK471315
Compound 71: Princeton BioMolecular Research, Inc., Ref #OSSL-226027
Compound 72: Vitas-M Laboratory, Ltd., Ref #STK468832
Compound 73: Vitas-M Laboratory, Ltd., Ref #STK471548
Compound 74: Vitas-M Laboratory, Ltd., Ref #STK471249
Compound 75: Enamine, Ref #Z283671592

Example #58. 1-[[3-[(4-chlorophenyl)carbamoyl]-5,6-dihydro-4H-cyclopenta[b]thiophen-2-yl]carbamoyl]piperidine-2-carboxylic acid (Compound 89)

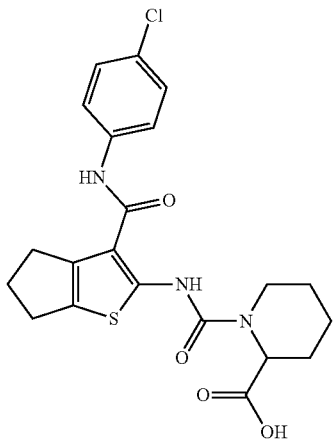 [SMILES: O=C(Nc1ccc(Cl)cc1)c1c(NC(=O)N2CCCCC2C(=O)O)sc2c1CCC2]

To a solution of 2-amino-N-(4-chlorophenyl)-5,6-dihydro-4H-cyclopenta[b]thiophene-3-carboxamide (*Indian Journal of Heterocyclic Chemistry*, 2003, 13(2), 185-186) (234 mg, 0.8 mmol) in DCM (5 mL) stirred at 0° C. was added pyridine (160 μl, 2 mmol), followed by 4-nitrophenylchloroformate (202 mg, 1 mmol). After 30 minutes, methyl pipecolinate hydrochloride (358 mg, 2 mmol) and Et₃N (427 μl, 3 mmol) were added to the stirred reaction mixture. The mixture was allowed to warm to rt and it was stirred for 1 h then concentrated in vacuo. The residue was diluted with MeOH/THF 1:1 (20 mL), 1N NaOH (3 mL) and water (5 mL) and the mixture was warmed to 50° C. for 1.5 h. EtOAc (70 mL) was added and the reaction mixture was extracted with 0.1N NaOH (2×). The combined aqueous phases were acidified with 1N HCl and extracted with EtOAc (2×). The combined organic phases were dried with MgSO₄ and concentrated in vacuo to provide a residue, which was suspended in EtOAc and filtered. The filtrate was concentrated to give 1-[[3-[(4-chlorophenyl)carbamoyl]-5,6-dihydro-4H-cyclopenta[b]thiophen-2-yl]carbamoyl]piperidine-2-carboxylic acid (25 mg, 8%) as a white solid. $^1$H NMR (DMSO-d$_6$, 400 MHz): δ 12.94 (br s, 1H), 11.19 (s, 1H), 9.02-8.96 (m, 1H), 7.67 (d, J=8.9 Hz, 2H), 7.41 (d, J=8.9 Hz, 2H), 4.81 (s, 1H), 3.69-3.68 (m, 1H), 3.20-3.10 (m, 1H), 3.07-2.99 (m, 2H), 2.81 (dd, J=7.0, 7.0 Hz, 2H), 2.42-2.33 (m, 2H), 2.18 (d, J=12.5 Hz, 1H), 1.77-1.65 (m, 3H), 1.47-1.37 (m, 1H), 1.26-1.07 (m, 1H). LC/MS (Table 1, Method D) R$_t$=5.43 min; MS m/z: 448 [M+H]$^+$.

Example #59. N1-[3-[(4-chlorophenyl)carbamoyl]-5,6-dihydro-4H-cyclopenta[b]-thiophen-2-yl]-N2-methoxy-cyclohexane-1,2-dicarboxamide (Compound 88)

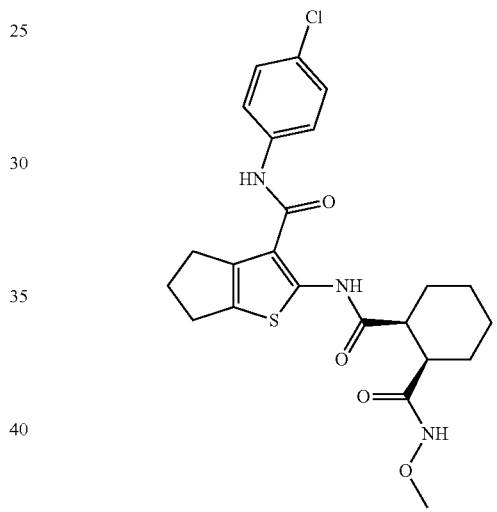

To a solution of N-(4-chlorophenyl)-2-(1,3-dioxo-3a,4,5,6,7,7a-hexahydroisoindol-2-yl)-5,6-dihydro-4H-cyclopenta[b]thiophene-3-carboxamide (Compound 54, 50 mg, 0.12 mmol) in DMF (1 mL) was added methoxyamine hydrochloride (97 mg, 1.17 mmol) and DIEA (203 μl, 1.17 mmol). The reaction mixture was stirred at 60° C. overnight. The mixture was cooled to rt diluted with water and extracted with a mixture of Et₂O/EtOAc 1:1 (3×). The combined organic phases were washed with brine, dried over MgSO₄ and concentrated in vacuo. The residue was partially purified by column chromatography on silica gel (eluting with 20-100% EtOAc in isohexane), then by RP-HPLC (Table 2, Method 3) to give N1-[3-[(4-chlorophenyl)carbamoyl]-5,6-dihydro-4H-cyclopenta[b]-thiophen-2-yl]-N2-methoxy-cyclohexane-1,2-dicarboxamide (15 mg, 27%) as a white solid. $^1$H NMR (400 MHz, DMSO-d$_6$) δ 11.28 (s, 1H), 10.95 (s, 1H), 9.16 (s, 1H), 7.69 (d, J=8.9 Hz, 2H), 7.42 (d, J=8.8 Hz, 2H), 3.46 (s, 3H), 3.01 (d, J=6.2 Hz, 2H), 2.82 (dd, J=7.0, 7.0 Hz, 2H), 2.75-2.64 (m, 2H), 2.43-2.32 (m, 2H), 2.15-2.07 (m, 1H), 1.94-1.86 (m, 1H), 1.79-1.68 (m, 2H), 1.63-1.47 (m, 2H), 1.44-1.28 (m, 2H). LC/MS (Table 1, Method D) R$_t$=5.37 min; MS m/z: 498.1 [M+Na]$^+$.

Example #60. N-(4-chlorophenyl)-2-[[2-(hydroxycarbamoyl)cyclohexanecarbonyl]amino]-5,6-dihydro-4H-cyclopenta[b]thiophene-3-carboxamide (Compound 90)

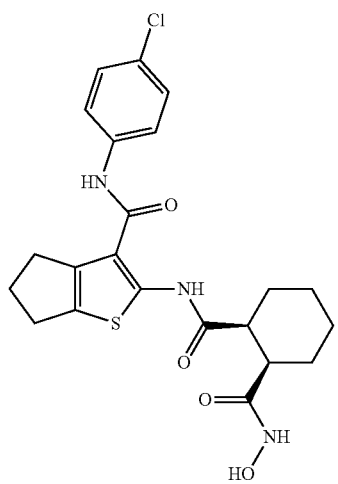 [SMILES: O=C(Nc1ccc(Cl)cc1)c1c(NC(=O)[C@H]2CCCC[C@H]2C(=O)NO)sc2c1CCC2]

To a solution of N-(4-chlorophenyl)-2-(1,3-dioxo-3a,4,5,6,7,7a-hexahydroisoindol-2-yl)-5,6-dihydro-4H-cyclopenta[b]thiophene-3-carboxamide (Compound 54, 105 mg, 0.24 mmol) in DMF (2.5 mL) was added hydroxylamine hydrochloride (170 mg, 2.45 mmol) and DIEA (426 µl, 2.45 mmol). The reaction mixture was stirred at rt over 2 days. The mixture was diluted with water and extracted with a mixture of EtOAc (3×). The combined organic phases were washed with brine, dried over MgSO4 and concentrated in vacuo. The residue was partially purified by column chromatography on silica gel (eluting with 0-100% EtOAc in isohexane, then with 10% 2M NH$_3$/DCM then by RP-HPLC (Table 2, Method 3) to give N-(4-chlorophenyl)-2-[[2-(hydroxycarbamoyl)cyclohexanecarbonyl] amino]-5,6-dihydro-4H-cyclopenta[b]thiophene-3-carboxamide (32 mg, 37%) as a pale yellow solid. $^1$H NMR (400 MHz, DMSO-d6) δ=11.33 (br s, 1H), 10.37 (br s, 1H), 9.13 (br s, 1H), 8.57 (br s, 1H), 7.69 (d, J=8.9 Hz, 2H), 7.40 (d, J=8.0 Hz, 2H), 3.07-2.95 (s, 2H), 2.84-2.67 (m, 3H), 2.39-2.31 (m, 2H), 2.22-2.14 (m, 1H), 2.00-1.90 (m, 1H), 1.83-1.76 (m, 1H), 1.74-1.68 (m, 1H), 1.64-1.56 (m, 1H), 1.50-1.28 (m, 4H). LC/MS (Table 1, Method D) Rt=5.06 min; MS m/z: 462 [M+H]+.

Example #61. N-(4-chlorophenyl)-2-[(2-tetrahydropyran-4-ylacetyl)amino]-5,6-dihydro-4H-cyclopenta[b]thiophene-3-carboxamide (Compound 81)

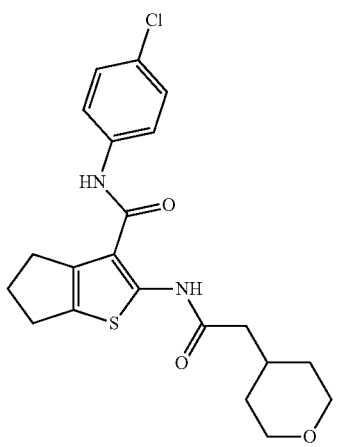 [SMILES: O=C(CC1CCOCC1)Nc1sc2c(c1C(=O)Nc1ccc(Cl)cc1)CCC2]

To a stirred suspension of 2-amino-N-(4-chlorophenyl)-5,6-dihydro-4H-cyclopenta[b]thiophene-3-carboxamide (*Indian Journal of Heterocyclic Chemistry*, 2003, 13(2), 185-186) (150 mg, 0.514 mmol), tetrahydropyran-4-carboxylic acid (134 mg, 1.02 mmol), 2-chloro-1-methylpyridinium iodide (275 mg, 1.08 mmol) and DMAP (19 mg, 0.154 mmol) in MeCN (2.5 mL) was added Et$_3$N (214 µl, 1.54 mmol). The reaction mixture was heated at 60° C. for 1 h. The mixture was diluted with EtOAc and washed with 1N HCl, sat NaHCO$_3$ and brine. The organic phase was dried with MgSO$_4$ and concentrated in vacuo. The residue was purified by RP-HPLC (Table 2, Method 3) to give N-(4-chlorophenyl)-2-[(2-tetrahydropyran-4-ylacetyl) amino]-5,6-dihydro-4H-cyclopenta[b]thiophene-3-carboxamide (57 mg, 26%) as an off-white solid. $^1$H NMR (DMSO-d$_6$, 400 MHz): δ 10.94 (s, 1H), 9.42 (s, 1H), 7.70 (d, J=8.9 Hz, 2H), 7.40 (d, J=8.9 Hz, 2H), 3.80 (dd, J=2.5, 11.4 Hz, 2H), 3.31-3.23 (m, 2H), 2.94 (dd, J=7.0, 7.0 Hz, 2H), 2.82 (dd, J=6.9, 6.9 Hz, 2H), 2.41-2.33 (m, 4H), 2.01-1.91 (m, 1H), 1.56 (dd, J=1.7, 12.7 Hz, 2H), 1.29-1.17 (m, 2H). LC/MS (Table 1, Method D) R$_t$=5.60 min; MS m/z: 441 [M+Na]+.

The following compounds were prepared using the same procedure with the appropriate starting material.

Example #62. N-[3-[(4-chlorophenyl)carbamoyl]-5,6-dihydro-4H-cyclopenta[b]thiophen-2-yl]oxetane-3-carboxamide (Compound 94)

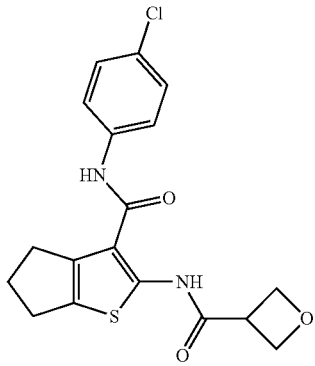 [SMILES: O=C(Nc1ccc(Cl)cc1)c1c(NC(=O)C2COC2)sc2c1CCC2]

The title compound was synthesized according to the procedure described in Example 61 using oxetane-3-carboxylic acid as a starting material (yield 12%). $^1$H NMR (DMSO-$d_6$, 400 MHz): δ=10.94-10.91 (m, 1H), 9.56-9.49 (m, 1H), 7.70 (d, J=8.9 Hz, 2H), 7.39 (d, J=8.9 Hz, 2H), 4.73-4.63 (m, 4H), 4.12-4.05 (m, 1H), 2.96-2.80 (m, 4H), 2.42-2.31 (m, 2H). LC/MS (Table 1, Method D) R$_t$=5.09 min; MS m/z: 377 [M+H]$^+$.

Example #63. N-(4-chlorophenyl)-2-[(2-pyrazin-2-ylacetyl)amino]-5,6-dihydro-4H-cyclopenta[b]thiophene-3-carboxamide (Compound 78)

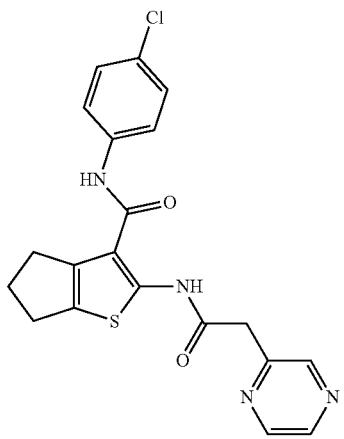 [SMILES: O=C(Cc1cnccn1)Nc1sc2c(c1C(=O)Nc1ccc(Cl)cc1)CCC2]

The title compound was synthesized according to the procedure described in Example 61 using 2-pyrazinecarboxylic acid as a starting material (yield 4%). $^1$H NMR (DMSO-$d_6$, 400 MHz): δ=11.33 (br s, 1H), 9.47 (s, 1H), 8.68 (s, 1H), 8.60-8.56 (m, 2H), 7.71 (d, J=8.8 Hz, 2H), 7.41 (d, J=8.7 Hz, 2H), 4.10 (s, 2H), 2.94 (dd, J=6.8, 6.8 Hz, 2H), 2.83 (dd, J=6.9, 6.9 Hz, 2H), 2.36 (dd, J=5.8, 13.3 Hz, 2H). LC/MS (Table 1, Method D) R$_t$=5.08 min; MS m/z: 413 [M+H]$^-$.

Example #64. N-[3-[(4-chlorophenyl)carbamoyl]-5,6-dihydro-4H-cyclopenta[b]thiophen-2-yl]-2-oxo-piperidine-4-carboxamide (Compound 101)

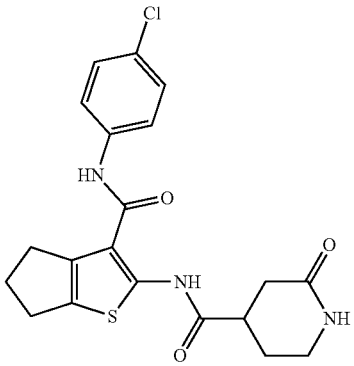 [SMILES: O=C1CC(C(=O)Nc2sc3c(c2C(=O)Nc2ccc(Cl)cc2)CCC3)CCN1]

The title compound was synthesized according to the procedure described in Example 61 using 2-oxopiperidine-4-carboxylic acid as a starting material (yield 42%). $^1$H NMR (DMSO-$d_6$, 400 MHz): δ=11.09 (s, 1H), 9.45 (s, 1H), 7.71 (d, J=8.9 Hz, 2H), 7.53 (s, 1H), 7.40 (d, J=8.8 Hz, 2H), 3.18-3.13 (m, 2H), 3.06-3.01 (m, 1H), 2.99-2.91 (m, 2H), 2.83 (dd, J=6.7, 6.7 Hz, 2H), 2.40-2.32 (m, 4H), 2.08-1.97 (m, 1H), 1.78-1.67 (m, 1H). LC/MS (Table 1, Method D) R$_t$=4.56 min; MS m/z: 418 [M+H]$^+$.

Example #65. 3-[[3-[(4-chlorophenyl)carbamoyl]-5,6-dihydro-4H-cyclopenta[b]thiophen-2-yl]carbamoyl]cyclohexanecarboxylic acid (Compound 99)

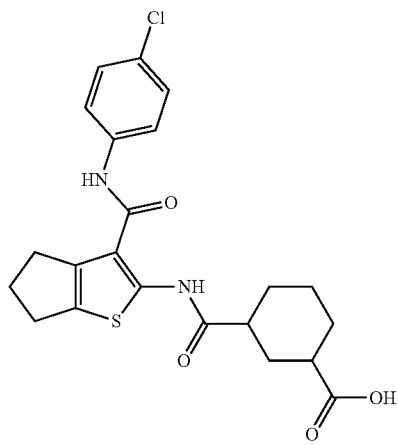 [SMILES: O=C(Nc1ccc(Cl)cc1)c1c(NC(=O)C2CCCC(C(=O)O)C2)sc2c1CCC2]

The title compound was synthesized according to the procedure described in Example 61 using 1,3-cyclohexanedicarboxylic acid, 1-methyl ester as a starting material. The residue (0.514 mmol) was diluted in THF/MeOH 1:1 (5 mL) and 1M NaOH (2.5 mL) was added. The reaction mixture was stirred at rt for 3 h, then diluted with DCM (30 mL). The organic phase was washed with 1N HCl (20 mL), brine (20 mL), dried over MgSO$_4$, filtered and concentrated in vacuo. The residue was purified by RP-HPLC (Table 2, Method 3) to give 3-[[3-[(4-chlorophenyl)carbamoyl]-5,6-dihydro-4H-cyclopenta[b] thiophen-2-yl]carbamoyl]cyclohexane carboxylic acid (57 mg, 25%) as pale yellow oil. $^1$H NMR (DMSO-d$_6$, 400 MHz): δ=12.14-12.13 (m, 1H), 11.09-11.08 (m, 1H), 9.36 (s, 1H), 7.72-7.69 (m, 2H), 7.41 (d, J=8.9 Hz, 2H), 2.97 (dd, J=7.0, 7.0 Hz, 2H), 2.82 (dd, J=7.1, 7.1 Hz, 2H), 2.56-2.54 (m, 1H), 2.42-2.26 (m, 3H), 2.11-2.06 (m, 1H), 1.91-1.78 (m, 3H), 1.46-1.19 (m, 4H). LC/MS (Table 1, Method D) R$_t$=5.36 min; MS m/z: 447.2 [M+H]$^+$.

Example #66 and Example #67. 4-[[3-[(4-chlorophenyl)carbamoyl]-5,6-dihydro-4H-cyclopenta[b]thiophen-2-yl]carbamoyl]cyclohexanecarboxylic acid, cis and trans isomers (Compound 97 and 98)

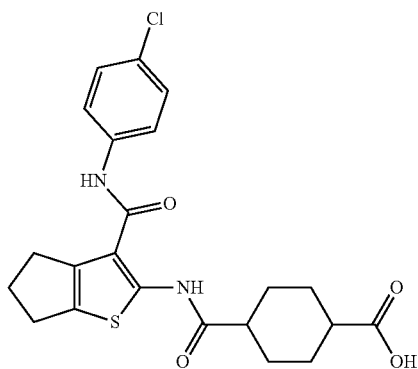 [SMILES: O=C(Nc1ccc(Cl)cc1)c1c(NC(=O)C2CCC(C(=O)O)CC2)sc2c1CCC2]

The title compound was synthesized according to the procedure described in Example 66 using 1,4-cyclohexanedicarboxylic acid, 1-methyl ester as a starting material. The residue (0.514 mmol) was diluted in THF/MeOH 1:1 (5 mL) and 1M NaOH (2.5 mL) was added. The reaction mixture was stirred at rt for 3 h, then diluted with DCM (30 mL). The organic phase was washed with 1N HCl (20 mL), brine (20 mL), dried over MgSO$_4$, filtered and concentrated in vacuo. The residue was purified by RP-HPLC (Table 2, Method 3) to give 2 isomers: isomer A, Compound 97 (24 mg, 10%) and isomer B Compound 98 (9 mg, 4%). Compound 97 $^1$H NMR (DMSO-d$_6$, 400 MHz): δ=12.07 (br s, 1H), 11.10 (br s, 1H), 9.35 (s, 1H), 7.71-7.68 (m, 2H), 7.42-7.39 (m, 2H), 2.97 (dd, J=7.0, 7.0 Hz, 2H), 2.82 (dd, J=7.1, 7.1 Hz, 2H), 2.47-2.33 (m, 3H), 2.24-2.16 (m, 1H), 1.98-1.91 (m, 3H), 1.46-1.32 (m, 4H). LC/MS (Table 1, Method D) R$_t$=5.27 min; MS m/z: 447.2 [M+H]$^+$.

Compound 98 $^1$H NMR (DMSO-d$_6$, 400 MHz): δ=12.13 (br s, 1H), 11.16 (br s, 1H), 9.31 (br s, 1H), 7.70 (d, J=8.9 Hz, 2H), 7.41 (d, J=8.9 Hz, 2H), 2.98 (dd, J=6.8, 6.8 Hz, 2H), 2.82 (dd, J=7.0, 7.0 Hz, 2H), 2.58 (d, J=3.6 Hz, 1H), 2.42-2.33 (m, 2H), 1.99-1.86 (m, 2H), 1.73-1.55 (m, 6H), 1.47-1.33 (m, 1H). LC/MS (Table 1, Method D) R$_t$=5.36 min; MS m/z: 447.2 [M+H]$^+$.

Example #68. N-[3-[(4-chlorophenyl)carbamoyl]-5,6-dihydro-4H-cyclopenta[b]thiophen-2-yl]morpholine-3-carboxamide (Compound 103)

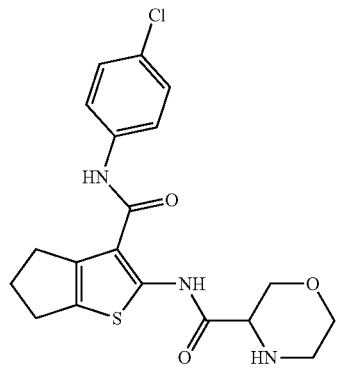 [SMILES: O=C(Nc1ccc(Cl)cc1)c1c(NC(=O)C2COCCN2)sc2c1CCC2]

The title compound was synthesized according to the procedure described in Example 61 using morpholine-3,4-dicarboxylic acid-4-tert-butyl ester as a starting material. The residue (0.139 mmol) was diluted in MeOH/DCM 3:1 (2 mL) and 4M HCl in dioxane (1.5 mL) was added. The reaction mixture was stirred at rt for 1.5 h. The reaction mixture was concentrated in vacuo, and diluted with DCM (30 mL). The organic phase was washed with sat NaHCO$_3$, dried over Na$_2$SO$_4$, filtered and concentrated in vacuo. The residue was purified by RP-HPLC (Table 2, Method 3) to give N-[3-[(4-chlorophenyl)carbamoyl]-5,6-dihydro-4H-cyclopenta[b]thiophen-2-yl]morpholine-3-carboxamide (38 mg, 67%) as pale yellow solid. $^1$H NMR (DMSO-d$_6$, 400 MHz): δ=10.04 (br s, 1H), 7.68 (d, J=8.9 Hz, 2H), 7.41-7.38 (m, 2H), 3.84 (dd, J=3.6, 11.2 Hz, 1H), 3.75-3.59 (m, 3H), 3.54-3.44 (m, 1H), 2.99-2.77 (m, 6H), 2.40-2.30 (m, 2H). LC/MS (Table 1, Method D) R$_t$=3.58 min; MS m/z: 406 [M+H]$^+$.

Example #69. N-[3-[(4-chlorophenyl)carbamoyl]-5,6-dihydro-4H-cyclopenta[b]thiophen-2-yl]-1-methylsulfonyl-piperidine-2-carboxamide (Compound 100)

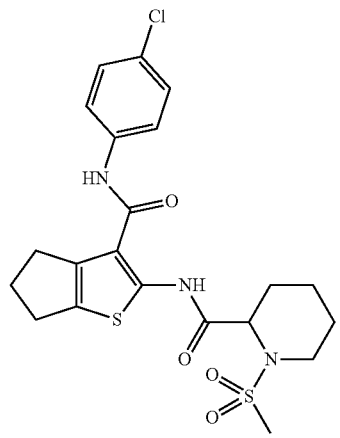

The title compound was synthesized according to the procedure described in Example 68 using 1-tert-butoxycarbonylpiperidine-2-carboxylic acid as a starting material. After treatment with 4N HCl in dioxane, the reaction mixture was concentrated in vacuo and used crude in the next step. The residue (0.197 mmol) was suspended in DCM (0.6 mL) and methanesulfonyl chloride (22.9 µl, 0.296 mmol) was added. The reaction mixture was stirred at rt for 1.5 h. The reaction mixture was concentrated in vacuo, and diluted with DCM (40 mL). The organic phase was washed with sat NaHCO$_3$, dried over Na$_2$SO$_4$, filtered and concentrated in vacuo. The residue was purified by RP-HPLC (Table 2, Method 3) to give N-[3-[(4-chlorophenyl)carbamoyl]-5,6-dihydro-4H-cyclopenta[b]thiophen-2-yl]-1-methylsulfonyl-piperidine-2-carboxamide (43 mg, 45%) as an off-white solid. $^1$H NMR (DMSO-d$_6$, 400 MHz): δ=11.55 (s, 1H), 9.32 (s, 1H), 7.69 (d, J=8.9 Hz, 2H), 7.41 (d, J=8.9 Hz, 2H), 4.77 (d, J=4.7 Hz, 1H), 3.74 (d, J=13.4 Hz, 1H), 3.19-3.10 (m, 1H), 3.08 (s, 3H), 3.00 (dd, J=7.0, 7.0 Hz, 2H), 2.85 (dd, J=7.1, 7.1 Hz, 2H), 2.44-2.34 (m, 2H), 2.18 (d, J=14.1 Hz, 1H), 1.76-1.54 (m, 3H), 1.52-1.42 (m, 1H), 1.35-1.23 (m, 1H). LC/MS (Table 1, Method D) R$_t$=5.61 min; MS m/z: 480 [M−H]$^−$.

Example #70. N-[3-[(4-chlorophenyl)carbamoyl]-5,6-dihydro-4H-cyclopenta[b]thiophen-2-yl]-4-methylsulfonyl-morpholine-3-carboxamide (Compound 93)

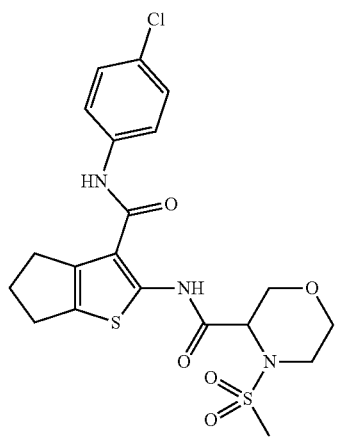 [SMILES: CS(=O)(=O)N1CCOCC1C(=O)Nc1sc2c(c1C(=O)Nc1ccc(Cl)cc1)CCC2]

The title compound was synthesized according to the procedure described in Example 69 using N-[3-[(4-chlorophenyl)carbamoyl]-5,6-dihydro-4H-cyclopenta[b]thiophen-2-yl]morpholine-3-carboxamide (Example #68) as a starting material in the sulfonylation step. The residue was purified by RP-HPLC (Table 2, Method 3) to give N-[3-[(4-chlorophenyl)carbamoyl]-5,6-dihydro-4H-cyclopenta[b]thiophen-2-yl]-4-methylsulfonyl-morpholine-3-carboxamide (15 mg, 15%) as an off-white solid. $^1$H NMR (DMSO-d$_6$, 400 MHz): δ=11.57 (s, 1H), 9.38 (s, 1H), 7.70 (d, J=8.9 Hz, 2H), 7.41 (d, J=8.7 Hz, 2H), 4.66 (d, J=1.7 Hz, 1H), 4.28 (d, J=11.9 Hz, 1H), 3.83-3.77 (m, 1H), 3.69 (dd, J=3.7, 12.1 Hz, 1H), 3.63-3.38 (m, 3H), 3.12 (s, 3H), 2.98 (d, J=6.4 Hz, 2H), 2.86 (dd, J=6.7, 6.7 Hz, 2H), 2.39 (dd, J=6.9, 6.9 Hz, 2H). LC/MS (Table 1, Method D) R$_t$=5.15 min; MS m/z: 506 [M+Na]$^+$.

Example #71. N-[3-[(4-chlorophenyl)carbamoyl]-5,6-dihydro-4H-cyclopenta[b]thiophen-2-yl]-1-methylsulfonyl-piperidine-3-carboxamide (Compound 95)

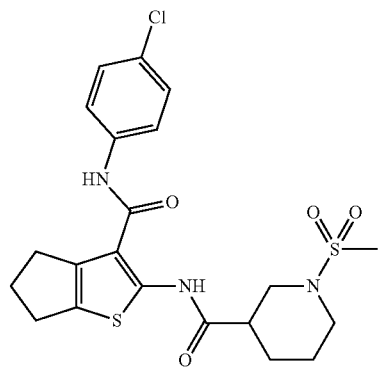

The title compound was synthesized according to the procedure described in Example 69 using 1-tert-butylcarbonylpiperidine-3-carboxylic acid as starting material. The residue was purified by RP-HPLC (Table 2, Method 3) to give N-[3-[(4-chlorophenyl)carbamoyl]-5,6-dihydro-4H-cyclopenta[b]thiophen-2-yl]-1-methylsulfonyl-piperidine-3-carboxamide (67 mg, 55%) as an off-white solid. $^1$H NMR (DMSO-d$_6$, 400 MHz): δ=11.14 (s, 1H), 9.46 (s, 1H), 7.71 (d, J=8.9 Hz, 2H), 7.40 (d, J=8.9 Hz, 2H), 3.70 (d, J=8.9 Hz, 1H), 3.51 (d, J=10.9 Hz, 1H), 2.97-2.91 (m, 2H), 2.88 (s, 3H), 2.87-2.78 (m, 4H), 2.78-2.66 (m, 1H), 2.41-2.33 (m, 2H), 2.00-1.90 (m, 1H), 1.81 (dd, J=3.2, 6.1 Hz, 1H), 1.54 (dd, J=9.2, 9.2 Hz, 2H). LC/MS (Table 1, Method D) R$_t$=5.36 min; MS m/z: 481.9 [M+H]$^+$.

Example #72. N-[3-[(4-chlorophenyl)carbamoyl]-5,6-dihydro-4H-cyclopenta[b]thiophen-2-yl]-4-methylsulfonyl-morpholine-2-carboxamide (Compound 86)

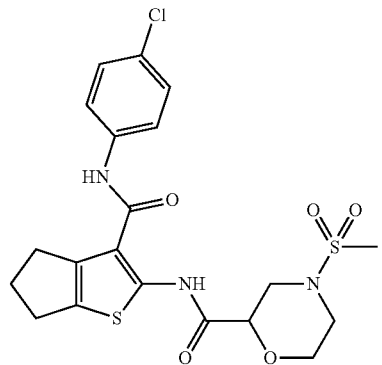

The title compound was synthesized according to the procedure described in Example 69 using 4-tert-butylcarbonylmorpholine-2-carboxylic acid as starting material. The residue was purified by RP-HPLC (Table 2, Method 3) to give N-[3-[(4-chlorophenyl)carbamoyl]-5,6-dihydro-4H-cyclopenta[b]thiophen-2-yl]-4-methylsulfonyl-morpholine-2-carboxamide (74 mg, 61%) as an off-white solid. $^1$H NMR (DMSO-d$_6$, 400 MHz): δ=11.68 (s, 1H), 9.24 (s, 1H), 7.67

(d, J=8.9 Hz, 2H), 7.42 (d, J=8.9 Hz, 2H), 4.41 (dd, J=3.0, 10.2 Hz, 1H), 4.14 (d, J=11.3 Hz, 1H), 3.76-3.70 (m, 2H), 3.39 (d, J=11.6 Hz, 1H), 3.04 (dd, J=6.8, 6.8 Hz, 2H), 2.97-2.83 (m, 7H), 2.45-2.35 (m, 2H). LC/MS (Table 1, Method E) $R_t$=5.23 min; MS m/z: 483.9 [M+H]$^+$.

Example #73. N3-[3-[(4-chlorophenyl)carbamoyl]-5,6-dihydro-4H-cyclopenta[b]thiophen-2-yl]morpholine-3,4-dicarboxamide (Compound 82)

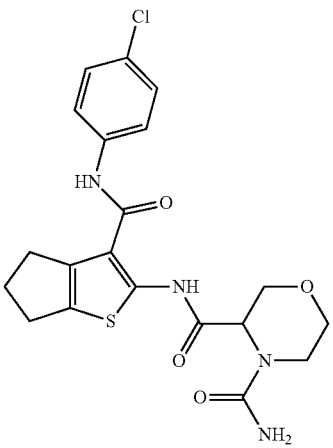 [SMILES: NC(=O)N1CCOCC1C(=O)Nc1sc2c(c1C(=O)Nc1ccc(Cl)cc1)CCC2]

To a stirred solution of Example 68 (89 mg, 0.197 mmol) in DCM (0.6 mL) was added trimethylsilyl isocyanate (40 µl, 0.296 mmol) and Et$_3$N (82 µl, 0.591 mmol). The reaction mixture was stirred at rt for 24 h. The mixture was diluted with DCM (40 mL), the organic phase was washed with NaHCO$_3$, dried over Na$_2$SO$_4$, filtered and concentrated in vacuo. The residue was purified by RP-HPLC (Table 2, Method 3) to give N3-[3-[(4-chlorophenyl)carbamoyl]-5,6-dihydro-4H-cyclopenta[b]thiophen-2-yl]morpholine-3,4-dicarboxamide (19 mg, 21%) as an off-white solid. $^1$H NMR (DMSO-d$_6$, 400 MHz): δ=11.41 (s, 1H), 9.28 (s, 1H), 7.69 (d, J=8.9 Hz, 2H), 7.41 (d, J=8.7 Hz, 2H), 6.34 (s, 2H), 4.73-4.73 (m, 1H), 4.26 (d, J=11.7 Hz, 1H), 3.79-3.71 (m, 2H), 3.57 (dd, J=3.9, 11.8 Hz, 1H), 3.40-3.35 (m, 1H), 3.24-3.18 (m, 1H), 3.00 (d, J=6.3 Hz, 2H), 2.84 (dd, J=7.1, 7.1 Hz, 2H), 2.43-2.32 (m, 2H). LC/MS (Table 1, Method D) Rt=4.42 min; MS m/z: 449 [M+H]$^+$.

Example #74. N3-[3-[(4-chlorophenyl)carbamoyl]-5,6-dihydro-4H-cyclopenta[b]thiophen-2-yl]piperidine-1,3-dicarboxamide (Compound 92)

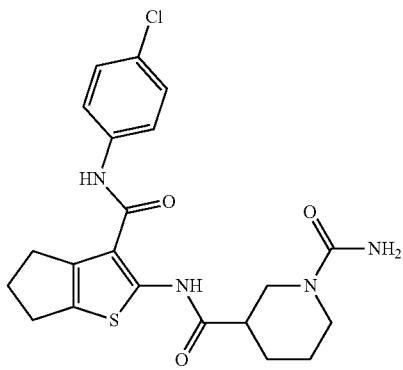 [SMILES: NC(=O)N1CCCC(C(=O)Nc2sc3c(c2C(=O)Nc2ccc(Cl)cc2)CCC3)C1]

The title compound was synthesized according to the procedure described in Example 73 using 1-tert-butylcarbonylpiperidine-3-carboxylic acid as starting material. The residue was purified by RP-HPLC (Table 2, Method 4) to give the title compound (74 mg, 64%) as an off-white solid. $^1$H NMR (DMSO-d$_6$, 400 MHz): δ=11.10 (s, 1H), 9.42 (s, 1H), 7.72 (d, J=8.9 Hz, 2H), 7.40 (d, J=8.7 Hz, 2H), 5.95 (s, 2H), 4.06 (d, J=13.3 Hz, 1H), 3.84 (d, J=12.8 Hz, 1H), 3.17 (d, J=5.2 Hz, 3H), 2.95 (dd, J=7.0, 7.0 Hz, 2H), 2.87-2.77 (m, 2H), 2.73-2.65 (m, 1H), 2.40-2.33 (m, 2H), 1.96 (d, J=10.8 Hz, 1H), 1.65-1.54 (m, 1H), 1.41-1.33 (m, 1H). LC/MS (Table 1, Method D) $R_t$=4.76 min; MS m/z: 447.3 [M+H]$^+$.

Example #75. N-[3-[(4-chlorophenyl)carbamoyl]-5,6-dihydro-4H-cyclopenta[b]thiophen-2-yl]-1-sulfamoyl-piperidine-2-carboxamide (Compound 80)

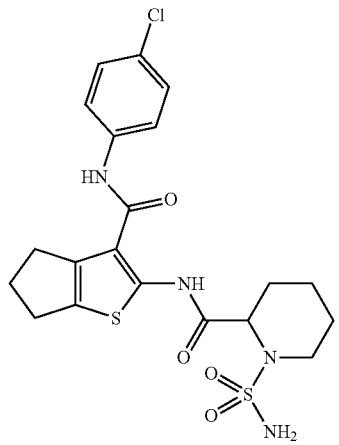 [SMILES: NS(=O)(=O)N1CCCCC1C(=O)Nc1sc2c(c1C(=O)Nc1ccc(Cl)cc1)CCC2]

To a stirred solution of chlorosulfonyl isocyanate (26 µl, 0.3 mmol) in DCM (2.5 mL) at 0° C., was added t-BuOH (29 µl, 0.3 mmol). The reaction mixture was stirred at 0° C. for 1 h, before the mixture was added to a solution of N-[3-[(4-chlorophenyl)carbamoyl]-5,6-dihydro-4H-cyclopenta[b]thiophen-2-yl]piperidine-2-carboxamide (88 mg, 0.2 mmol), which was synthesized according to the procedure described in Example 68, using 1-tert-butoxycarbonylpiperidine-2-carboxylic acid as a starting material, in DCM (2.5 mL). The reaction mixture was warmed to rt and stirred for 1 h. The reaction mixture was diluted with DCM (40 mL). The organic phase was washed with sat NaHCO$_3$, dried over Na$_2$SO$_4$, filtered and concentrated in vacuo. The residue was dissolved in DCM/MeOH 1:5 (1.2 mL) and 4N HCl in dioxane (1 mL) was added. The reaction mixture was stirred for 3 h at rt, then concentrated in vacuo. The residue was purified by RP-HPLC (Table 2, Method 3) to give the title compound (19 mg, 19%) as an off-white solid. $^1$H NMR (DMSO-d$_6$, 400 MHz): δ=11.53 (s, 1H), 9.26 (s, 1H), 7.68 (d, J=8.9 Hz, 2H), 7.41 (d, J=8.7 Hz, 2H), 6.94 (s, 2H), 4.54 (d, J=3.4 Hz, 1H), 3.69 (d, J=13.7 Hz, 1H), 3.11-2.93 (m, 3H), 2.89-2.81 (m, 2H), 2.42-2.36 (m, 2H), 2.13-2.07 (m, 1H), 1.87-1.81 (m, 1H), 1.65-1.57 (m, 2H), 1.44 (d, J=12.3 Hz, 1H), 1.29 (dd, J=13.0, 13.0 Hz, 1H). LC/MS (Table 1, Method D) $R_t$=1.46 min; MS m/z: 481 [M−H]$^-$.

Example #76. N-[3-[(4-chlorophenyl)carbamoyl]-5,6-dihydro-4H-cyclopenta[b]thiophen-2-yl]-1-sulfamoyl-azetidine-2-carboxamide (Compound 102)

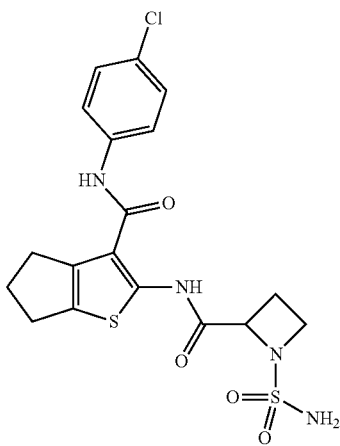 [SMILES: NS(=O)(=O)N1CCC1C(=O)Nc1sc2c(c1C(=O)Nc1ccc(Cl)cc1)CCC2]

The title compound was synthesized according to the procedure described in Example 75 using 1-(tert-Butoxycarbonyl)azetidine-2-carboxylic acid as starting material. The residue was purified by RP-HPLC (Table 2, Method 3) to give the title compound (29 mg, 18%) as an off-white solid. $^1$H NMR (DMSO-d$_6$, 400 MHz): δ=11.72 (s, 1H), 9.23 (s, 1H), 7.69 (d, J=8.4 Hz, 2H), 7.42 (d, J=8.3 Hz, 2H), 7.22 (s, 2H), 4.62 (dd, J=8.5, 8.5 Hz, 1H), 3.84 (q, J=8.5 Hz, 1H), 3.64-3.61 (m, 1H), 3.03 (d, J=5.4 Hz, 2H), 2.85-2.81 (m, 2H), 2.43-2.22 (m, 4H). LC/MS (Table 1, Method D) R$_t$=4.73 min; MS m/z: 455 [M+H]$^+$.

Example #77. N-[3-[(4-chlorophenyl)carbamoyl]-5,6-dihydro-4H-cyclopenta[b]thiophen-2-yl]azetidine-2-carboxamide (Compound 96)

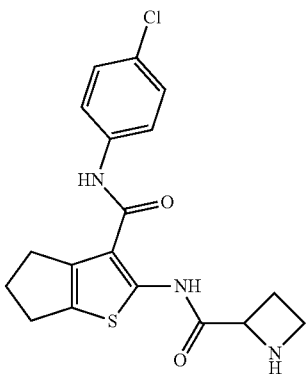 [SMILES: O=C(Nc1ccc(Cl)cc1)c1c(NC(=O)C2CCN2)sc2c1CCC2]

The title compound was synthesized according to the procedure described in Example 68 using 1-(tert-Butoxycarbonyl)azetidine-2-carboxylic acid as starting material. The residue was purified by RP-HPLC (Table 2, Method 3) to give the title compound (25 mg, 40%) as an off-white solid. $^1$H NMR (DMSO-d$_6$, 400 MHz): δ 11.60 (br s, 1H), 8.34 (br s, 1H), 7.68 (d, J=8.9 Hz, 2H), 7.34 (d, J=8.9 Hz, 2H), 4.75 (dd, J=8.6, 8.6 Hz, 1H), 3.83 (q, J=8.8 Hz, 1H), 3.54-3.46 (m, 1H), 2.97-2.90 (m, 2H), 2.78-2.64 (m, 3H), 2.47-2.25 (m, 4H). LC/MS (Table 1, Method D) R$_t$=3.43 min; MS m/z: 376 [M+H]$^+$.

Example #78. 1-acetyl-N-[3-[(4-chlorophenyl)carbamoyl]-5,6-dihydro-4H-cyclopenta[b]thiophen-2-yl]azetidine-2-carboxamide (Compound 84)

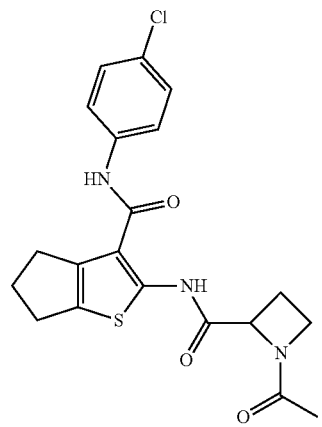 [SMILES: CC(=O)N1CCC1C(=O)Nc1sc2c(c1C(=O)Nc1ccc(Cl)cc1)CCC2]

To a stirred solution of N-[3-[(4-chlorophenyl)carbamoyl]-5,6-dihydro-4H-cyclopenta[b]thiophen-2-yl]azetidine-2-carboxamide (Example #77) (130 mg, 0.347 mmol) in DCM (1 mL) was added acetic anhydride (49 µl, 0.520 mmol). The reaction mixture was stirred at rt for 1 h, then diluted with DCM (20 mL). The organic phase was washed with brine, dried over Na$_2$SO$_4$, filtered and concentrated in vacuo. The residue was purified by RP-HPLC (Table 2, Method 3) to give the title compound (16 mg, 11%) as an off-white solid. $^1$H NMR (DMSO-d$_6$, 400 MHz): δ (mixture of rotamers) 11.43 (s, 1H), 9.43 (s, 0.3H), 9.33 (s, 0.7H), 7.69 (d, J=8.9 Hz, 2H), 7.41 (d, J=8.9 Hz, 2H), 5.13 (dd, J=5.4, 9.2 Hz, 0.3H), 4.80 (dd, J=6.0, 9.3 Hz, 0.7H), 4.17-4.04 (m, 1.4H), 3.86-3.78 (m, 0.6H), 2.98 (dd, J=7.0, 7.0 Hz, 2H), 2.85 (dd, J=7.0, 7.0 Hz, 2H), 2.60-2.56 (m, 1H), 2.43-2.23 (m, 3H), 1.84 (s, 2H), 1.72 (s, 1H). LC/MS (Table 1, Method D) R$_t$=4.78 min; MS m/z: 418 [M+H]$^+$.

Example #79. N-[3-[(4-chlorophenyl)carbamoyl]-5,6-dihydro-4H-cyclopenta[b]thiophen-2-yl]-4-sulfamoyl-morpholine-2-carboxamide (Compound 87)

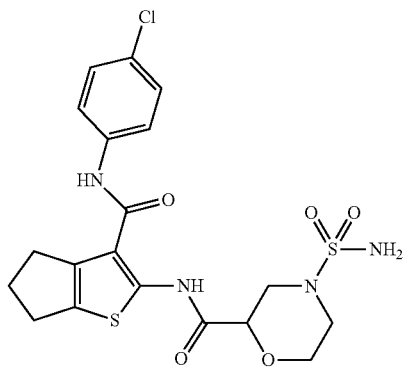 [SMILES: NS(=O)(=O)N1CCOC(C(=O)Nc2sc3c(c2C(=O)Nc2ccc(Cl)cc2)CCC3)C1]

The title compound was synthesized according to the procedure described in Example 75 using 4-(tert-Butoxycarbonyl)morpholine-2-carboxylic acid as starting material. The residue was purified by RP-HPLC (Table 2, Method 3) to give the title compound (61 mg, 50%) as an off-white solid. $^1$H NMR (DMSO-d$_6$, 400 MHz): δ=11.66 (s, 1H), 9.24 (s, 1H), 7.68 (d, J=8.9 Hz, 2H), 7.42 (d, J=8.8 Hz, 2H), 6.96 (s, 2H), 4.40 (dd, J=2.9, 10.3 Hz, 1H), 4.16-4.09 (m, 1H), 3.76-3.61 (m, 2H), 3.30-3.23 (m, 1H), 3.04 (dd, J=6.4, 6.4 Hz, 2H), 2.86 (dd, J=7.1, 7.1 Hz, 2H), 2.72 (dt, J=3.3, 11.7 Hz, 1H), 2.62 (t, J=11.1 Hz, 1H), 2.45-2.35 (m, 2H). LC/MS (Table 1, Method D) R$_t$=5.01 min; MS m/z: 485.2 [M+H]$^+$.

Example #80. N-[3-[(4-chlorophenyl)carbamoyl]-5,6-dihydro-4H-cyclopenta[b]thiophen-2-yl]-1-sulfamoyl-piperidine-3-carboxamide (Compound 83)

The title compound was synthesized according to the procedure described in Example 75 using 1-(tert-butoxycarbonyl)-3-piperidinecarboxylic acid as starting material. The residue was purified by RP-HPLC (Table 2, Method 3) to give the title compound (97 mg, 80%) as an off-white solid. $^1$H NMR (DMSO-d$_6$, 400 MHz): δ=11.15 (s, 1H), 9.44 (s, 1H), 7.71 (d, J=8.9 Hz, 2H), 7.41 (d, J=8.8 Hz, 2H), 6.78 (s, 2H), 3.61-3.58 (m, 1H), 3.40 (d, J=11.6 Hz, 1H), 2.95 (dd, J=6.1, 6.1 Hz, 2H), 2.87-2.76 (m, 3H), 2.69-2.61 (m, 1H), 2.54-2.53 (m, 1H), 2.42-2.33 (m, 2H), 1.93 (d, J=12.2 Hz, 1H), 1.82-1.76 (m, 1H), 1.61-1.42 (m, 2H). LC/MS (Table 1, Method D) R$_t$=5.07 min; MS m/z: 483.2 [M+H]$^+$.

Example #81. N-(4-chlorophenyl)-2-[[(1S,2R)-2-(methanesulfonamido)cyclohexane carbonyl]amino]-5,6-dihydro-4H-cyclopenta[b]thiophene-3-carboxamide (Compound 85)

The title compound was synthesized according to the procedure described in Example 61 using cis 2-[[(1,1-dimethylethoxy)carbonyl]amino]cyclohexanecarboxylic acid (0.7 mmol), as a starting material. The residue was dissolved in TFA/DCM 1:3 (4 mL) and the solution was stirred at rt for 1 h. The reaction mixture was then loaded onto a 2 g SCX-2 cartridge, washed with MeOH (2 CV) then eluted with 2N NH$_3$ in MeOH (2 CV). The fractions were concentrated in vacuo to yield 63 mg of compound, which was used crude in the next step. The residue (0.14 mmol) was suspended in DCM (1.5 mL) and methanesulfonyl chloride (13.3 μl, 0.17 mmol) and Et$_3$N (30 μl, 0.22 mmol) were added. The reaction mixture was stirred at rt for 2 h. The reaction mixture was concentrated in vacuo, and diluted with DCM (40 mL). The organic phase was washed with sat. NaHCO$_3$, dried over Na$_2$SO$_4$, filtered and concentrated in vacuo. The residue was purified by RP-HPLC (Table 2, Method 3) to give the title compound (15 mg, 21%) as an off-white solid. $^1$H NMR (DMSO-d$_6$, 400 MHz): δ=11.20 (s, 1H), 9.29 (s, 1H), 7.71-7.68 (m, 2H), 7.41 (d, J=8.8 Hz, 2H), 7.22 (d, J=8.6 Hz, 1H), 3.86-3.85 (m, 1H), 2.99 (dd, J=6.8, 6.8 Hz, 2H), 2.87-2.77 (m, 3H), 2.75 (s, 3H), 2.42-2.32 (m, 2H), 1.89-1.80 (m, 2H), 1.68-1.55 (m, 4H), 1.43-1.38 (m, 1H), 1.25-1.22 (m, 1H). LC/MS (Table 1, Method D) R$_t$=5.54 min; MS m/z: 496.1 [M+H]$^+$.

Example #82. 2-[[6-tert-butoxycarbonyl-3-[(4-chlorophenyl)carbamoyl]-5,7-dihydro-4H-thieno[2,3-c]pyridin-2-yl]carbamoyl]cyclohexanecarboxylic acid (Compound 91)

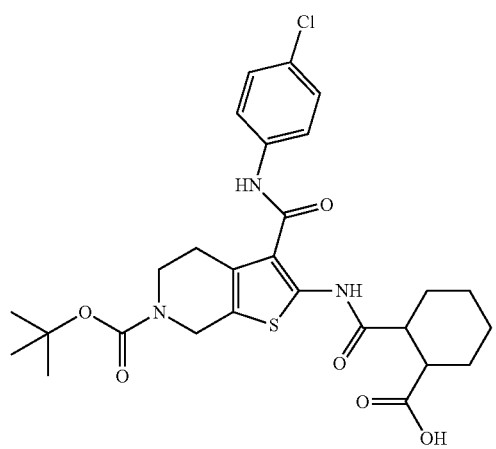 [SMILES: CC(C)(C)OC(=O)N1CCc2c(sc(NC(=O)C3CCCCC3C(=O)O)c2C(=O)Nc2ccc(Cl)cc2)C1]

Tert-butyl 2-amino-3-((4-chlorophenyl)carbamoyl)-4,7-dihydro thieno[2,3-c]pyridine-6 (5H)-carboxylate (Preparation #13, 1 g, 2.45 mmol) was dissolved in dioxane (10 mL) then cis-1,2-cyclohexane dicarboxylic anhydride (1.7 g, 11 mmol) was added and the mixture was stirred at 100° C. overnight. The mixture was cooled to rt then concentrated in vacuo. The residue was purified by column chromatography on silica gel (eluting with 0-60% EtOAc in isohexane) to give tert-butyl 3-((4-chlorophenyl)carbamoyl)-2-(1,3-dioxooctahydro-2H-isoindol-2-yl)-4,7-dihydrothieno[2,3-c]pyridine-6 (5H)-carboxylate (834 mg, 63%) as a yellow solid.

1N NaOH (2.3 mL, 2.3 mmol) was added to a solution of tert-butyl 3-((4-chlorophenyl)carbamoyl)-2-(1,3-dioxooctahydro-2H-isoindol-2-yl)-4,7-dihydrothieno[2,3-c]pyridine-6 (5H)-carboxylate (316 mg, 0.58 mmol) in THF (7 mL), and the reaction mixture was stirred at rt for 30 min. The reaction mixture was acidified with 1N HCl (pH 2) and extracted with EtOAc. The combined organic phases were washed with brine, dried over Na$_2$SO$_4$, filtered and concentrated in vacuo, to give the title compound (162 mg, 49%). $^1$H NMR (DMSO-d$_6$, 400 MHz): δ 12.13-12.08 (br s, 1H), 10.80 (s, 1H), 9.80 (s, 1H), 7.71-7.68 (m, 2H), 7.41-7.38 (m, 2H), 4.55-4.40 (m, 2H), 3.64-3.59 (m, 1H), 3.53-3.48 (m, 1H), 2.96-2.92 (m, 1H), 2.85-2.69 (m, 4H), 2.08-2.01 (m, 1H), 1.94-1.89 (m, 1H), 1.77-1.65 (m, 5H), 1.43 (s, 9H). LC/MS (Table 1, Method D) R$_t$=5.67 min; MS m/z: 562.0 [M+H]$^+$.

Example #83. 2-[[6-tert-butyl-3-[(4-chlorophenyl)carbamoyl]-4,5,6,7-tetrahydrobenzothiophen-2-yl]carbamoyl]cyclohexanecarboxylic acid (Compound 79)

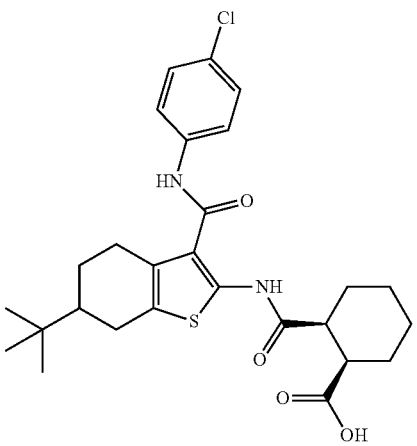 [SMILES: CC(C)(C)C1CCc2c(sc(NC(=O)[C@H]3CCCC[C@H]3C(=O)O)c2C(=O)Nc2ccc(Cl)cc2)C1]

Step A: 2-((6-(tert-butyl)-3-(methoxycarbonyl)-4,5,6,7-tetrahydrobenzo[b] thiophen-2-yl)carbamoyl)cyclohexane-1-carboxylic acid

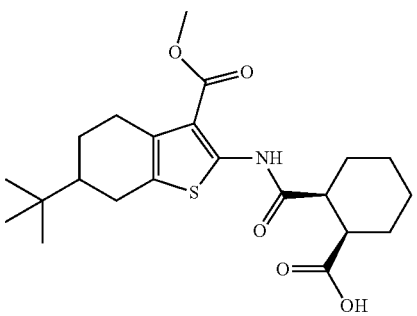 [SMILES: COC(=O)c1c(NC(=O)[C@H]2CCCC[C@H]2C(=O)O)sc2c1CCC(C(C)(C)C)C2]

A mixture of benzo[b]thiophene-3-carboxylic acid, 2-amino-6-(1,1-dimethylethyl)-4,5,6,7-tetrahydro-, methyl ester (774 mg, 2.9 mmol) and cis-1,2-cyclohexane dicarboxylic anhydride (2.25 g, 14.6 mmol) in dioxane (20 mL) was refluxed for 10 h. The reaction mixture was concentrated in vacuo, diluted with EtOAc (50 mL), washed with 0.1N HCl (50 mL). The organic phase was dried over $Na_2SO_4$, filtered, and concentrated in vacuo. The residue was used as such in the next step.

Step B: 6-(tert-butyl)-2-(2-carboxycyclohexane-1-carboxamido)-4,5,6,7-tetrahydrobenzo[b]thiophene-3-carboxylic acid

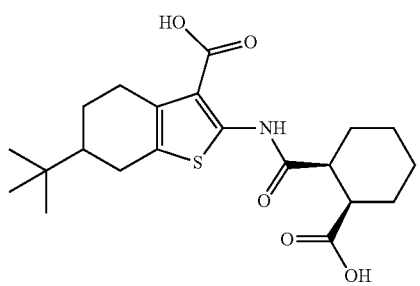 [SMILES: CC(C)(C)C1CCc2c(sc(NC(=O)[C@H]3CCCC[C@H]3C(=O)O)c2C(=O)O)C1]

2-((6-(tert-butyl)-3-(methoxycarbonyl)-4,5,6,7-tetrahydrobenzo[b] thiophen-2-yl)carbamoyl)cyclohexane-1-carboxylic acid (1.22 g, 2.9 mmol) was dissolved in MeOH/THF 1:1 (10 mL), and LiOH (750 mg, 17.6 mmol) in $H_2O$ (10 mL) was added. The reaction mixture was stirred at reflux for 2 h. The reaction mixture was cooled down to rt, and acidified with 0.1 N HCl. Water (50 mL) was added and the reaction mixture was extracted with EtOAc (50 mL). The organic phase was dried over $MgSO_4$, filtered and concentrated in vacuo. The residue was triturated in isohexane to yield 6-(tert-butyl)-2-(2-carboxycyclohexane-1-carboxamido)-4,5,6,7-tetrahydrobenzo[b]thiophene-3-carboxylic acid (1.2 g, 100%) and was used as such in the next step.

Step C: 2-[[6-tert-butyl-3-[(4-chlorophenyl)carbamoyl]-4,5,6,7-tetrahydrobenzo thiophen-2-yl]carbamoyl]cyclohexanecarboxylic acid (Compound 79)

To a mixture of 6-(tert-butyl)-2-(2-carboxycyclohexane-1-carboxamido)-4,5,6,7-tetrahydrobenzo[b]thiophene-3-carboxylic acid (200 mg, 0.49 mmol), DIEA (409 µl, 2.4 mmol) in DMF (5 mL), was added HATU (380 mg, 1 mmol). The reaction mixture was stirred at rt for 30 min, then 4-chloroaniline (102 mg, 0.8 mmol) was added. The reaction mixture was stirred at 50° C. for 1 h. 4-chloroaniline (102 mg, 0.8 mmol) and HATU (200 mg, 0.52 mmol) were added and the reaction mixture was stirred at 50° C. for 2 h. 1N NaOH (5 mL) was then added and the reaction mixture was stirred at 50° C. for 25 min. Water (50 mL) was added and the reaction mixture was extracted with EtOAc (50 mL). The organic phase was washed with Aq $NaHCO_3$, dried over $MgSO_4$, filtered and concentrated in vacuo. The residue was purified by trituration in EtOAc/isohexane to give the title compound as a white solid (25 mg, 10%). $^1$H NMR (DMSO-$d_6$, 400 MHz): δ 12.10 (s, 1H), 10.77 (s, 1H), 9.69 (s, 1H), 7.70 (d, J=8.8 Hz, 2H), 7.39 (d, J=8.9 Hz, 2H), 2.91-2.88 (m, 1H), 2.79-2.65 (m, 4H), 2.42-2.33 (m, 1H), 2.04-1.98 (m, 2H), 1.92-1.85 (m, 1H), 1.71-1.66 (m, 2H), 1.48-1.36 (m, 5H), 1.28-1.16 (m, 1H), 0.92 (s, 9H). LC/MS (Table 1, Method D) $R_t$=6.28 min; MS m/z: 517.3 [M+H]$^+$.

Biology

Antiviral Effect

The antiviral effect of the compounds of the invention have been tested on A549 cell lines infected with H1N1 (influenza A/New Caledonia/20/99). IC50 are reported in the following Tables 1 and 2. The results show that the compounds of the present invention present an antiviral effect.

TABLE 1
| Structure | Compound | IC50 (M) |
|---|---|---|
| 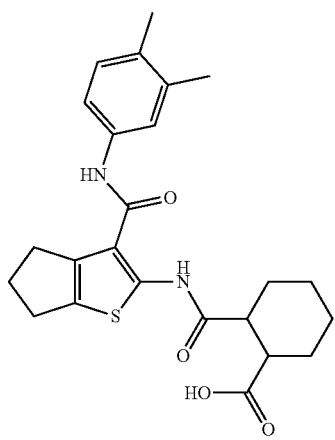 [SMILES: Cc1ccc(NC(=O)c2c(NC(=O)C3CCCCC3C(=O)O)sc3c2CCC3)cc1C] | Compound 1 | 7.78 10$^{-6}$ |
| 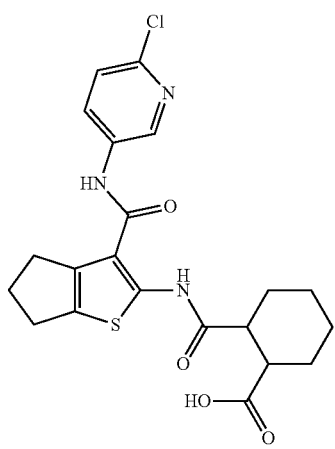 [SMILES: O=C(Nc1ccc(Cl)nc1)c1c(NC(=O)C2CCCCC2C(=O)O)sc2c1CCC2] | Compound 2 | 1.80 10$^{-5}$ |
| 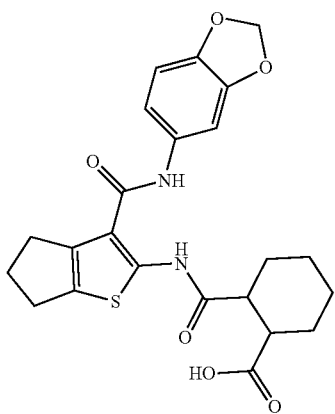 [SMILES: O=C(Nc1ccc2c(c1)OCO2)c1c(NC(=O)C2CCCCC2C(=O)O)sc2c1CCC2] | Compound 3 | 1.03 10$^{-5}$ |

TABLE 1-continued
| Structure | Compound | IC50 (M) |
|---|---|---|
| 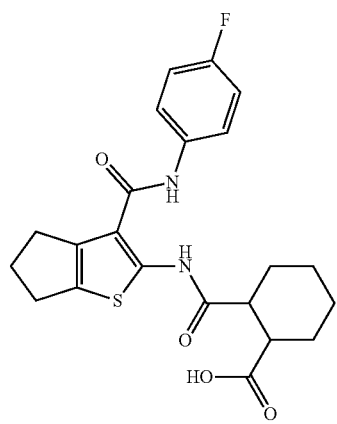 [SMILES: O=C(Nc1ccc(F)cc1)c1c(NC(=O)C2CCCCC2C(=O)O)sc2c1CCC2] | Compound 4 | 1.50 10<sup>−5</sup> |
| 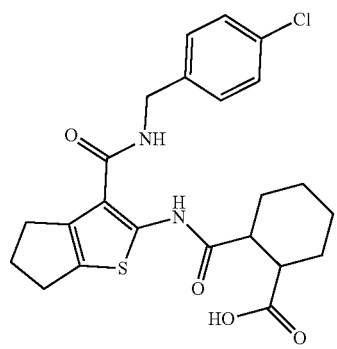 [SMILES: O=C(NCc1ccc(Cl)cc1)c1c(NC(=O)C2CCCCC2C(=O)O)sc2c1CCC2] | Compound 5 | 1.07 10<sup>−5</sup> |
| 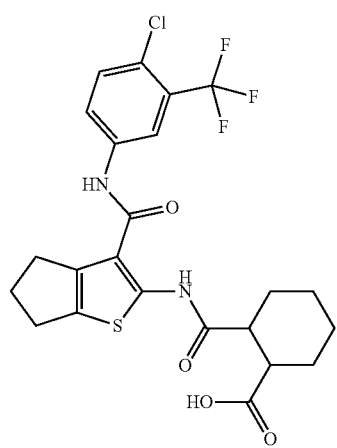 [SMILES: O=C(Nc1ccc(Cl)c(C(F)(F)F)c1)c1c(NC(=O)C2CCCCC2C(=O)O)sc2c1CCC2] | Compound 6 | 4.68 10<sup>−6</sup> |

TABLE 1-continued
| Structure | Compound | IC50 (M) |
|---|---|---|
| 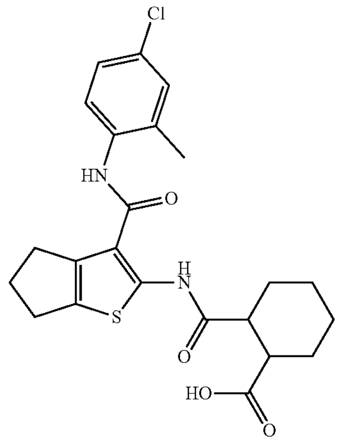 [SMILES: Cc1cc(Cl)ccc1NC(=O)c1c(NC(=O)C2CCCCC2C(=O)O)sc2c1CCC2] | Compound 7 | 1.01 10⁻⁵ |
| 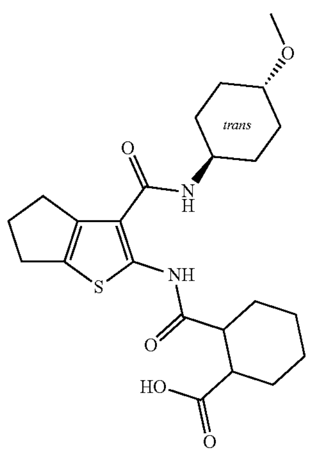 [SMILES: CO[C@H]1CC[C@H](NC(=O)c2c(NC(=O)C3CCCCC3C(=O)O)sc3c2CCC3)CC1] | Compound 8 | 2.74 10⁻⁵ |
| 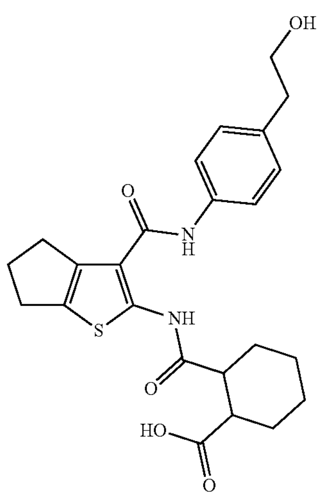 [SMILES: O=C(Nc1ccc(CCO)cc1)c1c(NC(=O)C2CCCCC2C(=O)O)sc2c1CCC2] | Compound 9 | 2.11 10⁻⁵ |
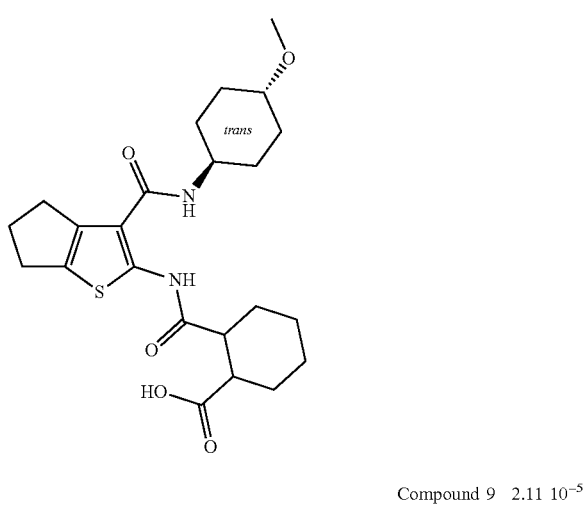
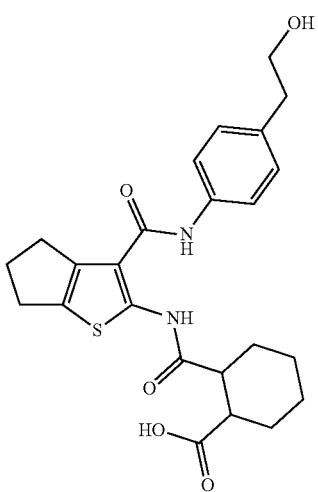

TABLE 1-continued
| Structure | Compound | IC50 (M) |
|---|---|---|
| 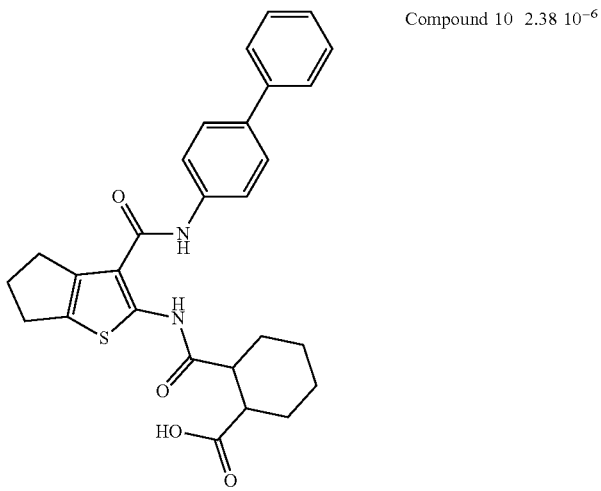 | Compound 10 | 2.38 10⁻⁶ |
| 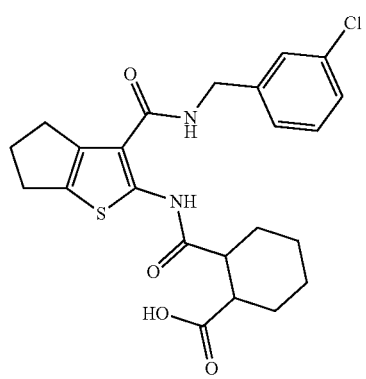 [SMILES: O=C(NCc1cccc(Cl)c1)c1c(NC(=O)C2CCCCC2C(=O)O)sc2c1CCC2] | Compound 11 | 8.63 10⁻⁶ |
| 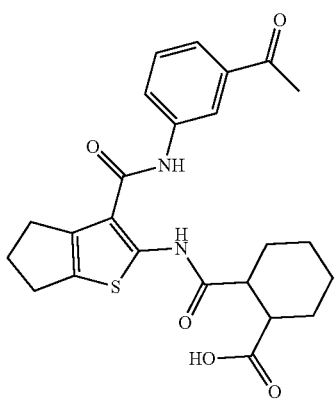 [SMILES: CC(=O)c1cccc(NC(=O)c2c(NC(=O)C3CCCCC3C(=O)O)sc3c2CCC3)c1] | Compound 12 | 2.12 10⁻⁵ |

TABLE 1-continued
| Structure | Compound | IC50 (M) |
|---|---|---|
| 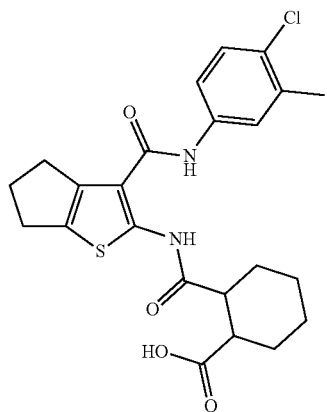 [SMILES: Cc1cc(NC(=O)c2c(NC(=O)C3CCCCC3C(=O)O)sc3c2CCC3)ccc1Cl] | Compound 13 | 4.68 10$^{-6}$ |
| 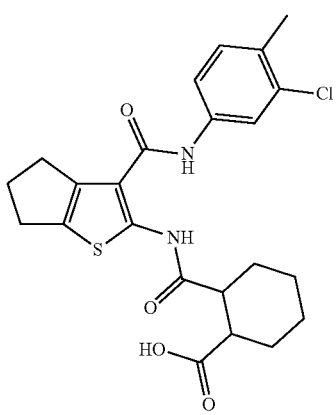 [SMILES: Cc1ccc(NC(=O)c2c(NC(=O)C3CCCCC3C(=O)O)sc3c2CCC3)cc1Cl] | Compound 14 | 4.78 10$^{-6}$ |
| 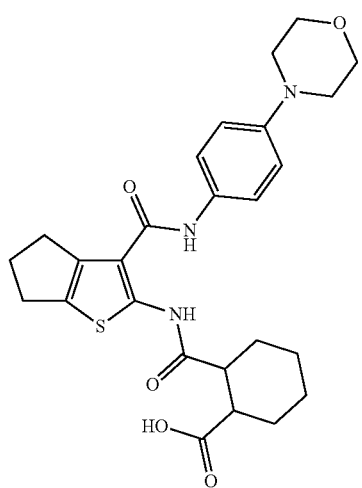 [SMILES: O=C(Nc1ccc(N2CCOCC2)cc1)c1c(NC(=O)C2CCCCC2C(=O)O)sc2c1CCC2] | Compound 15 | 1.12 10$^{-5}$ |

TABLE 1-continued
| Structure | Compound | IC50 (M) |
|---|---|---|
| 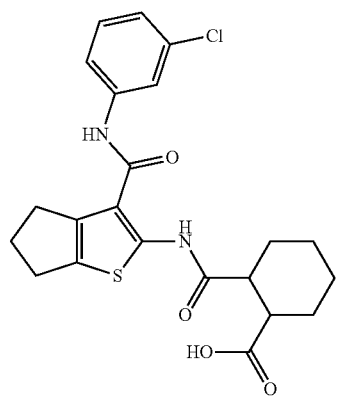 | Compound 16 | 1.04 10$^{-5}$ |
| 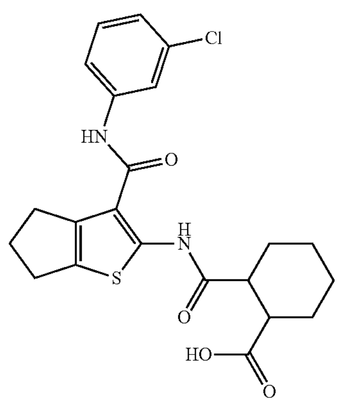 [SMILES: O=C(Nc1cccc(Cl)c1)c1c(NC(=O)C2CCCCC2C(=O)O)sc2c1CCC2] | Compound 17 | 4.88 10$^{-6}$ |
| 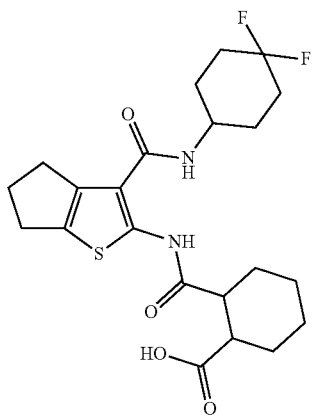 [SMILES: O=C(NC1CCC(F)(F)CC1)c1c(NC(=O)C2CCCCC2C(=O)O)sc2c1CCC2] | Compound 18 | 3.30 10$^{-5}$ |

TABLE 1-continued
| Structure | Compound | IC50 (M) |
|---|---|---|
| 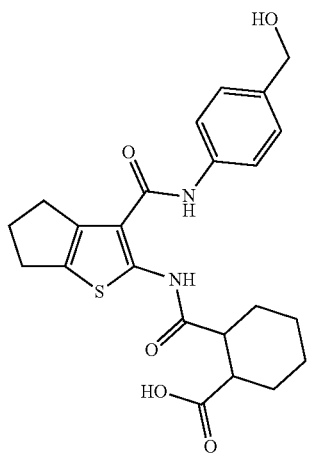 [SMILES: O=C(Nc1ccc(CO)cc1)c1c(NC(=O)C2CCCCC2C(=O)O)sc2c1CCC2] | Compound 19 | 3.08 10$^{-5}$ |
| 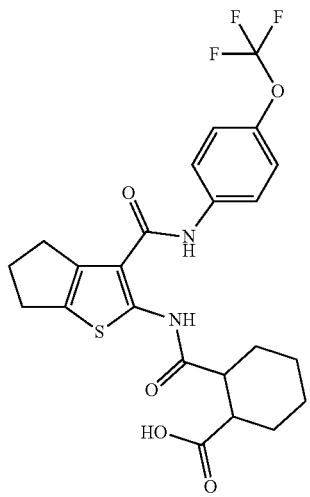 [SMILES: O=C(Nc1ccc(OC(F)(F)F)cc1)c1c(NC(=O)C2CCCCC2C(=O)O)sc2c1CCC2] | Compound 20 | 6.48 10$^{-6}$ |
| 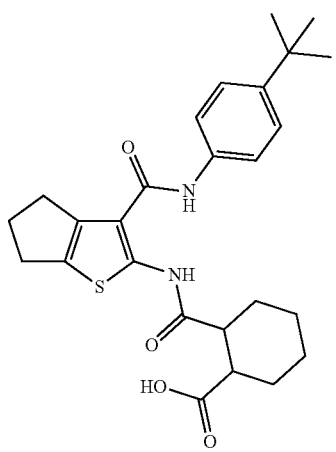 [SMILES: CC(C)(C)c1ccc(NC(=O)c2c(NC(=O)C3CCCCC3C(=O)O)sc3c2CCC3)cc1] | Compound 21 | 4.68 10$^{-6}$ |

TABLE 1-continued

| Structure | Compound | IC50 (M) |
|---|---|---|
| 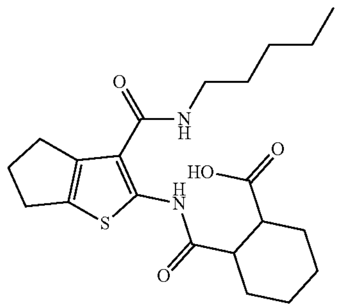 [SMILES: CCCCCNC(=O)c1c(NC(=O)C2CCCCC2C(=O)O)sc2c1CCC2] | Compound 22 | 2.03 10⁻⁵ |
| 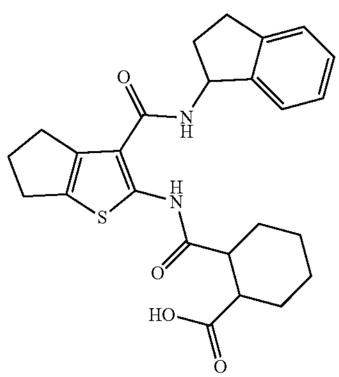 [SMILES: O=C(NC1CCc2ccccc21)c1c(NC(=O)C2CCCCC2C(=O)O)sc2c1CCC2] | Compound 23 | 6.28 10⁻⁶ |
| 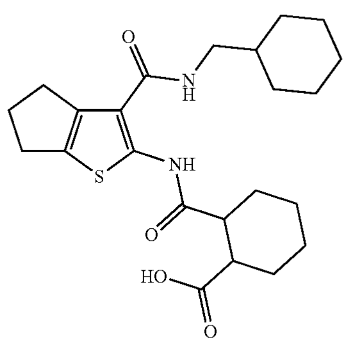 [SMILES: O=C(NCC1CCCCC1)c1c(NC(=O)C2CCCCC2C(=O)O)sc2c1CCC2] | Compound 24 | 1.23 10⁻⁵ |
| 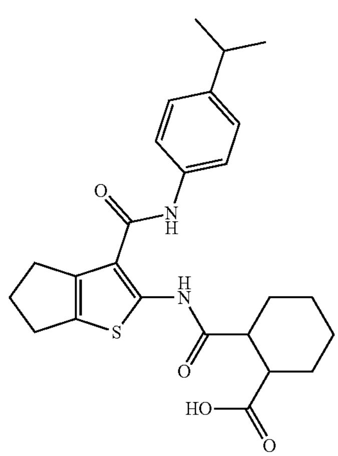 [SMILES: CC(C)c1ccc(NC(=O)c2c(NC(=O)C3CCCCC3C(=O)O)sc3c2CCC3)cc1] | Compound 25 | 4.68 10⁻⁶ |

TABLE 1-continued
| Structure | Compound | IC50 (M) |
|---|---|---|
| 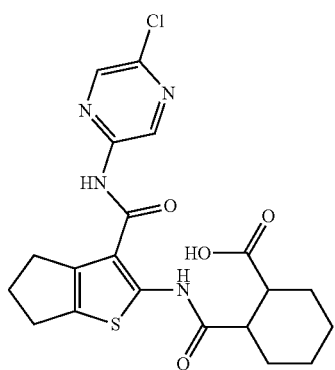 [SMILES: O=C(Nc1cnc(Cl)cn1)c1c(NC(=O)C2CCCCC2C(=O)O)sc2c1CCC2] | Compound 26 | 1.93 10$^{-5}$ |
| 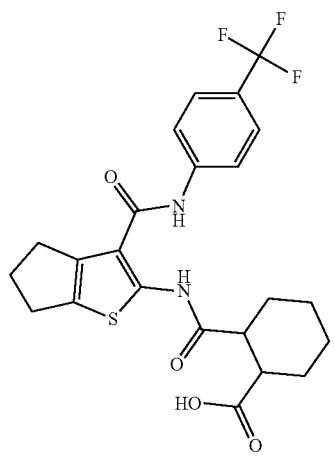 [SMILES: O=C(Nc1ccc(C(F)(F)F)cc1)c1c(NC(=O)C2CCCCC2C(=O)O)sc2c1CCC2] | Compound 27 | 1.81 10$^{-5}$ |
| 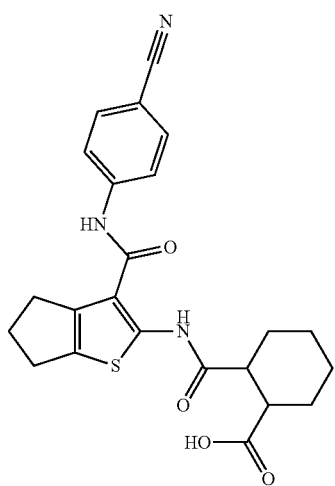 [SMILES: N#Cc1ccc(NC(=O)c2c(NC(=O)C3CCCCC3C(=O)O)sc3c2CCC3)cc1] | Compound 28 | 1.59 10$^{-5}$ |

TABLE 1-continued

| Structure | Compound | IC50 (M) |
|---|---|---|
| 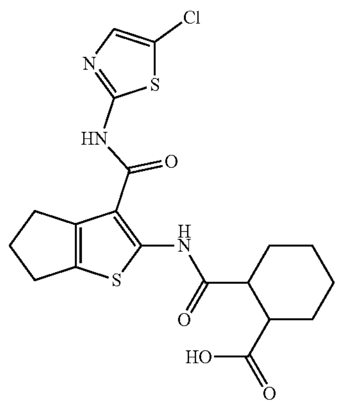 [SMILES: O=C(Nc1ncc(Cl)s1)c1c(NC(=O)C2CCCCC2C(=O)O)sc2c1CCC2] | Compound 29 | 6.78 10$^{-6}$ |
| 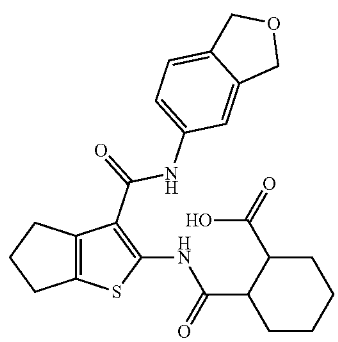 [SMILES: O=C(Nc1ccc2c(c1)COC2)c1c(NC(=O)C2CCCCC2C(=O)O)sc2c1CCC2] | Compound 30 | 1.96 10$^{-5}$ |
| 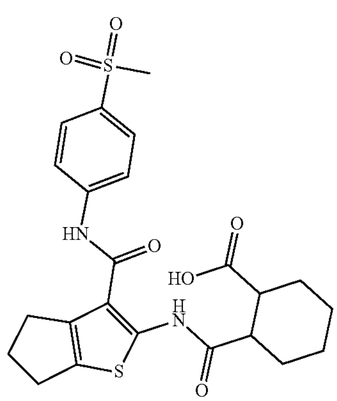 [SMILES: CS(=O)(=O)c1ccc(NC(=O)c2c(NC(=O)C3CCCCC3C(=O)O)sc3c2CCC3)cc1] | Compound 31 | 2.73 10$^{-5}$ |
| 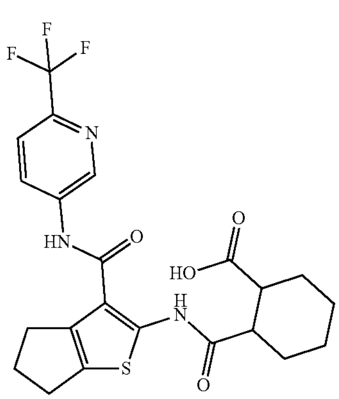 [SMILES: O=C(Nc1ccc(C(F)(F)F)nc1)c1c(NC(=O)C2CCCCC2C(=O)O)sc2c1CCC2] | Compound 32 | 2.20 10$^{-5}$ |

TABLE 1-continued
| Structure | Compound | IC50 (M) |
|---|---|---|
| 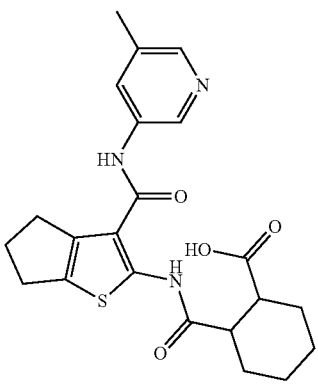 [SMILES: Cc1cncc(NC(=O)c2c(NC(=O)C3CCCCC3C(=O)O)sc3c2CCC3)c1] | Compound 33 | 2.74 10⁻⁵ |
| 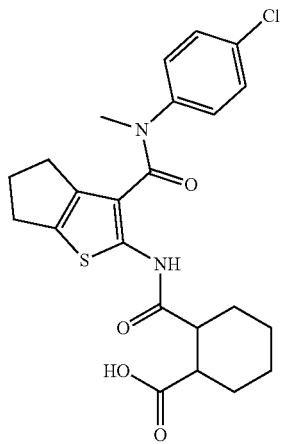 [SMILES: CN(C(=O)c1c(NC(=O)C2CCCCC2C(=O)O)sc2c1CCC2)c1ccc(Cl)cc1] | Compound 34 | 3.04 10⁻⁵ |
| 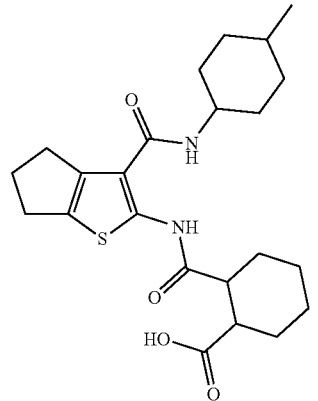 [SMILES: CC1CCC(NC(=O)c2c(NC(=O)C3CCCCC3C(=O)O)sc3c2CCC3)CC1] | Compound 35 | 1.24 10⁻⁵ |
| 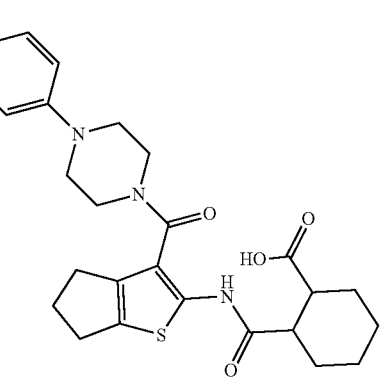 | Compound 36 | 2.10 10⁻⁵ |

TABLE 1-continued
| Structure | Compound | IC50 (M) |
|---|---|---|
| 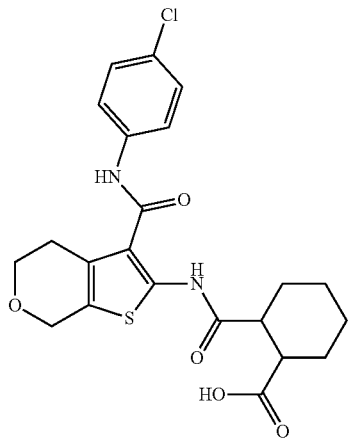 [SMILES: O=C(Nc1ccc(Cl)cc1)c1c(NC(=O)C2CCCCC2C(=O)O)sc2c1CCOC2] | Compound 37 | 4.34 10⁻⁵ |
| 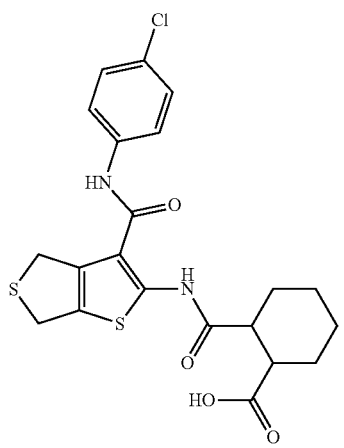 [SMILES: O=C(Nc1ccc(Cl)cc1)c1c(NC(=O)C2CCCCC2C(=O)O)sc2c1CSC2] | Compound 38 | 6.44 10⁻⁶ |
| 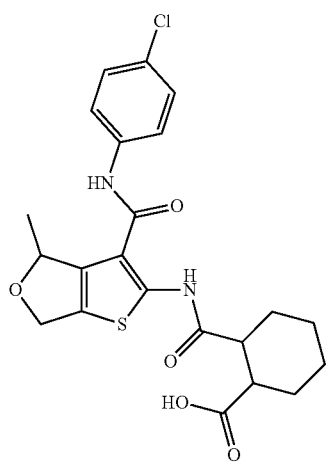 [SMILES: CC1OCc2sc(NC(=O)C3CCCCC3C(=O)O)c(C(=O)Nc3ccc(Cl)cc3)c21] | Compound 39 | 5.35 10⁻⁵ |

TABLE 1-continued
| Structure | Compound | IC50 (M) |
|---|---|---|
| 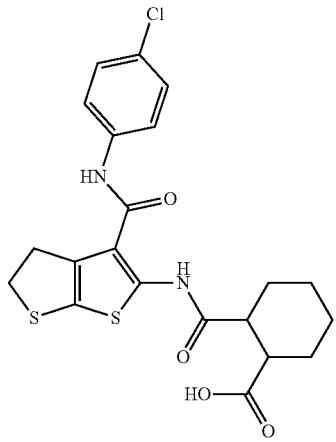 [SMILES: O=C(Nc1ccc(Cl)cc1)c1c(NC(=O)C2CCCCC2C(=O)O)sc2c1CCS2] | Compound 40 | 7.35 10⁻⁶ |
| 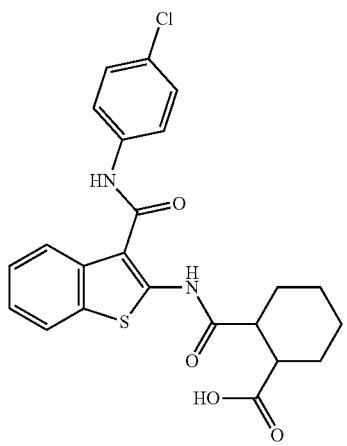 [SMILES: O=C(Nc1ccc(Cl)cc1)c1c(NC(=O)C2CCCCC2C(=O)O)sc2ccccc12] | Compound 41 | 3.53 10⁻⁶ |
| 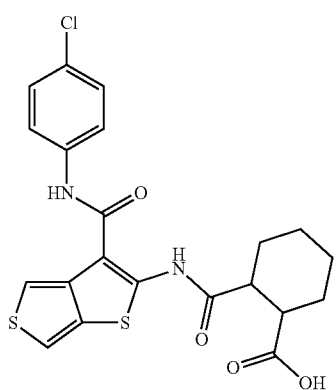 [SMILES: O=C(Nc1ccc(Cl)cc1)c1c(NC(=O)C2CCCCC2C(=O)O)sc2cscc12] | Compound 42 | 3.08 10⁻⁶ |

TABLE 1-continued
| Structure | Compound | IC50 (M) |
|---|---|---|
| 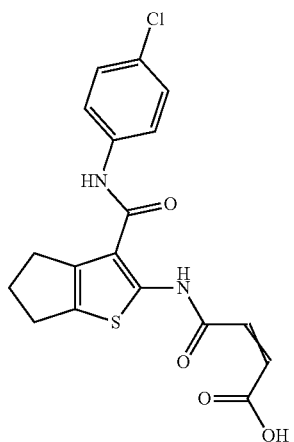 [SMILES: O=C(O)C=CC(=O)Nc1sc2c(c1C(=O)Nc1ccc(Cl)cc1)CCC2] | Compound 43 | 3.32 10$^{-5}$ |
| 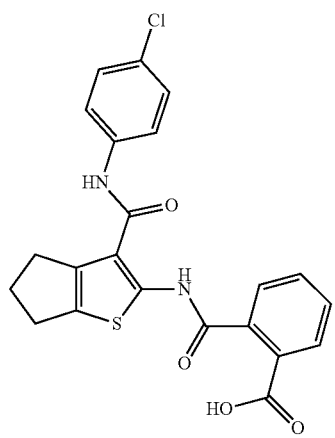 [SMILES: O=C(O)c1ccccc1C(=O)Nc1sc2c(c1C(=O)Nc1ccc(Cl)cc1)CCC2] | Compound 44 | 2.16 10$^{-5}$ |
| 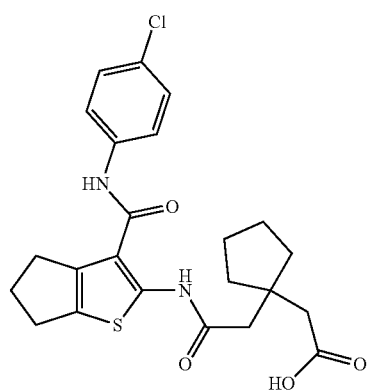 [SMILES: O=C(O)CC1(CC(=O)Nc2sc3c(c2C(=O)Nc2ccc(Cl)cc2)CCC3)CCCC1] | Compound 45 | 8.10 10$^{-6}$ |

TABLE 1-continued
| Structure | Compound | IC50 (M) |
|---|---|---|
| 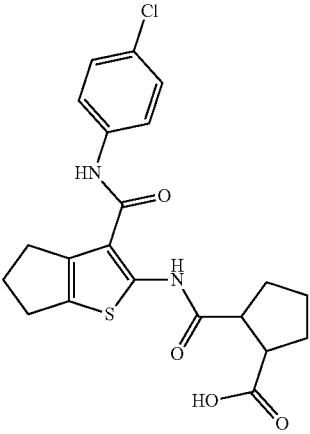 [SMILES: O=C(Nc1ccc(Cl)cc1)c1c(NC(=O)C2CCCC2C(=O)O)sc2c1CCC2] | Compound 46 | 1.74 10⁻⁵ |
| 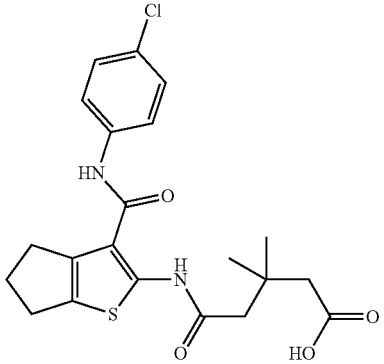 [SMILES: CC(C)(CC(=O)O)CC(=O)Nc1sc2c(c1C(=O)Nc1ccc(Cl)cc1)CCC2] | Compound 47 | 2.27 10⁻⁵ |
| 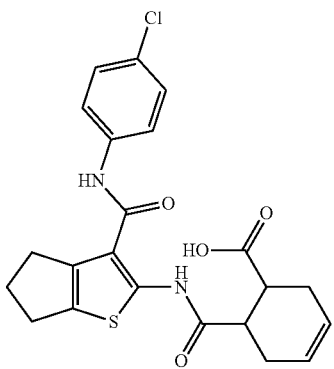 [SMILES: O=C(Nc1ccc(Cl)cc1)c1c(NC(=O)C2CC=CCC2C(=O)O)sc2c1CCC2] | Compound 48 | 1.12 10⁻⁵ |
| 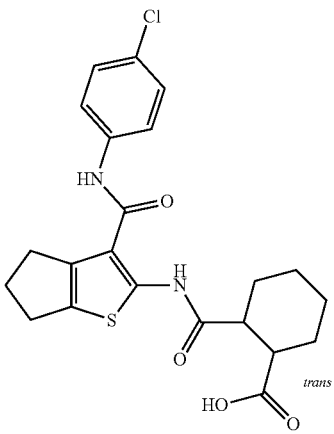 [SMILES: O=C(Nc1ccc(Cl)cc1)c1c(NC(=O)C2CCCCC2C(=O)O)sc2c1CCC2] | Compound 49 | 1.22 10⁻⁵ |

TABLE 1-continued
| Structure | Compound | IC50 (M) |
|---|---|---|
| 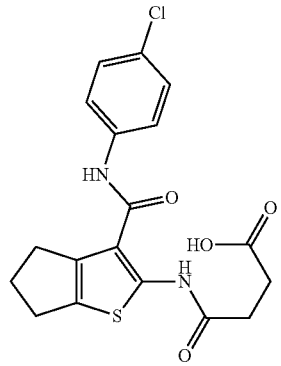 [SMILES: O=C(O)CCC(=O)Nc1sc2c(c1C(=O)Nc1ccc(Cl)cc1)CCC2] | Compound 50 | 3.32 10$^{-5}$ |
| 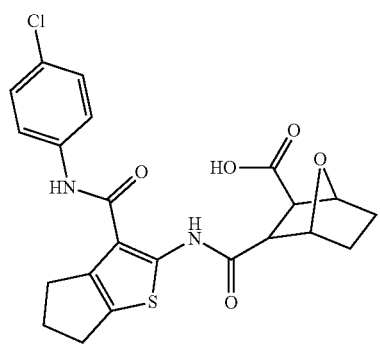 [SMILES: O=C(Nc1ccc(Cl)cc1)c1c(NC(=O)C2C3CCC(O3)C2C(=O)O)sc2c1CCC2] | Compound 51 | 2.97 10$^{-5}$ |
| 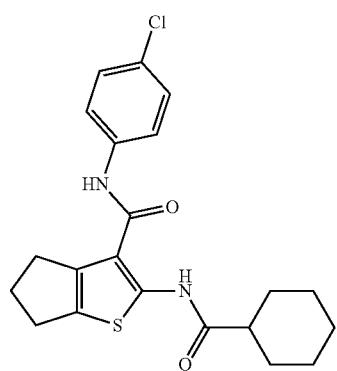 [SMILES: O=C(Nc1ccc(Cl)cc1)c1c(NC(=O)C2CCCCC2)sc2c1CCC2] | Compound 52 | 2.93 10$^{-5}$ |
| 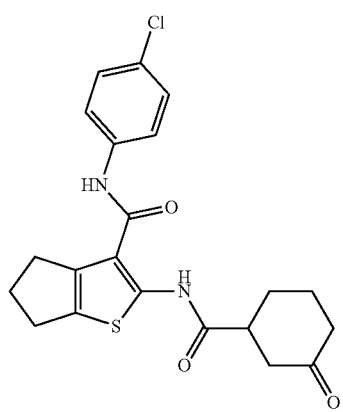 [SMILES: O=C1CCCC(C(=O)Nc2sc3c(c2C(=O)Nc2ccc(Cl)cc2)CCC3)C1] | Compound 53 | 1.28 10$^{-5}$ |

TABLE 1-continued

| Structure | Compound | IC50 (M) |
|---|---|---|
| 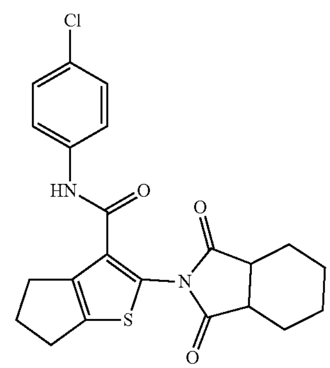 [SMILES: O=C(Nc1ccc(Cl)cc1)c1c(N2C(=O)C3CCCCC3C2=O)sc2c1CCC2] | Compound 54 | 5.98 10$^{-6}$ |
| 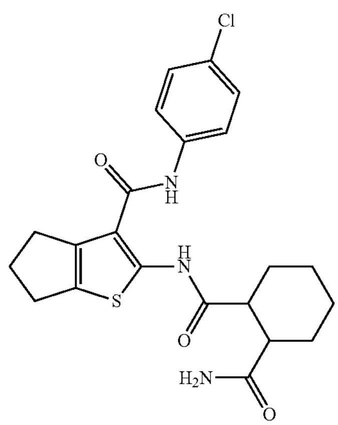 [SMILES: NC(=O)C1CCCCC1C(=O)Nc1sc2c(c1C(=O)Nc1ccc(Cl)cc1)CCC2] | Compound 55 | 2.70 10$^{-5}$ |
| 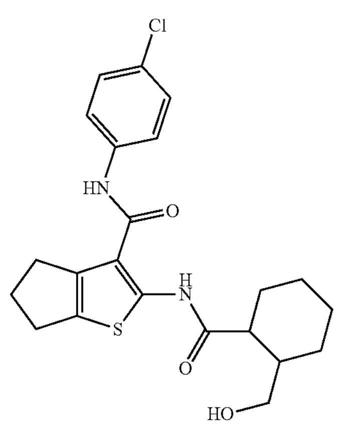 [SMILES: O=C(Nc1ccc(Cl)cc1)c1c(NC(=O)C2CCCCC2CO)sc2c1CCC2] | Compound 56 | 2.40 10$^{-5}$ |
| 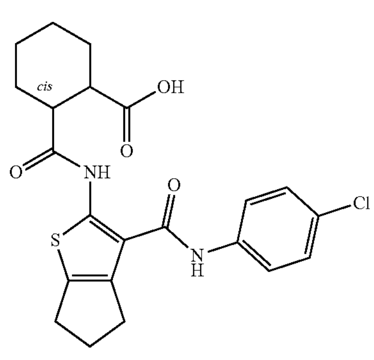 [SMILES: O=C(Nc1ccc(Cl)cc1)c1c(NC(=O)C2CCCCC2C(=O)O)sc2c1CCC2] | Compound 57 | 7.18 10$^{-6}$ |

TABLE 1-continued

| Structure | Compound | IC50 (M) |
|---|---|---|
| 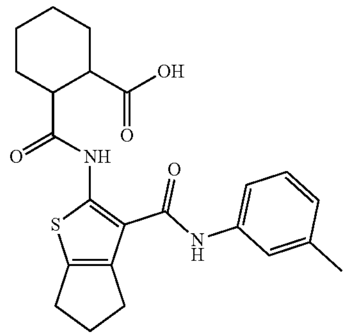 [SMILES: Cc1cccc(NC(=O)c2c(NC(=O)C3CCCCC3C(=O)O)sc3c2CCC3)c1] | Compound 58 | 2.76 10$^{-5}$ |
| 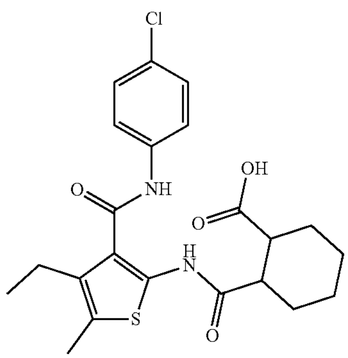 [SMILES: CCc1c(C)sc(NC(=O)C2CCCCC2C(=O)O)c1C(=O)Nc1ccc(Cl)cc1] | Compound 59 | 5.35 10$^{-5}$ |
| 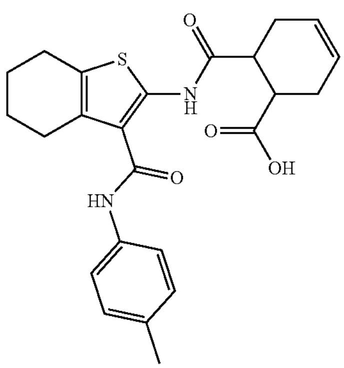 [SMILES: Cc1ccc(NC(=O)c2c(NC(=O)C3CC=CCC3C(=O)O)sc3c2CCCC3)cc1] | Compound 60 | 5.48 10$^{-5}$ |
| 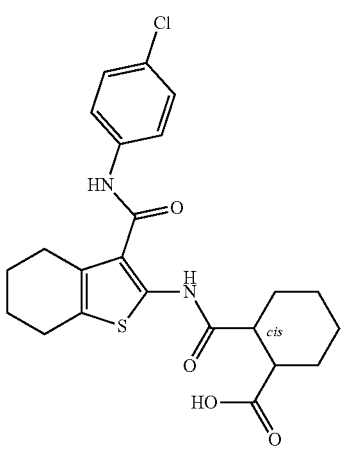 [SMILES: O=C(Nc1ccc(Cl)cc1)c1c(NC(=O)C2CCCCC2C(=O)O)sc2c1CCCC2] | Compound 61 | 8.59 10$^{-6}$ |

TABLE 1-continued
| Structure | Compound | IC50 (M) |
|---|---|---|
| 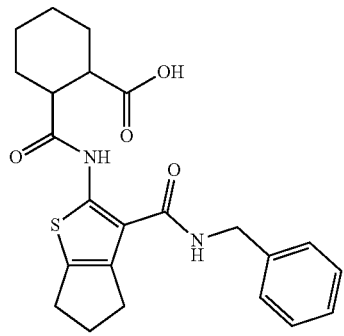 [SMILES: O=C(NCc1ccccc1)c1c(NC(=O)C2CCCCC2C(=O)O)sc2c1CCC2] | Compound 63 | 2.14 10$^{-5}$ |
| 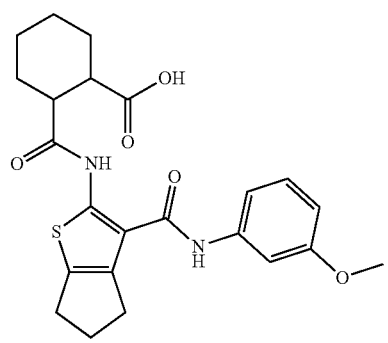 [SMILES: COc1cccc(NC(=O)c2c(NC(=O)C3CCCCC3C(=O)O)sc3c2CCC3)c1] | Compound 64 | 1.41 10$^{-5}$ |
| 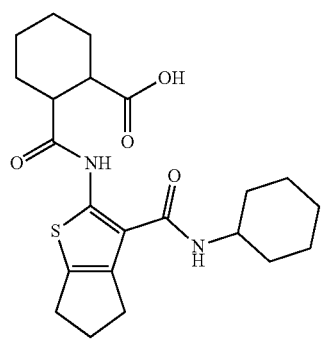 [SMILES: O=C(NC1CCCCC1)c1c(NC(=O)C2CCCCC2C(=O)O)sc2c1CCC2] | Compound 65 | 1.77 10$^{-5}$ |
| 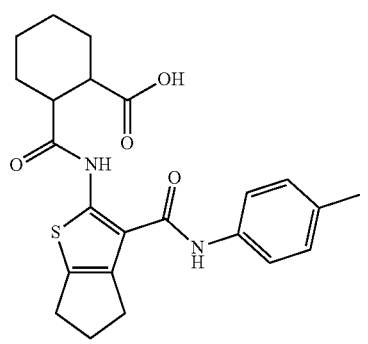 [SMILES: Cc1ccc(NC(=O)c2c(NC(=O)C3CCCCC3C(=O)O)sc3c2CCC3)cc1] | Compound 66 | 1.17 10$^{-5}$ |

TABLE 1-continued

| Structure | Compound | IC50 (M) |
|---|---|---|
| 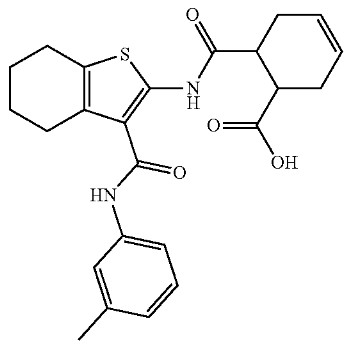 [SMILES: Cc1cccc(NC(=O)c2c(NC(=O)C3CC=CCC3C(=O)O)sc3c2CCCC3)c1] | Compound 68 | $1.17 \cdot 10^{-5}$ |
| 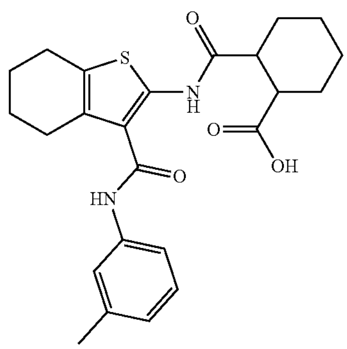 [SMILES: Cc1cccc(NC(=O)c2c(NC(=O)C3CCCCC3C(=O)O)sc3c2CCCC3)c1] | Compound 69 | $1.39 \cdot 10^{-5}$ |
| 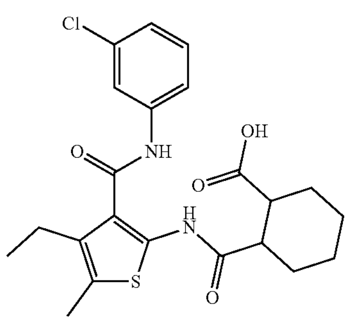 [SMILES: CCc1c(C)sc(NC(=O)C2CCCCC2C(=O)O)c1C(=O)Nc1cccc(Cl)c1] | Compound 70 | $1.47 \cdot 10^{-5}$ |
| 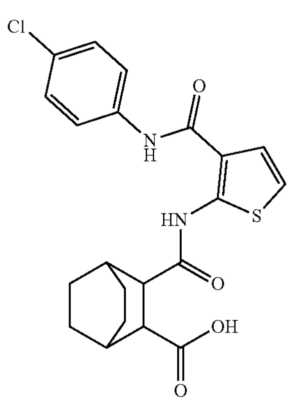 [SMILES: O=C(Nc1ccc(Cl)cc1)c1ccsc1NC(=O)C1C2CCC(CC2)C1C(=O)O] | Compound 71 | $1.22 \cdot 10^{-5}$ |

TABLE 1-continued

| Structure | Compound | IC50 (M) |
|---|---|---|
| 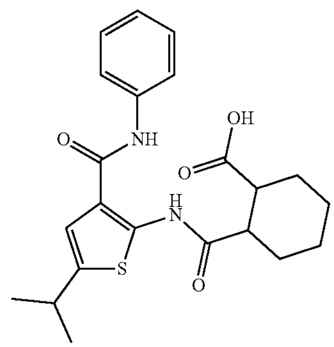 [SMILES: CC(C)c1cc(C(=O)Nc2ccccc2)c(NC(=O)C2CCCCC2C(=O)O)s1] | Compound 72 | 9.92 10⁻⁶ |
| 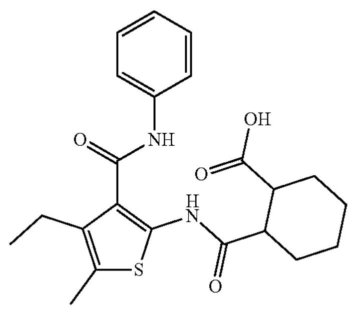 [SMILES: CCc1c(C)sc(NC(=O)C2CCCCC2C(=O)O)c1C(=O)Nc1ccccc1] | Compound 73 | 2.46 10⁻⁵ |
| 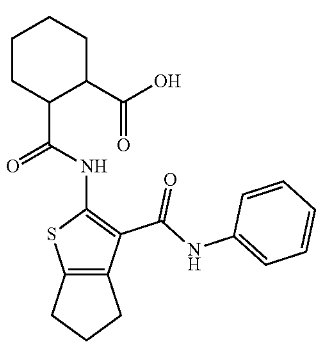 [SMILES: O=C(Nc1ccccc1)c1c(NC(=O)C2CCCCC2C(=O)O)sc2c1CCC2] | Compound 74 | 1.24 10⁻⁵ |
| 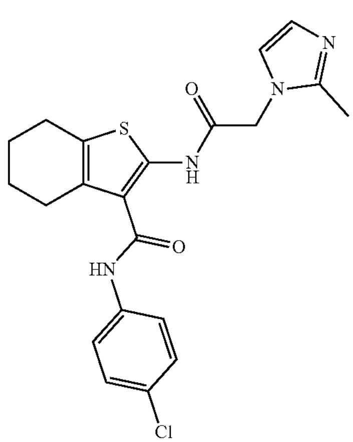 [SMILES: Cc1nccn1CC(=O)Nc1sc2c(c1C(=O)Nc1ccc(Cl)cc1)CCCC2] | Compound 75 | 1.71 10⁻⁵ |

TABLE 1-continued
| Structure | Compound | IC50 (M) |
|---|---|---|
| 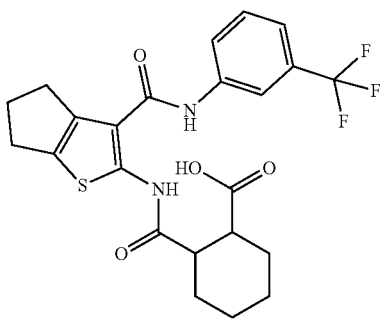 | Compound 76 | 1.41 10⁻⁵ |
| 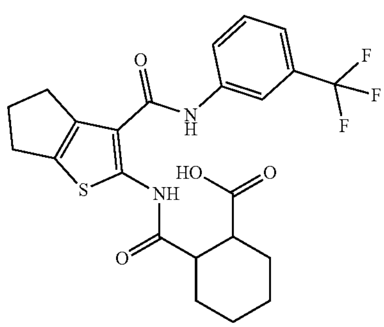 [SMILES: O=C(Nc1cccc(C(F)(F)F)c1)c1c(NC(=O)C2CCCCC2C(=O)O)sc2c1CCC2] | Compound 77 | 6.78 10⁻⁶ |
TABLE 2
| Structure | Compound | IC50 (M) |
|---|---|---|
| 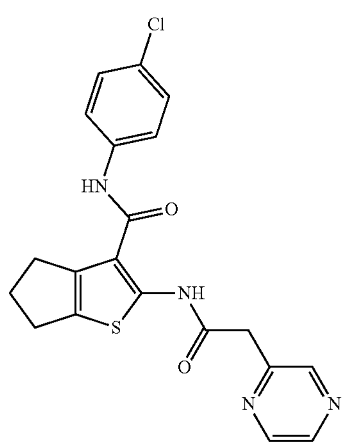 [SMILES: O=C(Cc1cnccn1)Nc1sc2c(c1C(=O)Nc1ccc(Cl)cc1)CCC2] | Compound 78 | 1.00 10⁻⁶ |

TABLE 2-continued
| Structure | Compound | IC50 (M) |
|---|---|---|
| 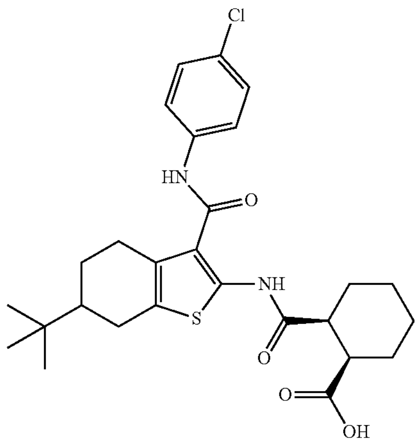 [SMILES: CC(C)(C)C1CCc2c(sc(NC(=O)[C@H]3CCCC[C@H]3C(=O)O)c2C(=O)Nc2ccc(Cl)cc2)C1] | Compound 79 | 1.85 10$^{-6}$ |
| 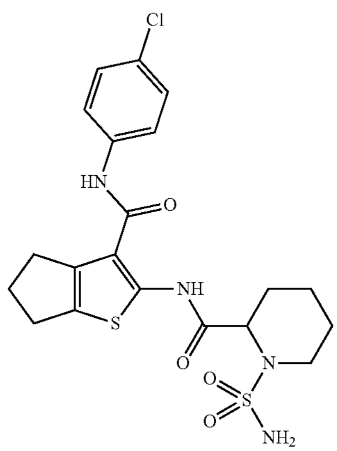 [SMILES: NS(=O)(=O)N1CCCCC1C(=O)Nc1sc2c(c1C(=O)Nc1ccc(Cl)cc1)CCC2] | Compound 80 | 2.25 10$^{-6}$ |
| 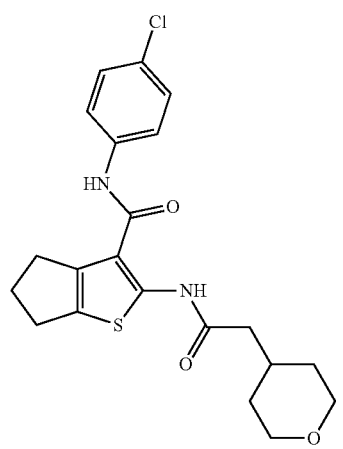 [SMILES: O=C(CC1CCOCC1)Nc1sc2c(c1C(=O)Nc1ccc(Cl)cc1)CCC2] | Compound 81 | 3.90 10$^{-6}$ |

TABLE 2-continued
| Structure | Compound | IC50 (M) |
|---|---|---|
| 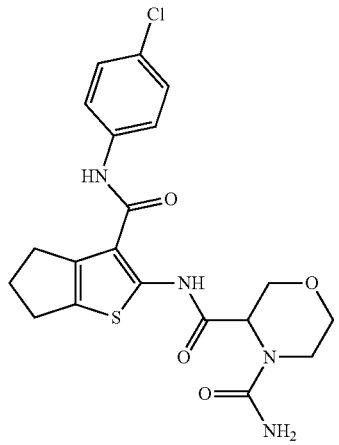 [SMILES: NC(=O)N1CCOCC1C(=O)Nc1sc2c(c1C(=O)Nc1ccc(Cl)cc1)CCC2] | Compound 82 | 4.40 10⁻⁶ |
| 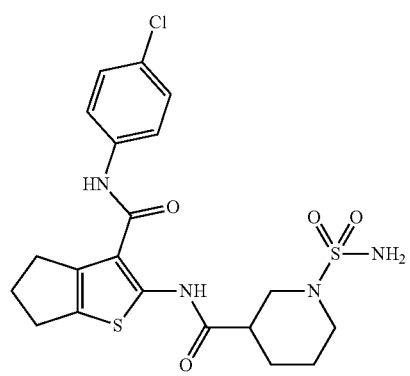 [SMILES: NS(=O)(=O)N1CCCC(C(=O)Nc2sc3c(c2C(=O)Nc2ccc(Cl)cc2)CCC3)C1] | Compound 83 | 5.05 10⁻⁶ |
| 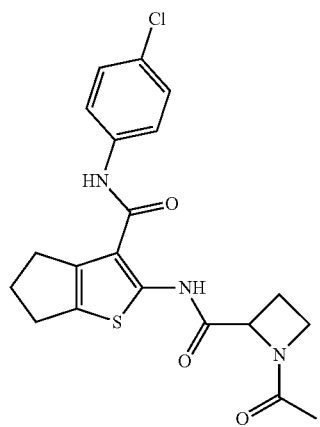 [SMILES: CC(=O)N1CCC1C(=O)Nc1sc2c(c1C(=O)Nc1ccc(Cl)cc1)CCC2] | Compound 84 | 2.96 10⁻⁵ |

TABLE 2-continued
| Structure | Compound | IC50 (M) |
| --- | --- | --- |
| 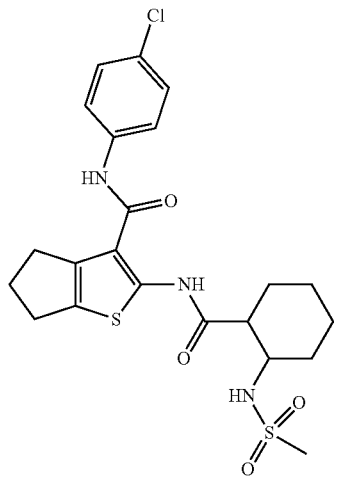 [SMILES: CS(=O)(=O)NC1CCCCC1C(=O)Nc1sc2c(c1C(=O)Nc1ccc(Cl)cc1)CCC2] | Compound 85 | 5.60 10$^{-6}$ |
| 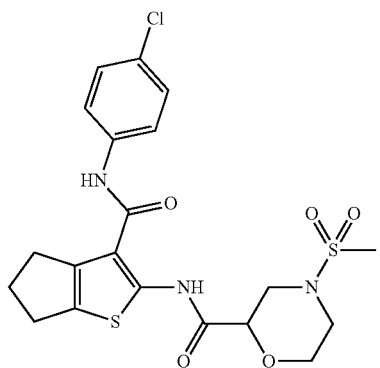 | Compound 86 | 6.30 10$^{-6}$ |
| 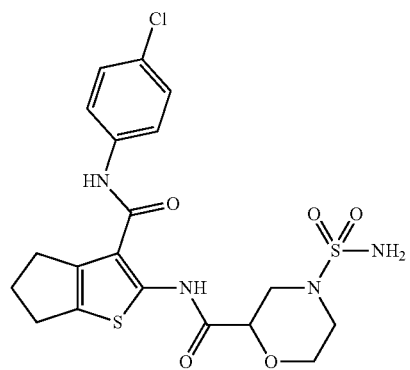 [SMILES: NS(=O)(=O)N1CCOC(C(=O)Nc2sc3c(c2C(=O)Nc2ccc(Cl)cc2)CCC3)C1] | Compound 87 | 6.75 10$^{-6}$ |

TABLE 2-continued
| Structure | Compound | IC50 (M) |
|---|---|---|
| 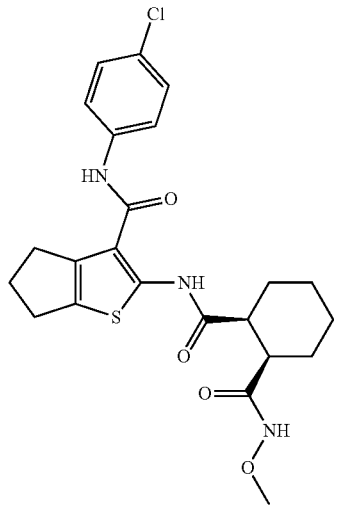 [SMILES: CONC(=O)[C@@H]1CCCC[C@@H]1C(=O)Nc1sc2c(c1C(=O)Nc1ccc(Cl)cc1)CCC2] | Compound 88 | 8.40 10⁻⁶ |
| 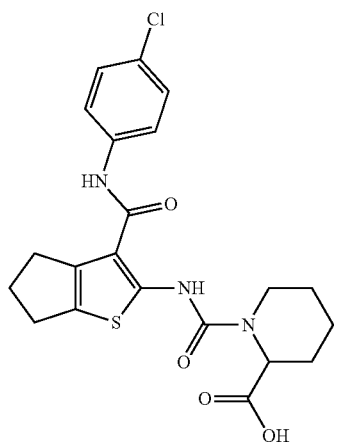 [SMILES: O=C(Nc1ccc(Cl)cc1)c1c(NC(=O)N2CCCCC2C(=O)O)sc2c1CCC2] | Compound 89 | 8.80 10⁻⁶ |
| 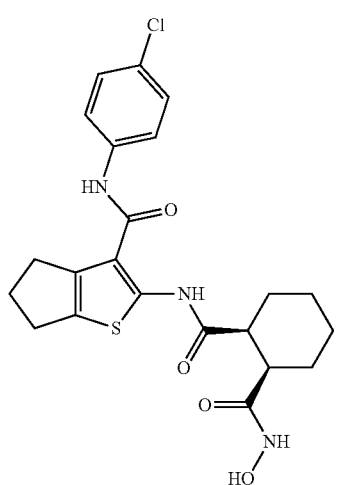 [SMILES: O=C(Nc1ccc(Cl)cc1)c1c(NC(=O)[C@H]2CCCC[C@H]2C(=O)NO)sc2c1CCC2] | Compound 90 | 9.00 10⁻⁶ |

TABLE 2-continued

| Structure | Compound | IC50 (M) |
|---|---|---|
| 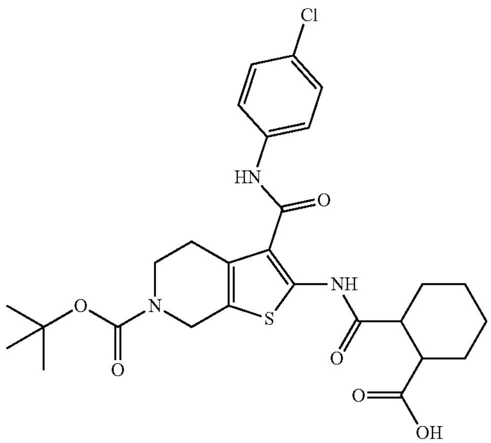 [SMILES: CC(C)(C)OC(=O)N1CCc2c(sc(NC(=O)C3CCCCC3C(=O)O)c2C(=O)Nc2ccc(Cl)cc2)C1] | Compound 91 | $1.00 \cdot 10^{-5}$ |
| 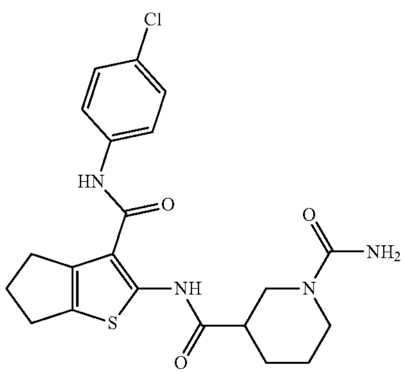 [SMILES: NC(=O)N1CCCC(C(=O)Nc2sc3c(c2C(=O)Nc2ccc(Cl)cc2)CCC3)C1] | Compound 92 | $1.14 \cdot 10^{-5}$ |
| 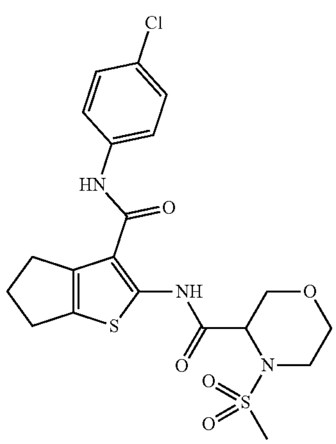 | Compound 93 | $1.27 \cdot 10^{-5}$ |
| 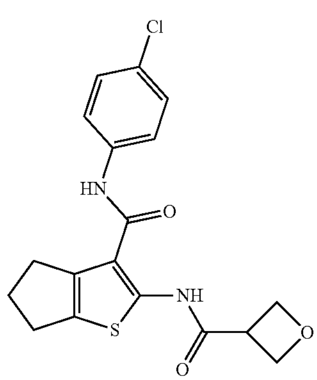 [SMILES: O=C(Nc1ccc(Cl)cc1)c1c(NC(=O)C2COC2)sc2c1CCC2] | Compound 94 | $1.29 \cdot 10^{-5}$ |

TABLE 2-continued
| Structure | Compound | IC50 (M) |
|---|---|---|
| 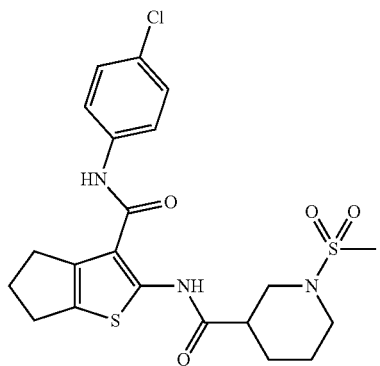 | Compound 95 | $1.37\ 10^{-5}$ |
| 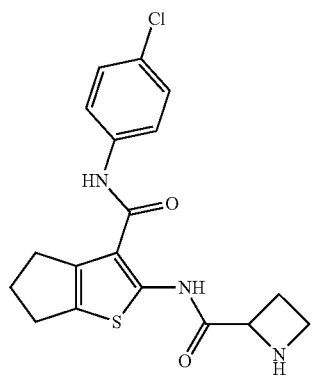 [SMILES: O=C(Nc1ccc(Cl)cc1)c1c(NC(=O)C2CCN2)sc2c1CCC2] | Compound 96 | $1.41\ 10^{-5}$ |
| 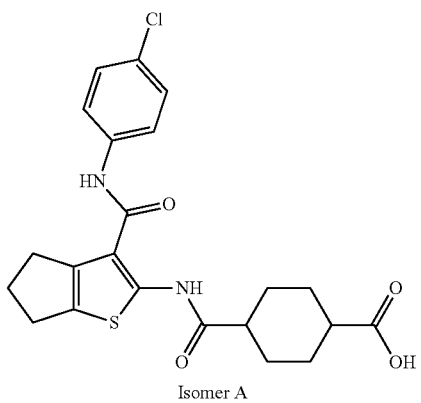 [SMILES: O=C(Nc1ccc(Cl)cc1)c1c(NC(=O)C2CCC(C(=O)O)CC2)sc2c1CCC2]  Isomer A | Compound 97 | $1.47\ 10^{-5}$ |
| 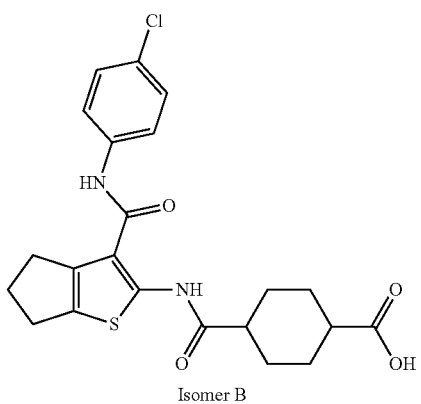 [SMILES: O=C(Nc1ccc(Cl)cc1)c1c(NC(=O)C2CCC(C(=O)O)CC2)sc2c1CCC2]  Isomer B | Compound 98 | $1.59\ 10^{-5}$ |

TABLE 2-continued
| Structure | Compound | IC50 (M) |
|---|---|---|
| 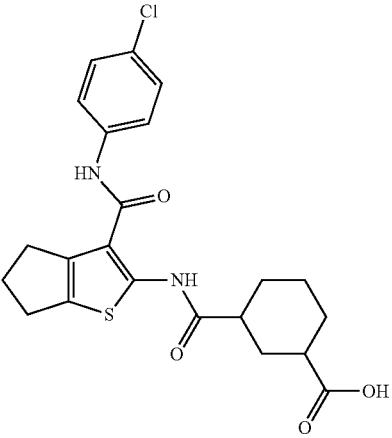 [SMILES: O=C(Nc1ccc(Cl)cc1)c1c(NC(=O)C2CCCC(C(=O)O)C2)sc2c1CCC2] | Compound 99 | 1.66 10$^{-5}$ |
| 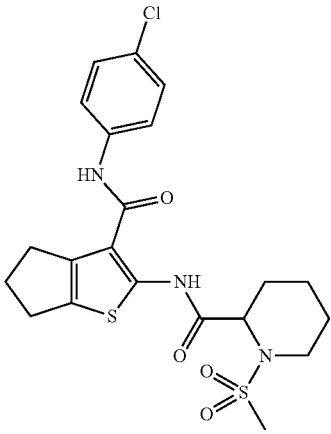 | Compound 100 | 1.66 10$^{-5}$ |
| 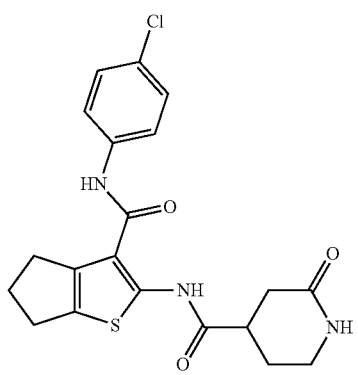 | Compound 101 | 1.90 10$^{-5}$ |

TABLE 2-continued

| Structure | Compound | IC50 (M) |
|---|---|---|
| (structure) | Compound 102 | $2.09 \cdot 10^{-5}$ |
| (structure) | Compound 103 | $2.42 \cdot 10^{-5}$ |

Autophagy-Inducing Effect

The autophagy-inducing effect has been assessed by LC3 lipidation assay and by p62 expression measurement. The results are shown in the following Table and show that the compounds of the invention present an autophagy-inducing effect.

| Compound | LC3 lipidation* | accumulation of LC3 positive cytoplasmic puncta* | p62 expression* | Mitochondria modification* |
|---|---|---|---|---|
| Compound 57 | + | | down | |
| Compound 41 | + | + | down | + |
| Compound 42 | + | | down | |

Materials and Methods
Cells and Virus

The A549 human lung epithelial cells line and the Madin-Darby canine kidney cells (ECACC) were grown in DMEM media (GibCo, 41966052) supplemented with 100U/ml penicillin/streptomycin (GibCo, 15140130) and 10% fetal calf serum (PAN, 3302-P221126) at 37° C. and 5% CO2.

The epidemic A/H1N1/New Caledonia/2006 and A/H3N2/Wyoming/2002 strains were propagated in MDCK cells in DMEM supplemented with 1 µg·ml-1 modified trypsin TPCK (Sigma, T3053) in absence of FCS. Virus stocks were titrated by standard plaque assay on MDCK cells using an agar overlay medium.

Molecules

All the molecules were solubilized in DMSO at a stock concentration of 10 mM. 8 serial 2-fold dilution of test compounds were prepared in DMEM in a final concentration range of 50 µM-195 nM.

Virus Infection

Cells (MDCK or A549) were washed twice with D-PBS 1× (GibCo, 14190). Molecules were added at indicated concentrations. MDCK and A549 cells were then infected with H1N1 (respectively MOI 0.01 and MOI 0.1), with H3N2 (MOI 0.1) in DMEM supplemented with 0.2 µg·ml-1 trypsin TPCK (infection medium) and incubated for 24h (MDCK) or 48 h (A549) in infection medium at 37° C. and 5% CO2.

Titer Measure by Neuraminidase Activity

Influenza virus neuraminidase is able to cleave the methyl-umbelliferyl-Nacetylneuraminic acid (4-MUNANA, Sigma M8639) modifying its emission wavelength in a dose-dependent manner. In 96-black plate (Corning, 3631), 25 µl infection supernatants were diluted in 25 µl DPBS1× containing calcium and magnesium (GibCo, 14040) and 50 µl of 20 µM 4-MUNANA.

After 1 h incubation at 37° C., 100 µl of glycine 0.1M 25% ethanol pH10.7 was added. Measures were done with TECAN infinite M1000 instrument at 365 nm excitation wavelength and 450 nm emission wavelength.

LC3 Lipidation Assay

The HeLa human cervical cancer cell line was grown in DMEM media (GibCo, 41966052) supplemented with 100U/ml penicillin/streptomycin (GibCo, 15140130) and 10% fetal calf serum (PAN, 3302-P221126) at 37° C. and 5% CO2.

For LC3 lipidation assay, cells were washed twice with EBSS and incubated with 10 μM Compound 57, Compound 41 and Compound 42 or with the vehicle alone (DMSO) in EBSS for 2h. Cells were then lysed in a cold extract buffer (20 mM Tris-HCl pH 8.0, 150 mM NaCl, 1 mM EDTA, 0.5% NP40 and a protease inhibitor cocktail (Roche)). Proteins were separated on a 12% Bis-tris gel and immunoblotted with anti-LC3 antibody (Sigma, L7543), anti-rabbit HRP antibody (Abcam, ab97080). Tubulin was used as an internal control.

The invention claimed is:

1. A compound having the following formula (I):

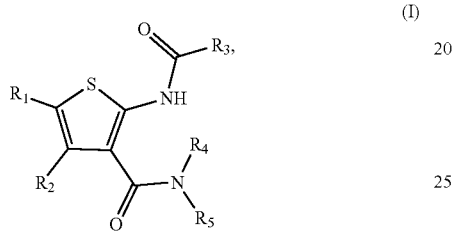

wherein:
$R_1$ and $R_2$ form together a 5-7 membered ring, saturated or unsaturated,
said 5-7 membered ring comprises one or more heteroatoms selected from the group consisting of:
N, optionally substituted by a radical selected from the group consisting of
a $(C_1-C_6)$alkyl, a $(C_2-C_6)$alkenyl, a $(C_2-C_6)$alkynyl,
a 5-10 membered ring, saturated or unsaturated, selected from the group consisting of cycloalkyl, aryl, heterocycloalkyl, and heteroaryl,
a saturated or unsaturated $(C_1-C_6)$alkylcycloalkyl, $(C_1-C_6)$alkylaryl, $(C_1-C_6)$alkylheterocycloalkyl), or $(C_1-C_6)$alkylheteroaryl, and
a CO—$(C_1-C_6)$alkyl, a $CO_2$—$(C_1-C_6)$alkyl, a CO—$(C_1-C_6)$alkylaryl, a CO-aryl, a CO-heteroaryl, a $SO_2$-aryl, or a $SO_2$-heteroaryl,
said radical is optionally substituted by at least one —OH, halogen, $(C_1-C_6)$alkyl, or $(C_1-C_6)$alkyloxy,
O, and
S, and
said 5-7 membered ring is optionally substituted by:
a $(C_1-C_6)$alkyl, a $(C_2-C_6)$alkenyl, a $(C_2-C_6)$alkynyl, optionally substituted by at least one halogen, or —OH,
a 5-10 membered ring, saturated or unsaturated, selected from the group consisting of cycloalkyl, aryl, heterocycloalkyl, and heteroaryl,
a saturated or unsaturated $(C_1-C_6)$alkylcycloalkyl, $(C_1-C_6)$alkylaryl, $(C_1-C_6)$alkylheterocycloalkyl), or $(C_1-C_6)$alkylheteroaryl,
a halogen, —CN, or —$NO_2$,
C(O)R, —$C(O)_2R$, —C(O)NRR', —CONHOR, —$CONHSO_2R$, —NRR', —N(R)C(O)R', —N(R)NR'R", —$N(R)C(O)_2R'$, —N(R)C(O)NR'R", —$N(R)S(O)_2R'$, —OR, —SR, —S(O)R, —$S(O_2)R$, —S(O)NRR', or —$S(O)_2NRR'$, R, R', and R" being independently H, $(C_1-C_6)$alkyl, cycloalkyl, aryl, heterocycloalkyl, heteroaryl, $(C_1-C_6)$alkylcycloalkyl, $(C_1-C_6)$alkylaryl, $(C_1-C_6)$alkylheterocycloalkyl), $(C_1-C_6)$alkylheteroaryl, or R and R' or R' and R" may form a 5-7 membered ring, optionally interrupted by one or several heteroatoms, said 5-7 membered ring is optionally substituted by at least one —OH, halogen, $(C_1-C_6)$alkyl or $(C_1-C_6)$alkyloxy;

$R_3$ represents:
a cyclohexyl being substituted in vicinal position with respect to the CO of the —NH—CO—$R_3$ group by at least one group (A) selected from the group consisting of: —C(O)R, —$C(O)_2R$, —C(O)NRR', —CONHOR, and —$CONHSO_2R$, R and R' are as defined above;

$R_4$ represents a radical selected from the group of:
a 5-14 membered ring, saturated or unsaturated, selected from the group consisting of a cycloalkyl, an aryl, a heterocycloalkyl, a heteroaryl, a fused arylheterocycloalkyl, and a fused arylcycloalkyl, and
a $(C_1-C_6)$alkylcycloalkyl, a $(C_1-C_6)$alkylaryl, a $(C_1-C_6)$alkylheterocycloalkyl, and a $(C_1-C_6)$alkylheteroaryl, and
a $(C_1-C_6)$alkyl,
said radicals being optionally substituted by at least one group (B) selected from the group consisting of:
a $(C_1-C_6)$alkyl or a $(C_1-C_6)$alkoxy, optionally substituted by at least one OH, one halogen or one —NRR', R, R', and R" are as defined above,
a halogen, —CN, or —$NO_2$,
a 5-10 membered ring, saturated or unsaturated, selected from the group consisting of a cycloalkyl, an aryl, a heterocycloalkyl, and a heteroaryl, optionally substituted by at least one OH, one halogen, one $(C_1-C_6)$alkyl, one $(C_1-C_6)$alkyloxy or one —NRR', R, R', and R" are as defined,
a saturated or unsaturated $(C_1-C_6)$alkylcycloalkyl, $(C_1-C_6)$alkylaryl, $(C_1-C_6)$alkylheterocycloalkyl, or $(C_1-C_6)$alkylheteroaryl, optionally substituted by at least one —OH, halogen, $(C_1-C_6)$alkyl, or $(C_1-C_6)$alkyloxy,
—C(O)R, —$C(O)_2R$, —C(O)NRR', —CONHOR, —$CONHSO_2R$, —NRR', —N(R)C(O)R', —N(R)NR'R", —$N(R)C(O)_2R'$, —N(R)C(O)NR'R", —$N(R)S(O)_2R'$, —OR, —SR, —S(O)R, —$S(O_2)R$, —S(O)NRR', or —$S(O)_2NRR'$, R, R', and R" are as defined above; and $R_5$ represents H, a $(C_1-C_6)$alkyl, a $(C_2-C_6)$alkenyl, or a $(C_2-C_6)$alkynyl; or $R_4$ and $R_5$ may form together a 5-14 membered ring, optionally interrupted by one or several heteroatoms, said 5-14 membered ring is optionally substituted by at least one —OH, halogen, $(C_1-C_6)$alkyl, $(C_1-C_6)$alkyloxy, cycloalkyl, or a 5-10 membered ring selected from the group of an aryl, a heterocycloalkyl, and a heteroaryl, optionally substituted by at least one —OH, halogen, $(C_1-C_6)$alkyl, or $(C_1-C_6)$alkyloxy;

and the pharmaceutical salts thereof.

2. The compound according to claim 1, wherein:
$R_1$ and $R_2$ form together a 5-7 membered ring, saturated or unsaturated,
said 5-7 membered ring comprises one or more heteroatoms selected from the group consisting of:

O, and
S, and
said 5-7 membered ring is optionally substituted by:
  a $(C_1\text{-}C_6)$alkyl;
$R_3$ represents:
  a cyclohexyl
being substituted in vicinal position with respect to the CO of the —NH—CO—$R_3$ group by at least one group (A), which is —C(O)$_2$R with R being H;
$R_4$ represents a radical selected from the group consisting of:
  a 5-10 membered ring, saturated or unsaturated, selected from the group consisting of:
    a cycloalkyl, optionally substituted by at least one group (B) selected from the group consisting of:
      a $(C_1\text{-}C_6)$alkyl, optionally substituted by at least one halogen, or one hydroxy,
      a $(C_1\text{-}C_6)$alkoxy, and
      a halogen,
      a cyano,
        a cycloalkyl, a heterocycloalkyl, an aryl, or a heteroaryl, optionally substituted by at least one —OH, halogen, $(C_1\text{-}C_6)$alkyl, or $(C_1\text{-}C_6)$alkyloxy,
        —C(O)R or —S(O$_2$)R with R being a $(C_1\text{-}C_6)$ alkyl,
    an aryl, optionally substituted by at least one group (B) selected from the group consisting of:
      a $(C_1\text{-}C_6)$alkyl, optionally substituted by at least one halogen or one hydroxy,
      a $(C_1\text{-}C_6)$alkoxy, optionally substituted by at least one fluorine,
      a halogen,
      a cyano,
      a cycloalkyl, a heterocycloalkyl, an aryl, or a heteroaryl, optionally substituted by at least one —OH, halogen, $(C_1\text{-}C_6)$alkyl, or $(C_1\text{-}C_6)$alkyloxy,
        —C(O)R or —S(O$_2$)R with R being a $(C_1\text{-}C_6)$ alkyl,
    a heteroaryl, a pyrazine, or a thiazole, optionally substituted by at least one group (B) selected from the group consisting of:
      a halogen,
      a $(C_1\text{-}C_6)$alkyl, or a $(C_1\text{-}C_6)$alkoxy, optionally substituted by at least one halogen or one hydroxy,
      a cyano,
        a cycloalkyl, a heterocycloalkyl, an aryl, or a heteroaryl, optionally substituted by at least one —OH, halogen, $(C_1\text{-}C_6)$alkyl, or $(C_1\text{-}C_6)$alkyloxy, and
        —C(O)R or —S(O$_2$)R with R being a $(C_1\text{-}C_6)$ alkyl,
    a fused arylheterocycloalkyl, and
    a fused arylcycloalkyl,
  a radical selected from the group consisting of:
    $(C_1\text{-}C_6)$alkylcycloalkyl, and
    a $(C_1\text{-}C_6)$alkylaryl,
  said radical is optionally substituted by at least one halogen, one $(C_1\text{-}C_6)$alkyl or one $(C_1\text{-}C_6)$alkoxy, optionally substituted by at least one halogen; and
  a $(C_1\text{-}C_6)$alkyl; and
$R_5$ represents H;
and the pharmaceutical salts thereof.

3. The compound according to claim 1, wherein $R_3$ represents a cyclohexyl substituted in vicinal position with respect to the CO of the —NH—CO—$R_3$ group by at least one group (A), which is —C(O)$_2$R with R being H.

4. The compound according to claim 1, wherein said compound is selected from the group consisting of:
  Compound 37, 2-[[3-[(4-Chlorophenyl)carbamoyl]-5,7-dihydro-4H-thieno[2,3-c]pyran-2-yl]carbamoyl]cyclohexanecarboxylic acid;
  Compound 38, 2-[[3-[(4-Chlorophenyl)carbamoyl]-4,6-dihydrothieno[3,4-b]thiophen-2-yl]carbamoyl]cyclohexanecarboxylic acid;
  Compound 39, 2-[[3-[(4-Chlorophenyl)carbamoyl]-4-methyl-4,6-dihydrothieno[2,3-c]furan-2-yl]carbamoyl] cyclohexanecarboxylic acid;
  Compound 40, 2-[[4-[(4-Chlorophenyl)carbamoyl]-2,3-dihydrothieno[2,3-b]thiophen-5-yl]carbamoyl] cyclohexanecarboxylic acid; and
  Compound 42, 2-[[3-[(4-Chlorophenyl)carbamoyl]thieno[3,4-b]thiophen-2-yl]carbamoyl] cyclohexanecarboxylic acid.

5. A compound selected from the group consisting of:
  Compound 1, 2-[[3-[(3,4-Dimethylphenyl)carbamoyl]-5,6-dihydro-4H-cyclopenta[b]thiophen-2-yl]carbamoyl] cyclohexanecarboxylic acid;
  Compound 2, 2-[[3-[(6-Chloro-3-pyridyl)carbamoyl]-5,6-dihydro-4H-cyclopenta[b]thiophen-2-yl]carbamoyl] cyclohexanecarboxylic acid;
  Compound 3, 2-[[3-(1,3-Benzodioxol-5-ylcarbamoyl)-5,6-dihydro-4H-cyclopenta[b]thiophen-2-yl]carbamoyl] cyclohexanecarboxylic acid;
  Compound 4, 2-[[3-[(4-Fluorophenyl)carbamoyl]-5,6-dihydro-4H-cyclopenta[b]thiophen-2-yl]carbamoyl]cyclohexanecarboxylic acid;
  Compound 5, 2-[[3-[(4-Chlorophenyl)methylcarbamoyl]-5,6-dihydro-4H-cyclopenta[b]thiophen-2-yl]carbamoyl]cyclohexanecarboxylic acid;
  Compound 6, 2-[[3-[[4-Chloro-3-(trifluoromethyl)phenyl]carbamoyl]-5,6-dihydro-4H-cyclopenta[b]thiophen-2-yl]carbamoyl]cyclohexanecarboxylic acid;
  Compound 7, 2-[[3-[(4-Chloro-2-methyl-phenyl)carbamoyl]-5,6-dihydro-4H-cyclopenta[b]thiophen-2-yl]carbamoyl]cyclohexanecarboxylic acid;
  Compound 8, 2-[[3-[(Trans-4-methoxycyclohexyl)carbamoyl]-5,6-dihydro-4H-cyclopenta[b]thiophen-2-yl] carbamoyl]cyclohexanecarboxylic acid;
  Compound 9, 2-[[3-[[4-(2-Hydroxyethyl)phenyl]carbamoyl]-5,6-dihydro-4H-cyclopenta[b]thiophen-2-yl]carbamoyl]cyclohexanecarboxylic acid;
  Compound 10, 2-[[3-[(4-Phenylphenyl)carbamoyl]-5,6-dihydro-4H-cyclopenta[b]thiophen-2-yl]carbamoyl] cyclohexanecarboxylic acid;
  Compound 11, 2-[[3-[(3-Chlorophenyl)methylcarbamoyl]-5,6-dihydro-4H-cyclopenta[b]thiophen-2-yl]carbamoyl]cyclohexanecarboxylic acid;
  Compound 12, 2-[[3-[(3-Acetylphenyl)carbamoyl]-5,6-dihydro-4H-cyclopenta[b]thiophen-2-yl]carbamoyl] cyclohexanecarboxylic acid;
  Compound 13, 2-[[3-[(4-Chloro-3-methyl-phenyl)carbamoyl]-5,6-dihydro-4H-cyclopenta[b]thiophen-2-yl] carbamoyl]cyclohexanecarboxylic acid;
  Compound 14, 2-[[3-[(3-chloro-4-methyl-phenyl)carbamoyl]-5,6-dihydro-4H-cyclopenta[b]thiophen-2-yl] carbamoyl]cyclohexanecarboxylic acid;
  Compound 15, 2-[[3-[(4-Morpholinophenyl)carbamoyl]-5,6-dihydro-4H-cyclopenta[b]thiophen-2-yl]carbamoyl]cyclohexanecarboxylic acid;

Compound 16, 2-[[3-[(3,4-Difluorophenyl)carbamoyl]-5,6-dihydro-4H-cyclopenta[b]thiophen-2-yl]carbamoyl]cyclohexanecarboxylic acid;

Compound 17, 2-[ [3-[(3-Chlorophenyl)carbamoyl]-5,6-dihydro-4H-cyclopenta[b]thiophen-2-yl]carbamoyl]cyclohexanecarboxylic acid;

Compound 18, 2-[[3-[(4,4-Difluorocyclohexyl)carbamoyl]-5,6-dihydro-4H-cyclopenta[b]thiophen-2-yl]carbamoyl]cyclohexanecarboxylic acid;

Compound 19, 2-[[3-[[4-(Hydroxymethyl)phenyl]carbamoyl]-5,6-dihydro-4H-cyclopenta[b]thiophen-2-yl]carbamoyl]cyclohexanecarboxylic acid;

Compound 20, 2-[[3-[[4-(Trifluoromethoxy)phenyl]carbamoyl]-5,6-dihydro-4H-cyclopenta[b]thiophen-2-yl]carbamoyl]cyclohexanecarboxylic acid;

Compound 21, 2-[[3-[(4-tert-Butylphenyl)carbamoyl]-5,6-dihydro-4H-cyclopenta[b]thiophen-2-yl]carbamoyl]cyclohexanecarboxylic acid;

Compound 22, 2-[[3-(pentylcarbamoyl)-5,6-dihydro-4H-cyclopenta[b]thiophen-2-yl]carbamoyl]cyclohexanecarboxylic acid;

Compound 23, 2-[[3-(Indan-1-ylcarbamoyl)-5,6-dihydro-4H-cyclopenta[b]thiophen-2-yl]carbamoyl]cyclohexanecarboxylic acid;

Compound 24, 2-[[3-(Cyclohexylmethylcarbamoyl)-5,6-dihydro-4H-cyclopenta[b]thiophen-2-yl]carbamoyl]cyclohexanecarboxylic acid;

Compound 25, 2-[ [3-[(4-Isopropylphenyl)carbamoyl]-5,6-dihydro-4H-cyclopenta[b]thiophen-2-yl]carbamoyl]cyclohexanecarboxylic acid;

Compound 26, 2-[[3-[(5-Chloropyrazin-2-yl)carbamoyl]-5,6-dihydro-4H-cyclopenta[b]thiophen-2-yl]carbamoyl]cyclohexanecarboxylic acid;

Compound 27, 2-[[3-[[4-(Trifluoromethyl)phenyl]carbamoyl]-5,6-dihydro-4H-cyclopenta[b] thiophen-2-yl]carbamoyl]cyclohexanecarboxylic acid;

Compound 28, 2-[[3-[(4-Cyanophenyl)carbamoyl]-5,6-dihydro-4H-cyclopenta[b]thiophen-2-yl]carbamoyl]cyclohexanecarboxylic acid;

Compound 29, 2-[[3-[(5-Chlorothiazol-2-yl)carbamoyl]-5,6-dihydro-4H-cyclopenta[b]thiophen-2-yl]carbamoyl]cyclohexanecarboxylic acid;

Compound 30, 2-[ [3-(1,3-Dihydroisobenzofuran-5-yl-carbamoyl)-5,6-dihydro-4H-cyclopenta[b]thiophen-2-yl]carbamoyl]cyclohexanecarboxylic acid;

Compound 31, 2-[[3-[(4-Methylsulfonylphenyl)carbamoyl]-5,6-dihydro-4H-cyclopenta[b]thiophen-2-yl]carbamoyl]cyclohexanecarboxylic acid;

Compound 32, 2-[[3-[[6-(Trifluoromethyl)-3-pyridyl]carbamoyl]-5,6-dihydro-4H-cyclopenta[b]thiophen-2-yl]carbamoyl]cyclohexanecarboxylic acid;

Compound 33, 2-[[3-[(5-Methyl-3-pyridyl)carbamoyl]-5,6-dihydro-4H-cyclopenta[b]thiophen-2-yl] carbamoyl]cyclohexanecarboxylic acid;

Compound 34, 2-[[3-[(4-Chlorophenyl)-methyl-carbamoyl]-5,6-dihydro-4H-cyclopenta[b]thiophen-2-yl]carbamoyl]cyclohexanecarboxylic acid;

Compound 35, 2-[[3-[(4-Methylcyclohexyl)carbamoyl]-5,6-dihydro-4H-cyclopenta[b]thiophen-2-yl]carbamoyl]cyclohexanecarboxylic acid;

Compound 36, 2-[[3-[4-(4-chlorophenyl)piperazine-1-carbonyl]-5,6-dihydro-4H-cyclopenta[b]thiophen-2-yl]carbamoyl]cyclohexanecarboxylic acid;

Compound 41, 2-[[3-[(4-Chlorophenyl)carbamoyl]benzothiophen-2-yl]carbamoyl] cyclohexane carboxylic acid;

Compound 49, 2-[[3-[(4-Chlorophenyl)carbamoyl]-5,6-dihydro-4H-cyclopenta[b]thiophen-2-yl]carbamoyl]cyclohexane-trans-carboxylic acid;

Compound 55, N2-[3-[(4-Chlorophenyl)carbamoyl]-5,6-dihydro-4H-cyclopenta[b]thiophen-2-yl]cyclohexane-1,2-dicarboxamide;

Compound 57, 2-[[3-[(4-Chlorophenyl)carbamoyl]-5,6-dihydro-4H-cyclopenta[b]thiophen-2-yl]carbamoyl]cyclohexane-cis-carboxylic acid; and Compound 61, 2-[[3-[(4-Chlorophenyl)carbamoyl]-4,5,6,7-tetrahydrobenzothiophen-2-yl]carbamoyl]cyclohexane-cis-carboxylic acid.

6. A pharmaceutical composition comprising a compound as defined in claim 1, and a pharmaceutically acceptable excipient.

7. A pharmaceutical composition comprising a compound as defined in claim 5, and a pharmaceutically acceptable excipient.

* * * * *

UNITED STATES PATENT AND TRADEMARK OFFICE
CERTIFICATE OF CORRECTION

PATENT NO. : 11,807,618 B2
APPLICATION NO. : 17/697981
DATED : November 7, 2023
INVENTOR(S) : Eric Meldrum et al.

It is certified that error appears in the above-identified patent and that said Letters Patent is hereby corrected as shown below:

In the Specification

Column 67,
Line 36, "all H" should read --all $^1$H--.
Line 38, "AVII" should read --AVIII--.
Line 39, "AVII" should read --AVIII--.

Column 68,
Line 33, "on oPLC" should read --on HPLC--.

Column 75,
Line 1, "in THE" should read --in THF--.
Line 52, "in THE" should read --in THF--.

Column 77,
Line 3, "in THE" should read --in THF--.
Line 59, "THF/Et$_{20}$" should read --THF/Et$_2$O--.

Column 78,
Line 25, "in THE" should read --in THF--.
Line 65, "in THE" should read --in THF--.

Column 82,
Line 32, "[M+H]$^-$" should read --[M+H]$^+$--.

Column 87,
Line 3, "[M+H]$^-$" should read --[M+H]$^+$--.

Signed and Sealed this
Sixteenth Day of July, 2024

Katherine Kelly Vidal
*Director of the United States Patent and Trademark Office*

Column 95,

Lines 40-55, " 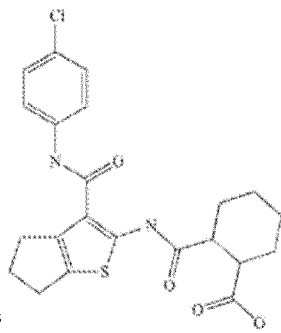 " should read -- 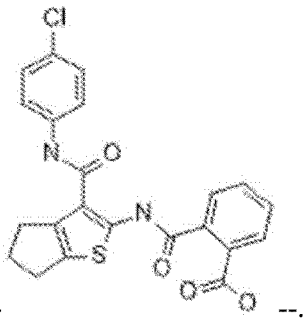 --.

Column 95,
Line 60, "in THE" should read --in THF--.

Column 97,
Line 56, "in Et$_{20}$" should read --in Et$_2$O--.

Column 98,
Line 25, "with THE" should read --with THF--.

Column 99,
Line 4, "with THE" should read --with THF--.

Column 100,
Line 50, "in THE" should read --in THF--.

Column 101,
Line 24, "in THE" should read --in THF--.
Line 26, "in THE" should read --in THF--.

Column 104,
Line 2, "dissolved in THE" should read --dissolved in THF--.
Line 3, "2M in THE" should read --2M in THF--.

Column 105,

Lines 33-48, " 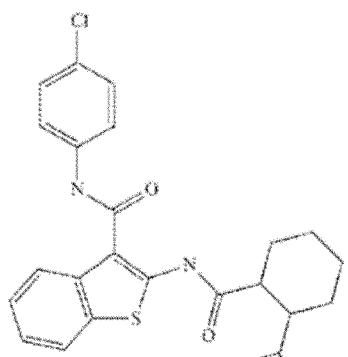 " should read -- 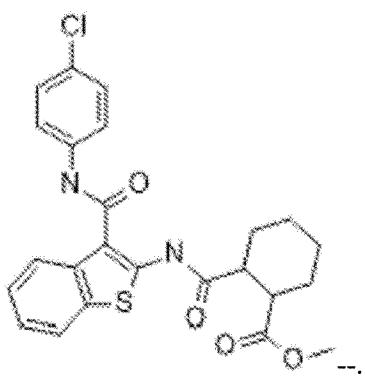 --.

Column 106,

Lines 30-44, " 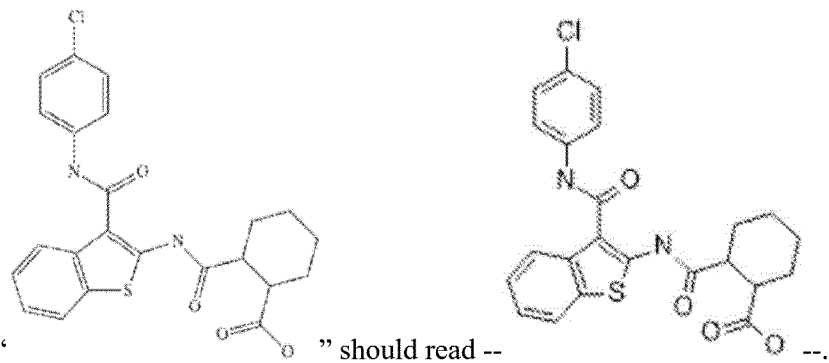 " should read -- --.

Column 106,
Line 49, "of THE" should read --of THF--.
Line 53, "THE was" should read --THF was--.

Column 108,
Line 20, "in THE" should read --in THF--.

Column 111,
Line 13, "pink powder." should read --pink powder. $^1$H NMR (DMSO-$d_6$, 400MHz): δ = 12.25 (s, 1H), 11.89 (s, 1H), 9.70 (s, 1H), 7.75 (br s, 2H), 7.74 (d, $J$=8.9 Hz, 2H), 7.44 (d, $J$=8.9 Hz, 2H), 2.92 (m, 2H), 1.98-2.08 (m, 1H), 1.82-1.98 (m, 2H), 1.65-1.74 (m, 1H), 1.55-1.63 (m, 1H), 1.29-1.51 ppm (m, 3H). LC/MS (Table 1, Method C) $R_t$ = 4.21 min; MS *m/z*: 463 [M+H]$^+$.--.

Column 112,
Line 61, "220%)" should read --22%)--.

Column 115,
Line 64, "in THE" should read --in THF--.

Column 118,

Lines 29-39, " 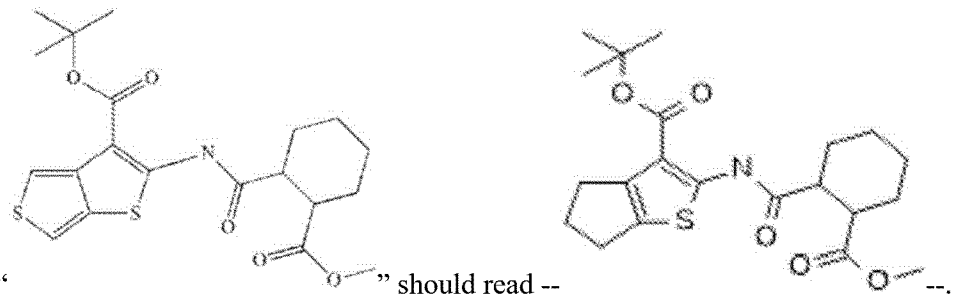 " should read -- --.

Column 125,
Line 67, "[M+H]$^-$" should read --[M+H]$^+$--.

Column 137,
Line 57, "in THE" should read --in THF--.